(12) United States Patent
Hoffmann et al.

(10) Patent No.: US 8,912,173 B2
(45) Date of Patent: Dec. 16, 2014

(54) SUBSTITUTED QUINOLINES AND THEIR USE AS MEDICAMENTS

(75) Inventors: Matthias Hoffmann, Mittelbiberach (DE); Daniel Bischoff, Biberach an der Riss (DE); Georg Dahmann, Warthausen-Birkenhard (DE); Jasna Klicic, Biberach an der Riss (DE); Gerhard Schaenzle, Biberach an der Riss (DE); Stefan Ludwig Michael Wollin, Bad Waldsee (DE); Serge Gaston Convers-Reignier, Abingdon (GB); Stephen Peter East, Wallingford (GB); Frederic Jacques Marlin, Sutton Courtenay (GB); Clive McCarthy, Wantage (GB); John Scott, Abingdon (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/553,898

(22) Filed: Jul. 20, 2012

(65) Prior Publication Data

US 2013/0029949 A1  Jan. 31, 2013

(30) Foreign Application Priority Data

Jul. 26, 2011 (EP) ..................... 11175444

(51) Int. Cl.
| | | |
|---|---|---|
| *A61K 31/56* | (2006.01) | |
| *C07D 401/14* | (2006.01) | |
| *C07D 491/04* | (2006.01) | |
| *C07D 401/12* | (2006.01) | |
| *C07D 413/12* | (2006.01) | |
| *C07D 471/04* | (2006.01) | |
| *C07D 413/14* | (2006.01) | |
| *C07D 417/14* | (2006.01) | |
| *C07D 215/20* | (2006.01) | |

(52) U.S. Cl.
CPC ............ *C07D 215/20* (2013.01); *C07D 401/14* (2013.01); *C07D 491/04* (2013.01); *C07D 401/12* (2013.01); *C07D 413/12* (2013.01); *C07D 471/04* (2013.01); *C07D 413/14* (2013.01); *C07D 417/14* (2013.01)
USPC ....................................................... 514/171

(58) Field of Classification Search
USPC ....................................................... 514/171
See application file for complete search history.

(56) References Cited

U.S. PATENT DOCUMENTS

| | | | |
|---|---|---|---|
| 4,329,349 A | 5/1982 | Damon, II et al. | |
| 7,321,041 B2 | 1/2008 | Cywin et al. | |
| 8,604,049 B2 | 12/2013 | Fiegen et al. | |
| 2003/0158195 A1 | 8/2003 | Cywin et al. | |
| 2003/0229090 A1 | 12/2003 | Cywin et al. | |
| 2008/0188467 A1 | 8/2008 | Wong et al. | |
| 2011/0201608 A1 | 8/2011 | Hoffmann et al. | |
| 2011/0263549 A1 | 10/2011 | Fiegen et al. | |
| 2012/0028939 A1 | 2/2012 | Hoffmann et al. | |
| 2014/0142135 A1 | 5/2014 | Fiegen et al. | |

FOREIGN PATENT DOCUMENTS

| | | |
|---|---|---|
| EP | 1396488 A1 | 3/2004 |
| JP | 56020588 | 2/1981 |
| WO | 03057695 A1 | 7/2003 |
| WO | 2008133753 A2 | 11/2008 |
| WO | 2010015518 A2 | 2/2010 |
| WO | 2010015520 A1 | 2/2010 |
| WO | 2011092128 A1 | 8/2011 |

OTHER PUBLICATIONS

Politanskaya et al 'Regioselectivity and relative substrate activity of difluoroquinolines contaning fluorine atoms in benzene ring in reaction with sodium methoxide' Journal of Fluorine Chemistry, vol. 126, p. 1502-1509, 2005.*
Cywin, C.L. et al., "Discovery and SAR of Novel [1,6]Naphthyridines as Potent Inhibitors of Spleen Tyrosine Kinase (SYK)". Bioorganice & Medicinal Chemistry Letters, 13, 2003, 1415-1418.
Brun, E.M. et al., "New approach to condensed pyrid-2-ones". ARKIVOC (Gainesville, FL, U.S.) [online computer file], coden: AGFUAR URL: HTTP://WWW.ARKAT-USA.ORG/ARK/JOURNAL/2002/PART(X)_GENERAL/2-615C/615C.PDF, vol. 2002, No. (x), Jan. 22, 2003, pp. 80-89.
Ames, D.E., "Condensation of beta-Dicarbonyl Compounds with Halogenopyridinecarboxylic Acids. A Convenient sythesis of Some Naphthridine Derivatives". Journal of the Chemical Society, Perkin Transactions 1, Chemical Society, Letchworth; GB LNKD-DOI:10. 1029/P19720000705, Jan. 1, 1972, pp. 705-710.
Li, Jianke et al. "Synthesis of 5-hydroxyquinolines" Tetrahedron Letters (2010) 51, pp. 3876-3878.

(Continued)

*Primary Examiner* — Wu-Cheng Winston Shen
*Assistant Examiner* — Christopher R Stone
(74) *Attorney, Agent, or Firm* — Michael P. Morris; Anthony Bottino; Usha R. Patel

(57) ABSTRACT

Disclosed are substituted quinolines of formula 1

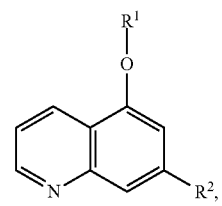

wherein
$R^1$ and $R^2$ are defined herein, the processing of making and using the same.

35 Claims, No Drawings

(56) References Cited

OTHER PUBLICATIONS

Weinblatt et al.; Treatment of Rheumatoid Arthritis With a Syk Kinase Inhibitor, A Twelve-Week, Randomized, Placebo-Controlled Trial; Arthritis & Rheumatism; Nov. 2008; vol. 58; No. 11; pp. 3309-3318.

Xie et al.; Pharmacophore modeling study based on known Spleen tyrosine kinase inhibitors together with virtual screening for identifying novel inhibitors; Bioorganic & Medicinal Chemistry Letters; 2009; No. 19; pp. 1944-1949.

* cited by examiner

SUBSTITUTED QUINOLINES AND THEIR USE AS MEDICAMENTS

The invention relates to new substituted quinolines of formula 1

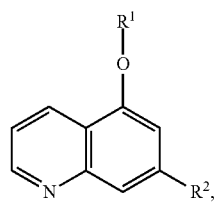

wherein
$R^1$ is a linear or branched $C_{1-6}$-alkyl,
wherein $R^1$ may optionally be substituted by $R^3$ which is selected from the group consisting of a three-, four-, five-, six- or seven-membered cycloalkl; a five-, six- or seven-membered, saturated heterocycle comprising one, two or three heteroatoms each independently selected from the group consisting of N, S and O; and a five- or six-membered heteroaryl comprising one, two or three heteroatoms each independently selected from the group consisting of N, S and O;
wherein $R^3$ may optionally be substituted by one, two, three or four substituents each independently from the other selected from the group consisting of oxo, OH, —CO—$NH_2$, —CO—NH($CH_3$), —CO—N($CH_3$)$_2$, —$C_{1-5}$-alkyl, —$C_{1-3}$-alkylene-CO—$NH_2$, —$C_{1-3}$-alkylene-CO—NH($CH_3$), $C_{1-3}$-alkylene-CO—N($CH_3$)$_2$, —$C_{1-3}$-alkylene-CN and —CN,
and wherein
$R^2$ is selected from the group consisting of halogen, phenyl, a five- or six-membered monocyclic heteroaryl comprising one, two or three heteroatoms each independently selected from the group consisting of N, S and O; a bicyclic, nine-, ten- or eleven-membered, either aromatic or non-aromatic, but not fully saturated heterocycle comprising one, two, three or four heteroatoms each independently selected from the group consisting of N, S and O;
wherein $R^2$ may optionally be substituted by one, two, three or four substituents $R^4$ which independently from one another are selected from the group consisting of linear or branched —O—$C_{1-5}$-alkyl, —OH, oxo, halogen, —$C_{1-5}$-haloalkyl, —$SO_2CH_3$, —$C_{1-3}$-alkylene-$SO_2$—($C_{1-3}$-alkyl), —$SO_2$—$CF_3$, —CN, $C_{3-6}$-cycloalkyl, linear or branched —$C_{1-5}$-alkyl, a five- or six-membered saturated heterocycle comprising one, two or three heteroatoms each independently from one another selected from the group of N, S, —$SO_2$ and O;
—$C_{1-3}$-alkylene-N($C_{1-3}$-alkyl)-CO—$C_{1-3}$-alkyl, —NH—CO—$C_{1-3}$-alkyl, —CO—NH($CH_3$), —CO—$NH_2$, —CO—N($CH_3$)$_2$, —O—$R^5$, —CO—$R^5$, —$C_{1-3}$-alkylene-O—CO—$C_{1-3}$-alkyl and

wherein $R^4$ may optionally be substituted by one or two substituents $R^5$,
wherein each
$R^5$ is independently from one another selected from the group consisting of linear or branched —$C_{1-4}$-alkyl, oxo; —$C_{1-3}$- haloalkyl, —OH, halogen, —$C_{1-2}$-alkylene-$C_{1-3}$-haloalkyl, a five- or six-membered saturated heterocycle comprising one, two or three heteroatoms each independently selected from the group of N, S and O; a three, four-, five-, six- or seven-membered cycloalkyl; a five- or six-membered heteroaryl comprising one or two heteroatoms each independently selected from the group of N, S and O,
wherein $R^5$ may optionally be substituted by a group consisting of oxo, $C_{1-3}$-alkyl and —$C_{1-3}$-haloalkyl,
and the pharmacologically acceptable salts of the aforementioned compounds.

1. BACKGROUND TO THE INVENTION

1.1 SYK-Inhibitors

The present invention describes new substituted quinolines that inhibit the protein kinase Syk (spleen tyrosine kinase), the preparation and formulation thereof and their use for preparing a medicament.

Syk is an intracellular tyrosine kinase that has an important mediator function in the signal transduction of different receptors in B-cells, mast cells, monocytes, macrophages, neutrophils, T-cells, dendritic cells and epithelial cells. The receptors in which Syk performs an important function in signal transduction include for example the receptors for IgE (FcεRI) and IgG (FcγR1) on mast cells and B cells, the B-cell receptor (BCR) and the T-cell receptor (TCR) on B- and T-cells, the ICAM1 receptor (ICAM1R) on epithelial cells of the respiratory tract, the DAP12-receptor on natural killer cells, dendritic cells and osteoclasts, the dectin 1-receptor on a subpopulation of T-helper cells (Th-17 cells), as well as the integrin receptors for β1-, β2- and β3-integrins on neutrophils, monocytes and macrophages (Wong et al.; Expert Opin. Investig. Drugs (2004) 13(7), 743-762; Ulanova et al.; Expert Opion. Ther. Target (2005) 9(5); 901-921; Wang et al.; J. Immunol. (2006) 177, 6859-6870; Leib and Gut-Landmann et al.; Nature Immunology (2007) 8, 630-638; Slack et al., European J. Immunol. (2007) 37, 1600-1612). The molecular processes are described best for the signal transduction of the FcεRI. In mast cells the binding of IgE to FcεRI causes the cross-linking of IgE-receptors and the recruiting and activation of Lyn (a tyrosine kinase from the Src family). Active Lyn phoshorylates so-called ITAM motifs, which are present in many of the receptors listed above, and thereby generates binding sites for the SH2-domain of Syk. As a result of the binding to the ITAM motif Syk is activated and then phosphorylates various substrates which are needed for the release of allergic and inflammatory mediators such as e.g. histamine and β-hexosamidase (BHA), as well as for the synthesis of lipid mediators, such as e.g. prostaglandins and leukotrienes.

In view of its central function in different signal transduction pathways Syk has been discussed as a therapeutic target for different diseases such as e.g. allergic rhinitis, asthma, autoimmune diseases, rheumatoid arthritis, osteopenia, osteoporosis, COPD and various leukaemias and lymphomas (Wong et al.; Expert Opin. Investig. Drugs (2004) 13(7), 743-762; Ulanova et al.; Expert Opion. Ther. Target (2005) 9(5); 901-921; Sigh and Masuda. Annual Reports in Medicinal Chemistry (2007) Vol 42; 379-391; Bajpai et al.; Expert Opin. Investig. Drugs (2008) Vol 15 (5); 641-659; Masuda and Schmitz; PPT (2008) Vol 21; 461-467; Riccaboni et al., Drug Discovery Today (2010) Vol 00 (O); 517-530; Efremov and Luarenti, Expert Opin Investig Drugs. (2011) 20(5):623-36).

Allergic rhinitis and asthma are diseases associated with allergic reactions and inflammatory processes and involving different cell types such as e.g. Mast cells, eosinophils, T-cells and dendritic cells. After exposure to allergens has occurred, the high affinity immunoglobulin receptors for IgE (FcεRI) and IgG (FcγR1) are activated and induce the release of pro-inflammatory mediators and bronchoconstrictors. An inhibitor of the Syk kinase activity should thus be able to inhibit these steps.

Rheumatoid arthritis (RA) is an autoimmune disease in which the bones and ligaments structures surrounding the joints are progressively destroyed. In the pathophysiology of RA, B-cells play a significant role, as has been demonstrated for example by the therapeutic use of rituximab, a B cell-depleting antibody. In addition to the function of Syk in the signal transduction of the BCR (which after being stimulated also induces the release of pro-inflammatory mediators), Syk also plays an important part in the maturation and proliferation of B cells (Cheng et al. Nature (1995) 378, 303-306, Cornall et al., PNAS (2000) 97(4), 1713-1718). An inhibitor of the Syk kinase activity may thus offer a therapeutic option for the treatment of autoimmune diseases such as RA and diseases with an increased proliferation of B cells, such as e.g. B-cell lymphomas.

Chronic obstructive pulmonary disease (COPD) is characterised by a successive deterioration in lung function and chronic inflammation of the airways, which is initiated and produced by noxious substances of all kinds and contributes to the maintenance of the course of the disease. At a cellular level, in COPD there is in particular a multiplication of T-lymphocytes, neutrophils, granulocytes and macrophages. In particular, there is an increase in the number of CD8-positive lymphocytes, that is directly connected with the impairment of lung function. Another characteristic of COPD are acute deteriorations in lung function (exacerbations), characterised by viral (e.g. Rhinovirus), or bacterial (e.g. *Streptococcus pneumoniae, Haemophilus influenzae* and *Moraxella catarrhalis*) infections.

In view of the pro-inflammatory function of Syk in macrophages, T-cells and neutrophils as described above (see: Wong et al.; Expert Opin. Investig. Drugs (2004) 13(7), 743-762; and references cited therein) an inhibitor of the Syk kinase activity could be a new therapeutic approach to the treatment of the inflammatory processes that underlie COPD. It has also been shown that Syk in epithelial cells of the respiratory tract is involved in the ICAM1R-mediated uptake and subsequent replication of the Rhinovirus and that a si-RNA against Syk blocks these steps (Wang et al.; J. Immunol. (2006) 177, 6859-6870; Lau et al.; J. Immunol. (2008) 180, 870-880). Thus, an inhibitor of the Syk kinase activity could also be used therapeutically in exacerbations caused by Rhinoviruses.

Various studies suggest that Syk is involved in the malignant transformation of lymphocytes (summarised in Sigh and Masuda, Annual Reports in Medicinal Chemistry (2007) Vol 42; 379-391). A TEL-Syk fusion protein with a constitutive Syk activity transformed B cells of a patient with myelodysplastic syndrome, a constitutively active ITK-Syk fusion protein was isolated from patients with peripheral T-cell lymphomas (PTCL). Moreover, constitutively active Syk was found in B-cell lymphoma cells of patients, especially in B-lineage acute lymphoblastic leukemia (B-ALL), follicular lymphoma (FL), diffuse large B-cell lymphoma (DLBCL), mantle cell lymphomas and B cell Non-Hodgkin Lymphomas (NHLs) as well as in acute myeloid leukemia (AML). On the basis of these data it seems that Syk is a proto-oncogene in haematopoietic cells and represents a potential target for the treatment of certain leukaemias and lymphomas.

Idiophathic thrombocytoenic purpura (ITP) is an autoimmune disease in which IgG autoantibodies against antigens present on platelets bind to and destroy platelets. Patients with ITP have an accelerated clearance of circulating IgG-coated platelets via macrophages in the spleen and the liver. In view of the pro-inflammatory FcγR-mediated function of Syk in macrophages an inhibitor of Syk is considered to have a therapeutic benefit in FcγR-mediated cytopenias like ITP. Indeed the Syk inhibitor R788 (R406) improved platelet counts in a single center, oben label study in patients with ITP (Podolanczuk et al; Blood (2009) 113, 3154-3169).

Bullous pemphigoid (Ujiie et al. Journal of Dermatology 2010; 37: 194-204) is a chronic, autoimmune, subepidermal, blistering skin disease that rarely involves mucous membranes. Bullous pemphigoid is characterized by the presence of immunoglobulin G (IgG) autoantibodies specific for the hemidesmosomal bullous pemphigoid antigens BP230 (BPAg1) and BP180 (BPAg2). Pemphigus vulgaris (Venugopal et al. Dermatol. Clin. 2011; 29:373-80) is a chronic blistering skin disease with skin lesions that are rarely pruritic, but which are often painful. Pemphigus vulgaris is an autoimmune disease caused by IgG autoantibodies directed against both desmoglein 1 and desmoglein 3 resulting in the loss of cohesion between keratinocytes in the epidermis. It is characterized by extensive flaccid blisters and mucocutaneous erosions. In both diseases IgG autoantibodies bind to Fc receptor gamma (FcR9) and activate FcR9 and downstream signaling via Syk kinase. Thus, an inhibitor of the Syk kinase activity which blocks downstream signalling of the FcR9 could be used therapeutically to treat patients with bullous pemphigoid and pemphigus vulgaris. Systemic lupus erythematosus (SLE) is a chronic autoimmune disease which can affect basically any organ of the body. It is characterised by a multisystem inflammation of the microvascular and the presence of autoantibodies. FcγR-deficient mice are protected from several aspects of SLE in disease-related preclinical models, suggesting that an inhibitor of Syk can have a therapeutic benefit in SLE in view of the pro-inflammatory FcγR-mediated function of Syk in various cells.

1.2 Prior Art

U.S. Pat. No. 3,928,367, U.S. Pat. No. 4,017,500, U.S. Pat. No. 4,115,395 and U.S. Pat. No. 4,260,759 describe 5-amino-1,6-naphthyridines with an antifungal and antibacterial activity. WO 9918077 describes 5-piperazinyl-1,6-naphthyridines as serotonin antagonists. U.S. Pat. No. 7,321,041 describes substituted 1,6-naphthyridines as SYK-inhibitors, however these 1,6-naphthyridines have a completely different substitution pattern from the compounds according to the invention. PCT/EP1011050871 discloses 1,6-naphthyridines which are substituted in 5- and in 7-position. In contrast to that the instant invention concerns 5-,7-disubstituted quinolines instead of naphthyridines.

WO 2006038041 discloses quinoline-compounds which are substituted in the 5- and 7-position, however the substitution pattern—in particular in the 7-position—is completely different from the one of the quinolines of formula 1 of the instant invention.

Surprisingly it has now been found that quinolines of formula 1 are particularly suitable for the treatment of respiratory complaints, allergic diseases, osteoporosis, gastrointestinal diseases, autoimmune diseases, inflammatory diseases and diseases of the peripheral or central nervous system, particularly for the treatment of asthma, allergic rhinitis, rheumatoid arthritis, allergic dermatitis and COPD.

2. DESCRIPTION OF THE INVENTION

The present invention therefore relates to compounds of formula 1,

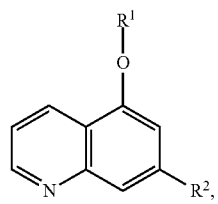

wherein
$R^1$ is a linear or branched $C_{1-6}$-alkyl,
wherein $R^1$ may optionally be substituted by $R^3$ which is selected from the group consisting of a three-, four-, five-, six- or seven-membered cycloalkyl; a five-, six- or seven-membered, saturated heterocycle comprising one, two or three heteroatoms each independently selected from the group consisting of N, S and O; and a five- or six-membered heteroaryl comprising one, two or three heteroatoms each independently selected from the group consisting of N, S and O;
wherein $R^3$ may optionally be substituted by one, two, three or four substituents each independently selected from the group consisting of oxo, OH, —CO—$NH_2$, —CO—NH($CH_3$), —CO—N($CH_3$)$_2$, —$C_{1-5}$-alkyl, —$C_{1-3}$-alkylene-CO—$NH_2$, —$C_{1-3}$-alkylene-CO—NH($CH_3$), —$C_{1-3}$-alkylene-CO—N($CH_3$)$_2$, —$C_{1-3}$-alkylene-CN and —CN,
and wherein
$R^2$ is selected from the group consisting of halogen, phenyl, a five- or six-membered monocyclic heteroaryl comprising one, two or three heteroatoms each independently selected from the group consisting of N, S and O; a bicyclic nine-, ten- or eleven-membered, either aromatic or non-aromatic, but not fully saturated heterocycle comprising one, two, three or four heteroatoms each independently selected from the group consisting of N, S and O;
wherein $R^2$ may optionally be substituted by one, two, three or four substituents $R^4$ which independently from one another are selected from the group consisting of linear or branched —O—$C_{1-5}$-alkyl, —OH, oxo, halogen, —$C_{1-5}$-haloalkyl, —$SO_2CH_3$, —$C_{1-3}$-alkylene-$SO_2$—$C_{1-3}$-alkyl), —$SO_2$—$CF_3$, —CN, —$C_{3-6}$-cycloalkyl, linear or branched —$C_{1-5}$-alkyl, a four, five- or six-membered saturated heterocycle comprising one, two or three heteroatoms each independently from one another selected from the group of N, S, —$SO_2$ and O;
—$C_{1-3}$-alkylene-N($C_{1-3}$-alkyl)-CO—$C_{1-3}$-alkyl, —NH—CO—$C_{1-3}$-alkyl, —CO—NH($CH_3$), —CO—$NH_2$, —CO—N($CH_3$)$_2$, —O—$R^5$, —CO—$R^5$, —$C_{1-3}$-alkylene-O—CO—$C_{1-3}$-alkyl and

wherein $R^4$ may optionally be substituted by one or two substituents $R^5$, wherein each
$R^5$ is independently from one another selected from the group consisting of linear or branched —$C_{1-4}$-alkyl, oxo, —$C_{1-3}$-haloalkyl, —OH, halogen, —$C_{1-2}$-alkylene-$C_{1-3}$-haloalkyl, a five- or six-membered saturated heterocycle comprising one, two or three heteroatoms each independently selected from the group of N, S and O, a three, four-, five-, six- or seven-membered cycloalkyl, a five- or six-membered heteroaryl comprising one or two heteroatoms each independently selected from the group consisting of N, O and S,
wherein $R^5$ may optionally be substituted by a group consisting of oxo, —$C_{1-3}$-alkyl and —$C_{1-3}$-haloalkyl,
and the pharmacologically acceptable salts of the aforementioned compounds.

In another embodiment the invention relates to the above-mentioned compounds of formula 1, wherein
$R^1$ is selected from the group consisting of —$CH_3$ and —$CH_2$—($CH_3$) which may optionally be substituted by $R^3$ which is selected from the group consisting of a three-, four-, five-, six- or seven-membered cycloalkl; a five-, six- or seven-membered, saturated heterocycle comprising one, two or three heteroatoms each independently selected from the group consisting of N, S and O; and a five- or six-membered heteroaryl comprising one, two or three heteroatoms each independently selected from the group consisting of N, S and O;
wherein $R^3$ may optionally be substituted by one, two, three or four substituents each independently selected from the group consisting of oxo, OH, —CO—$NH_2$, —CO—NH ($CH_3$), —CO—N($CH_3$)$_2$, —$C_{1-5}$-alkyl, —$C_{1-3}$-alkylene-CO—$NH_2$, —$C_{1-3}$-alkylene-CO—NH($CH_3$), —$C_{1-3}$-alkylene-CO—N($CH_3$)$_2$, —$C_{1-3}$-alkylene-CN and —CN,
and the pharmacologically acceptable salts of the aforementioned compounds.

In a further aspect the instant invention relates to the above compounds of formula 1, wherein $R^1$ is substituted by $R^3$ which is selected from the group consisting of a five- or six-membered saturated heterocycle comprising one or two heteroatoms each independently selected from the group consisting of N, S and O,
wherein $R^3$ may optionally be substituted by one, two, three or four substituents each independently selected from the group consisting of oxo, OH, —CO—$NH_2$, —CO—NH ($CH_3$), —CO—N($CH_3$)$_2$, —$C_{1-5}$-alkyl, —$C_{1-3}$-alkylene-CO—$NH_2$, —$C_{1-3}$-alkylene-CO—NH($CH_3$), —$C_{1-3}$-alkylene-CO—N($CH_3$)$_2$, —$C_{1-3}$-alkylene-CN and —CN,
and the pharmacologically acceptable salts of the aforementioned compounds.

Further, the instant invention refers to the above compounds of formula 1, wherein $R^1$ is substituted by $R^3$ which is selected from the group consisting of a five- or six-membered heteroaryl comprising one or two heteroatoms each independently selected from the group consisting of N, S and O,
wherein $R^3$ may optionally be substituted by one, two, three or four substituents each independently selected from the group consisting of oxo, OH, —CO—$NH_2$, —CO—NH ($CH_3$), —CO—N($CH_3$)$_2$, —$C_{1-5}$-alkyl, —$C_{1-3}$-alkylene-CO—$NH_2$, —$C_{1-3}$-alkylene-CO—NH($CH_3$), —$C_{1-3}$-alkylene-CO—N($CH_3$)$_2$, —$C_{1-3}$-alkylene-CN and —CN,
and the pharmacologically acceptable salts of the aforementioned compounds.

In another embodiment the instant invention relates to the above-mentioned compounds of formula 1, wherein
$R^1$ is a selected from the group consisting of —$CH_3$ or —$CH_2$ ($CH_3$),
wherein $R^1$ may optionally be substituted by $R^3$ which is selected from the group consisting of a three-, four-, five- or six-membered cycloalkl; a five- or six-membered saturated heterocycle comprising one or two heteroatoms each independently selected from the group consisting of N, S and O; and a five- or six-membered heteroaryl comprising one or two heteroatoms each independently selected from the group consisting of N, S and O;
wherein $R^3$ may optionally be substituted by one, two, three or four substituents each independently selected from the group consisting of oxo, —CO—NH$_2$, —CH$_2$—CO—NH$_2$, methyl and —CH$_2$—CN,
and the pharmacologically acceptable salts of the aforementioned compounds.

In a preferred embodiment the instant invention refers to the compounds of formula 1, wherein
$R^1$ is selected from the group consisting of —CH$_3$ and —CH$_2$—CH$_3$,
wherein $R^1$ is substituted by $R^3$ which is a five-membered saturated heterocycle comprising one nitrogen-atom,
wherein $R^3$ is substituted by one oxo-group
and the pharmacologically acceptable salts of the aforementioned compounds.

In a further particularly preferred embodiment the invention relates to the above compound of formula 1, wherein $R^1$ is the group

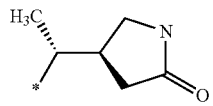

and the pharmacologically acceptable salts of the aforementioned compounds.

In a further preferred embodiment the instant invention refers to the above compounds of formula 1, wherein
$R^1$ is selected from the group consisting of —CH$_3$ and —CH$_2$—CH$_3$,
wherein $R^1$ is substituted by $R^3$ which is a six-membered heteroaryl comprising one nitrogen-atom,
wherein $R^3$ is substituted by —CO—NH$_2$,
and the pharmacologically acceptable salts of the aforementioned compounds.

In a further particularly preferred embodiment the instant invention relates to compounds of formula 1, wherein $R^1$ is the group

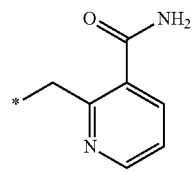 [SMILES: *Cc1ncccc1C(N)=O]

and the pharmacologically acceptable salts of the aforementioned compounds.

In a further embodiment the invention relates to the above compounds of formula 1, wherein
$R^2$ is selected from the group consisting of
$R^2$ is selected from the group consisting of phenyl, a five- or six-membered monocyclic heteroaryl comprising one, two or three heteroatoms each independently selected from the group consisting of N, S and O; a bicyclic, nine- or ten-membered, either aromatic or non-aromatic, but not fully saturated heterocycle comprising one, two, three or four heteroatoms each independently selected from the group consisting of N, S and O;

wherein $R^2$ may optionally be substituted by one, two, three or four substituents $R^4$ which independently from one another are selected from the group consisting of linear or branched —O—C$_{1-3}$-alkyl, oxo, —OH, —F, —Cl, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently selected from the group of N, S, SO$_2$ and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein $R^4$ may optionally be substituted by one or two substituents $R^5$,
wherein each
$R^5$ is independently from one another selected from the group consisting of methyl, ethyl, propyl, isopropyl, isopropyl, n-butyl, isobutyl, tert-butyl, —C$_{1-3}$-haloalkyl, oxo, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl, a five- or six-membered heteroaryl comprising one or two heteratoms each independently selected from the group consisting of N, S and O,
wherein $R^5$ may optionally be substituted by a group consisting of oxo, methyl, ethyl, —CF$_3$,
and the pharmacologically acceptable salts of the aforementioned compounds.

The instant invention further relates to the above compounds of formula 1, wherein
$R^2$ is phenyl,
wherein $R^2$ may optionally be substituted by one, two, three or four substituents $R^4$ which independently from one another are selected from the group consisting of linear or branched —O—C$_{1-3}$-alkyl, oxo, —OH, —F, —Cl, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently selected from the group of N, S and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein $R^4$ may optionally be substituted by one or two substituents $R^{59}$
wherein each
$R^5$ is independently selected from the group consisting of methyl, ethyl, propyl, isopropyl, m isopropyl, n-butyl, isobutyl, tert-butyl, oxo, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl, a five- or six-membered heteroaryl comprising one or two heteroatoms each independently selected from the group consisting of N, S and O, wherein $R^5$ may optionally be substituted by a group consisting of oxo, methyl, and the pharmacologically acceptable salts of the aforementioned compounds.

In another embodiment the instant invention refers to the above-mentioned compounds of formula 1, wherein $R^2$ is phenyl, and wherein $R^2$ may optionally be substituted by one, two, three or four substituents $R^4$ which independently from one another are selected from the group consisting of —OCH$_3$, oxo, —OH, —F, Cl, —CF$_3$, —CHF$_2$, —SO$_2$CH$_3$, —SO$_2$—CF$_3$, —CH$_3$, —CH$_2$—CH$_3$, propyl, isopropyl; —NH—CO—CH$_3$, —C$_{1-3}$-alkylene-N(C$_{1-3}$-alkyl)-CO—CH$_3$, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein $R^4$ may optionally be substituted by one or two substituents $R^5$, wherein each $R^5$ is independently selected from the group consisting of methyl, ethyl, propyl, isopropyl, isopropyl, n-butyl, isobutyl, tert-butyl, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently from one another selected from the group of N, S and O, a three, four-, five-, six- or seven-membered cycloalkyl, wherein $R^5$ may optionally be substituted by a group consisting of oxo, methyl, and the pharmacologically acceptable salts of the aforementioned compounds.

The invention further relates to the above compounds of formula 1, wherein $R^2$ is a five- or six-membered monocyclic heteroaryl comprising one, two or three heteroatoms each independently selected from the group consisting of N, S and O;

wherein $R^2$ may optionally be substituted by one, two, three or four substituents $R^4$ which independently from one another are selected from the group consisting of —O-methyl, —O-ethyl, —O-propyl, —O-isopropyl, oxo, —OH, —F, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently selected from the group of N, S and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein $R^4$ may optionally be substituted by one or two substituents $R^5$, wherein each $R^5$ is independently selected from the group consisting of methyl, ethyl, propyl, isopropyl, n-butyl, isobutyl, tert-butyl, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl, wherein $R^5$ may optionally be substituted by a group consisting of oxo, methyl and —CF$_3$, and the pharmacologically acceptable salts of the aforementioned compounds.

The invention concerns in another embodiment the above compounds of formula 1, wherein $R^2$ is a five- or six-membered monocyclic heteroaryl comprising one, two or three heteroatoms each independently selected from the group consisting of N, S and O;

wherein $R^2$ may optionally be substituted by one, two, three or four substituents $R^4$ which independently from one another are selected from the group consisting of —O—CH$_3$, oxo, —OH, —F, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently from one another selected from the group of N, S and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, wherein $R^4$ may optionally be substituted by one or two substituents $R^5$, wherein each $R^5$ is independently selected from the group consisting of methyl, ethyl, propyl, isopropyl, n-butyl, isobutyl, tert-butyl, —CF$_3$, —CH$_2$—CF$_3$, —CHF$_2$, CH$_2$F, —CF$_2$—CF$_3$, —OH, halogen, -ethylen-CF$_3$, a five- or six-membered saturated heterocycle comprising one, two or three heteroatoms each independently from one another selected from the group of N, S and O, a three, four-, five-, six- or seven-membered cycloalkyl, wherein $R^5$ may optionally be substituted by a group consisting of oxo, methyl and —CF$_3$, and the pharmacologically acceptable salts of the aforementioned compounds.

The instant invention further concerns the above compounds of formula 1, wherein $R^2$ is a five-membered monocyclic heteroaryl comprising one, two or three heteroatoms each independently selected from the group consisting of N, S and O;

whereby this five-membered monocyclic heteroaryl is linked to the quinoline-core-structure via a carbon atom and wherein this five-membered monocyclic heteroaryl optionally may be further substituted as identified in claim 14, and the pharmacologically acceptable salts of the aforementioned compounds.

The instant invention also relates to compounds of formula 1, wherein $R^2$ is a five-membered monocyclic heteroaryl comprising at least one nitrogen atom and optionally one or two further heteroatoms each independently selected from the group consisting of N, S and O;

whereby this five-membered monocyclic heteroaryl is linked to the quinoline-core-structure via a nitrogen atom, and wherein this five-membered monocyclic heteroaryl optionally may be further substituted as identified in claim 14, and the pharmacologically acceptable salts of the aforementioned compounds.

In another embodiment the instant invention relates to the above compounds of formula 1, wherein
$R^2$ is a bicyclic, nine- or ten-membered, either aromatic or non-aromatic, but not fully saturated heterocycle comprising one, two, three or four heteroatoms each independently selected from the group consisting of N, S and O;
wherein $R^2$ may optionally be substituted by one, two, three or four substituents $R^4$ which independently from one another are selected from the group consisting of linear or branched —O—$C_{1-3}$-alkyl, oxo, —OH, —F, —$CF_3$, —$CHF_2$, —$SO_2CH_3$, —$CH_2$—$SO_2$—$CH_3$, —$SO_2$—$CF_3$, —$CH_3$, —$CH_2$—$CH_3$, propyl, isopropyl, a five- or six-membered saturated heterocycle comprising one or two heteroatoms each independently from one another selected from the group of N, S and O; —NH—CO—$CH_3$, —$C_{1-3}$-alkylene-N($C_{1-3}$-alkyl)-CO—$C_{1-3}$-alkyl, —CO—NH($CH_3$), —($C_{1-3}$-alkylene)-O—CO—$CH_3$, —CO—$NH_2$, —CO—N($CH_3$)$_2$, —O—$R^5$, —CO—$R^5$, —$C_{1-3}$-alkylene-O—CO—$C_{1-3}$-alkyl and

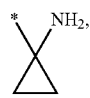

wherein $R^4$ may optionally be substituted by one or two substituents $R^5$,
wherein each
$R^5$ is independently selected from the group consisting of methyl, ethyl, propyl, isopropyl, —$C_{1-3}$-haloalkyl, —OH, halogen, —$C_{1-2}$-alkylene-$C_{1-3}$-haloalkyl, a five- or six-membered saturated heterocycle comprising one, two or three heteroatoms each independently from one another selected from the group of N, S and O, a three, four-, five-, six- or seven-membered cycloalkyl,
wherein $R^5$ may optionally be substituted by a group consisting of oxo, methyl and —$CF_3$,
and the pharmacologically acceptable salts of the aforementioned compounds.

The invention further relates to the above compounds of formula 1, wherein
$R^2$ is a bicyclic, nine- or ten-membered, either aromatic or non-aromatic, but not fully saturated heterocycle comprising one, two, three or four heteroatoms each independently selected from the group consisting of N, S and O;
wherein $R^2$ may optionally be substituted by one, two, three or four substituents $R^4$ which independently from one another are selected from the group consisting of —O—$CH_3$, —O-ethyl, —O-propyl, —O-isopropyl, oxo, —OH, —F, —$CF_3$, methyl, ethyl, propyl and isopropyl, and the pharmacologically acceptable salts of the aforementioned compounds.

In a preferred embodiment the invention refers to the above compounds of formula 1, wherein
$R^2$ is pyridine,
wherein $R^2$ may optionally be substituted by one, two, three or four substituents $R^4$ which independently from one another are selected from the group consisting of —O—$CH_3$, oxo, —OH, —F, —$CF_3$, —$CHF_2$, —$SO_2CH_3$, —$CH_2$—$SO_2$—$CH_3$, —$SO_2$—$CF_3$, —$CH_3$, —$CH_2$—$CH_3$, propyl, isopropyl, a five- or six-membered saturated heterocycle comprising one or two heteroatoms each independently selected from the group of N, S and O; —NH—CO—$CH_3$, —$C_{1-3}$-alkylene-N($C_{1-3}$-alkyl)-CO—$C_{1-3}$-alkyl, —CO—NH($CH_3$), —($C_{1-3}$-alkylene)-O—CO—$CH_3$, —CO—$NH_2$, —CO—N($CH_3$)$_2$, —O—$R^5$, —CO—$R^5$,
wherein $R^4$ may optionally be substituted by one or two substituents $R^5$,
wherein each
$R^5$ is independently from one another selected from the group consisting of methyl, ethyl, propyl, isopropyl, n-butyl, isobutyl, tert-butyl, —$CF_3$, —$CH_2$—$CF_3$, —$CHF_2$, $CH_2F$, —$CF_2$—$CF_3$, —OH, halogen, —$C_{1-2}$-alkylene-$CF_3$, a five- or six-membered saturated heterocycle comprising one, two or three heteroatoms each independently from one another selected from the group of N, S and O, a three, four-, five-, six- or seven-membered cycloalkyl,
wherein $R^5$ may optionally be substituted by a group consisting of oxo, methyl and —$CF_3$
and the pharmacologically acceptable salts of the aforementioned compounds.

In a further preferred embodiment the invention relates to the above compounds of formula 1, wherein
$R^2$ is pyridine,
wherein $R^2$ is substituted by one or two $R^4$ which independently from one another are selected from the group consisting of —O—$CH_3$, —OH, —F, —$CF_3$, —$CHF_2$, —$CH_3$, —$CH_2$—$CH_3$, propyl, isopropyl and —O—$R^5$,
wherein
$R^5$ is selected from the group consisting of methyl, ethyl, propyl, isopropyl, —$CF_3$, —$CHF_2$, $CH_2F$, —$CH_2$—$CF_3$, —$CF_2$—$CF_3$
and the pharmacologically acceptable salts of the aforementioned compounds.

In a particularly preferred embodiment the instant invention relates to the above compounds according to formula 1, wherein
$R^1$ is selected from the group consisting of

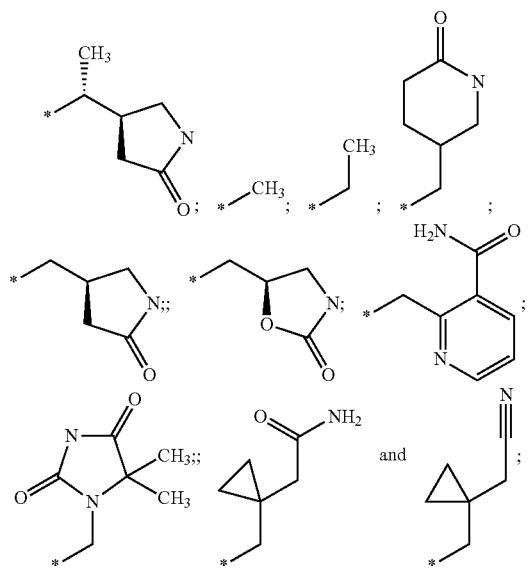

and wherein
$R^2$ is selected from the group consisting of
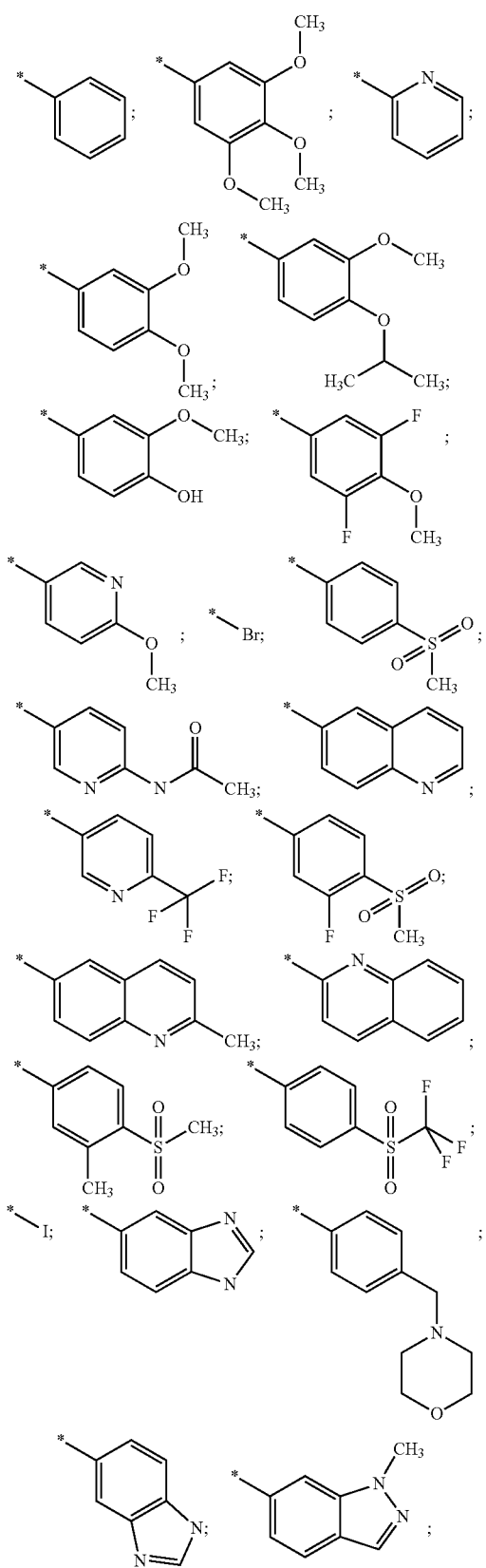
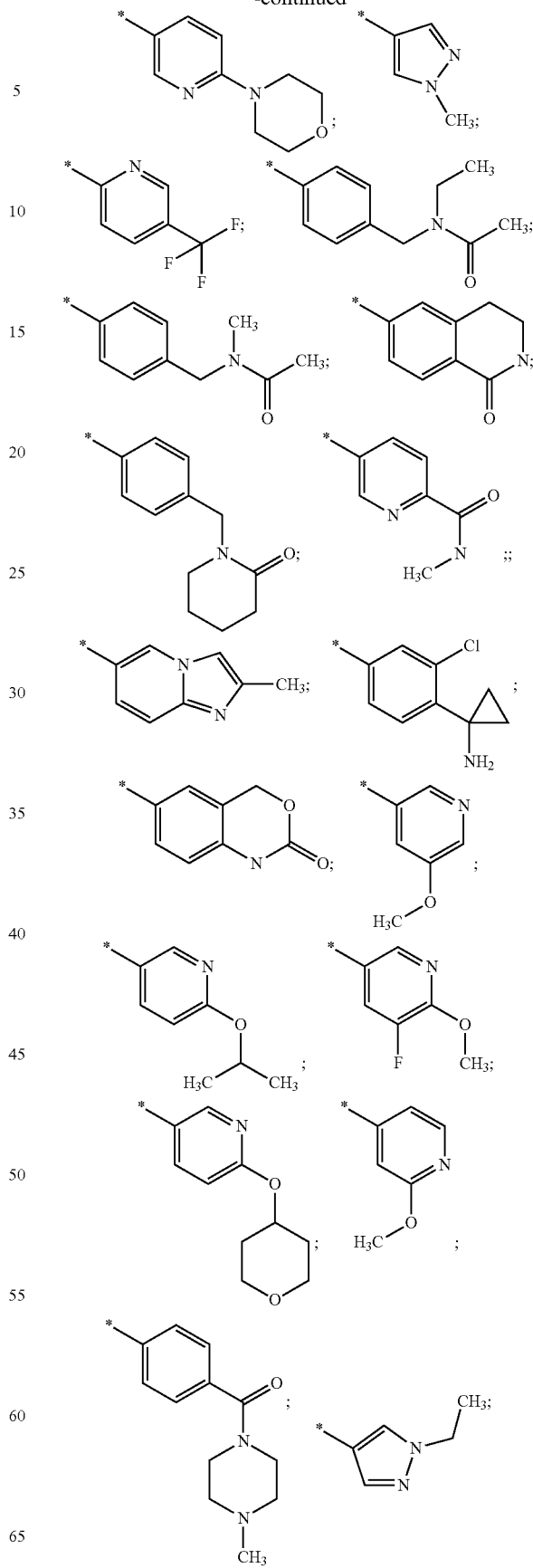

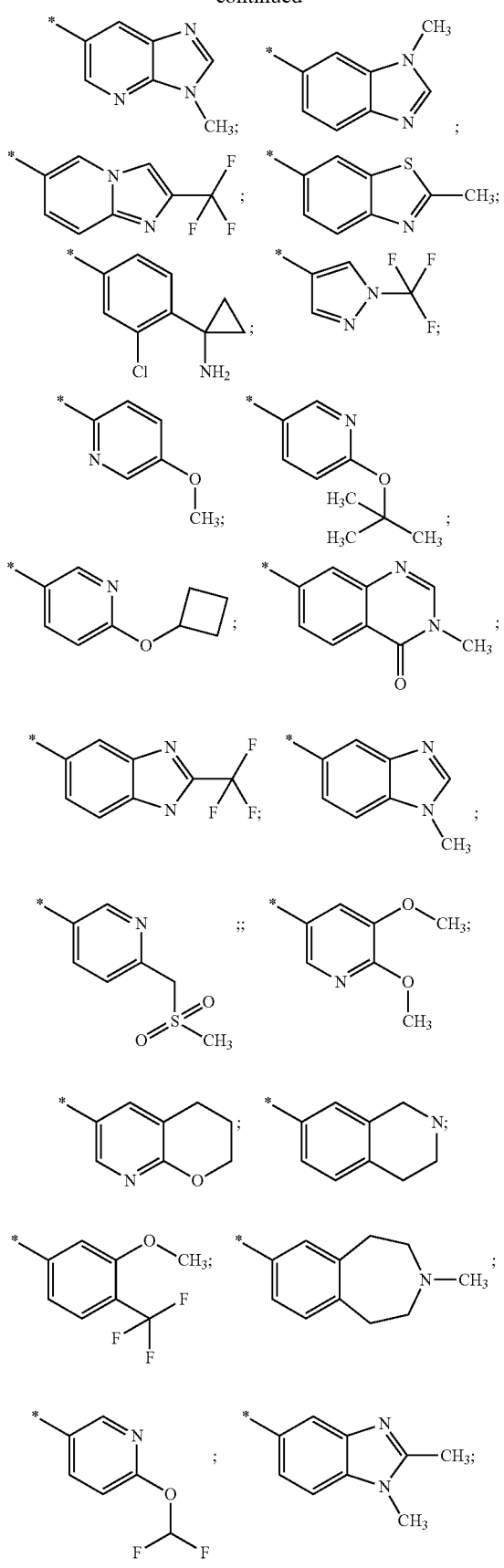
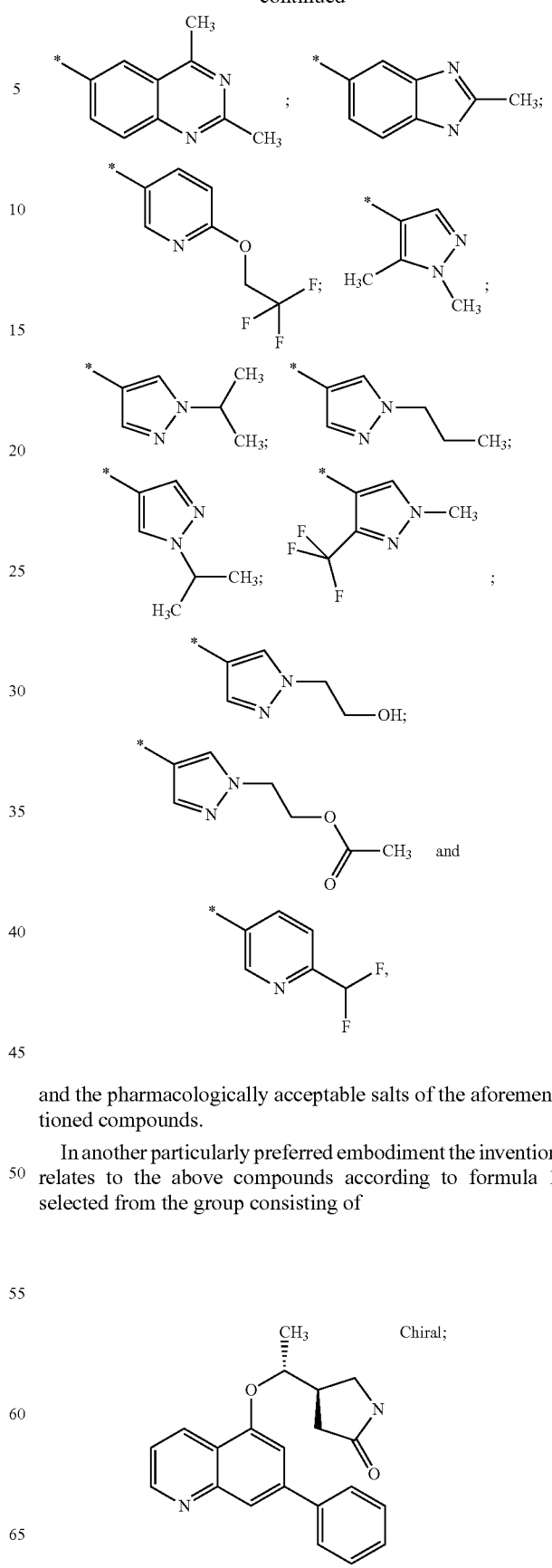
and the pharmacologically acceptable salts of the aforementioned compounds.
In another particularly preferred embodiment the invention relates to the above compounds according to formula 1 selected from the group consisting of

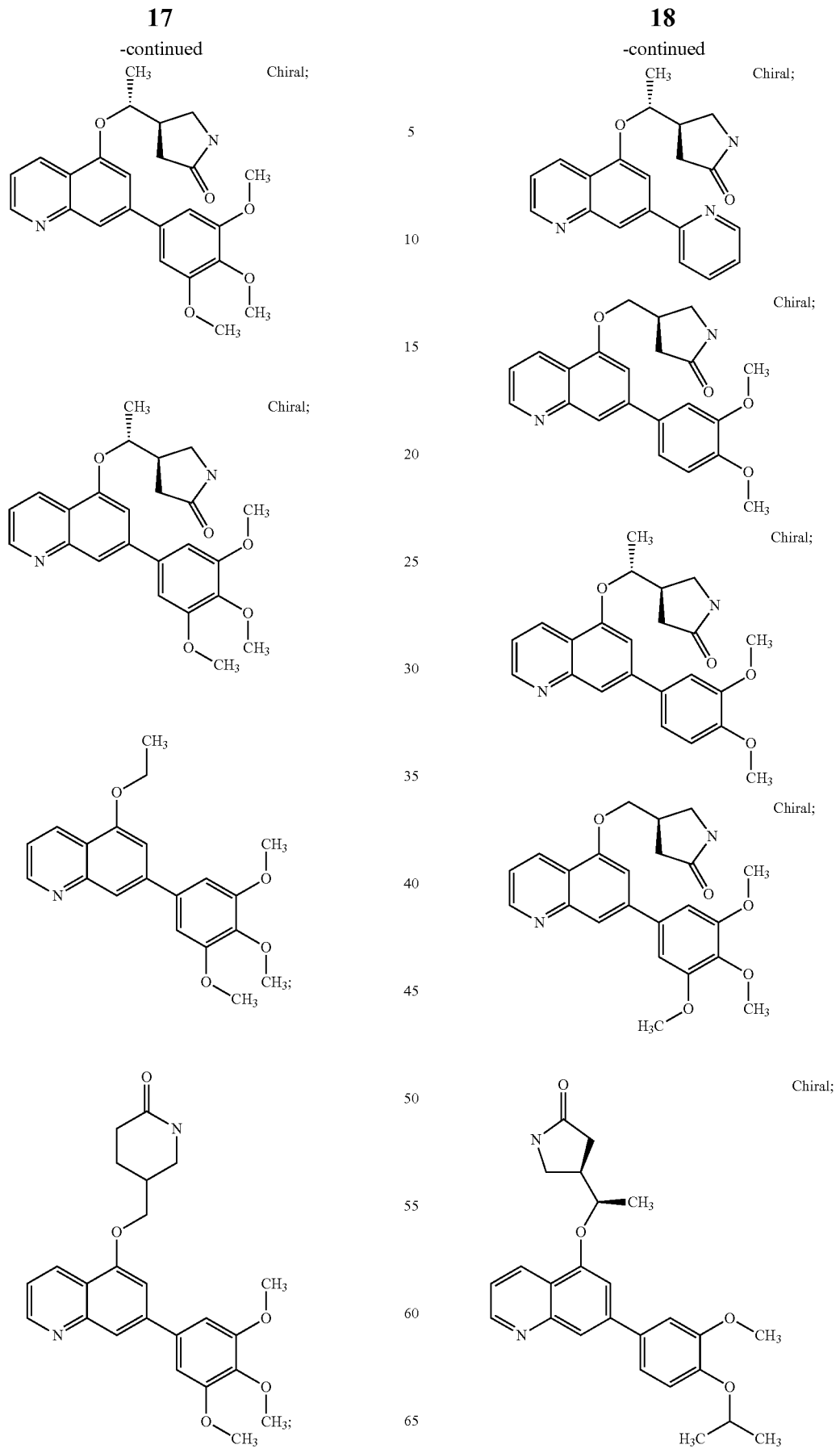

-continued
Chiral;
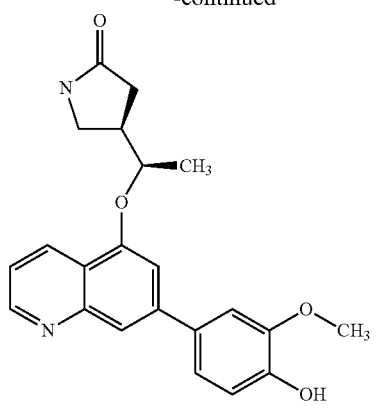
Chiral;
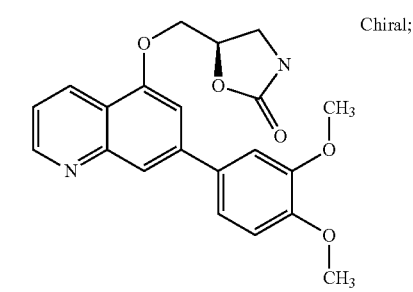
Chiral;
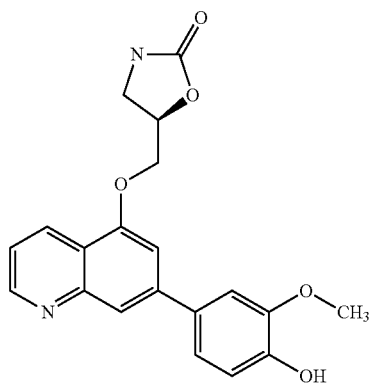
Chiral;
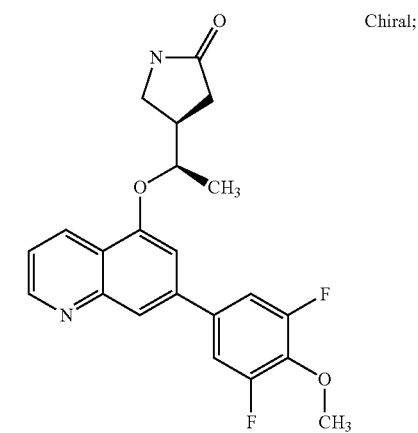
-continued
Chiral;
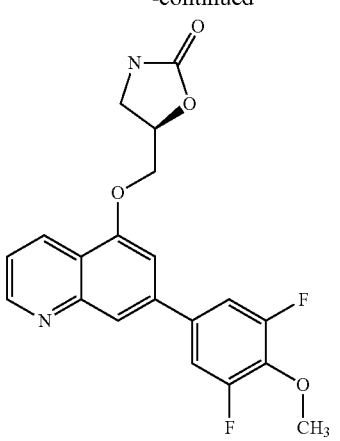
Chiral;
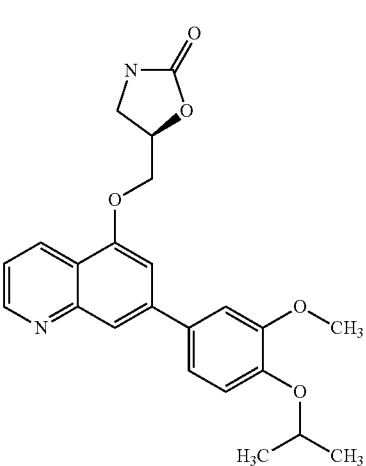
Chiral;
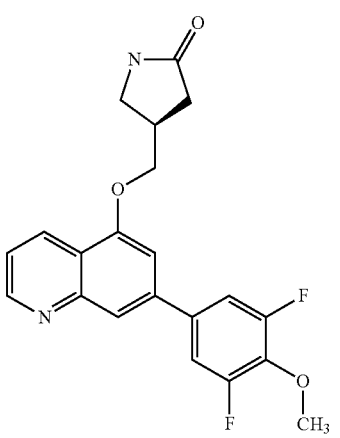
Chiral;
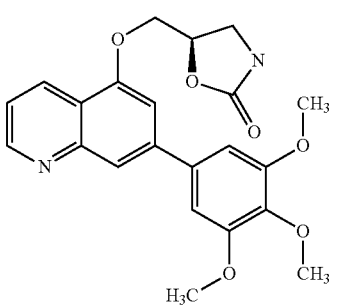

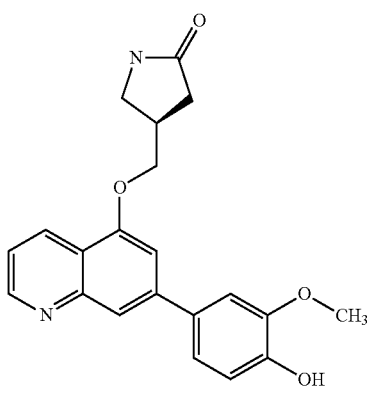 Chiral;
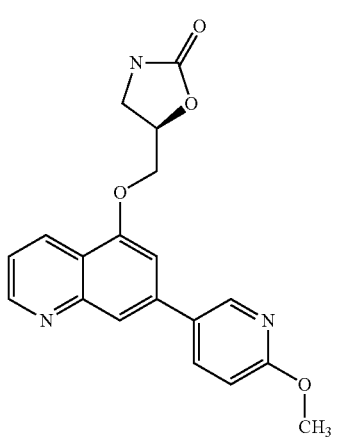 Chiral;
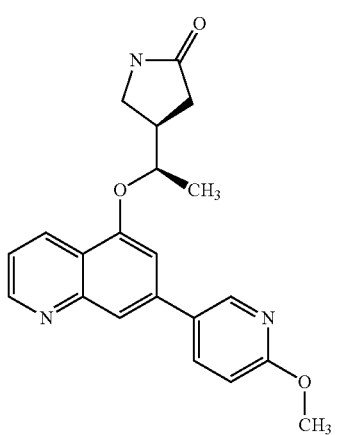 Chiral;
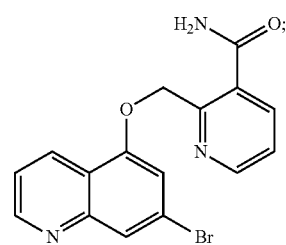
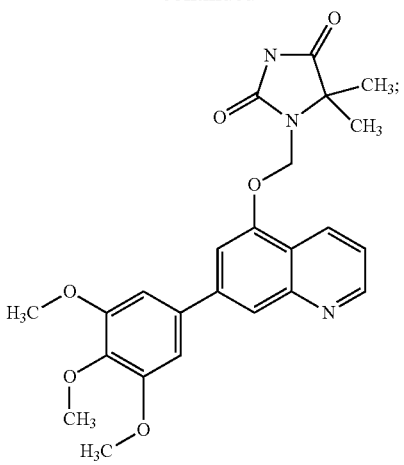
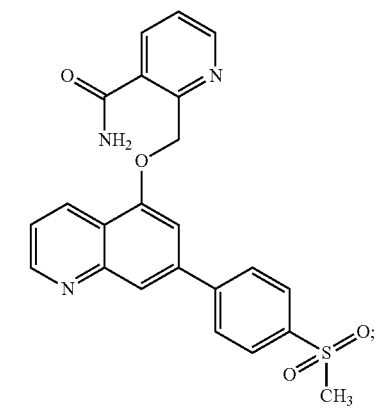
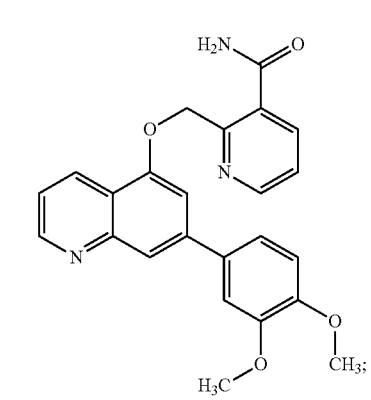
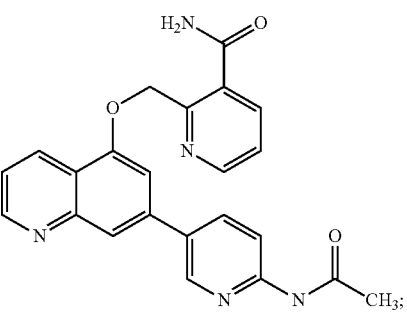

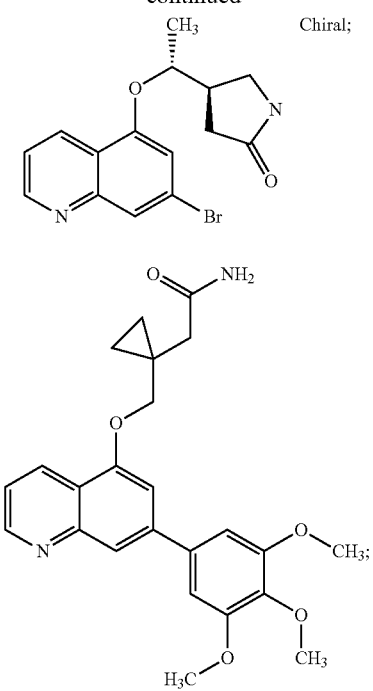
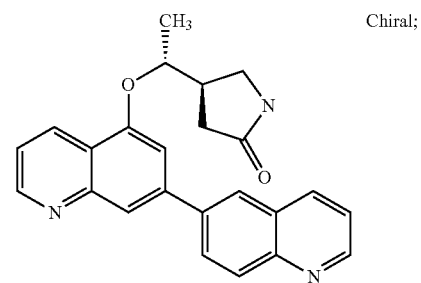
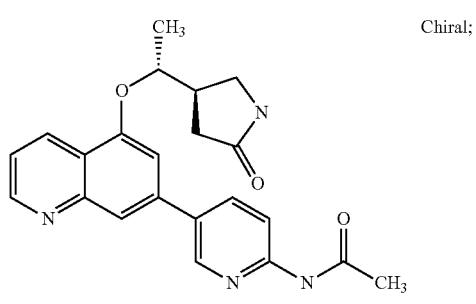
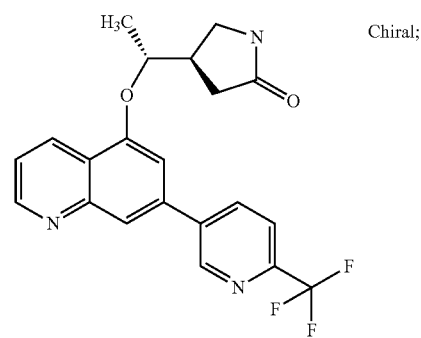
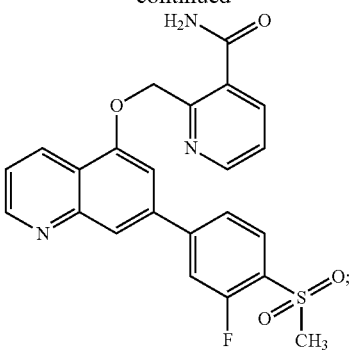
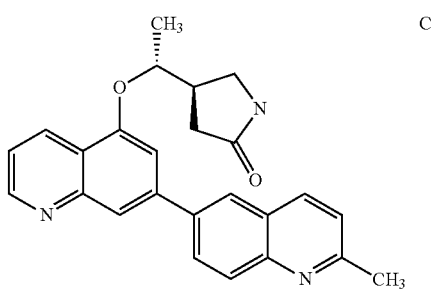
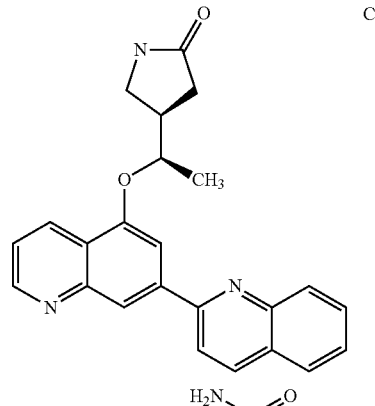
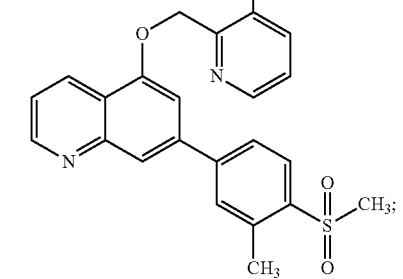
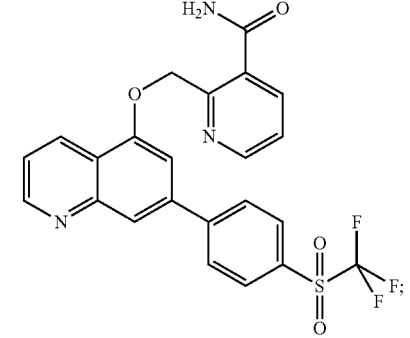

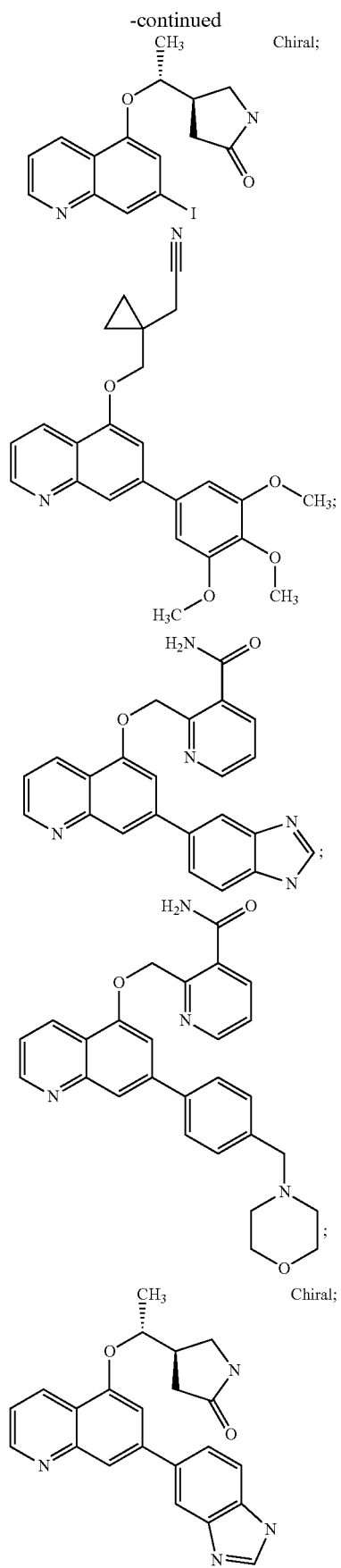
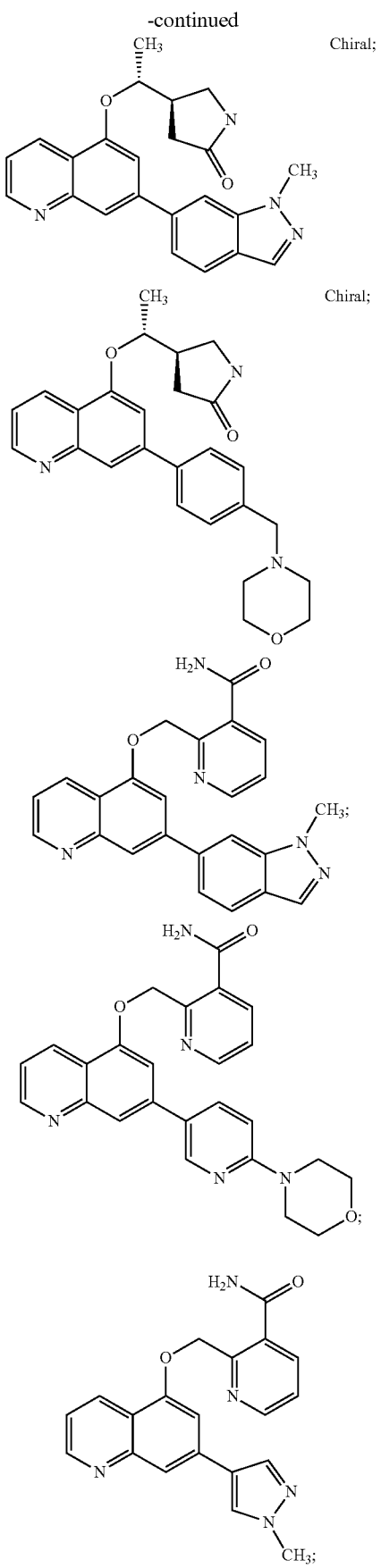

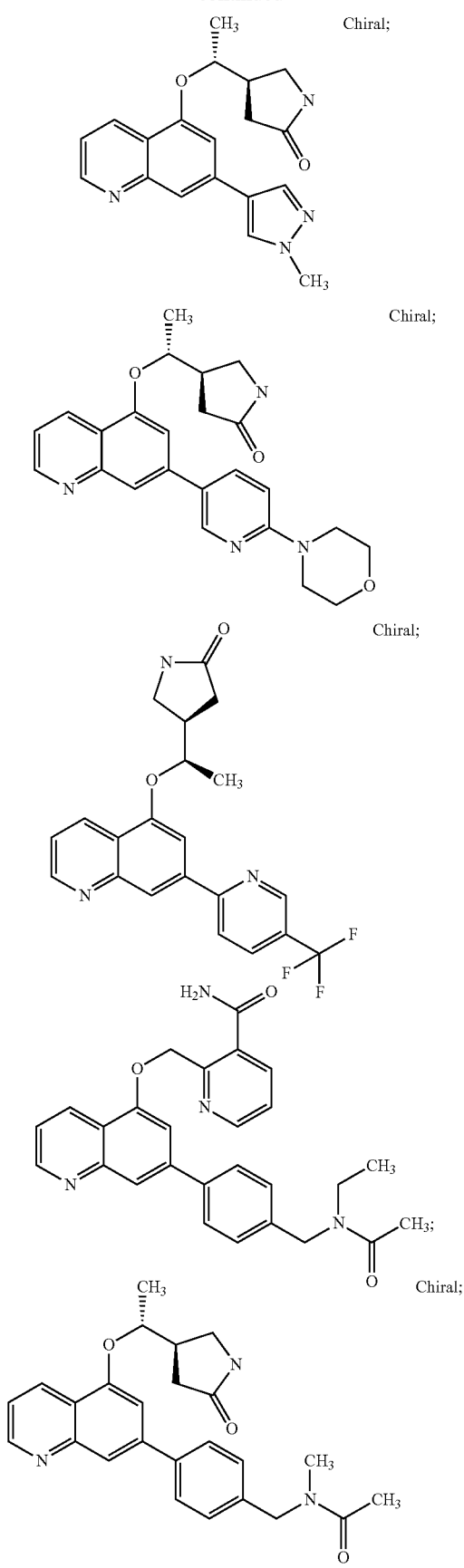
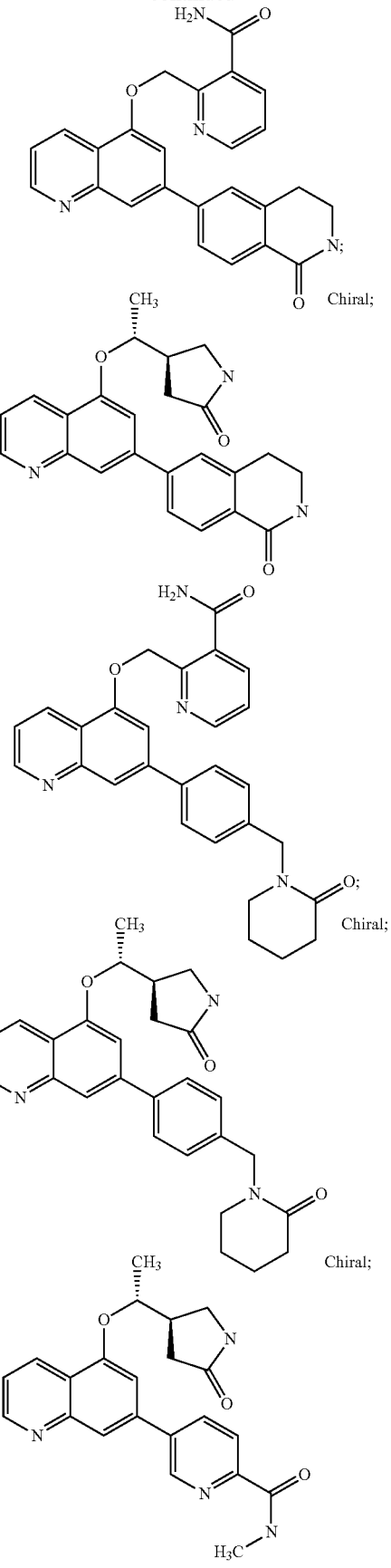

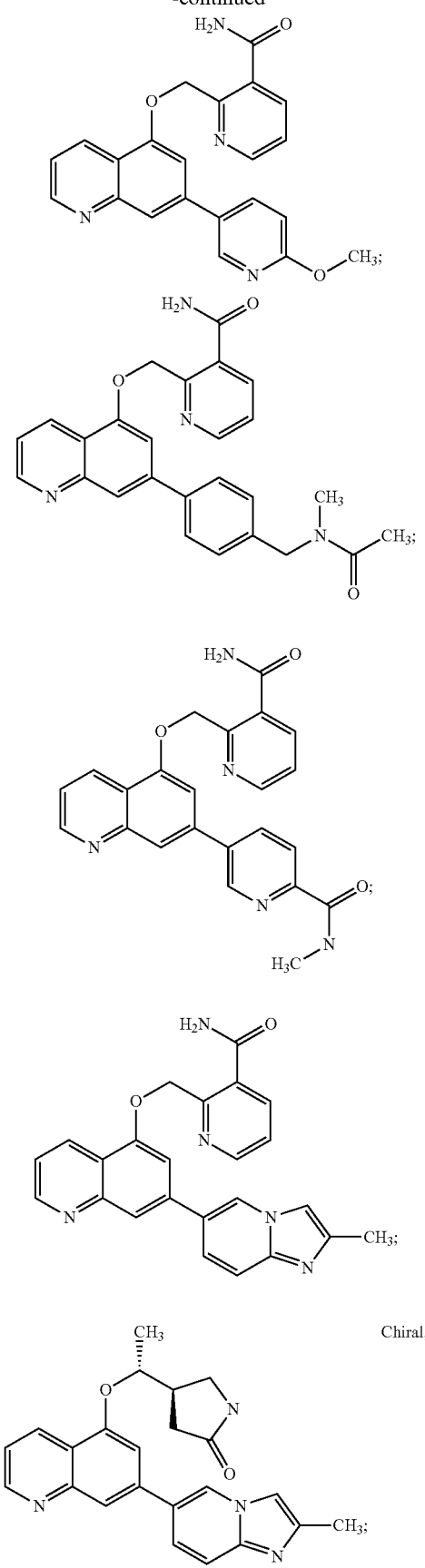
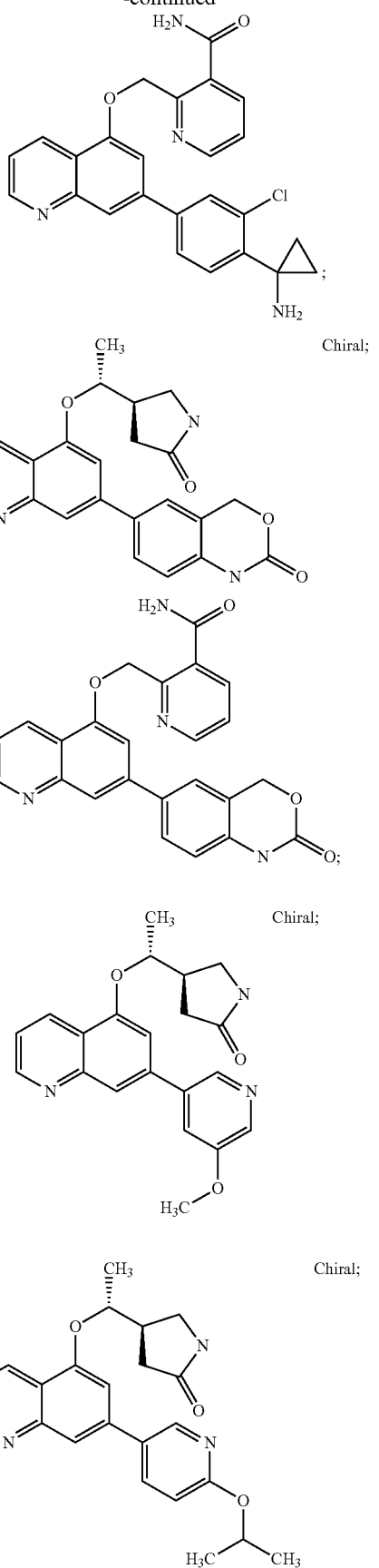

-continued
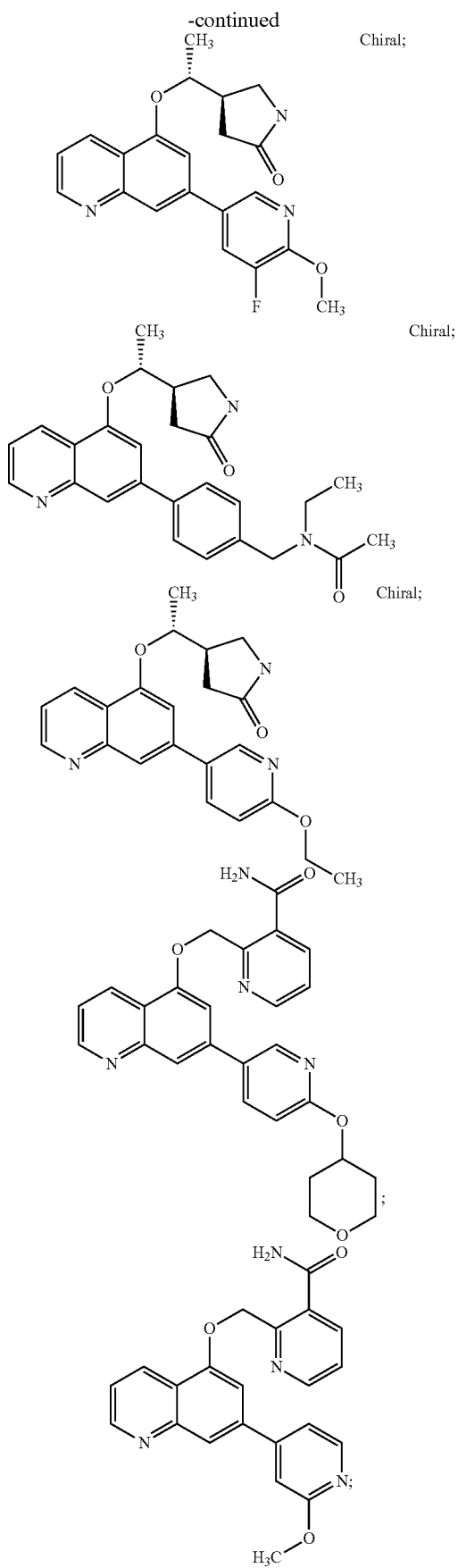
-continued
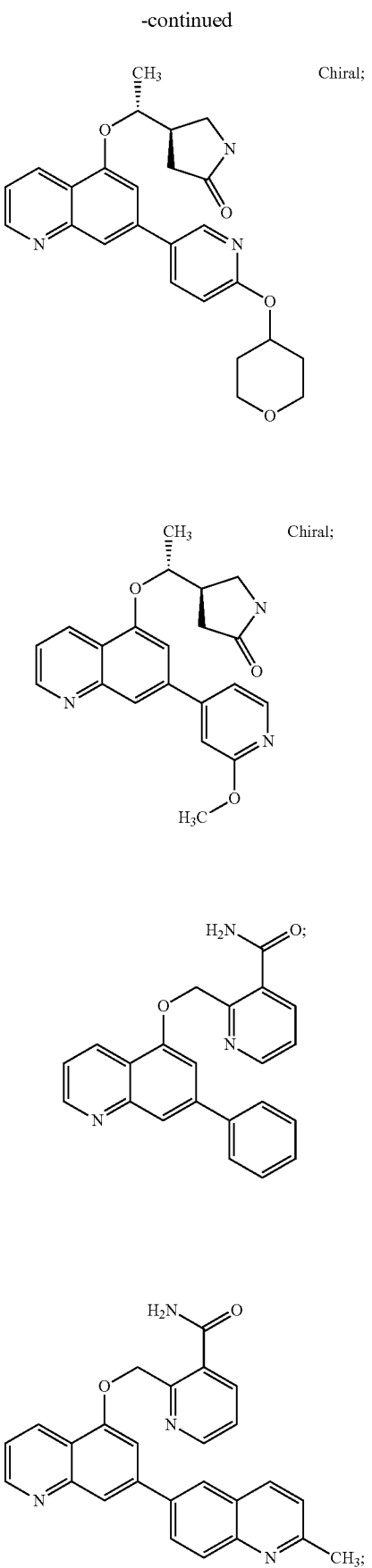

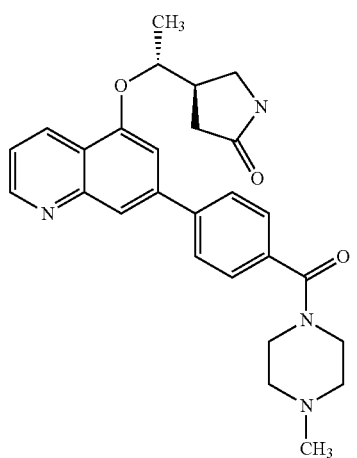
Chiral;
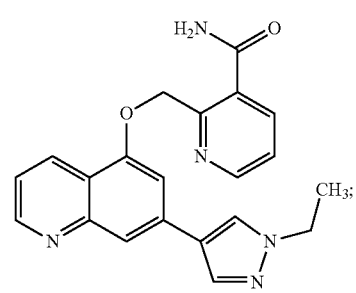
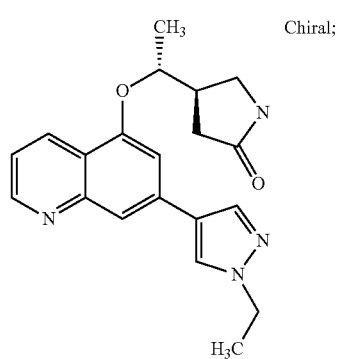
Chiral;
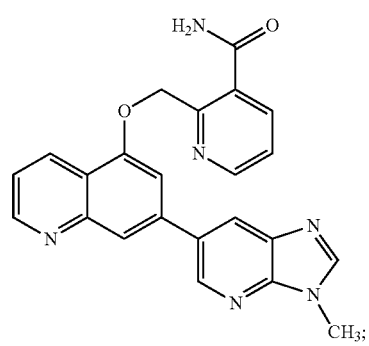
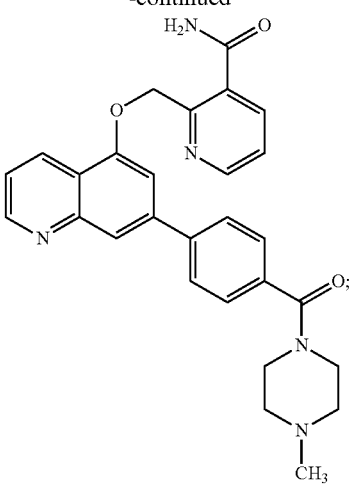
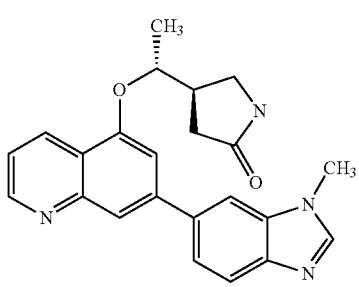
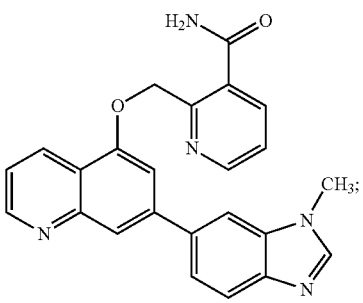
Chiral;
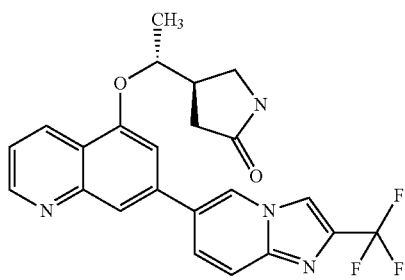
Chiral;
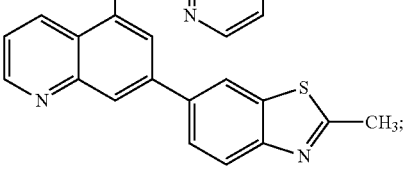

35
-continued
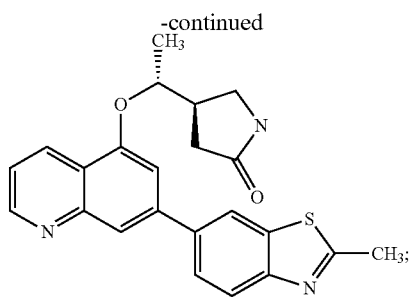
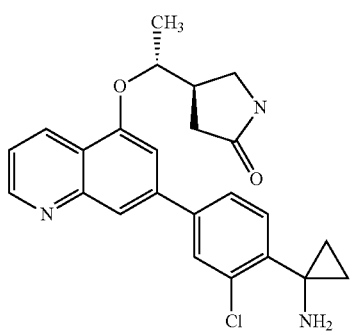
Chiral;
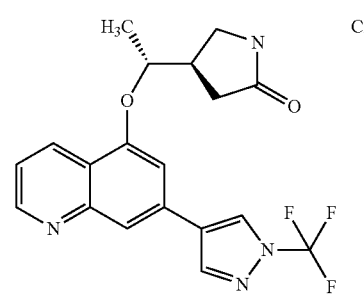
Chiral;
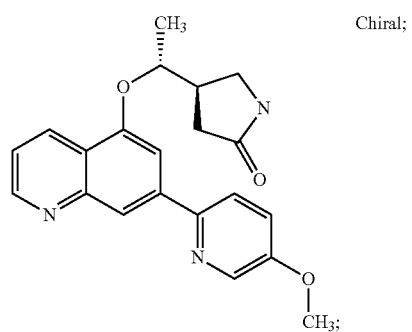
Chiral;
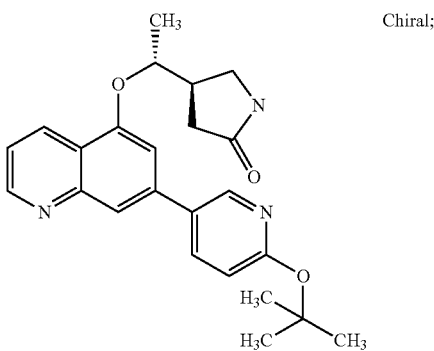
Chiral;
36
-continued
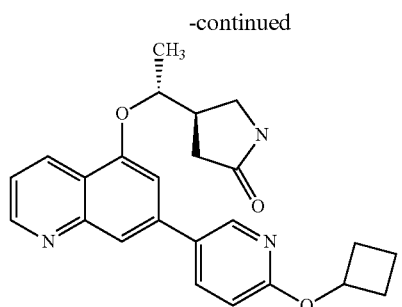
Chiral;
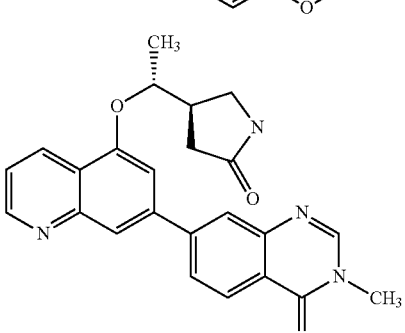
Chiral;
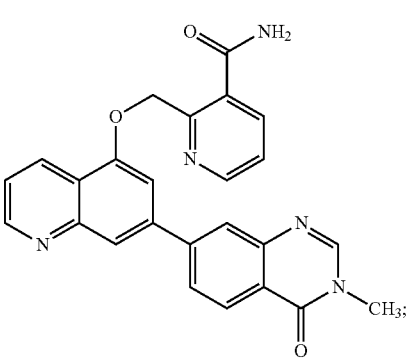
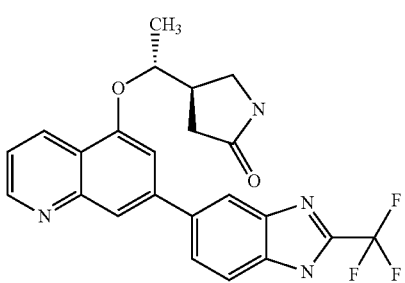
Chiral;
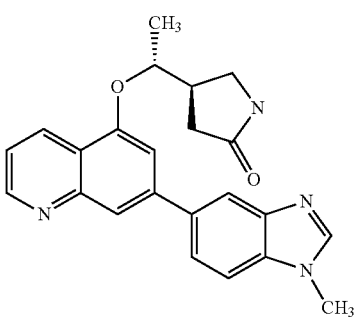
Chiral;

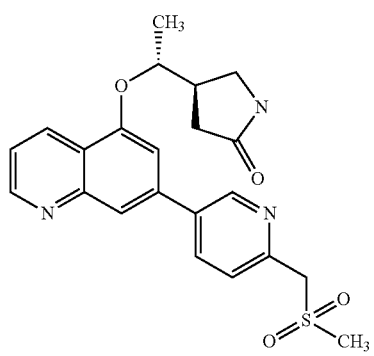
Chiral;
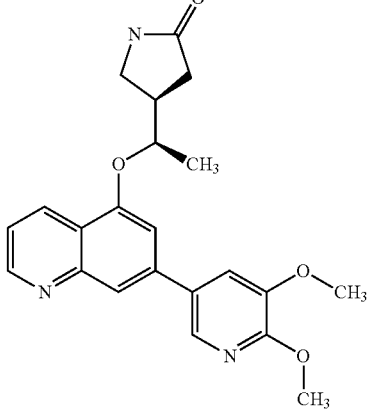
Chiral;
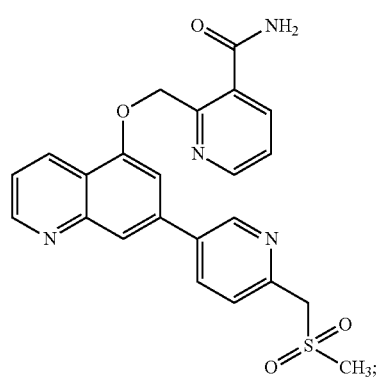
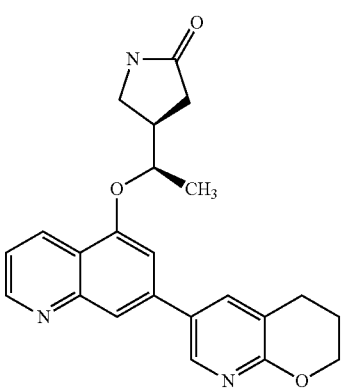
Chiral;
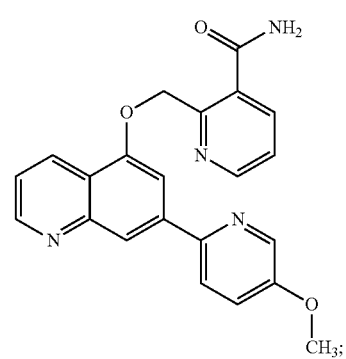
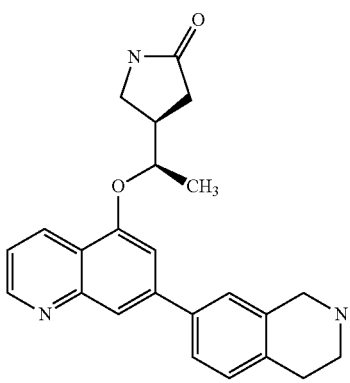
Chiral;
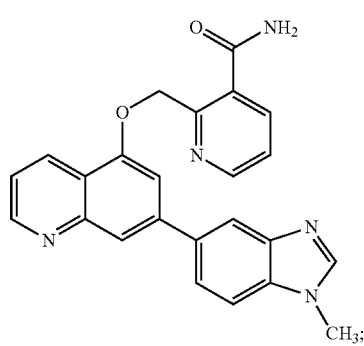
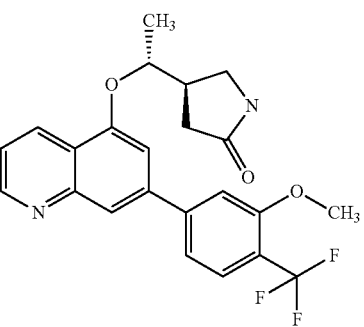
Chiral;

-continued
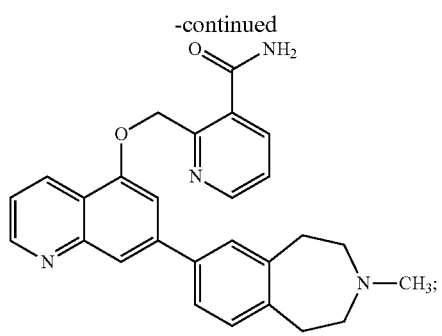
Chiral;
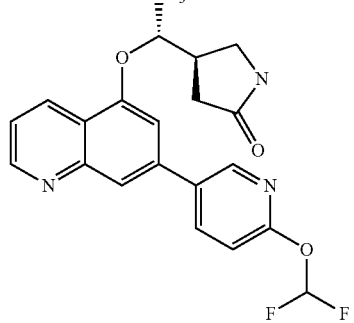
Chiral;
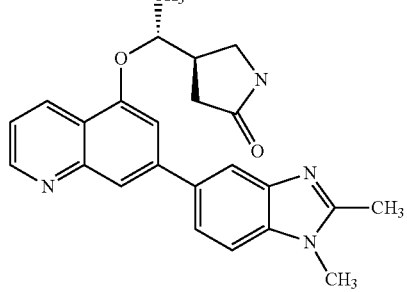
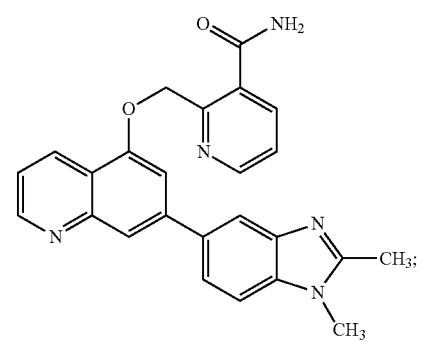
Chiral;
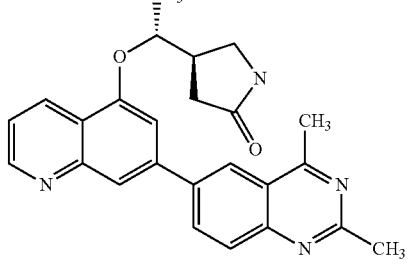
-continued
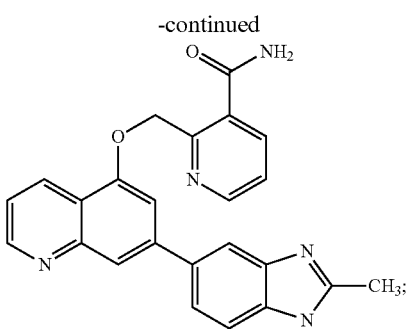
Chiral;
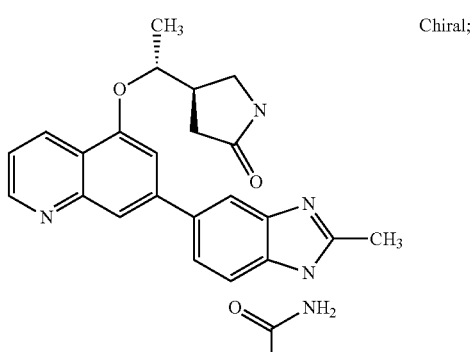
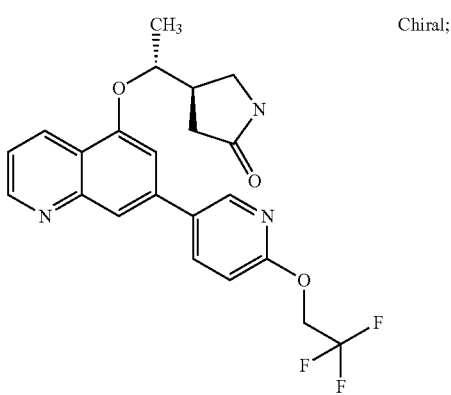
Chiral;
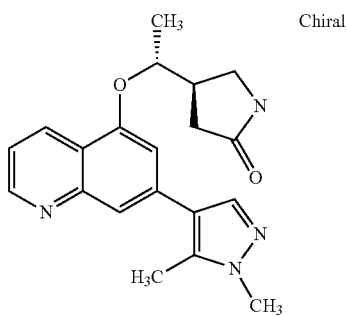
Chiral;

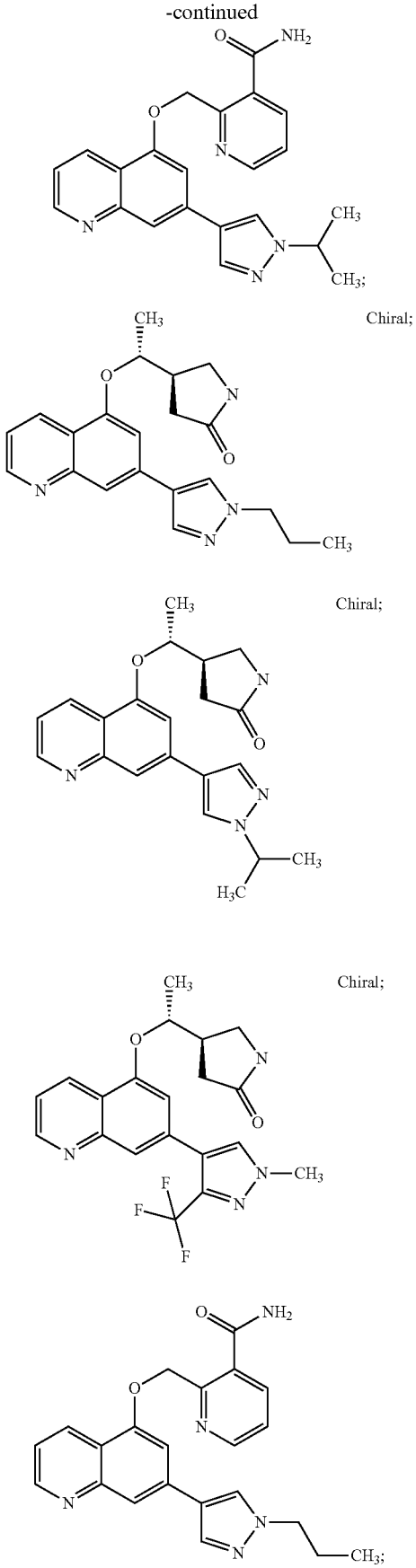
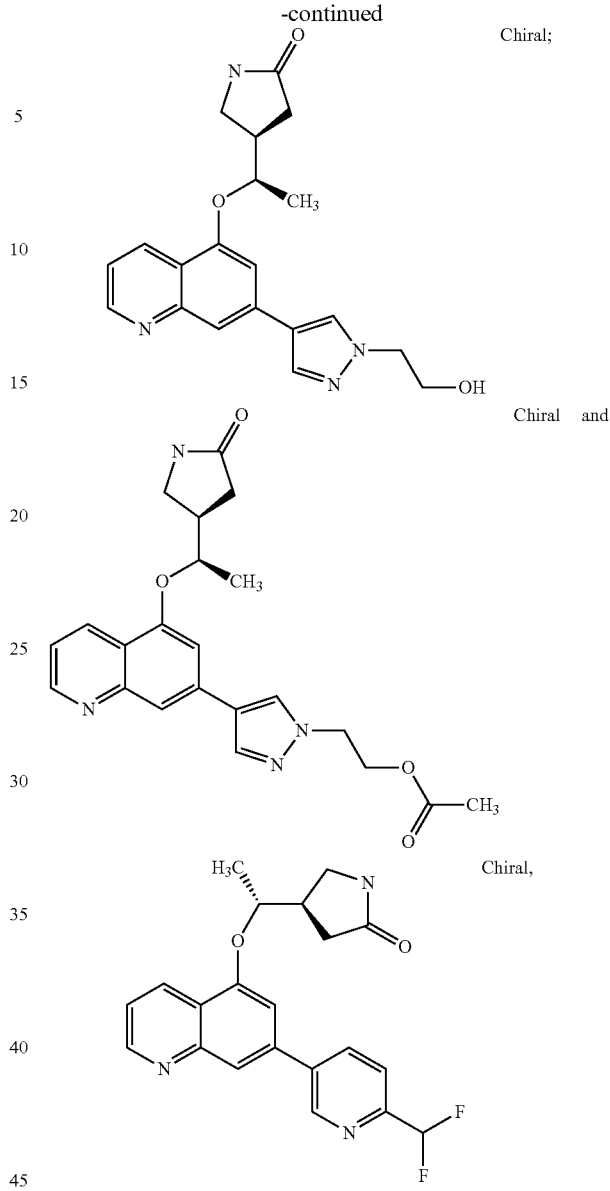

and the pharmacologically acceptable salts of the aforementioned compounds.

The instant invention further concerns the above-mentioned compounds of formula 1 as medicaments.

In a further embodiment the invention concerns the use of the above compounds according to formula 1 for the treatment of a disease which can be treated by inhibition of the SYK enzyme.

In a preferred embodiment the instant invention relates to the use of the above compounds of formula 1 for the treatment of a disease selected from the group consisting of allergic rhinitis, asthma, COPD, adult respiratory distress syndrome, bronchitis, B-cell lymphoma, dermatitis and contact dermatitis, allergic dermatitis, allergic rhinoconjunctivitis, rheumatoid arthritis, anti-phospholipid syndrome, Berger's disease, Evans's syndrome, ulcerative colitis, allergic antibody-based glomerulonephritis, granulocytopenia, Goodpasture's syndrome, hepatitis, Henoch-Schönlein purpura, hypersensitivity vasculitis, immunohaemolytic anaemia, autoimmune haemolytic anemia, idiopathic thrombocytopenic purpura, Kawasaki syndrome, allergic conjunctivitis, lupus erythematodes, capsule cell lymphoma, neutropenia, non-familial lateral sclerosis, Crohn's disease, multiple sclerosis, myasthenia gravis, osteoporosis, osteolytic diseases, osteopenia, psoriasis, Sjögren's syndrome, sclerodermy, T-cell lymphoma, urticaria/angiooedema, Wegener's granulomatosis and coeliac disease.

In a further preferred embodiment the instant invention relates to the use of the above compounds of formula 1, wherein the disease is selected from the group consisting of asthma, COPD, allergic rhinitis, adult espiratory distress syndrome, bronchitis, allergic dermatitis, contact dermatitis, idiopathic thrombocytopenic purpura, rheumatoid arthritis and allergic rhinoconjunctivitis.

In a particularly preferred embodiment the instant invention relates to the use of the above compounds of formula 1, wherein the disease is selected from the group consisting of asthma, COPD, allergic rhinitis, allergic dermatitis and rheumatoid arthritis.

Further, the instant invention concerns pharmaceutical formulations characterised in that they contain one or more compounds of formula 1.

In a further embodiment the instant invention relates to a pharmaceutical formulation characterised in that it contains one or more compounds of formula 1 in combination with an active substance selected from the group consisting of anticholinergics, betamimetics, corticosteroids, PDE4-inhibitors, EGFR-inhibitors, LTD4-antagonists, CCR3-inhibitors, iNOS-inhibitors and HMG-CoA reductase inhibitors.

In another embodiment the invention concerns compounds selected from formula 6

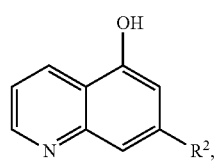
6 from formula 7

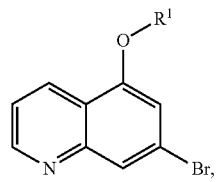
7 from formula A

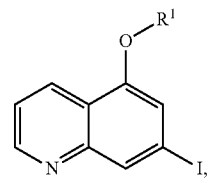
A from formula B

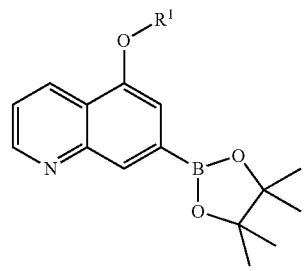
B and from formula C

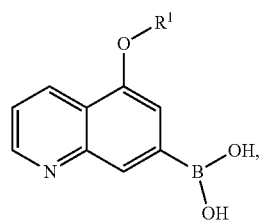
C wherein $R^1$ and $R^2$ are defined as mentioned above.

3. TERMS AND DEFINITIONS USED

Unless stated otherwise, all the substituents are independent of one another. If for example a number of $C_{1-6}$-alkyl groups are possible substituents at a group, in the case of three substituents, for example, $C_{1-6}$-alkyl could represent, independently of one another, a methyl, an n-propyl and a tert-butyl.

Within the scope of this application, in the definition of possible substituents, these may also be presented in the form of a structural formula. An asterisk (*) in the structural formula of the substituent is to be understood as being the linking point to the rest of the molecule. Moreover, the atom of the substituent following the linking point is understood as being the atom in position number 1. Thus for example the groups N-piperidinyl (I), 4-piperidinyl (II), 2-tolyl (III), 3-tolyl (IV) and 4-tolyl (V) are represented as follows:

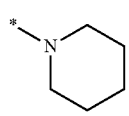
I

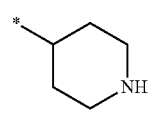
II

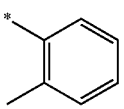
III

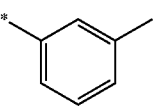
IV

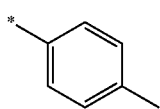

V

If there is no asterisk (*) in the structural formula of the substituent, each hydrogen atom may be removed at the substituent and the valency thus freed may serve as a binding site to the rest of a molecule. Thus, for example, VI

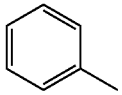

VI may represent 2-tolyl, 3-tolyl, 4-tolyl and benzyl.

Alternatively to the * within the scope of this application $X_1$ is also understood as being the linking point of the group $R^1$ to the structure of formula 1 and $X_2$ as being the linking point of the group $R^2$ to the structure of formula 1.

By the term "$C_{1-6}$-alkyl" (including those which are part of other groups) are meant branched and unbranched alkyl groups with 1 to 6 carbon atoms and by the term "$C_{1-3}$-alkyl" are meant branched and unbranched alkyl groups with 1 to 3 carbon atoms. "$C_{1-4}$-alkyl" accordingly denotes branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc., may also optionally be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples of these include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene include all the possible isomeric forms of the groups in question with the same number of carbons. Thus, for example, propyl includes also 1-methylethylene and butylene includes 1-methylpropylene, 1,1-dimethylethylene, 1,2-dimethylethylene.

If the carbon chain is substituted by a group which together with one or two carbon atoms of the alkylene chain forms a carbocyclic ring with 3, 5 or 6 carbon atoms, this includes, inter alia, the following examples of the rings:

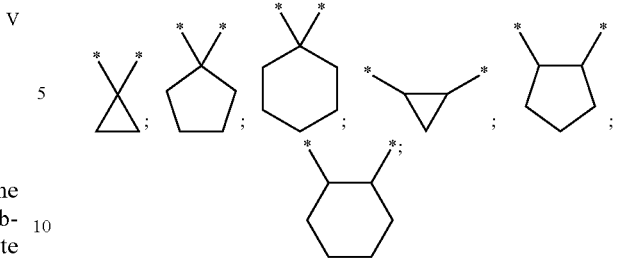

By the term "$C_{2-6}$-alkenyl" (including those which are part of other groups) are meant branched and unbranched alkenyl groups with 2 to 6 carbon atoms and by the term "$C_{2-4}$-alkenyl" are meant branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples of these include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the groups in question with the same number of carbons. Thus, for example, propenyl also includes 1-methylethenylene and butenylene includes 1-methylpropenylene, 1,1-dimethylethenylene, 1,2-dimethylethenylene. By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Preferred are alkynylene groups with 2 to 4 carbon atoms. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the groups in question with the same number of carbons. Thus for example propynyl also includes 1-methylethynylene and butynylene includes 1-methylpropynylene, 1,1-dimethylethynylene, 1,2-dimethylethynylene.

By the term "aryl" (including those which are part of other groups) are meant aromatic ring systems with 6 or 10 carbon atoms. Examples include: phenyl or naphthyl, the preferred aryl group being phenyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl-$C_{1-6}$-alkylene" (including those which are part of other groups) are meant branched and unbranched alkylene groups with 1 to 6 carbon atoms, which are substituted by an aromatic ring system with 6 or 10 carbon atoms. Examples include: benzyl, 1- or 2-phenylethyl or 1- or 2-naphthylethyl. Unless otherwise stated, the aromatic groups may be substituted by one or more groups selected from among methyl, ethyl, iso-propyl, tert-butyl, hydroxy, fluorine, chlorine, bromine and iodine.

By the term "heteroaryl-$C_{1-6}$-alkylene" (including those which are part of other groups) are meant—even though they are already included under "aryl-$C_{1-6}$-alkylene"—branched and unbranched alkylene groups with 1 to 6 carbon atoms, which are substituted by a heteroaryl.

A heteroaryl of this kind includes five- or six-membered heterocyclic aromatic groups or 5-10-membered, bicyclic heteroaryl rings which may contain one, two, three or four heteroatoms selected from among oxygen, sulphur and nitrogen, and contain so many conjugated double bonds that an aromatic system is formed. The following are examples of five- or six-membered heterocyclic aromatic groups or bicyclic heteroaryl rings:

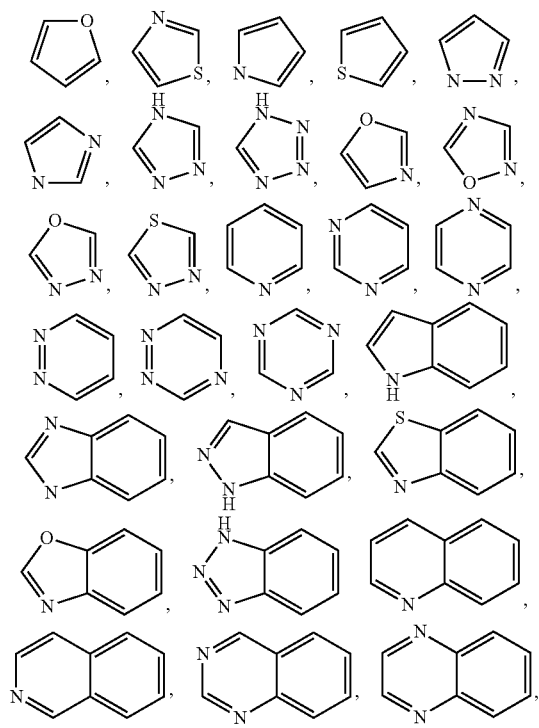

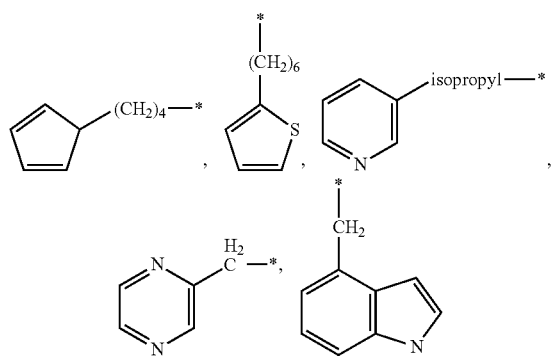

Unless otherwise stated, these heteroaryls may be substituted by one or more groups selected from among methyl, ethyl, iso-propyl, tert-butyl, hydroxy, fluorine, chlorine, bromine and iodine.

The following are examples of heteroaryl-$C_{1-6}$-alkylenes:

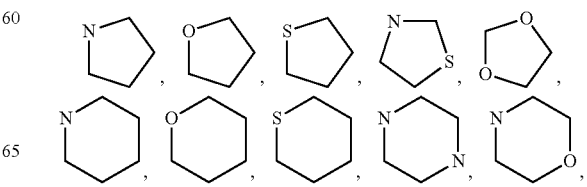

By the term "$C_{1-6}$-haloalkyl" (including those which are part of other groups) are meant branched and unbranched alkyl groups with 1 to 6 carbon atoms, which are substituted by one or more halogen atoms. By the term "$C_{1-4}$-alkyl" are meant branched and unbranched alkyl groups with 1 to 4 carbon atoms, which are substituted by one or more halogen atoms. Alkyl groups with 1 to 4 carbon atoms are preferred. Examples include: $CF_3$, $CHF_2$, $CH_2F$, $CH_2CF_3$.

By the term "$C_{3-7}$-cycloalkyl" (including those which are part of other groups) are meant cyclic alkyl groups with 3 to 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-10}$-cycloalkyl" are also meant monocyclic alkyl groups with 3 to 7 carbon atoms and also bicyclic alkyl groups with 7 to 10 carbon atoms, or monocyclic alkyl groups which are bridged by at least one $C_{1-3}$-carbon bridge.

By the term "heterocyclic rings" or "heterocycle" are meant, unless stated otherwise, five-, six- or seven-membered, saturated, partially saturated or unsaturated heterocyclic rings which may contain one, two or three heteroatoms, selected from among oxygen, sulphur and nitrogen, while the ring may be linked to the molecule through a carbon atom or through a nitrogen atom, if there is one. Although included by the term "heterocyclic rings" or "heterocycles", the term "saturated heterocyclic ring" refers to five-, six- or seven-membered saturated rings. Examples include:

-continued

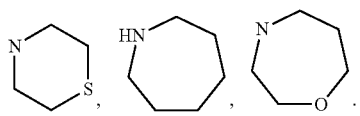

Although included by the term "heterocyclic rings" or "heterocyclic group", the term "partially saturated heterocyclic group" refers to five-, six- or seven-membered partially saturated rings which contain one or two double bonds, without so many double bonds being produced that an aromatic system is formed. Examples include:

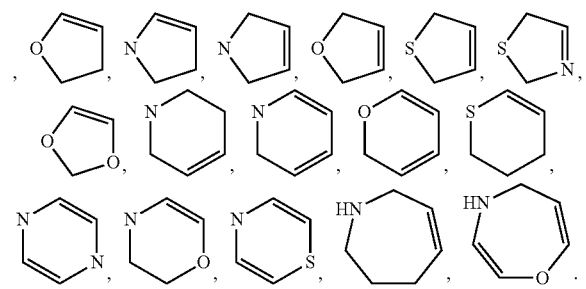

Although included by the term "heterocyclic rings" or "heterocycles", the term "heterocyclic aromatic rings", "unsaturated heterocyclic group" or "heteroaryl" refers to five- or six-membered heterocyclic aromatic groups or 5-10-membered, bicyclic heteroaryl rings which may contain one, two, three or four heteroatoms, selected from among oxygen, sulphur and nitrogen, and contain so many conjugated double bonds that an aromatic system is formed. Examples of five- or six-membered heterocyclic aromatic groups include:

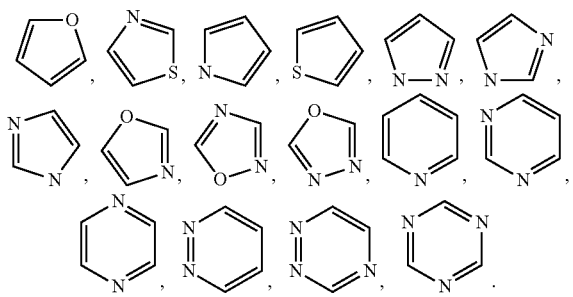

Unless otherwise mentioned, a heterocyclic ring (or heterocycle) may be provided with a keto group. Examples include:

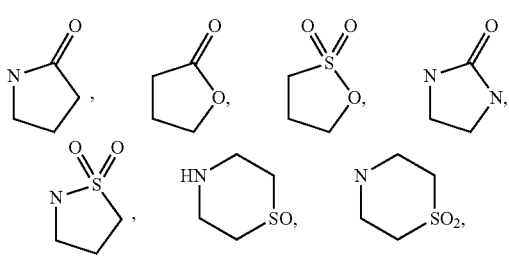

-continued

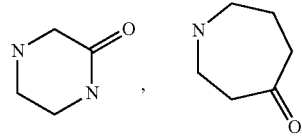

Although covered by the term "cycloalkyl", the term "bicyclic cycloalkyls" generally denotes eight-, nine- or ten-membered bicyclic carbon rings. Examples include

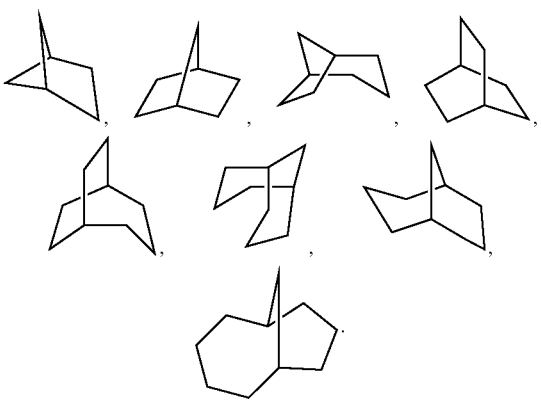

Although already included by the term "heterocycle", the term "bicyclic heterocycles" generally denotes eight-, nine- or ten-membered bicyclic rings which may contain one or more heteroatoms, preferably 1-4, more preferably 1-3, even more preferably 1-2, particularly one heteroatom, selected from among oxygen, sulphur and nitrogen. The ring may be linked to the molecule through a carbon atom of the ring or through a nitrogen atom of the ring, if there is one. Examples include:

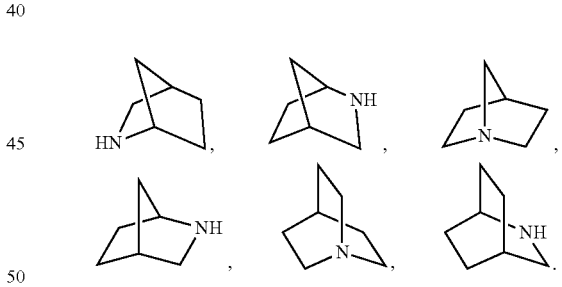

Although already included by the term "aryl", the term "bicyclic aryl" denotes a 5-10 membered, bicyclic aryl ring which contains sufficient conjugated double bonds to form an aromatic system. One example of a bicyclic aryl is naphthyl.

Although already included under "heteroaryl", the term "bicyclic heteroaryl" denotes a 5-10 membered, bicyclic heteroaryl ring which may contain one, two, three or four heteroatoms, selected from among oxygen, sulphur and nitrogen, and contains sufficient conjugated double bonds to form an aromatic system.

Although included by the term "bicyclic cycloalkyls" or "bicyclic aryl", the term "fused cycloalkyl" or "fused aryl" denotes bicyclic rings wherein the bridge separating the rings denotes a direct single bond. The following are examples of a fused, bicyclic cycloalkyl:

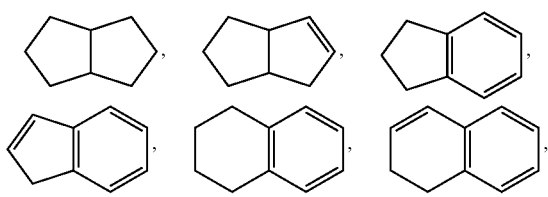

Although included by the term "bicyclic heterocycles" or "bicyclic heteroaryls", the term "fused bicyclic heterocycles" of "fused bicyclic heteroaryls" denotes bicyclic 5-10 membered heterorings which contain one, two, three or four heteroatoms, selected from among oxygen, sulphur and nitrogen and wherein the bridge separating the rings denotes a direct single bond. The "fused bicyclic heteroaryls" moreover contain sufficient conjugated double bonds to form an aromatic system. Examples include pyrrolizine, indole, indolizine, isoindole, indazole, purine, quinoline, isoquinoline, benzimidazole, benzofuran, benzopyran, benzothiazole, benzothiazole, benzoisothiazole, pyridopyrimidine, pteridine, pyrimidopyrimidine,

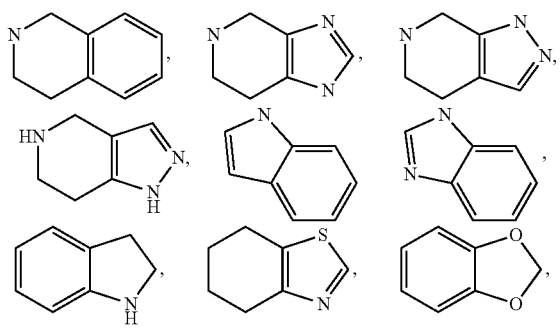

By the term "spiro group" (spiro) are meant 5-10 membered, spirocyclic rings which may optionally contain one, two or three heteroatoms, selected from among oxygen, sulphur and nitrogen, while the ring may be linked to the molecule through a carbon atom or if available through a nitrogen atom. Unless otherwise mentioned, a spirocyclic ring may be provided with an oxo, methyl or ethyl group. Examples of this include:

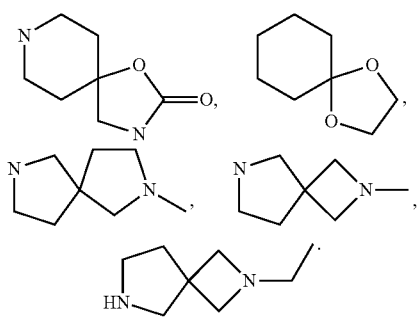

"Halogen" within the scope of the present invention denotes fluorine, chlorine, bromine or iodine. Unless stated to the contrary, fluorine, chlorine and bromine are regarded as preferred halogens.

Compounds of general formula 1 may have acid groups, mainly carboxyl groups, and/or basic groups such as e.g. Amino functions. Compounds of general formula 1 may therefore be present as internal salts, as salts with pharmaceutically usable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically usable bases such as alkali metal or alkaline earth metal hydroxides or carbonates, zinc or ammonium hydroxides or organic amines such as e.g. diethylamine, triethylamine, triethanolamine, inter alia.

As mentioned previously, the compounds of formula 1 may be converted into the salts thereof, particularly for pharmaceutical use into the physiologically and pharmacologically acceptable salts thereof. These salts may be present on the one hand as physiologically and pharmacologically acceptable acid addition salts of the compounds of formula 1 with inorganic or organic acids. On the other hand, the compound of formula 1 when R is hydrogen may be converted by reaction with inorganic bases into physiologically and pharmacologically acceptable salts with alkali or alkaline earth metal cations as counter-ion. The acid addition salts may be prepared for example using hydrochloric acid, hydrobromic acid, sulphuric acid, phosphoric acid, methanesulphonic acid, acetic acid, fumaric acid, succinic acid, lactic acid, citric acid, tartaric acid or maleic acid. It is also possible to use mixtures of the above-mentioned acids. To prepare the alkali and alkaline earth metal salts of the compound of formula 1 wherein R denotes hydrogen, it is preferable to use the alkali and alkaline earth metal hydroxides and hydrides, of which the hydroxides and hydrides of the alkali metals, particularly sodium and potassium, are preferred, while sodium and potassium hydroxide are particularly preferred.

The compounds of general formula 1 may optionally be converted into the salts thereof, particularly for pharmaceutical use into the pharmacologically acceptable acid addition salts with an inorganic or organic acid. Examples of suitable acids for this purpose include succinic acid, hydrobromic acid, acetic acid, fumaric acid, maleic acid, methanesulphonic acid, lactic acid, phosphoric acid, hydrochloric acid, sulphuric acid, tartaric acid or citric acid. It is also possible to use mixtures of the above-mentioned acids.

The invention relates to the compounds in question, optionally in the form of the individual optical isomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The compounds according to the invention may optionally be present as racemates, but may also be obtained as pure enantiomers, i.e. In the (R) or (S) form.

The invention relates to the compounds in question, optionally in the form of the individual optical isomers, diastereomers, mixtures of diastereomers, mixtures of the individual enantiomers or racemates, in the form of the tautomers as well as in the form of the free bases or the corresponding acid addition salts with pharmacologically acceptable acids—such as for example acid addition salts with hydrohalic acids—for example hydrochloric or hydrobromic acid—or organic acids—such as for example oxalic, fumaric, diglycolic or methanesulphonic acid.

The invention relates to the respective compounds of formula 1 in the form of the pharmacologically acceptable salts thereof. These pharmacologically acceptable salts of the compounds of formula 1 may also be present in the form of their respective hydrates (e.g. Monohydrates, dihydrates, etc.) as well as in the form of their respective solvates.

By a hydrate of the compound according to the formula 1 is meant, for the purposes of the invention, a crystalline salt of the compound according to formula 1, containing water of crystallisation.

By a solvate of the compound according to formula 1 is meant, for the purposes of the invention, a crystalline salt of the compound according to formula 1, which contains solvent molecules (e.g. Ethanol, methanol etc) in the crystal lattice.

The skilled man will be familiar with the standard methods of obtaining hydrates and solvates (e.g. recrystallisation from the corresponding solvent or from water).

4. METHODS OF PREPARATION

The Examples according to the invention were prepared as shown in Schemes 1, 2 or 3.

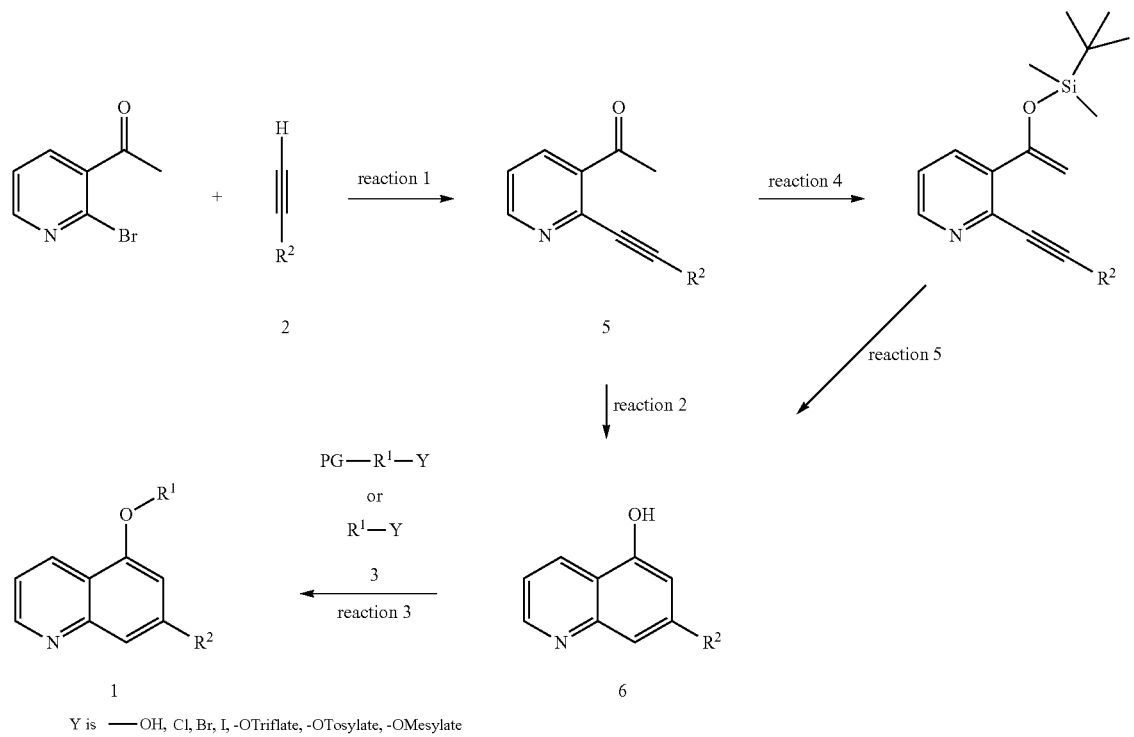

Scheme 1

Y is —OH, Cl, Br, I, -OTriflate, -OTosylate, -OMesylate

PG is protecting group (e.g. benzyl, 1-phenylethyl, 1-(4-methoxyphenyl)ethyl)

and $R^1$ and $R^2$ are as herein before defined.

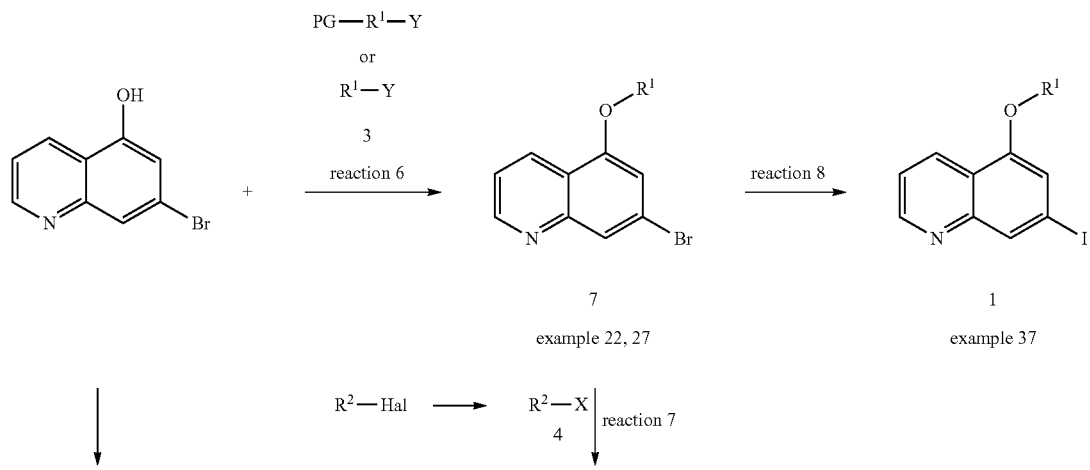

Scheme 2

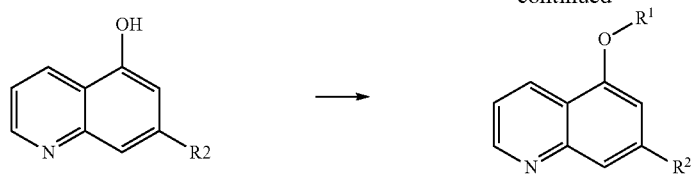

with X being —B(OH)₂, -boronic acid pinacolester, -trifluoroborate, —SnBu₃;

Y being —OH, Cl, Br, I, -OTriflate, -OTosylate, -Omesylate, with Hal being Cl, Br, I, PG is a protecting group (e.g. benzyl, 1-phenylethyl, 1-(4-methoxyphenyl)ethyl)

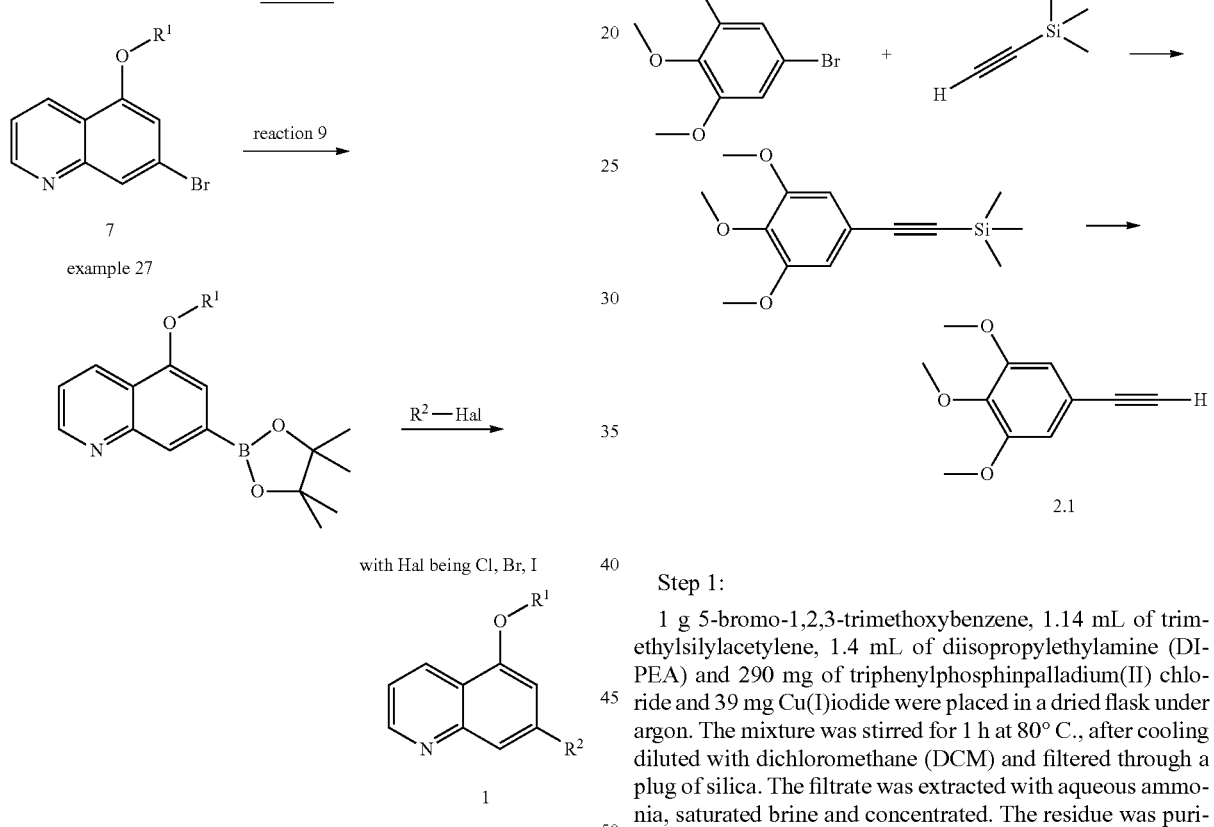

4.1. Starting Materials and Intermediates of Formula 2, 3 and 4

4.1.1. Synthesis of Arylalkines 2 from Scheme 1

Synthesis of 5-ethynyl-1,2,3-trimethoxybenzene (2.1) for Examples 2, 3, 4, 5, 9, 18, 23, 38

The synthesis of 5-ethynyl-1,2,3-trimethoxybenzene was carried out according to the method of Rasolofonjatovo, Evelia; Provot, Olivier; Hamze, Abdallah; Brion, Jean-Daniel; Alami, Mouad; Bignon, Jerome; Thoret, Sylviane European Journal of Medicinal Chemistry, 2010, vol. 45, 3617-3626.

Step 1:

1 g 5-bromo-1,2,3-trimethoxybenzene, 1.14 mL of trimethylsilylacetylene, 1.4 mL of diisopropylethylamine (DIPEA) and 290 mg of triphenylphosphinpalladium(II) chloride and 39 mg Cu(I)iodide were placed in a dried flask under argon. The mixture was stirred for 1 h at 80° C., after cooling diluted with dichloromethane (DCM) and filtered through a plug of silica. The filtrate was extracted with aqueous ammonia, saturated brine and concentrated. The residue was purified via flash chromatography (SiO₂: cyclohexane→cyclohexane/ethylacetate 9:1) to give trimethyl((3,4,5-trimethoxyphenyl)ethynyl)silane.

Yield: 970 mg (oil)

Analysis: HPLC-MS (method E) Rt=1.55 min; M+H=265.

Step 2:

230 mg Trimethyl((3,4,5-trimethoxyphenyl)ethynyl)silane, 0.9 mL tetrabutylammoniumfluoride (1 mol/l in THF) were dissolved in 3 mL of THF and stirred for 1 h at 25° C. The solution was diluted with DCM and extracted with water. The solvent of the organic phase was distilled off and the residue purified via flash chromatography (10 g SiO₂; cyclohexane→cyclohexane/ethylacetate 7:3).

Yield: 135 mg (90% of theory)

Analysis: HPLC-MS (method E): Rt: 1.15 min M+H=193

Synthesis of
5-Ethynyl-1,3-difluoro-2-methoxy-benzene (2.2) for
Examples 14, 15, 17

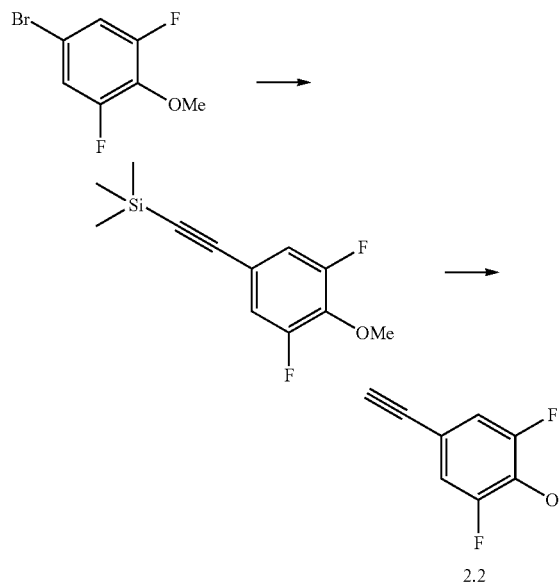

2.2

A mixture of 2 g 5-bromo-1,3-difluoro-2-methoxy-benzene, 1.76 g ethynyl-trimethyl-silane, 629 mg bis(triphenylphosphine)palladium(II) dichloride, 3.1 ml diisopropyl-ethylamine, and 85 mg copper iodide in 20 ml acetonitrile was degassed then heated at 80° C. for 2 hours. The mixture was diluted with dichloromethane and filtered through a plug of silica, washed with dilute ammonia and brine then dried over sodium sulphate, filtered and concentrated in vacuo. Purification over silica afforded 1.71 g (3,5-difluoro-4-methoxy-phenylethynyl)-trimethyl-silane.

$^1$H NMR (250 MHz, CDCl$_3$) δ ppm 0.24 (9H, s), 4.02 (3H, t, J=1.29 Hz), 6.91-7.09 (2H, m).

1N tetrabutylammonium fluoride (TBAF) in THF was added to 1.71 g (3,5-Difluoro-4-methoxy-phenylethynyl)-trimethyl-silane and the mixture stirred at 25° C. overnight. The solvent was removed in vacuo and the residue purified by flash chromatography over silica eluting with 20:1 heptane:ethyl acetate to give 866 mg 5-Ethynyl-1,3-difluoro-2-methoxy-benzene in 72% yield.

$^1$H NMR (250 MHz, CDCl$_3$) δ ppm 3.08 (1H, s), 4.02 (3H, d, J=1.22 Hz), 6.89-7.15 (2H, m), 4-Ethynyl-1-isopropoxy-2-methoxy-benzene (2.3)
(for Examples 10, 11, 13, 16, 19)

4-Ethynyl-1-isopropoxy-2-methoxy-benzene 2.3 was synthesized in 2 steps from 4-Bromo-1-isopropoxy-2-methoxy-benzene in analogy to 2.2.

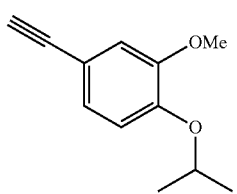

2.3

$^1$H NMR (250 MHz, CDCl$_3$) δ ppm 1.38 (6H, d, J=6.09 Hz), 3.01 (1H, s), 3.85 (3H, s), 4.56 (1H, m), 6.82 (1H, d, J=8.22 Hz), 7.00 (1H, d, J=1.83 Hz), 7.07 (1H, dd, J=8.30, 1.90 Hz).

2-Ethynyl-quinoline (2.4) for Example 34

2-Ethynyl-quinoline 2.4 for Example 34 was synthesized in 2 steps from 2-bromo-quinoline in analogy to 2.2.

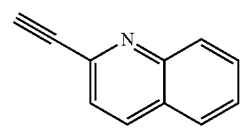

2.4

Analysis: HPLC-MS: Rt=1.25 (method M), M+H=154.

5-Ethynyl-2-methoxypyridine (2.5) for Examples 20, 21

5-Ethynyl-2-methoxypyridine for Example 20, 21 was synthesized in 2 steps from 5-Bromo-2-methoxy-pyridine in analogy to 2.2.

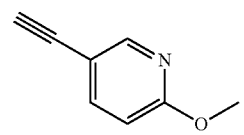

2.5

$^1$H NMR (500 MHz, CHLOROFORM-d) δ ppm 3.11 (1H, s), 3.92-3.98 (3H, m), 6.70 (1H, dd, J=8.62, 0.53 Hz), 7.64 (1H, dd, J=8.54, 2.29 Hz), 8.32 (1H, d, J=2.14 Hz)

The following arylalkines were commercially available:
4-Ethynyl-1,2-dimethoxybenzene 2.6 for Example 7, 8, 12
1-Ethynyl-benzene 2.7 for Example 1
2-Ethynylpyridine 2.8 for Example 6

4.1.2. Synthesis of 5-hydroxy-7-bromo-quinoline from Scheme 2

The title compound can be purchased by Shanghai Haoyuan Chemexpress Co., Ltd. CHINA or synthesized via known 3-bromo-5-methoxyaniline (Liedholm, Brita. Acta Chemica Scandinavica, Series B: Organic Chemistry and Biochemistry (1984), B38(10), 877-84 or Hodgson, H. H.; Wignall, J. S Journal of the Chemical Society (1926)) in two steps.

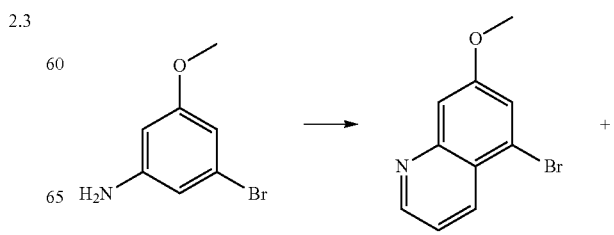

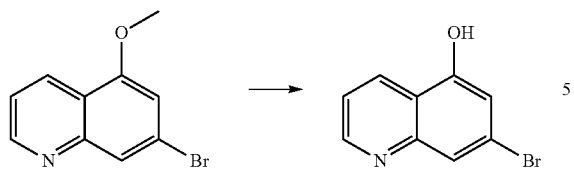

Step 1:

4.0 g (0.02 mol) of 3-Bromo-5-methoxy-aniline, 4.6 g (0.05 mol) of glycerol, 2.46 g (0.02 mol) of nitrobenzene and 12 ml of 75% sulfuric acid were stirred for 3 h at 150° C. After this dark solution was poured onto 100 g of crushed ice, 100 ml of ethylacetate (EtOAc) and 30 ml of 30% solution of NaOH. After 1 hour brown solid was filtered off and the organic layer was separated. After filtering through $SiO_2$ and evaporation of solvent 7-bromo-5-methoxy-quinoline and 5-bromo-7-methoxy-quinoline were separated as mixture approximately 60:40 (total 3.5 g, 74%) This mixture was separated to individual 7-bromo-5-methoxy-quinoline and 5-bromo-7-methoxy-quinoline with column chromatography on silica-gel with benzene-EtOAc (3:1) as eluent. Yield of pure 7-bromo-5-methoxy-quinoline was 950 mg (27% from mixture).

Step 2:

1.5 g (0.0064 mol) of 7-bromo-5-methoxy-quinoline were refluxed with 48% HBr (30 ml) for 20 h. After cooling to room temperature reaction mixture was poured into 100 ml of water and basified with saturated ammonia solution. Product was filtered off, washed with water and dried at 50° C. in vacuo. Yield of 7-bromo-5-hydroxy-quinoline was 600 mg (41%).

$^1$H-NMR (400 MHz, d6-DMSO): δ=11.1 (1H, s(broad)), 8.88 (1H, s), 8.49 (1H, d), 7.68 (1H,$), 7.48 (1H, m), 7.18 (1H,$) ppm.

4.1.3. Synthesis of Alcohols 3 from Scheme 1 and 2

Synthesis of (R)-4-((R)-1-hydroxyethyl)-1-(R)-1-phenylethyl)pyrrolidine-2-one (3.1) and (R)-4-((S)-1-hydroxyethyl)-1-(R)-1-phenylethyl)pyrrolidine-2-one (3.2) (for Examples 1, 2, 6, 8, 14)

Step 1:

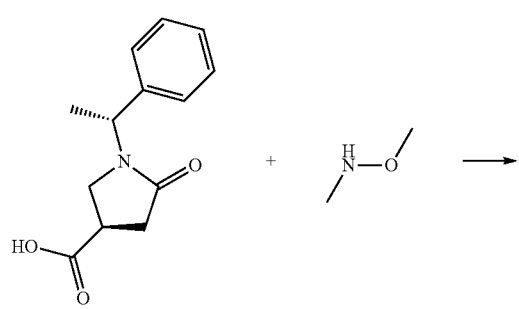

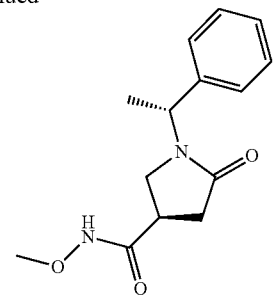

20 g (1'R,3R)-1-(1'-Phenylethyl)-5-oxo-3-pyrrolidinecarboxylic acid and N,O-dimethylhydroxylamine hydrochloride was dissolved in 100 mL dimethylformamide at 0° C. 13.9 g Hydroxybenzotriazole, 19.8 g 1-ethyl-3-(3-dimethylamino-propyl)carbodiimide (EDC) and 20 mL N-methylmorpholine were added and the mixture stirred at 0° C. for 2 h and overnight at ambient temperature. The reaction mixture was diluted with ethyl acetate and the organic phase was washed with 10% citric acid solution, 5% sodium bicarbonate and saturated sodium chloride solution. The organic phase was dried and concentrated.

Yield: 23.8 g (95% of theory)

Analysis (method E): Rt: 1.12 min, (M+H)$^+$: 277

Step 2:

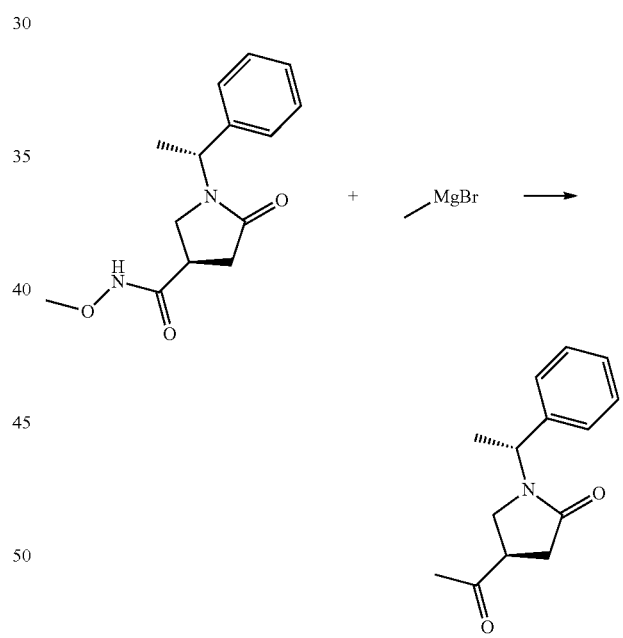

The reaction was carried out under a nitrogen atmosphere.

11.95 g (R)—N-methoxy-5-oxo-1-((R)-1-phenylethyl) pyrrolidine-3-carboxamide (were placed in 100 mL tetrahydrofuran at −10° C. 30 mL Methylmagnesium bromide in diethyl ether solution was added within 15 min (white suspension, temperature at +10° C.) and the mixture was stirred at −10° C. for 2 h and then warmed to ambient temperature. The mixture was diluted with ethyl acetate and washed with 1N hydrochloric acid, saturated sodium bicarbonate and saturated sodium chloride solution. The organic phase was dried and concentrated.

Yield: 9.45 g (95% of theory)

Step 3:

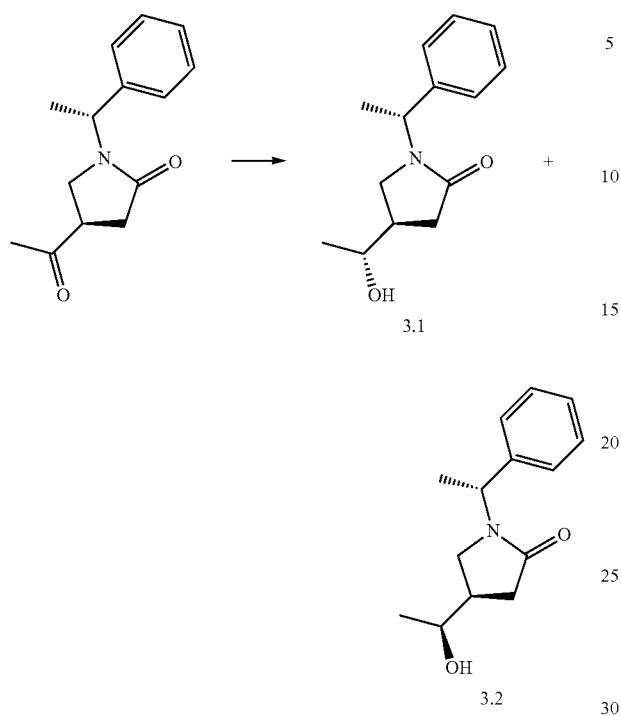

Reaction was carried out under argon atmosphere.

8.5 g (26.8 mmol) (R)-4-acetyl-1-((R)-1-phenylethyl)pyrrolidine-2-one were placed in 40 mL dichloromethane at −50° C. and 40.5 mL (40.5 mmol) lithium 9-BBN hydride in tetrahydrofuran was added dropwise. During the addition the temperature increased to −30° C. The mixture was then stirred at −45° C. for 1 h. After this time, phosphate buffer was added and the mixture was warmed to ambient temperature, diluted with dichloromethane and extracted with water. The organic phase was dried over magnesium sulfate, concentrated and purified via prep HPLC(X-bridge C18).

Yield: 2.60 g of 3.1 (30% of theory)
Analysis (method E): Rt: 1.08 min, (M+H)+: 234
Yield: 2.60 g of 3.2 (30% of theory)
Analysis (method E): Rt: 1.12 min, (M+H)+: 234

5-(Hydroxymethyl)piperidine-2-one (3.3) (for Example 5)

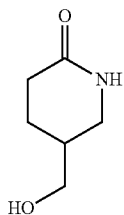

5-(Hydroxymethyl)piperidine-2-one (3.3) may be synthesised according to the following literature:
Lerchner, Andreas; Carreira, Erick M. *Chemistry A European Journal* (2006), 12(32), 8208-8219.

Synthesis of (R)-4-[(S)-1-hydroxyethyl]-1-[(S)-1-(4-methoxyphenyl)-ethyl]-pyrrolidin-2-one 3.4 for Examples 21, 27, 29-31, 33, 34, 37, 41-43, 47-49, 51, 53, 55, 56, 61, 63, 65, 66-69, 72, 73, 76, 78, 81, 83, 85-91, 93-95, 99-102, 104, 105, 107, 109, 111, 112, 114-116, 118-120

Step 1: Synthesis of (1'R,3R/S)-1-(1'-(4-Methoxyphenylethyl)-5-oxo-3-pyrrolidine carboxylic acid (mixture of diastereoisomers)

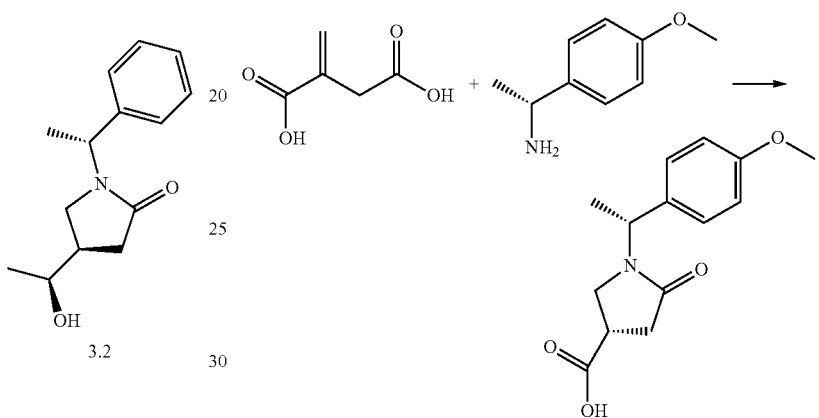

A suspension of 100 g of (R)-1-(4-methoxy-phenyl)-ethylamine and 95 g itaconic acid in 0.5 L 1-methyl-2-pyrrolidinone is heated to 80° C. for 1 hour. The solution is stirred for additional 4 hours at 120° C. The reaction mixture is cooled to 25° C. and poured into 1.5 L of demineralized water. The precipitate is filtered, washed with demineralized water and dried at 50° C.

Yield: 195 g (quantitative yield) solid as a mixture of diastereoisomers
Analysis (method G): Rt: 2.6 min and 2.7 min, (M+H)+: 264

In analogy is prepared
(1'S,3R/S)-1-(1'-(4-Methoxyphenylethyl)-5-oxo-3-pyrrolidine carboxylic acid as a mixture of diastereoisomers
Analysis (method G): Rt: 2.6 min and 2.7 min, (M+H)+: 264

Step 2: Synthesis of (R/S)—N-Methoxy-5-oxo-1-[(S)-1-(4-methoxyphenyl)-ethyl]-pyrrolidine-3-carboxamide as a mixture of diastereoisomers

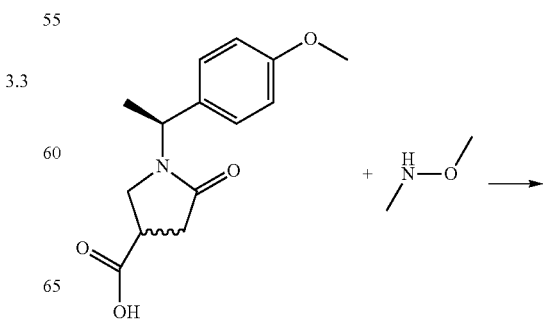

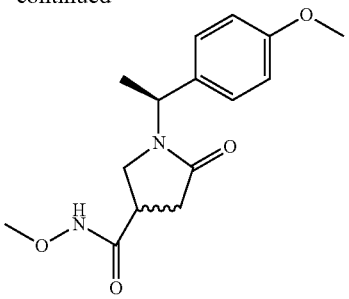

260 g of 1,1'-Carbonyldiimidazole (CDI) are added to a solution of 285 g (1'R,3R/S)-1-(1'-(4-methoxyphenylethyl)-5-oxo-3-pyrrolidine carboxylic acid (mixture of diastereoisomers) in 1.4 L 2-methyltetrahydrofuran at 20° C. The suspension is stirred at 20° C. for 80 minutes. 235 mL ethyldiisopropylamine (DIPEA) and 130 g of N,O-dimethyl-hydroxylamine hydrochloride are added. The suspension is stirred for 3 hours at 20° C. Under cooling 850 mL 4 N hydrochloric acid is added. The organic phase is separated and washed two times with 500 mL 1 N hydrochloric acid. The aqueous phase is reextracted two times with 500 mL ethyl acetate. The combined organic phases are dried over sodium sulfate. After filtration the solvent is evaporated under reduced pressure.

Yield: 271 g (82% of theory) of (R/S)—N-Methoxy-5-oxo-1-[(S)-1-(4-methoxyphenyl)-ethyl]-pyrrolidine-3-carboxamide (mixture of diastereoisomers) as an oil.

Analysis (method H): Rt: 11.1 min (41 area %) and 13.8 min (59 area %), (M+H)$^+$: 307

Step 3: Synthesis of (R/S)-4-acetyl-1-[(S)-1-(4-methoxyphenyl)-ethyl]-pyrrolidine-2-one as a mixture of diastereoisomers

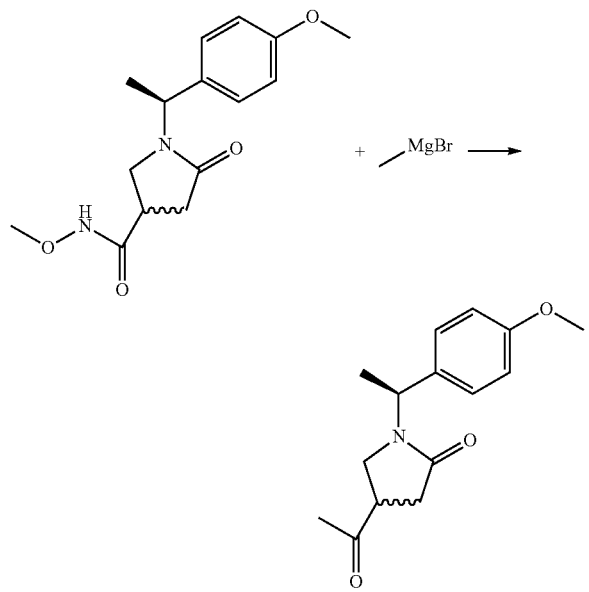

530 mL of a 3 M solution of methylmagnesium bromide in diethylether is added slowly to a cooled solution of 271 g of (R/S)—N-Methoxy-5-oxo-1-[(S)-1-(4-methoxyphenyl)-ethyl]-pyrrolidine-3-carboxamide (mixture of diastereoisomers) in 1.4 L of 2-methyltetrahydrofuran so that the temperature remains under 0° C. After complete addition the temperature is kept for 75 minutes at 0° C. and then warmed up to 20° C. The suspension is stirred 16 hours at 20° C. Under cooling 650 mL of a 4 M hydrochloric acid are added. The organic phase is separated and washed with 500 mL saturated sodium carbonate solution and with 500 mL saturated brine. The organic phase is dried over sodium sulfate. After filtration the solvent is evaporated under reduced pressure.

Yield: 188 g (81% of theory) of (R/S)-4-acetyl-1-[(S)-1-(4-methoxyphenyl)-ethyl]-pyrrolidine-2-one (mixture of diastereoisomers) as an oil.

Analysis (method H): Rt: 7.4 min and 9.6 min, (M+H)$^+$: 262

Step 4: Crystallization of (R)-4-acetyl-1-[(S)-1-(4-methoxyphenyl)-ethyl]-pyrrolidine-2-one under base induced epimerization conditions

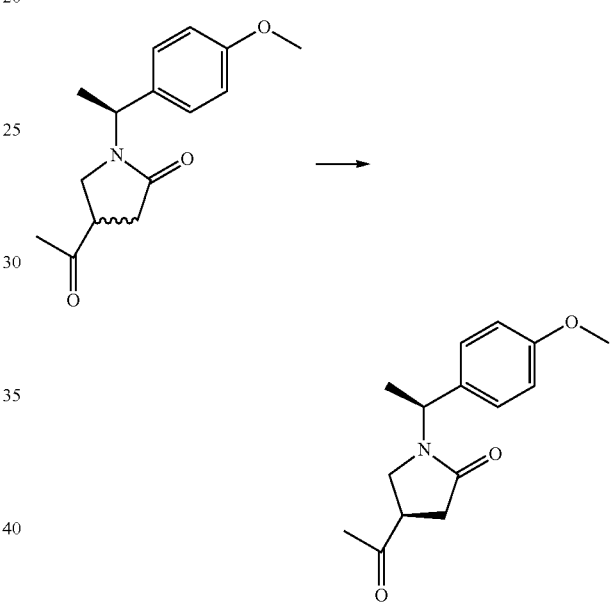

103 g of a mixture of diastereoisomers (R/S)-4-acetyl-1-[(S)-1-(4-methoxyphenyl)-ethyl]-pyrrolidine-2-one is dissolved in 155 mL 1-butanol at 25° C. 18 mL benzyltrimethylammonium hydroxide (40% solution in methanol) is added. The solution is stirred for 30 minutes at 25° C. The solution is cooled to 0° C. Precipitation starts. The suspension is stirred for 15 minutes at 0° C. 100 mL n-heptane is added slowly and the suspension is stirred for 30 minutes at 0° C. The addition of 100 mL portions of n-heptane is repeated 4 times with subsequent stirring of the suspension at 0° C. for 30 minutes. The precipitate is isolated, washed with n-heptane and dried at 50° C.

Yield: 77.1 g of a beige solid (75% of theory) with a diastereoisomeric purity of ~95:5 (method H).

For further purification the crude product is dissolved in 310 mL 2-methyl-2-butanol at 40° C. (temperature <50° C.). The solution is slowly cooled to 0° C. Precipitation starts. At 0° C. 385 mL of n-heptane is added and the suspension is stirred for 1 hour. The precipitate is filtrated, washed with n-heptane and dried at 50° C.

Yield: 68.7 g (67% of theory) of a colorless solid with a diastereoisomeric purity of >99:1.

Analysis (method H): Rt: 6.8 min, (M+H)$^+$: 262

Step 5: Synthesis of (R)-4-[(S)-1-hydroxyethyl]-1-[(S)-1-(4-methoxyphenyl)-ethyl]-pyrrolidin-2-one

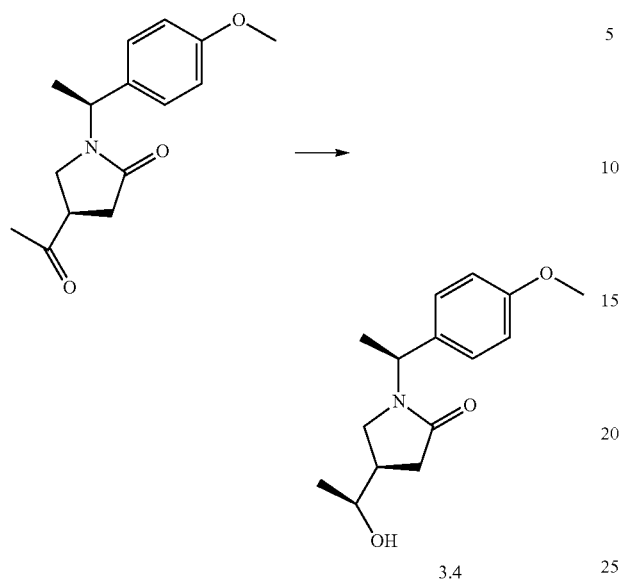

3.4

2.4 g of Dichloro-(pentamethylcyclopentadienyl)-rhodium-(III)-dimer and 2.8 g (R,R)—N-(p-toluenesulfonyl)-1,2-diphenylethylendiamine [(R,R)-TsDPEN] is added to a solution of 50 g (R)-4-acetyl-1-[(S)-1-(4-methoxyphenyl)-ethyl]-pyrrolidin-2-one in acetonitril at 25° C. The solution is cooled to −15° C. At this temperature a mixture of 22 mL formic acid and 135 mL triethylamine is added. The reaction mixture is stirred for 22 hours at −15° C. and then warmed up to 20° C. 230 mL of a 4 molar hydrochloric acid is added under cooling. The aqueous phase is extracted 3 times with ethyl acetate. The organic phase is washed with diluted and concentrated brine and treated with activated carbon. The organic phase is dried over sodium sulfate. The solvent is evaporated under reduced pressure to obtain 57.1 g of a beige solid with a diastereomeric purity of ~97:3.

For further purification the crude product is crystallized from isopropyl acetate.

Yield: 37.8 g (75% of theory) of a beige solid with a diastereoisomeric purity of >99:1.

Analysis (method I): Rt: 12.9 min, (M+H)+: 264

The transfer hydrogenation reaction can also be performed in 2-propanol at 20° C.

Synthesis of (R)-4-(hydroxymethyl)-1-((R)-1-phenylethyl)pyrrolidin-2-one (for Example 7, 9, 17, 19)

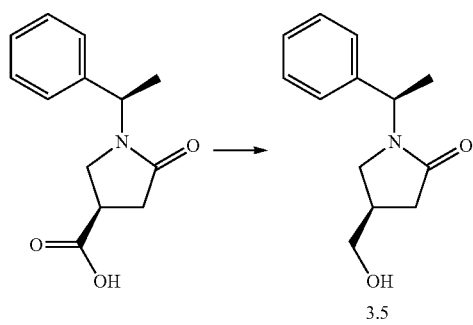 [SMILES: C[C@H](c1ccccc1)N1C[C@H](C(=O)O)CC1=O ; C[C@H](c1ccccc1)N1C[C@H](CO)CC1=O]

3.5

5 g (1'R,3R)-1-(1'Phenylethyl)-5-oxo-3-pyrrolidine carboxylic acid was dissolved in 50 mL tetrahydrofuran, then the solution was cooled to 0° C. 16.5 mL borane dimethyl sulfide (2 M in tetrahydrofuran) was added dropwise over 30 min and the reaction solution was slowly warmed to 25° C. and stirred for a further 2 h at 25° C. The reaction mixture was concentrated, diluted in dichloromethane and washed with sodium bicarbonate solution. The water phase was extracted with dichloromethane (×2) and the combined organic phases were dried over magnesium sulfate and concentrated.

Yield: 5.5 g (content 80%, 94% of theory)

Analysis: HPLC-MS (method D): Rt=1.20 min (M+H)+=220

(R)-5-(Hydroxymethyl)-3-[(R)-α-methylbenzyl-2-oxazolidinone (3.5) (for Example 12, 13, 15, 16, 18, 20)

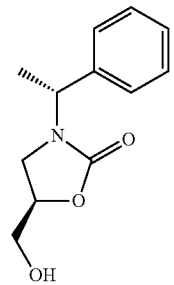

3.6

Commercially available from Sigma-Aldrich 2-(Hydroxymethyl)nicotinamide for Example 22, 24-26, 32, 35, 36, 39, 40, 44-46, 50, 52, 54, 57-60, 62, 64, 70, 71, 74-75, 77, 79, 80, 82, 84, 92, 96-98, 103, 106, 108, 110, 113, 117

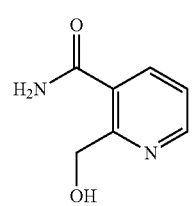

3.7

2-(Hydroxymethyl)nicotinamide may be synthesized according to the following literature: Goto, Takehiko; Saito, Minoru; Sato, Ryu *Bulletin of the Chemical Society of Japan*, 1987, 60, 4178-4180

Synthesis of 1-Chloromethyl-5,5-dimethyl-imidazolidine-2,4-dione for Example 23

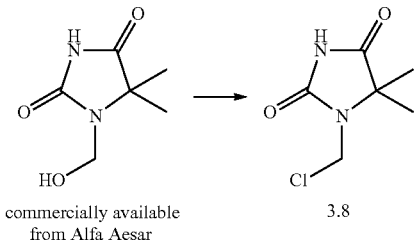

0.69 ml Thionyl chloride was added to a solution of 500 mg 1-Hydroxymethyl-5,5-dimethyl-imidazolidine-2,4-dione in 5 ml DCM at 0° C. for 30 minutes, then left to stir at 25° C. for 16 hours. The mixture was evaporated to dryness and used crude in the synthesis of example 23.

4.1.4. Synthesis of boronic acids, boronic esters and stannanes 4 in Scheme 2

4.1.4.1. Synthesis of R²-Hal

4-Bromo-2-methyl-1-(methylsulfonyl)benzene for Example 35

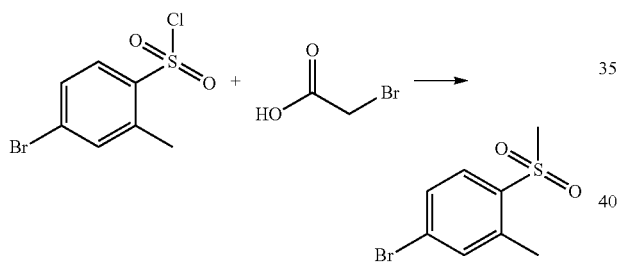

235 mg Sodium sulfite and 470 mg $NaHCO_3$ were dissolved in 1.75 mL of water and heated to 75° C. 500 mg of 4-Bromo-2-methyl-benzenesulfonyl chloride were added in portions within 10 min (gas formation) and the mixture stirred for 1 h at 75° C. 387 mg of Bromoacetic acid and 150 µL of water was added in small portions and the mixture stirred at 105° C. overnight. After cooling to 25° C. the mixture was acidified to pH 1 using 4N HCl. The resulting precipitate was collected and washed with water to yield 205 mg solid.

Analysis: HPLC-MS: Rt=0.73 (method X001_002) M+H=249/251

1-Bromo-4-(trifluoromethylsulfonyl)benzene for Example 36

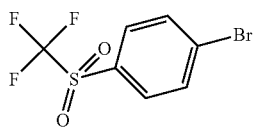

1-Bromo-4-(trifluoromethylsulfonyl)benzene is described in: Mongin, Olivier; Pones, Laurent; Charlot, Marina; Katan, Claudine; Blanchard-Desce, Mireille *Chemistry—A European Journal,* 2007, 13, p. 1481-1498.

N-(4-Bromobenzyl)-N-ethylacetamide for Examples 50, 68

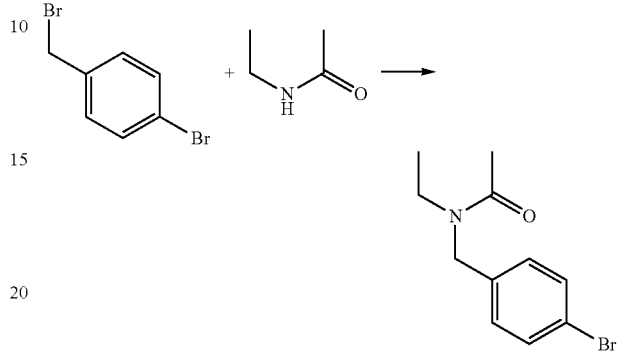

0.568 mL N-ethylacetamide was dissolved in 20 mL THF. 0.67 g Potassium tert-butoxide was added and the mixture stirred for 20 min at 50° C. Then 1 g of 4-bromobenzylbromide dissolved in 5 mL THF was added and the suspension stirred for 2 h at 50° C. After cooling, ethylacetate and water were added and the organic phase extracted with water (1×), dried and the solvent distilled off. The product was purified via FCC (cyclohexane/ethylacetate: 90/10→50/50) to yield 830 mg N-(4-bromobenzyl)-N-ethylacetamide as an oil.

Analysis: HPLC-MS: Rt=2.67 min (method C), M+H=256

N-(4-Bromobenzyl)-N-methylacetamide for Examples 51, 58

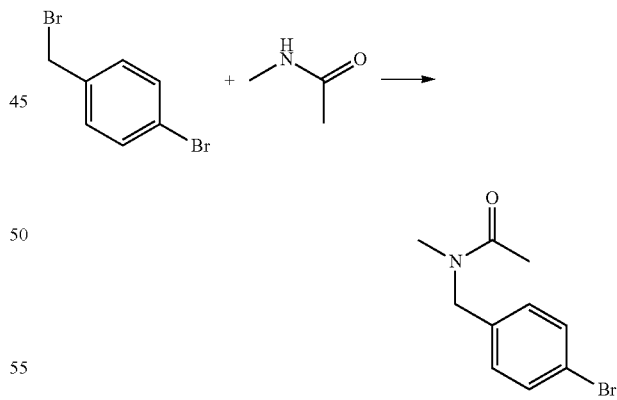

1.316 g N-methylacetamide was dissolved in 60 mL THF. 2.02 g Potassium tert-butoxide was added and the mixture stirred for 20 min at 50° C. Then 3 g of 4-bromobenzylbromide dissolved in 10 mL THF was added and the mixture stirred for 2 h at 50° C. After cooling ethylacetate and water were added and the organic phase extracted with water (1×), dried and the solvent distilled off to yield 2.8 g N-(4-bromobenzyl)-N-methylacetamide as an oil.

Analysis: MS: M+H=242.

4-Bromo-1-(trifluoromethyl)-1H-pyrazole for Example 87

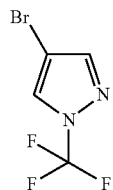

was obtained as described in WO2008/95944.

7-Bromo-3-methylquinazolin-4(3H)-one for Examples 91, 92

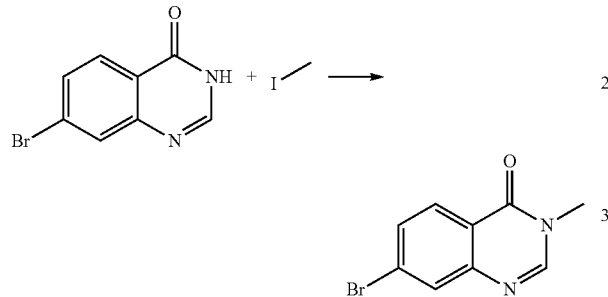

7-Bromoquinazolin-4(3H)-one can be obtained as described in WO2010/146173.

400 mg 7-Bromoquinazolin-4(3H)-one was dissolved in DMF and 720 mg of CsCO$_3$ and 130 µL of methyliodide were added and the mixture stirred for 3 h at 25° C. Additional 50 µL methyliodide were added and stirred overnight at 25° C. The mixture was filtered off and the mother liquor diluted with DCM and extracted with water. The solvent was removed to yield 490 mg of 7-bromo-3-methylquinazolin-4(3H)-one as solid.

Analysis: HPLC-MS: Rt=0.66 min (method X001_004) M+H=239/241

7-Bromo-3-methyl-2,3,4,5-tetrahydro-1H-benzo[d]azepine for Example 103

7-Bromo-2,3,4,5-tetrahydro-1H-benzo[d]azepine can be obtained as described in Shah, Unmesh; Lankin, Claire M.; Boyle, Craig D.; Chackalamannil, Samuel; Greenlee, William J.; Neustadt, Bernard R.; Cohen-Williams, Mary E.; Higgins, Guy A.; Ng, Kwokei; Varty, Geoffrey B.; Zhang, Hongtao; Lachowicz, Jean E. Bioorganic and Medicinal Chemistry Letters, 2008, 18, 4204-4209.

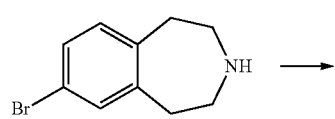

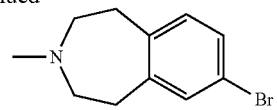

2.43 g 7-Bromo-2,3,4,5-tetrahydro-1H-benzo[d]azepine are dissolved in 4.055 g of formic acid and 3.2 mL of formaldehyde solution was added. The mixture was stirred at 70° C. for 3.5 h and continued overnight at 25° C. The mixture was concentrated, diluted with water and 10 N NaOH to adjust to a basic pH. The mixture was then extracted with tertbutylmethylether (3×) and the organic phase dried (Na$_2$SO$_4$), filtered and concentrated to yield 2.48 g 7-bromo-3-methyl-2,3,4,5-tetrahydro-1H-benzo[d]azepine as oil.

Analysis: MS: M+H=240/242

6-Bromo-2,4-dimethylquinazoline for Example 107

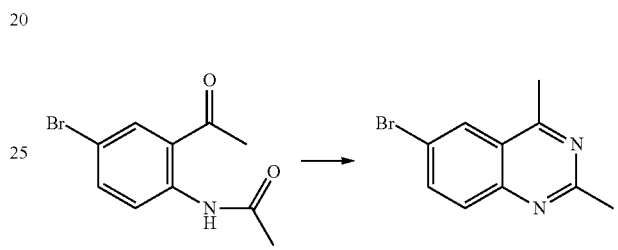

N-(2-acetyl-4-bromophenyl)acetamide can be obtained as described in: Woods, Keith W.; Fischer, John P.; Claiborne, Akiyo; Li, Tongmei; Thomas, Sheela A.; Zhu, Gui-Dong; Diebold, Robert B.; Liu, Xuesong; Shi, Yan; Klinghofer, Vered; Han, Edward K.; et al. *Bioorganic & Medicinal Chemistry*, 2006, 14, p. 6832-6846

415 mg N-(2-acetyl-4-bromophenyl)acetamide and 0.624 g of ammonium acetate was dissolved in 5 mL of glacial acetic acid and heated for 2 days at 100° C. The solvent was removed and the residue suspended in water and extracted with DCM. The organic phase was concentrated and purified via FCC (25 g SiO$_2$, DCM:MeOH 100:0→70:30) to yield 90 mg of 6-bromo-2,4-dimethylquinazoline as oil. Analysis: HPLC-MS: Rt=1.26 min (method V003_003), M+H=237/239.

5-Bromo-2-(difluoromethyl)pyridine for Example 120

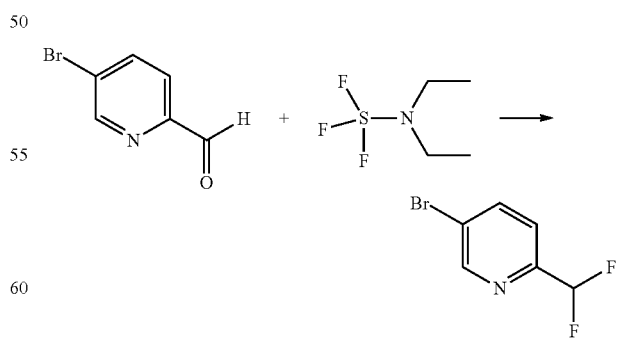

1 g 5-Bromo-pyridine-2-carboxaldehyde was dissolved in 50 mL DCM. The solution was cooled to −70° C., then 1.55 mL diethylaminosulfurtrifluoride was added dropwise over 20 minutes. The suspension was stirred for 30 minutes at room temperature, then 10 mL water was added at 0° C. followed by slow addition of 20 mL saturated NaHCO$_3$ (gas formation). The phases were separated and 2 mL of 4N HCl in dioxane is added to the organic phase which was concentrated in vacuo to provide 1.06 g product as yellow solid. HPLC-MS: Rt=0.72 min (method X001_004), M+H=208/210.

4.1.4.2. Synthesis of Compounds of Formula 4 (R$^2$—X) (Scheme 2)

Synthesis of 2-methyl-6-(4,4,5,5-tetramethyl-1,3,2-dioxaborolan-2-yl)quinoline for Examples 33, 75

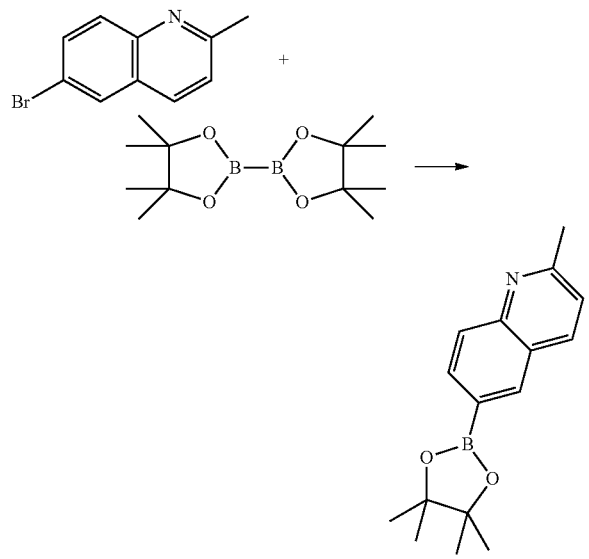

100 mg 6-Bromoquinaldine, 133 mg bis-(pinacolato)-diboron, 16 mg Pd(II)Cl$_2$ (PPh$_3$)$_2$ and 86 mg potassium acetate were suspended in 1 mL dioxane and the mixture heated at 100° C. in the microwave for 1 h. The mixture was diluted after cooling with DCM and extracted with water (2×). The organic phase was concentrated to yield 200 mg (94%, content 55%) 2-methyl-6-(4,4,5,5-tetramethyl-1,3,2-dioxaborolan-2-yl)quinoline as oil.

Analysis: HPLC-MS (method X001_002) Rt=0.48 min, M+H=188

The following boronic esters were synthesized in analogy and were used without further purification:
- 4,4,5,5-Tetramethyl-2-(3-methyl-4-(methylsulfonyl)phenyl)-1,3,2-dioxaborolane for Example 35. Reaction conditions: 1 h, 100° C. Yield: 74% (content 50%). Analysis: HPLC-MS: Rt=0.42 min (method X001_003), M+H=215 (boronic acid)
- 4,4,5,5-Tetramethyl-2-(4-(trifluoromethylsulfonyl)phenyl)-1,3,2-dioxaborolane for Example 36. Reaction conditions: 1 h, 100° C. Yield: 93% (content 45%). Analysis: HPLC-MS: Rt=0.72 min (method X001_003)
- N-Ethyl-N-(4-(4,4,5,5-tetramethyl-1,3,2-dioxaborolan-2-yl)benzyl)acetamide for Example 50, 68. Reaction conditions: 2 h, 100° C. Yield: 93% (content 55%). Analysis: HPLC-MS: Rt=0.87 min (method X001_002), M+H=304
- N-Methyl-N-(4-(4,4,5,5-tetramethyl-1,3,2-dioxaborolan-2-yl)benzyl)acetamide for Example 51, 58. Reaction conditions: 2 h, 100° C. Yield: 94% (content 45%). Analysis: HPLC-MS: Rt=0.83 min (method X001_002), M+H=290
- 6-(4,4,5,5-Tetramethyl-1,3,2-dioxaborolan-2-yl)-3,4-dihydroisoquinolin-1(2H)-one for Example 52, 53. Reaction conditions: 1 h, 100° C. Yield: 87% (content 35%). Analysis: HPLC-MS: Rt=0.81 min (method X001_002), M+H=274
- 1-(4-(4,4,5,5-Tetramethyl-1,3,2-dioxaborolan-2-yl)benzyl)piperidin-2-on for Example 54, 55. Reaction conditions: 1 h, 100° C. Yield: 92% (content 45%). Analysis: HPLC-MS: Rt=0.87 min (method X001_003), M+H=316
- 2-Methyl-6-(4,4,5,5-tetramethyl-1,3,2-dioxaborolan-2-yl)imidazo[1,2-a]pyridine for Example 60, 61. Reaction conditions: 6 h, 100° C. Yield: 98% (content 50%). Analysis: HPLC-MS: Rt=0.40 min (method X001_004), M+H=177 (boronic acid)
- 1-(2-Chloro-4-(4,4,5,5-tetramethyl-1,3,2-dioxaborolan-2-yl)phenyl)cyclopropanamine for Example 62, 86. Reaction conditions: 1 h, 100° C. Yield: 85% (content 40%). Analysis: HPLC-MS: Rt=0.67 min (method X001_004), M+H=294 and 0.24 min M+H=212 (boronic acid).
- 6-(4,4,5,5-Tetramethyl-1,3,2-dioxaborolan-2-yl)-1H-benzo[d][1,3]oxazin-2(4H)-one for Example 63, 64. Reaction conditions: 1 h, 100° C. Yield: 87% (content 50%). Analysis: HPLC-MS: Rt=0.67 min (method X001_004), M+H=276

The following examples were synthesized in analogy to the described example but without using a microwave:
- 6-(4,4,5,5-Tetramethyl-1,3,2-dioxaborolan-2-yl)-2-(trifluoromethyl)imidazo[1,2-a]pyridine for Example 83. Reaction conditions: 1 h, 100° C. Yield: 94% (content 45%). Analysis: HPLC-MS: Rt=0.49 min (method X001_004), M+H=231 (boronic acid)
- 4-(4,4,5,5-Tetramethyl-1,3,2-dioxaborolan-2-yl)-1-(trifluoromethyl)-1H-pyrazole for Example 87. Reaction conditions: 3.5 h, 100° C. Yield: 98% (content 55%). Analysis: HPLC-MS: Rt=1.66 min (method V003_002), M+H=263
- 2-Cyclobutyloxy-5-(4,4,5,5-tetramethyl-1,3,2-dioxaborolan-2-yl)pyridine for Example 90. Reaction conditions: 1 h, 100° C. Yield: 90% (content 40%). Analysis: HPLC-MS: Rt=0.50 min (method X001_004), M+H=194 (boronic acid)
- 3-Methyl-7-(4,4,5,5-tetramethyl-1,3,2-dioxaborolan-2-yl)quinazolin-4(3H)-one for example 91, 92 Reaction conditions: (1 h, 100° C.). Yield 98% (content 50%). HPLC-MS: Rt=0.34 min (method X001_004).
- 5-(4,4,5,5-Tetramethyl-1,3,2-dioxaborolan-2-yl)-2-(trifluoromethyl)-1H-benzo[d]imidazole for Example 93. Reaction conditions: 11 h, 100° C. Yield: 97% (content 60%). Analysis: HPLC-MS: Rt=0.70 min (method X001_004), M+H=313
- 1-Methyl-5-(4,4,5,5-tetramethyl-1,3,2-dioxaborolan-2-yl)-1H-benzo[d]imidazole for Example 94, 98. Reaction conditions: 1 h, 100° C. Yield: 96% (content 50%). Analysis: HPLC-MS: Rt=0.58 min (method X001_004), M+H=259
- 2-(Methylsulfonylmethyl)-5-(4,4,5,5-tetramethyl-1,3,2-dioxaborolan-2-yl)pyridine for Example 95, 96. Reaction conditions: 1 h, 100° C. Yield: 98% (content 45%). Analysis: MS: M+H=298
- 2-(3-Methoxy-4-(trifluoromethyl)phenyl)-4,4,5,5-tetramethyl-1,3,2-dioxaborolane for Example 102. Reaction conditions: 7 h, 100° C. Yield: 88% (content 55%). Analysis: HPLC-MS: Rt=0.90 min (method X001_004), M+H=303

3-Methyl-7-(4,4,5,5-tetramethyl-1,3,2-dioxaborolan-2-yl)-2,3,4,5-tetrahydro-1H-benzo[d]azepine for Example 103. Reaction conditions (1 h, 100° C.). Yield: 88% (content 50%) HPLC-MS: Rt=0.61 min (method X001_004), M+H=288

2-(Difluoromethoxy)-5-(4,4,5,5-tetramethyl-1,3,2-dioxaborolan-2-yl)pyridine for Example 104

1,2-Dimethyl-5-(4,4,5,5-tetramethyl-1,3,2-dioxaborolan-2-yl)-1H-benzo[d]imidazole for Example 105, 106. Reaction conditions (2 h, 100° C.) Yield: 91% (content 50%). Analysis: HPLC-MS: Rt=0.57 min (method X001_004), M+H=273.

2,4-Dimethyl-6-(4,4,5,5-tetramethyl-1,3,2-dioxaborolan-2-yl)quinazoline for example 107. Reaction conditions (7 h, 100° C.). Yield: 95% (content 40%). Analysis: HPLC-MS: Rt=0.29 min (method X001_004)

2-(Difluoromethyl)-5-(4,4,5,5-tetramethyl-1,3,2-dioxaborolan-2-yl)pyridine for Example 120. Reaction conditions (1 h, 100° C.). Yield: 97% (content 38%). Analysis: HPLC-MS: Rt=0.27 min (method X001_004)

The following boronic acids, trifluoroborates or boronic esters were commercially available:

4-(Methanesulfonyl)benzeneboronic acid for Example 24
3,4-Dimethoxyphenylboronic acid for Example 25
N-[5-(4,4,5,5-Tetramethyl-1,3,2-dioxaborolan-2-yl)-pyridin-2-yl]-acetamide for Examples 26, 30
Quinoline-6-boronic acid for Example 29
2-(Trifluoromethyl)pyridin-5-ylboronic acid for Example 31
3-Fluoro-4-(methylsulfonyl)phenylboronic acid for Example 32
1H-Benzimidazol-5-boronic acid, pinacol ester for Examples 39, 41
4-(4-Morpholinylmethyl)phenylboronic acid for Examples 40, 43
1-Methylindazol-6-boronic acid for Examples 42, 44
4-[5-(4,4,5,5-Tetratmethyl-[1,3,2]dioxaborolan-2-yl)pyridin-2-yl]morpholine for Examples 45, 48
1-Methyl-4(4,4,5,5-tetramethyl-1,3,2-dioxaborolan-2-yl-1H pyrazole for Examples 46, 47
6-(N-Methylamidocarbonyl)pyridine-3-boronic acid pinacol ester for Example 56, 59
2-Methoxy-5-pyridineboronic acid for Example 57
5-Methyoxy-3-pyridinylboronic acid for Example 65
2-Isopropoxy-5-(4,4,5,5-tetramethyl-1,3,2-dioxaborolan-2-yl)pyridine for Example 66
3-Fluoro-2-,ethoxypyridine-5-boronic acid for Example 67
2-Ethoxy-5-pyridineboronic acid for Example 69
2-(Tetrahydropyran-4-yloxy)-5-(4,4,5,5-tetramethyl-1,3,2-dioxaborolan-2-yl)pyridine for Examples 70, 72
2-Methoxypyridine-4-boronic acid for Examples 71, 73
Phenylboronic acid for Example 74
(4-Methyl-piperazin-1-yl)-[4-(4,4,5,5-tetramethyl-[1,3,2]dioxaborolan-2-yl)-phenyl]-methanone for Examples 76, 80
1-Ethyl-1H-pyrazole-4-boronic acid, pinacol ester for Examples 77, 78
3-Methyl-6-(4,4,5,5-tetramethyl-1,3,2-dioxaborolan-2-yl)-3H-imidazo[4,5-B]pyridine for Example 79
1-Methyl-1H-benzoimidazole-6-boronic acid for Examples 81, 82
2-Methylbenzo[D]thiazol-6-ylboronic acid, pinacol ester for Examples 84, 85

Potassium 5-methoxypyridine-2-trifluoroborate for Examples 88, 97
2-Tert-butoxy-5-(4,4,5,5-tetramethyl-1,3,2-dioxyborolan-2-yl)pyridine for Example 89
2-Methyl-1-H-benziomidazole-5-boronic acid, pinacol ester for Examples 108, 109
6-(2,2,2-Trifluoroethoxy)pyridine-3-boronic acid, pinacol ester for Examples 110, 111
1,5-Dimethyl-1H-pyrazole-4-boronic acid, pinacol ester for Example 112
1-Isopropyl-1H-pyrazole-4-boronic acid, pinacol ester for Examples 113, 115
1-Propyl-1H-pyrazole-4-boronic acid, pinacol ester for Examples 114, 117
1-Methyl-3-trifluoromethylpyrazole-4-boronic acid for Example 116
2,3-Dimethoxy-5-(4,4,5,5-tetramethyl-[1,3,2]dioxaborolan-2-yl)-pyridine for Example 99
6-(4,4,5,5-Tetramethyl-[1,3,2]dioxaborolan-2-yl)-3,4-dihydro-2H-pyrano[2,3-b]pyridine for Example 100
(4,4,5,5-Tetramethyl-[1,3,2]dioxaborolan-2-yl)-3,4-dihydro-1H-isoquinoline-2-carboxylic acid tert-butyl ester for Example 101
Acetic acid 2-[4-(4,4,5,5-tetramethyl-[1,3,2]dioxaborolan-2-yl)-pyrazol-1-yl]-ethyl ester for Examples 118, 119

4.2. Synthesis of compounds with formula 6: Reaction 1, 2, 4 and 5 of Scheme 1

The first step was made according to the following literature: M. Tiano, P. Belmont J. Organic Chem. 2008, 73, 4101-4109. The second step was carried out according to N. Nishiwaki, S. Minakata, M. Komatsu, Y. Ohshiro, Synlett 1990, 5, 273-275.

Synthesis of 7-phenylquinolin-5-ol (6.1) for Example 1

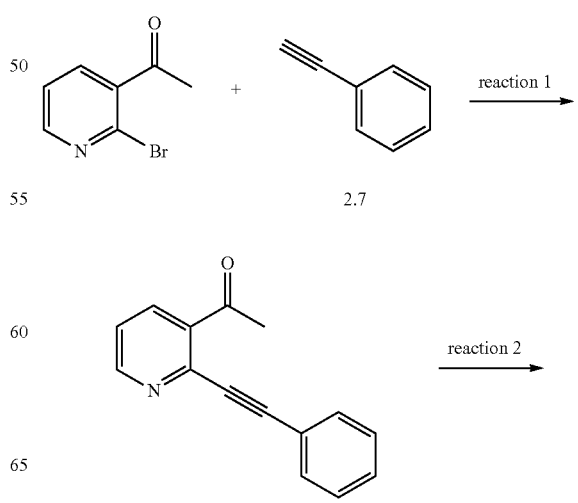

-continued

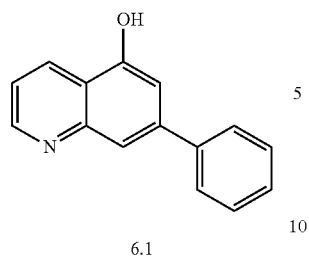

6.1

-continued

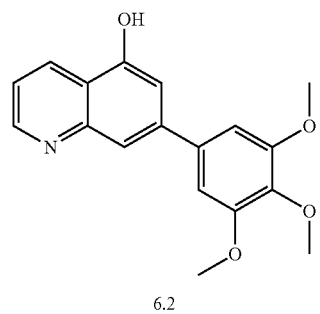

6.2

Step 1 (=Reaction 1):

66 mg 3-Acetyl-2-bromopyridine, 56 µL phenylacetylene, 170 µL DIPEA, 22.5 mg triphenylphosphinpalladium(II) chlorid, 3 mg Cu(I)I were suspended in 1 mL DMF under argon atmosphere and stirred for 16 h at 25° C. The mixture was diluted with DCM and extracted with diluted aq. NH$_3$ and brine. The organic phase was concentrated and the mixture separated via flash chromatography (10 g SiO$_2$, cyclohexane→cyclohexane/ethylacetate 70:30) to yield 40 mg 1-(2-(phenylethynyl)pyridin-3-yl)ethanone as solid. Analysis: HPLC-MS: Rt=1.21 min (method E), M+H=222.

Step 2 (=Reaction 2):

30 mg 1-(2-(Phenylethynyl)pyridin-3-yl)ethanone were suspended in 350 µL 1N sulfuric acid and 2.147 mg mercuric chloride and stirred for 30 min at 60° C. Then 1 mL of NaOH was added and the mixture stirred for additional 1 h at 25° C. Water was added and a neutral pH adjusted with NaHCO$_3$ solution. The precipitate was filtered off and washed with water and dried to yield 30 mg 7-phenylquinolin-5-ol 6.1 as solid. Analysis: HPLC-MS: Rt=1.18 min (method D), M+H=240.

Synthesis of
7-(3,4,5-trimethoxyphenyl)quinolin-5-ol (6.2) for
Examples 2, 3, 4, 5, 9, 18, 23

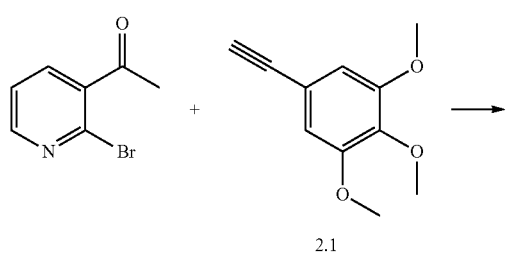

2.1

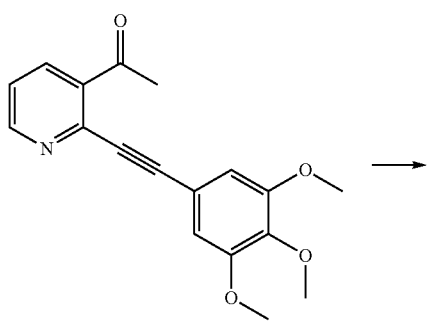

Step 1 (=Reaction 1):

100 mg 3-Acetyl-2-bromopyridine, 140 mg 5-ethynyl-1,2,3-trimethoxybenzene 2.1, 101 µL triethylamine, 17 mg triphenylphosphinpalladium(II) chlorid, 1 mg Cu(I)I were suspended in 4 mL THF under argon atmosphere and stirred for 1 h at 25° C. The mixture was diluted with DCM and extracted with diluted aq. NH$_3$ and saturated NH$_4$Cl solution. The organic phase was concentrated and the mixture separated via FCC (10 g SiO$_2$, Cyclohexane→cyclohexane/ethylacetate 70:30) to yield 90 mg 1-(2-(3,4,5-trimethoxyphenylethynyl)pyridin-3-yl)ethanone as solid. Analysis: HPLC-MS: Rt=1.21 min (method E) M+H=312.

Step 2 (=Reaction 2):

90 mg 1-(2-(3,4,5-trimethoxyphenylethynyl)pyridin-3-yl)ethanone were suspended in 750 µL 1N sulfuric acid and 4 mg mercuric chloride and stirred for 1 h 45 minutes at 60° C. Then 2 mL of NaOH was added and the mixture stirred for additional 1 h at 25° C. Water was added and a neutral pH was adjusted with KHSO$_4$ solution. The precipitate was filtered off and washed with water and dried to yield 80 mg 7-(3,4,5-trimethoxyphenyl)quinolin-5-ol 6.2 as solid. Analysis: HPLC-MS: Rt=1.18 min (method D), M+H=330.

7-(pyridin-2-yl)quinolin-5-ol (6.3) for Example 6

7-(pyridin-2-yl)quinolin-5-ol (6.3) for Example 6 was synthesized in analogy to 6.2.

Yield: 4% (over two steps) as solid. Analysis: HPLC-MS: Rt=0.78 min (method E), M+H=223.

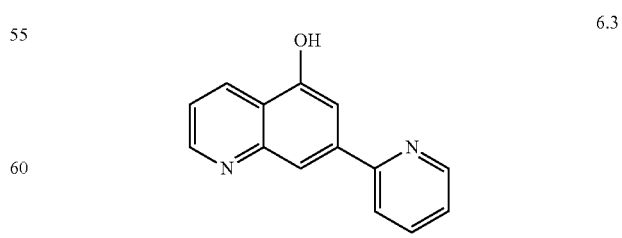

6.3

Alternatively 6.3 can be synthesized as described in: Godet, Thomas; Belmont, Philippe Synlett, 2008, 16, 2513-2517

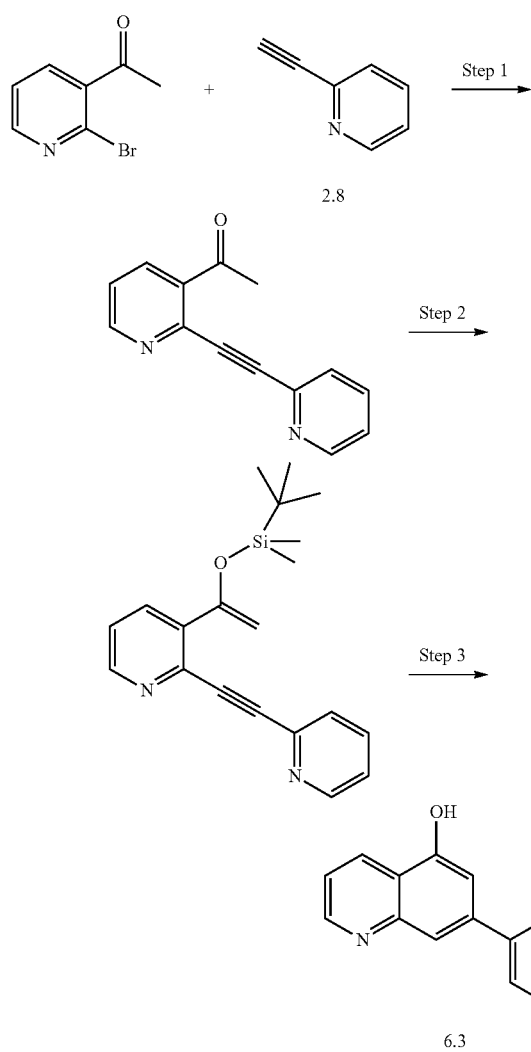

Step 1 (=Reaction 1):

750 mg 3-Acetyl-2-bromopyridin, 550 µL 2-ethynyl-pyridine, 765 µL triethylamin, 255 mg triphenylphosphinpalladium(II) chlorid, 17 mg Cu(I)I were suspended in 10 mL DMF under argon atmosphere and stirred for 2 h at 25° C. The mixture was diluted with DCM and extracted with diluted aq. $NH_3$ and saturated $NH_4Cl$ solution. The organic phase was concentrated and the mixture separated via FCC (100 g $SiO_2$, cyclohexane→cyclohexane/ethylacetate 35:65) to yield 455 mg 1-(2-(pyridin-2-ylethynyl)pyridin-3-yl)ethanone as solid. Analysis: HPLC-MS: Rt=0.88 min (method E) M+H=223.

Step 2 (=Reaction 4):

455 mg 1-(2-(pyridin-2-ylethynyl)pyridin-3-yl)ethanone was dissolved in 10 mL DCM, 1.069 mL of DIPEA was added, the solution was cooled 0° C. and 1.42 mL of tert-butyldimethylsilyltrifluormethansulfonate added slowly. The mixture was stirred 30 min at 0° C., warmed to 25° C. and filtrated over a plug of silica (cyclohexane/ethylacetate 1:1+ small amount of TEA) to yield 1.025 g 3-(1-(tert-butyldimethylsilyloxy)vinyl)-2-(pyridin-2-ylethynyl)pyridine as oil. Analysis: HPLC-MS: Rt=1.59 min (method E) m+H=337.

Step 3 (=Reaction 5):

1.025 g 3-(1-(tert-butyldimethylsilyloxy)vinyl)-2-(pyridin-2-ylethynyl)pyridine was dissolved in 100 mL dimethoxyethane and 126 mg of trifluormethanesulfonic acid silver salt added and stirred 7 h at 70° C. The mixture is diluted with DCM and extracted with saturated $NaHCO_3$ solution (3×). The organic phase was dried ($MgSO_4$) and concentrated in vacuo. The residual mixture was dissolved in 10 mL THF, 1.2 mL of tertbutylammoniumfluoride in THF (1N) was added and the mixture stirred for 2 h at 25° C. The mixture was diluted with DCM and extracted with water (1×) and the organic phase concentrated in vacuo and purified via FCC (100 g $SiO_2$, DCM→DCM 93:7) to yield 165 mg of 7-(pyridin-2-yl)quinolin-5-ol 6.3 as solid. HPLC-MS: Rt=0.78 min (method E), M+H=223.

Synthesis of 7-(3,4-dimethoxyphenyl)quinolin-5-ol (6.4) for Examples 7, 8, 12

7-(3,4-dimethoxyphenyl)quinolin-5-ol 6.4 for Example 7, 8, 12 was synthesized in analogy to 6.2 Yield: 76% (over two steps) as solid. Analysis: HPLC-MS: Rt=0.96 min (method E), M+H=300.

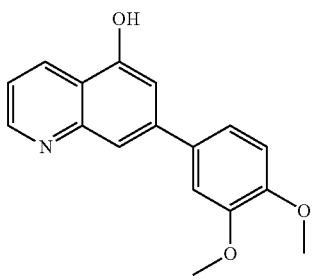

Synthesis of 7-(3,5-Difluoro-4-methoxy-phenyl)-quinolin-5-ol (6.5) for Examples 14, 15, 17 and 38

7-(3,5-Difluoro-4-methoxy-phenyl)-quinolin-5-ol 6.5 for Example 14, 15, 17 and 38 was synthesized in analogy to 6.3 Yield: 19% (over two steps) as brown solid. Analysis: HPLC-MS: Rt=1.13 (method M), M+H=288.

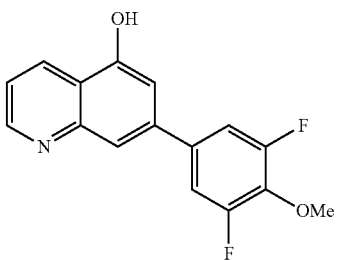

$^1$H NMR (500 MHz, METHANOL-d4) δ ppm 4.03 (3H, s), 7.13 (1H, d, J=1.68 Hz), 7.36-7.43 (2H, m), 7.48 (1H, dd, J=8.39, 4.43 Hz), 7.68 (1H, s), 8.64-8.67 (1H, m), 8.83 (1H, dd, J=4.42, 1.68 Hz)

7-(4-Isopropoxy-3-methoxy-phenyl)-quinolin-5-ol (6.6) for Examples 10, 11, 13 and 16

7-(4-Isopropoxy-3-methoxy-phenyl)-quinolin-5-ol 6.6 for Examples 10, 11, 13 and 16 was synthesized in analogy to 6.3. Yield: 27% (over two steps) as brown solid. Analysis: HPLC-MS: Rt=1.54 min (method B), M+H=310.

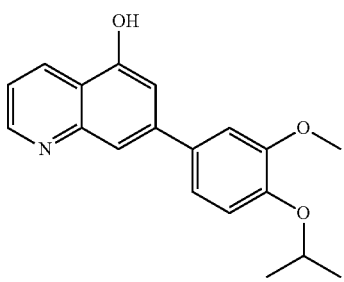

7-(6-methoxypyridin-3-yl)quinolin-5-ol (6.7) for
Examples 20, 21

7-(6-methoxypyridin-3-yl)quinolin-5-ol for Example 20, 21 was synthesized in analogy to 6.2. Yield: 73% (over two steps) as solid. Analysis: HPLC-MS: Rt=0.98 min (method M), M+H=253.

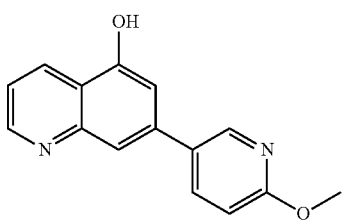

[2,7']Biquinolinyl-5'-ol (6.8) for Example 34

[2,7']Biquinolinyl-5'-ol (6.8) for Example 34 was synthesized in analogy to 6.3 using the method of Godet, Thomas; Belmont, Philippe Synlett, 2008, 16, 2513-2517.
Yield: 43% (over three steps) as brown solid. Analysis: HPLC-MS: Rt=1.02 min (method M), M+H=272.

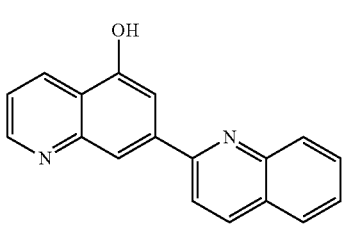

4.3. Synthesis of the Patent Examples of Formula 7 and Formula 1

Synthesis of (R)-4-((R)-1-(7-phenylquinolin-5-yloxy)ethyl)pyrrolidin-2-one (Example 1)

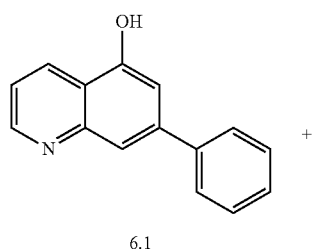

+

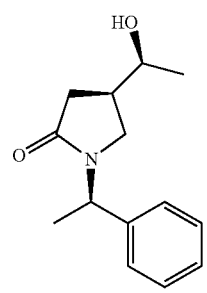

3.2

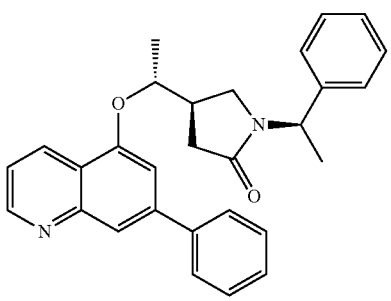

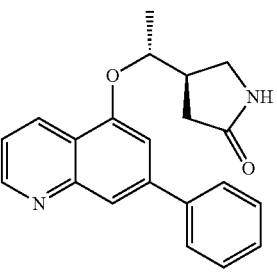

Example 1

30 mg of 7-Phenylquinolin-5-ol, 32.5 mg of (R)-4-((S)-1-hydroxyethyl)-1-((R)-1-phenylethyl)pyrrolidin-2-one and 150 mg of triphenylphosphine were dissolved in 3 mL of DCM. 125.5 mg of Di-tertbutyl-azodicarboxylate (DBAD) was added and the mixture stirred for 21 h at room temperature. The mixture was diluted with DCM and extracted with 1N NaOH and water. The organic phase was concentrated in vacuo and purified via flash column chromatography (FCC) (20 SiO$_2$; cyclohexane→cyclohexane:ethylacetate:MeOH 58:40:2). Product containing fractions were concentrated, dissolved in 2 mL of trifluoroacetic acid (TFA) and heated 45 min at 150° C. in the microwave. The mixture was purified with rpHPLC (XbridgeC18, MeOH/water, TFA) to yield after lyophilisation 8 mg of Example 1 as solid. Analysis: HPLC-MS: Rt=1.21 min (method D), M+H=333.

Synthesis of (R)-4-((R)-1-(7-(3,4,5-trimethoxyphenyl)quinolin-5-yloxy)ethyl)pyrrolidin-2-one (Example 2)

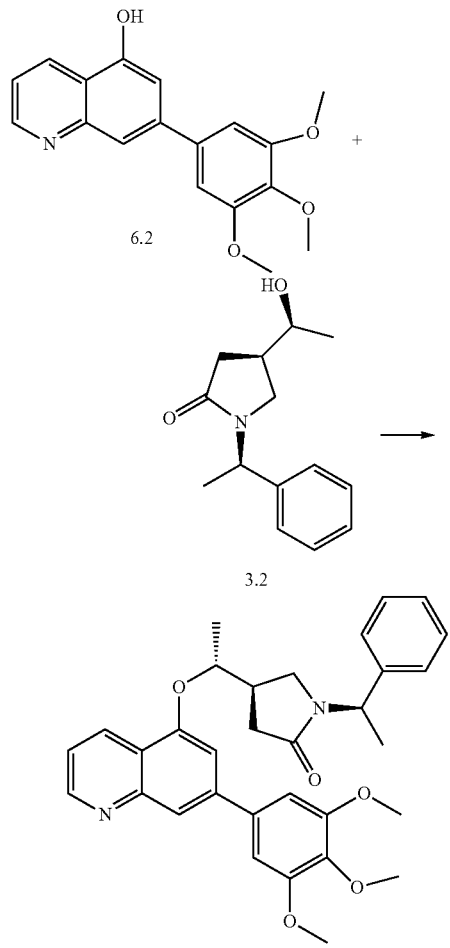

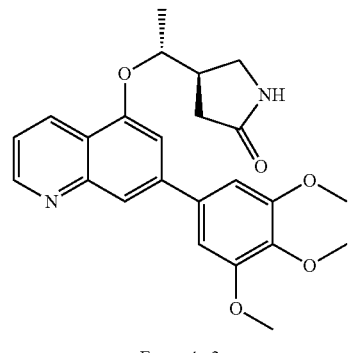

Example 2

80 mg of 7-(3,4,5-Trimethoxyphenyl)quinolin-5-ol, 62 mg of (R)-4-((S)-1-hydroxyethyl)-1-((R)-1-phenylethyl)pyrrolidin-2-one and 142 mg of triphenylphosphine was dissolved in 5 mL of DCM. 125.5 mg of DBAD was added and the mixture stirred for 6 h at room temperature. The mixture was diluted with DCM and extracted with 1N NaOH and water. The organic phase was concentrated in vacuo and purified via flash chromatography (10 $SiO_2$; cyclohexane→cyclohexane:ethylacetate:MeOH 58:40:2). Product containing fractions were concentrated, dissolved in 1.5 mL of TFA and heated 75 min at 150° C. in the microwave. The mixture was purified with HPLC (XbridgeC18, MeOH/water, TFA) to yield after lyophilisation 21 mg of Example 2 as solid.

Analysis: HPLC-MS: Rt=1.20 min (method D), M+H=423.

$^1$H-NMR (400 MHz, DMSO-d6): δ=9.05 (1H, d), 8.75 (1H, d), 7.88 (1H,$), 7.68 (1H, dd), 7.60 (1H, s), 7.45 (1H, s), 7.10 (2H,$), 5.05 (1H, m), 3.95 (6H, s), 3.77 (3H,$), 3.40 (1H, t), 3.25-3.05 (1H, m), 2.85 (1H, m), 2.45-2.22 (2H, m), 1.35 (3H, d) ppm.

The following Examples were synthesized in analogous manner to Examples 1 and 2.

| Example | Quinoline (corresponding to formula 6) | Alcohol for Conversion (corresponding to formula 3) | Yield | Analysis |
|---|---|---|---|---|
| Example 7 (R)-4-((7-(3,4-dimethoxyphenyl)quinolin-5-yloxy)methyl)pyrrolidin-2-one | 7-(3,4-dimethoxy-phenyl)quinolin-5-ol | (R)-4-(hydroxymethyl)-1-((R)-1-phenylethyl)pyrrolidin-2-one | 58 mg (24%) | HPLC-MS: Rt = 1.22 min (method XBM), M + H = 379 |
| Example 9 (R)-4-((7-(3,4,5-trimethoxyphenyl)quinolin-5-yloxy)methyl)pyrrolidin-2-one | 7-(3,4,5-trimethoxy-phenyl)quinolin-5-ol | R)-4-(hydroxymethyl)-1-((R)-1-phenylethyl)pyrrolidin-2-one | 25 mg (11%) | HPLC-MS: Rt = 1.24 min (method XBM), M + H = 409 |
| Example 14 (R)-4-{(R)-1-[7-(3,5-Difluoro-4-methoxy-phenyl)-quinolin-5-yloxy]-ethyl}-pyrrolidin-2-one | 7-(3,5-Difluoro-4-methoxy-phenyl)-quinolin-5-ol | (R)-4-((S)-1-hydroxyethyl)-1-((R)-1-phenylethyl)pyrrolidin-2-one | 15 mg (11%) | HPLC-MS: Rt = 3.49 min (method A), M + H = 399 |
| Example 17 (R)-4-[7-(3,5-Difluoro-4-methoxy-phenyl)-quinolin-5- | 7-(3,5-Difluoro-4-methoxy-phenyl)-quinolin-5-ol | (R)-4-Hydroxymethyl-pyrrolidin-2-one | 6 mg (4%) | HPLC-MS: Rt = 3.40 min (method A), |

-continued

| Example | Quinoline (corresponding to formula 6) | Alcohol for Conversion (corresponding to formula 3) | Yield | Analysis |
|---|---|---|---|---|
| yloxymethyl]-pyrrolidin-2-one | | | | M + H = 385 |
| Example 20 (R)-5-[7-(6-Methoxy-pyridin-3-yl)-quinolin-5-yloxymethyl]-oxazolidin-2-one | 7-(6-Methoxy-pyridin-3-yl)-quinolin-5-ol | (R)-5-Hydroxymethyl-3-((R)-1-phenyl-ethyl)-oxazolidin-2-one | 34 mg (15%) | HPLC-MS: Rt = 2.78 min (method A), M + H = 352 |

Synthesis of 5-methoxy-7-(3,4,5-trimethoxyphenyl)quinoline (Example 3)

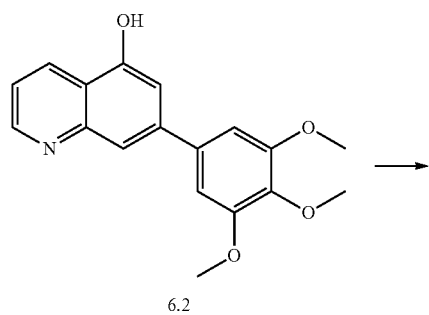

6.2

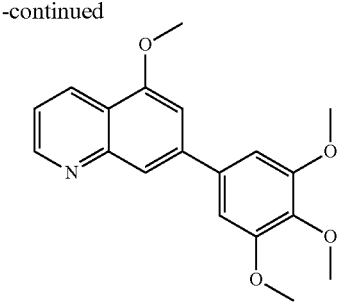

Example 3

100 mg of 7-(3,4,5-Trimethoxyphenyl)quinolin-5-ol, 42 µL of MeOH and 480 mg of triphenylphosphine was dissolved in 5 mL of DCM. 435 mg of DBAD was added and the mixture stirred for 3 days at room temperature. The mixture was diluted with DCM and extracted with 1N NaOH and water. The organic phase was concentrated in vacuo and purified with HPLC (XbridgeC18, MeOH/water, TFA) to yield after lyophilisation 12 mg of Example 3 as solid.

Analysis: HPLC-MS: Rt=1.11 min (method E), M+H=326.

The following Examples were synthesized in analogous manner to Example 3.

| Example | Quinoline (corresponding to formula 6) | Alcohol for Conversion (corresponding to formula 3) | Yield | Analysis |
|---|---|---|---|---|
| Example 4 5-ethoxy-7-(3,4,5-trimethoxyphenyl)quinoline | 7-(3,4,5-trimethoxyphenyl)quinolin-5-ol | EtOH | 15 mg (15%) | HPLC-MS: Rt = 1.20 min (method E), M + H = 340 |
| Example 5 5-((7-(3,4,5-trimethoxyphenyl)quinolin-5-yloxy)methyl)piperidin-2-one | 7-(3,4,5-trimethoxyphenyl)quinolin-5-ol | 5-(Hydroxymethyl)piperidine-2-one | 7 mg (6%) as white solid | HPLC-MS: Rt = 1.03 min (method E), M + H = 423 |
| Example 12 (R)-5-((7-(3,4-dimethoxyphenyl)-quinolin-5-yloxy)methyl)-oxazolidin-2-one | 7-(3,4-dimethoxyphenyl)quinolin-5-ol | (R)-5-(hydroxymethyl)oxazolidin-2-one | 16 mg (7%) | HPLC-MS: Rt = 0.94 min (method E), M + H = 381 |
| Example 18 (R)-5-((7-(3,4,5-trimethoxyphenyl)-quinolin5yloxy)methyl)-oxazolidin-2-one | 7-(3,4,5-trimethoxyphenyl)quinolin-5-ol | (R)-5-(hydroxymethyl)oxazolidin-2-one | 6 mg (5%) | HPLC-MS: Rt = 1.02 min (method E), M + H = 411 |
| Example 38 {1-[7-(3,4,5-Trimethoxy-phenyl)-quinolin-5yloxy methyl]-cyclopropyl}acetonitrile | 7-(3,4,5-Trimethoxy-phenyl)-quinolin-5-ol | (1-Hydroxymethyl-cyclopropyl)-acetonitrile | 4 mg (1%) | HPLC-MS: Rt = 3.62 (method A), M + H = 405 |

Synthesis of (R)-4-((R)-1-(7-(pyridin-2-yl)quinolin-5-yloxy)ethyl)pyrrolidin-2-one (Example 6)

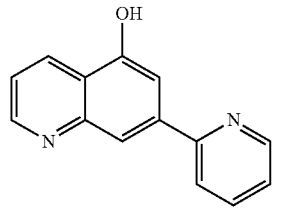

6.3

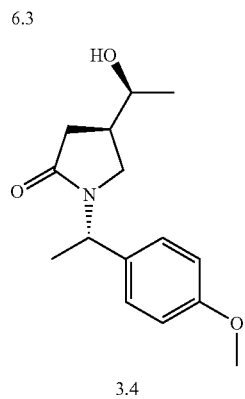

3.4

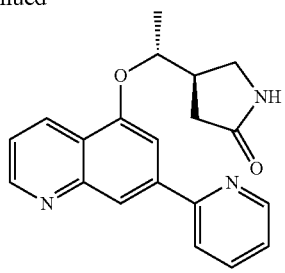

Example 6

20 mg of 7-(Pyridin-2-yl)quinolin-5-ol, 30 mg of ((R)-4-((S)-1-hydroxyethyl)-1-((S)-1-(4-methoxyphenyl)ethyl)pyrrolidin-2-one and 50 mg of triphenylphosphin was dissolved in 2 mL of DCM. 45 mg of DBAD was added and the mixture stirred for 14 h at room temperature. The mixture was diluted with DCM and extracted with 1N NaOH and water. The organic phase was concentrated in vacuo and dissolved in 0.5 mL of TFA and heated 30 min at 90° C. in the microwave. The mixture was purified with HPLC (XbridgeC18, MeOH/water, TFA) to yield after lyophilisation 21 mg of Example 6 as solid.

Analysis: HPLC-MS: Rt=0.9 min (method E), M+H=334.

The following Examples were synthesized in analogous manner to Example 6.

| Example | Quinoline (corresponding to formula 6) | Alcohol for Conversion (corresponding to formula 3) | Yield | Analysis |
|---|---|---|---|---|
| Example 8 (R)-4-((R)-1-(7-(3,4-dimethoxyphenyl)-quinolin-5-yloxy)-ethyl)pyrrolidin-2-one | 7-(3,4-dimethoxyphenyl)quinolin-5-ol | (R)-4-((S)-1-hydroxyethyl)-1-((S)-1-(4-methoxyphenyl)ethyl)-pyrrolidin-2-one | 23 mg (9%) | HPLC-MS: Rt = 1.26 min (method XBM), M + H = 393 |
| Example 34 R)-4-[(R)-1-([2,7']Biquinolinyl-5'-yloxy)-ethyl]-pyrrolidin-2-one | [2,7']Bi-quinolinyl-5'-ol | (R)-4-((S)-1-hydroxy-ethyl)-1-((S)-1-(4-methoxyphenyl)ethyl)-pyrrolidin-2-one | 6 mg (1.5%) | HPLC-MS: Rt = 3.28 min (method A), M + H = 384 |

Synthesis of (R)-5-[7-(4-Hydroxy-3-methoxy-phenyl)-quinolin-5-yloxymethyl]-oxazolidin-2-one (Example 13)

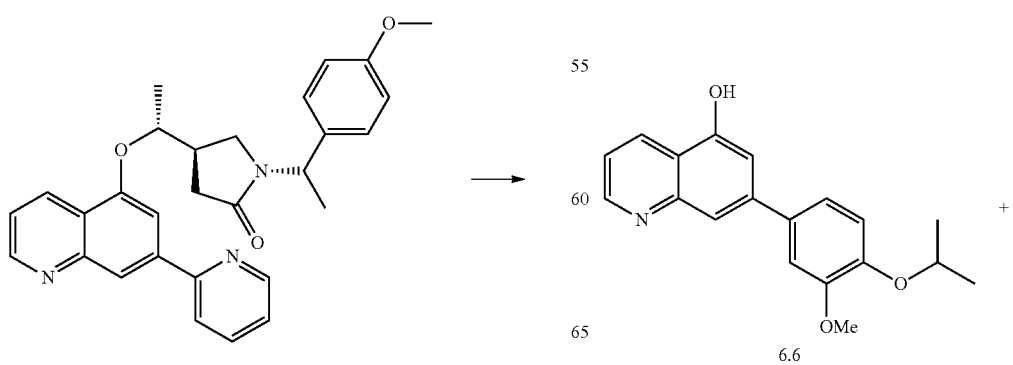

6.6

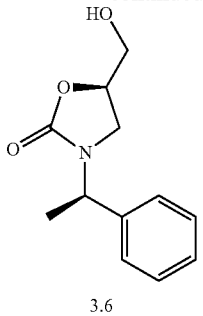

3.6

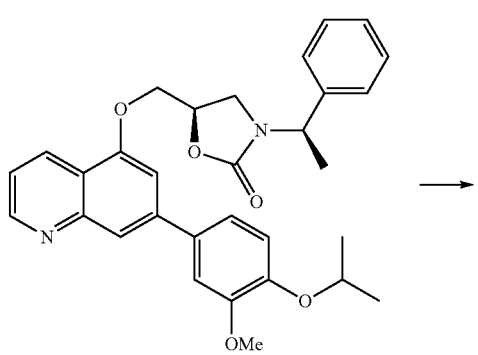

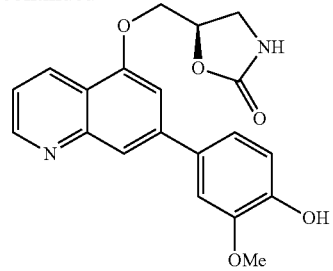

Example 13

A solution of 0.085 ml of diisopropylazodicarboxylate (DIAD) in THF (2 ml) was added to a mixture of 150 mg of 7-(4-Isopropoxy-3-methoxy-phenyl)-quinolin-5-ol, 128 mg of (R)-5-Hydroxymethyl-3-((R)-1-phenyl-ethyl)-oxazolidin-2-one and 161 mg of PS-triphenylphosphine in THF (15 mL) and stirred for 14 h at room temperature. A further 161 mg of PS-triphenylphosphine and 0.085 ml of DIAD were added and stirring continued for a further 4 hr. The mixture was filtered then diluted with EtOAc and extracted with water. The organic phase was concentrated in vacuo and dissolved in 1 mL of TFA and heated 30 min at 150° C. in the microwave. The mixture was purified over $SiO_2$ eluting with 1-10% 7N $NH_3$/MeOH:DCM to afford 17 mg of Example 13 as a solid.

Analysis: HPLC-MS: Rt=2.61 (method A), M+H=367

The following Examples were synthesized in analogous manner to Example 13.

| Example | Quinoline (corresponding to formula 6) | Alcohol (corresponding to formula 3) | Yield | Analysis |
|---|---|---|---|---|
| Example 10 (R)-4-{(R)-1-[7-(4-Isopropoxy-3-methoxy-phenyl)-quinolin-5-yloxy]-ethyl}-pyrrolidin-2-one | 7-(4-Isopropoxy-3-methoxy-phenyl)-quinolin-5-ol | (1S,4R)-1-[1-(4-Methoxy-phenyl)-ethyl]-4-{(R)-1-[7-(6-methoxy-pyridin-3-yl)-quinolin-5-yloxy]-ethyl}-pyrrolidin-2-one | 32 mg (64%) TFA treatment for 30 mins @ 50° C. | HPLC-MS: Rt = 3.23 min (method A), M + H = 421 |
| Example 11 (R)-4-{(R)-1-[7-(4-Hydroxy-3-methoxy-phenyl)-quinolin-5-yloxy]-ethyl}-pyrrolidin-2-one | 7-(4-Isopropoxy-3-methoxy-phenyl)-quinolin-5-ol | (1S,4R)-1-[1-(4-Methoxy-phenyl)-ethyl]-4-{(R)-1-[7-(6-methoxy-pyridin-3-yl)-quinolin-5-yloxy]-ethyl}-pyrrolidin-2-one | 100 mg (36%) TFA treatment for 60 mins @ 110° C. | HPLC-MS: Rt = 2.73 min (method A), M + H = 379 |
| Example 15 (R)-5-[7-(3,5-Difluoro-4-methoxy-phenyl)-quinolin-5-yloxymethyl]-oxazolidin-2-one | 7-(3,5-Difluoro-4-methoxy-phenyl)-quinolin-5-ol | (R)-5-Hydroxymethyl-3-((R)-1-phenyl-ethyl)-oxazolidin-2-one | 28 mg (18%) | HPLC-MS: Rt = 3.38 min (method A), M + H = 387 |
| Example 19 (R)-4-[7-(4-Hydroxy-3-methoxy-phenyl)- | 7-(4-Isopropoxy-3-methoxy-phenyl)-quinolin-5-ol | (R)-4-(hydroxymethyl)-1-((R)-1-phenylethyl)- | 23 mg (12%) | HPLC-MS: Rt = 2.65 min (method A), M + H = 365 |

| Example | Quinoline (corresponding to formula 6) | Alcohol (corresponding to formula 3) | Yield | Analysis |
|---|---|---|---|---|
| quinolin-5-yloxymethyl]-pyrrolidin-2-one | | pyrrolidine-2-one | | |

Synthesis of (R)-5-((7-(4-isopropoxy-3-methoxyphenyl)quinolin-5-yloxy)methyl) oxazolidin-2-one (Example 16)

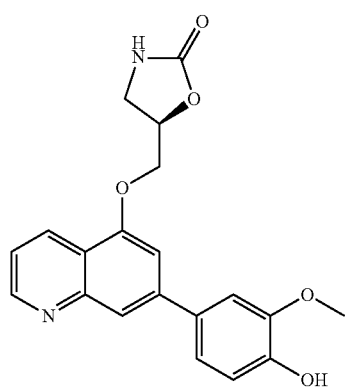

Example 13

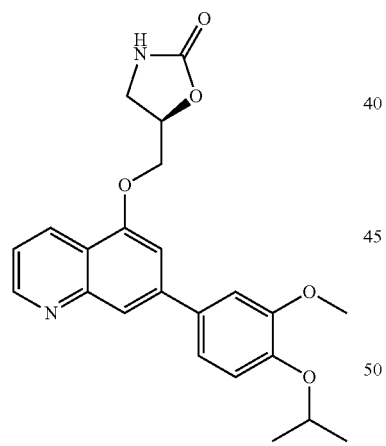

Example 16

A mixture of 59 mg (R)-5-[7-(4-hydroxy-3-methoxy-phenyl)-quinolin-5-yloxymethyl]-oxazolidin-2-one (Example 13), 19.3 µl 2-iodopropane and 44 mg potassium carbonate in DMF (10 ml) was stirred at 50° C. for 16 hours. The mixture was poured into EtOAc and washed with water then brine and dried over $Na_2SO_4$. Purification by FCC over $SiO_2$, eluting with EtOAc-MeOH from 100:0 to 95:5 yielded 56 mg (85%) of (R)-5-[7-(4-Isopropoxy-3-methoxy-phenyl)-quinolin-5-yloxymethyl]-oxazolidin-2-one (Example 16) as an oily residue.

Analysis HPLC-MS: Rt=1.09 min (method M), M+H=409.

Synthesis of (R)-4-{(R)-1-[7-(6-Methoxy-pyridin-3-yl)-quinolin-5-yloxy]-ethyl}-pyrrolidin-2-one (Example 21)

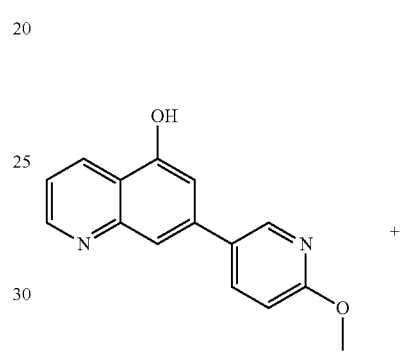

6.7

3.4

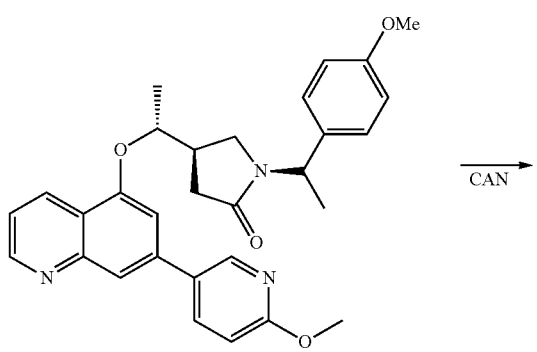

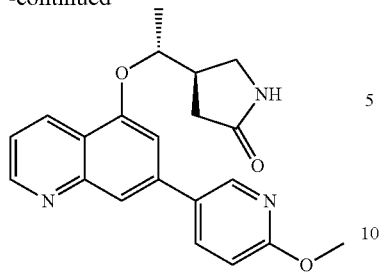

Example 21

1020 mg of 7-(6-Methoxy-pyridin-3-yl)-quinolin-5-ol 6.7, 1171 mg of (R)-4-((S)-1-Hydroxy-ethyl)-1-[(R)-1-(4-methoxy-phenyl)-ethyl]-pyrrolidin-2-one 3.4 and 1590 mg of triphenylphosphine were dissolved in 20 mL of THF. 1.19 ml of DIAD- was added and the mixture stirred for 24 h at room temperature. The mixture was concentrated in vacuo and purified over $SiO_2$ (1-5% MeOH:DCM) to give 1300 mg of (1S,4R)-1-[1-(4-Methoxy-phenyl)-ethyl]-4-{(R)-1-[7-(6-methoxy-pyridin-3-yl)-quinolin-5-yloxy]-ethyl}-pyrrolidin-2-one. 727 mg of this product was dissolved in acetonitrile (7 ml) at 0° C. and a solution of 2339 mg ceric ammonium nitrate (CAN) in water (7 ml) was added. The mixture was stirred for 6 hours, then poured onto sat $NaHCO_3$ (150 ml), diluted with water, then extracted with DCM. Purification over a plug of silica using 1-3% 2N $MeOH/NH_3$:DCM afforded 137 mg of required product as a pale brown foam in 26% yield.

Analysis: HPLC-MS: Rt=2.94 min (method A), M+H=364

Synthesis of
2-((7-bromoquinolin-5-yloxy)methyl)nicotinamide
(Example 22)

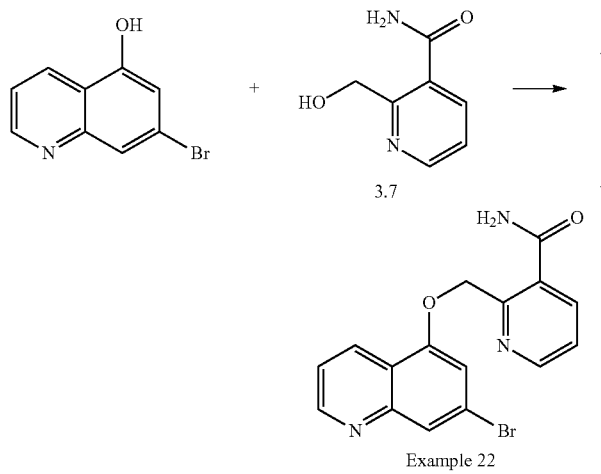

Example 22

100 mg 7-Bromo-quinolin-5-ol, 77.5 mg of 2-(hydroxymethyl)nicotinamide 3.7, 233.5 mg of triphenylphosphine and 205 mg of Di-tertbutyl-azodicarboxylate (DBAD) were dissolved in 2.5 mL of DCM and 7.5 mL of THF under Argon at room temperature. After 14 h the precipitate was collected and dried. The mother liquor was concentrated and the formed precipitate again collected to yield 72 mg Example 22.

Analysis: HPLC-MS: Rt=0.48 min (method X001_002), M+H=358/360.

$^1$H-NMR (400 MHz, DMSO-d6): δ=8.91 (1H, d), 8.65 (1H, d), 8.48 (1H, d), 8.05 (1H, s), 7.95 (1H, d), 7.80 (1H, s), 6.65-7.50 (3H, m), 7.31 (1H,$), 5.58 (2H,$) ppm.

Synthesis of 5,5-Dimethyl-1-[7-(3,4,5-trimethoxyphenyl)-quinolin-5-yloxymethyl]-imidazolidine-2,4-dione (Example 23)

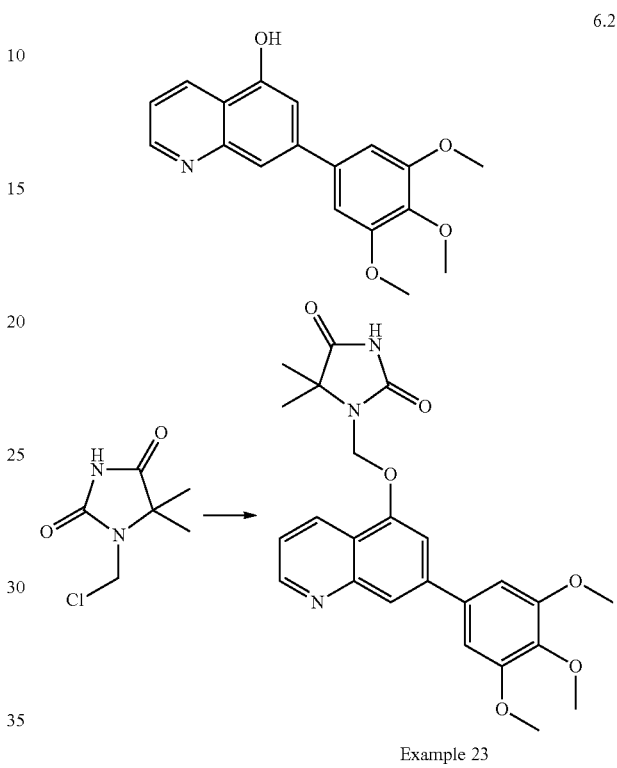

Example 23

150 mg 7-(3,4,5-Trimethoxy-phenyl)-quinolin-4-ol (6.2), 65 mg 1-chloromethyl-5,5-dimethyl-imidazolidine-2,4-dione (3.7) and 51 mg potassium carbonate were dissolved in 1.5 ml DMF and heated at 70° C. for 2 hrs. Water was added and the mixture extracted with EtOAc. The combined organic extracts were washed with brine, dried over sodium sulphate, filtered and concentrated in vacuo.

Purification by HPLC afforded 33 mg 5,5-Dimethyl-1-[7-(3,4,5-trimethoxy-phenyl)-quinolin-5-yloxymethyl]-imidazolidine-2,4-dione in 21% yield.

HPLC-MS: Rt=3.46 min (method A), M+H=452.

Synthesis of 2-((7-(4-(methylsulfonyl)phenyl)quinolin-5-yloxy)methyl)nicotinamide according to Scheme 2 (Example 24)

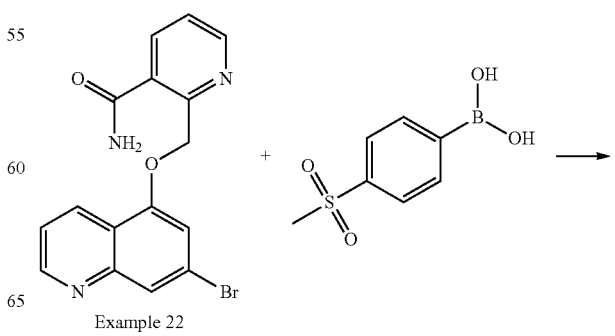

Example 22

-continued

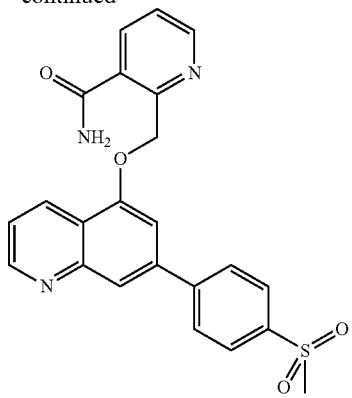

Example 24

50 mg Example 22, 33.5 mg 4-methanesulphonyl)benzeneboronic acid, 17.5 mg tetrakis-(triphenylphosphin)-palladium(0), 140 μL 2N aqueous sodium carbonate and 0.5 mL dioxan were heated in the microwave (MW) for 15 min at 140° C. The mixture was purified with HPLC (XbridgeC18, MeOH/water, TFA) and the desired fractions lyophilized to yield 60 mg (75%) of Example 24 as yellow solid.

HPLC-MS: Rt=0.49 min (method X001_002), M+H=434.

$^{1}$H-NMR (400 MHz, DMSO-d6): δ=9.05 (1H, d), 8.70-8.64 (2H, m), 8.15 (2H, d), 8.10-8.02 (3H, m), 8.0-7.9 (2H, m), 7.65-7.55 (3H, m), 7.52 (1H, dd), 5.7 (2H, s), 3.30 (3H, s) ppm.

The following Examples were synthesized in analogous manner to Example 24.

| Example | Boronic acid/ester (corresponding to formula 4) | Yield | Analysis |
|---|---|---|---|
| Example 25 2-((7-(3,4-dimethoxyphenyl)quinolin-5-yloxy)-methyl)nicotinamide | 3,4-dimethoxyphenyl-boronic acid | 30 mg (48%) | HPLC-MS: Rt = 0.65 min (method X001_002), M + H = 416 |
| Example 26 2-((7-(6-acetamido-pyridin-3-yl)quinolin-5-yloxy)methyl)-nicotinamide | N-(5-(4,4,5,5-tetramethyl-1,3,2-dioxaborolan-2-yl)pyridin-2-yl)acetamide | 14 mg (22%) | HPLC-MS: Rt = 0.57 min (method X001_002), M + H = 414 |
| Example 32 2-((7-(3-fluoro-4-(methylsulfonyl)phenyl)quinolin-5-yloxy)methyl)nicotinamide | 3-fluoro-4-(methyl-sulfonyl)phenylboronic acid | 33 mg (41%) | HPLC-MS: Rt = 0.60 min (method X001_002), M + H = 452 |
| Example 35 2-((7-(3-methyl-4-(methylsulfonyl)phenyl)quinolin-5-yloxy)methyl)nicotinamide | 4,4,5,5-tetramethyl-2-(3-methyl-4-(methylsulfonyl)phenyl)-1,3,2-dioxaborolane | 35 mg (47%) | HPLC-MS: Rt = 0.51 min (method X001_003), M + H = 448 |
| Example 36 2-((7-(4-(trifluoromethyl sulfonyl)phenyl)quinolin-5-yloxy)methyl)nicotinamide | 4,4,5,5-tetramethyl-2-(4-(trifluoromethyl-sulfonyl)phenyl)-1,3,2-dioxaborolane | 25 mg (37%) | HPLC-MS: Rt = 0.70 min (method X001_003), M + H = 488 |
| Example 39 2-((7-(1H-benzo[d]imidazol-5-yl)quinolin-5-yloxy)methyl)nicotinamide | 5-(4,4,5,5-tetramethyl-1,3,2-dioxaborolan-2-yl)-1H-benzo[d]imidazole | 25 mg (59%) | HPLC-MS: Rt = 0.39 min (method X001_003), M + H = 396 $^{1}$H-NMR (400 MHz, DMSO-d6): δ = 9.45 (1H, s), 9.0 (1H, s), 8.7-8.55 (2H, m), 8.25 (1H, s), 8.10-7.93 (6H, m), 7.65-7.55 (3H, m), 7.52 (1H, dd), 5.75 (2H, s) ppm. |
| Example 40 2-((7-(4-(morpholinomethyl)phenyl)quinolin-5-yloxy)methyl)nicotinamide | 4-(morpholinomethyl)phenylboronic acid | 34 mg (71%) | HPLC-MS: Rt = 0.39 min (method X001_003), M + H = 455 |
| Example 44 2-((7-(1-methyl-1H-indazol-6-yl)quinolin-5-yloxy)methyl)nicotinamide | 1-methyl-1H-indazol-6-ylboronic acid | 25 mg (57%) | HPLC-MS: Rt = 0.55 min (method X001_003), M + H = 410 |
| Example 45 2-((7-(6-morpholino-pyridin-3-yl)quinolin-5-yloxy)methyl)nicotinamide | 4-(5-(4,4,5,5-tetramethyl-1,3,2-dioxaborolan-2-yl)pyridin-2-yl)morpholine | 38 mg (82%) | HPLC-MS: Rt = 0.46 min (method X001_002), M + H = 442 |

-continued

| Example | Boronic acid/ester (corresponding to formula 4) | Yield | Analysis |
|---|---|---|---|
| Example 46 2-((7-(1-methyl-1H-pyrazol-4-yl)quinolin-5-yloxy)methyl)nicotinAmide | 1-methyl-4-(4,4,5,5-tetramethyl-1,3,2-dioxaborolan-2-yl)-1H-pyrazole | 32 mg (81%) | HPLC-MS: Rt = 0.46 min (method X001_002), M + H = 360 |
| Example 50 2-((7-(4-((N-ethylacetamido)methyl)phenyl)quinolin-5-yloxy)methyl)nicotinamide | N-ethyl-N-(4-(4,4,5,5-tetramethyl-1,3,2-dioxaborolan-2-yl)benzyl)acetamide | 18 mg (36%) | HPLC-MS: Rt = 0.60 min (method X001_002), M + H = 455 |
| Example 52 2-((7-(1-oxo-1,2,3,4-tetrahydroisoquinolin-6-yl)quinolin-5-yloxy)methyl)nicotinamide | 6-(4,4,5,5-tetramethyl-1,3,2-dioxaborolan-2-yl)-3,4-dihydroiso-quinolin-1(2H)-one | 14 mg (39%) | HPLC-MS: Rt = 0.51 min (method X001_002), M + H = 425 |
| Example 54 6-(5-((R)-1-((R)-5-oxopyrrolidin-3-yl)ethoxy)quinolin-7-yl)-3,4-dihydroiso-quinolin-1(2H)-one | 6-(4,4,5,5-tetramethyl-1,3,2-dioxaborolan-2-yl)-3,4-dihydroiso-quinolin-1(2H)-one | 6 mg (15%) | HPLC-MS: Rt = 0.60 min (method X001_002), M + H = 467 |
| Example 57 2-((7-(6-methoxypyridin-3-yl)quinolin-5-yloxy)methyl)nicotinamide | 6-methoxypyridin-3-ylboronic acid | 38 mg (91%) | HPLC-MS: Rt = 0.57 min (method X001_002), M + H = 387 |
| Example 58 2-((7-(4-((N-methylacetamido)methyl)phenyl)quinolin-5-yloxy)methyl)nicotinamide | N-methyl-N-(4-(4,4,5,5-tetramethyl-1,3,2-dioxaborolan-2-yl)benzyl)acetamide | 10 mg (27%) | HPLC-MS: Rt = 0.55 min (method X001_002), M + H = 441 |
| Example 59 5-(5-((3-carbamoylpyridin-2-yl)methoxy)quinolin-7-yl)-N-methylpicolin-amide | N-methyl-5-(4,4,5,5-tetramethyl-1,3,2-dioxaborolan-2-yl)picolinamide | 37 mg (84%) | HPLC-MS: Rt = 0.51 min (method X001_002), M + H = 414 |
| Example 60 2-((7-(2-methyl-imidazo[1,2-a]pyridin-6-yl)quinolin-5-yloxy)methyl)nicotinamide | 2-methyl-6-(4,4,5,5-tetramethyl-1,3,2-dioxaborolan-2-yl)imidazo[1,2-a]pyridine | 28 mg (64%) | HPLC-MS: Rt = 0.50 min (method X001_002), M + H = 410 |
| Example 62 2-((7-(4-(1-amino-cyclopropyl)-3-chlorophenyl)quinolin-5-yloxy)methyl)nicotinamide | 1-(2-chloro-4-(4,4,5,5-tetramethyl-1,3,2-dioxaborolan-2-yl)phenyl)cyclopropan amine | 5 mg (13%) | HPLC-MS: Rt = 0.53 min (method X001_004), M + H = 445 |
| Example 64 2-((7-(2-oxo-2,4-dihydro-1H-benzo[d][1,3]oxazin-6-yl)quinolin-5-yloxy)methyl)nicotinamide | 6-(4,4,5,5-tetramethyl-1,3,2-dioxaborolan-2-yl)-1H-benzo[d][1,3]oxazin-2(4H)-one | 10 mg (28%) | HPLC-MS: Rt = 0.42 min (method X001_004), M + H = 427 |
| Example 70 2-((7-(6-(tetrahydro-2H-pyran-4-yloxy)pyridin-3-yl)quinolin-5-yloxy)methyl)nicotinamide | 2-(tetrahydro-2H-pyran-4-yloxy)-5-(4,4,5,5-tetramethyl-1,3,2-dioxaborolan-2-yl)pyridine | 26 mg (54%) | HPLC-MS: Rt = 0.61 min (method X001_004), M + H = 457 |
| Example 71 2-((7-(2-methoxy pyridin-4-yl)quinolin-5-yloxy)methyl)nicotinamide | 2-methoxypyridin-4-ylboronic acid | 23 mg (55%) | HPLC-MS: Rt = 0.56 min (method X001_004), M + H = 387 |
| Example 74 2-((7-phenylquinolin-5-yloxy)methyl)nicotinamide | phenylboronic acid | 23 mg (59%) | HPLC-MS: Rt = 0.59 min (method X001_004), M + H = 356 |
| Example 75 2-((2-methyl-6,7'-biquinolin-5'-yloxy)methyl)nicotinamide | 2-methyl-6-(4,4,5,5-tetramethyl-1,3,2-dioxaborolan-2-yl)quinoline | 85 mg (39%) | HPLC-MS: Rt = 0.52 min (method X001_004), M + H = 421 |

| Example | Boronic acid/ester (corresponding to formula 4) | Yield | Analysis |
|---|---|---|---|
| Example 77 2-((7-(1-ethyl-1H-pyrazol-4-yl)quinolin-5-yloxy)methyl)nicotinamide | 1-ethyl-4-(4,4,5,5-tetramethyl-1,3,2-dioxaborolan-2-yl)-1H-pyrazole | 24 mg (55%) | HPLC-MS: Rt = 0.50 min (method X001_004), M + H = 374 |
| Example 79 2-((7-(3-methyl-3H-imidazo[4,5-b]pyridin-6-yl)quinolin-5-yloxy)methyl)nicotinamide | 3-methyl-6-(4,4,5,5-tetramethyl-1,3,2-dioxaborolan-2-yl)-3H-imidazo[4,5-b]pyridine | 18 mg (43%) | HPLC-MS: Rt = 0.46 min (method X001_004), M + H = 411 |
| Example 80 2-((7-(4-(4-methyl piperazine-1-carbonyl)phenyl)quinolin-5-yloxy)methyl)nicotinamide | (4-methylpiperazin-1-yl)(4-(4,4,5,5-tetramethyl-1,3,2-dioxaborolan-2-yl)phenyl)methanone hydrochloride | 34 mg (71%) | HPLC-MS: Rt = 0.44 min (method X001_004), M + H = 482 |
| Example 82 2-((7-(1-methyl-1H-benzo[d]imidazol-6-yl)quinolin-5-yloxy)methyl)nicotinamide | 1-methyl-1H-benzo[d]imidazol-6-ylboronic acid | 17 mg (40%) | HPLC-MS: Rt = 0.48 min (method X001_004), M + H = 410 |
| Example 84 2-((7-(2-methylbenzo[d]thiazol-6-yl)quinolin-5yloxy)methyl)nicotinamide | 2-methyl-6-(4,4,5,5-tetramethyl-1,3,2-dioxaborolan-2-yl)benzo[d]thiazole | 28 mg (62%) | HPLC-MS: Rt = 0.55 min (method X001_004), M + H = 427 |
| Example 92 2-((7-(3-methyl-4-oxo-3,4-dihydroquinazolin-7-yl)quinolin-5-yloxy)methyl)nicotinamide | 3-methyl-7-(4,4,5,5-tetramethyl-1,3,2-dioxaborolan-2-yl)quinazolin-4(3H)-one | 18 mg (37%) | HPLC-MS: Rt = 0.47 min (method X001_004), M + H = 438 |
| Example 96 2-((7-(6-(methyl sulfonylmethyl)pyridin-3-yl)quinolin-5-yloxy)methyl)nicotinamide | 2-(methylsulfonyl methyl)-5-(4,4,5,5-tetramethyl-1,3,2-dioxaborolan-2-yl)pyridine | 22 mg (35%) | HPLC-MS: Rt = 0.39 min (method X001_004), M + H = 449 |
| Example 97 2-(methylsulfonyl-methyl)-5-(4,4,5,5-tetramethyl-1,3,2-dioxaborolan-2-yl)pyridine | potassium trifluoro(5-methoxypyridin-2-yl)borate | 45 mg (81%) | HPLC-MS: Rt = 0.50 min (method X001_004), M + H = 387 |
| Example 98 2-((7-(1-methyl-1H-benzo[d]imidazol-5-yl)quinolin-5-yloxy)methyl)nicotin-amide | 1-methyl-5-(4,4,5,5-tetramethyl-1,3,2-dioxaborolan-2-yl)-1H-benzo[d]imidazole | 12 mg (26%) | HPLC-MS: Rt = 0.39 min (method X001_004), M + H = 410 |
| Example 103 2-((7-(3-methyl-2,3,4,5-tetrahydro-1H-benzo[d]azepin-7-yl)quinolin-5-yloxy)methyl)nicotinamide | 3-methyl-7-(4,4,5,5-tetramethyl-1,3,2-dioxaborolan-2-yl)-2,3,4,5-tetrahydro-1H-benzo[d]azepine | 7 mg (14%) Reaction time: 30 min | HPLC-MS: Rt = 0.38 min (method X001_004), M + H = 439 |
| Example 106 2-((7-(1,2-dimethyl-1H-benzo[d]imidazol-5-yl)quinolin-5-yloxy)methyl)nicotin-amide | 1,2-dimethyl-5-(4,4,5,5-tetramethyl-1,3,2-dioxaborolan-2-yl)-1H-benzo[d]imidazole | 15 mg (32%) | HPLC-MS: Rt = 0.35 min (method X001_004), M + H = 424 |
| Example 108 2-((7-(2-methyl-1H-benzo[d]imidazol-5-yl)quinolin-5-yloxy)methyl)nicotinamide | 2-methyl-5-(4,4,5,5-tetramethyl-1,3,2-dioxaborolan-2-yl)-1H-benzo[d]imidazole | 30 mg (51%) | HPLC-MS: Rt = 0.69 min (method X001_004), M + H = 410 |
| Example 110 2-((7-(6-(2,2,2-trifluoroethoxy)pyridin-3-yl)quinolin-5-yloxy)methyl)nicotin-amide | 5-(4,4,5,5-tetramethyl-1,3,2-dioxaborolan-2-yl)-2-(2,2,2-trifluoro-ethoxy)pyridine | 39 mg (61%) | HPLC-MS: Rt = 0.59 min (method X001_004), M + H = 455 |

| Example | Boronic acid/ester (corresponding to formula 4) | Yield | Analysis |
|---|---|---|---|
| Example 113 2-((7-(1-isopropyl-1H-pyrazol-4-yl)quinolin-5-yloxy)methyl)nicotinamide | 1-isopropyl-4-(4,4,5,5-tetramethyl-1,3,2-dioxaborolan-2-yl)-1H-pyrazole | 36 mg (64%) | HPLC-MS: Rt = 0.46 min (method X001_004), M + H = 388 |
| Example 117 2-((7-(1-propyl-1H-pyrazol-4-yl)quinolin-5-yloxy)methyl)nicotinamide | 1-propyl-4-(4,4,5,5-tetramethyl-1,3,2-dioxaborolan-2-yl)-1H-pyrazole | 38 mg (67%) | HPLC-MS: Rt = 0.47 min (method X001_004), M + H = 388 |

Synthesis of (R)-4-((R)-1-(7-bromoquinolin-5-yloxy)ethyl)pyrrolidin-2-one (Example 27)

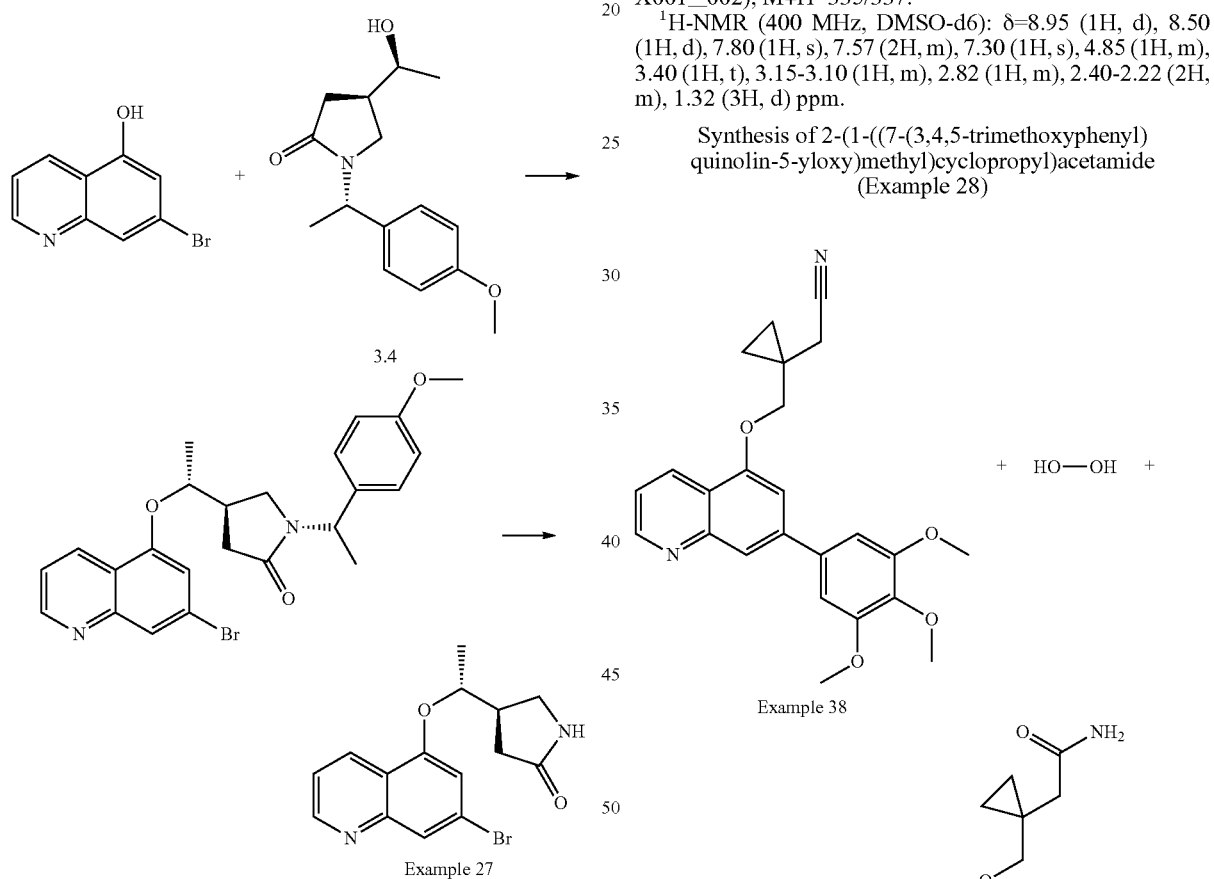

Example 27

100 mg of 7-Bromo-quinolin-5-ol, 234 mg triphenylphosphine and 133 mg of (R)-4-((S)-1-hydroxyethyl)-1-((S)-1-(4-methoxyphenyl)ethyl)pyrrolidin-2-one was dissolved in 2.5 mL of DCM and 7.5 mL of THF. 205 mg DBAD was added (slightly exothermic) and the mixture was stirred overnight at room temperature. Then additional 234 mg triphenylphosphine and 205 mg DBAD was added and the mixture stirred over the weekend. The mixture was diluted with DCM and extracted with 1 N NaOH and water and the organic phase was concentrated in vacuo.

The remaining material was treated with 2 mL of trifluoracetic acid (TFA) and heated 2 h and 15 min at 90° C. in the microwave. The mixture was concentrated and purified with HPLC (XbridgeC18, MeOH/water, TFA) to yield 165 mg yellow solid which was purified by FCC over silica (20 g SiO₂; DCM→DCM:MeOH 90:10) to yield 90 mg solid as Example 27. Analysis: HPLC-MS: Rt=0.56 min (method X001_002), M+H=335/337.

¹H-NMR (400 MHz, DMSO-d6): δ=8.95 (1H, d), 8.50 (1H, d), 7.80 (1H, s), 7.57 (2H, m), 7.30 (1H, s), 4.85 (1H, m), 3.40 (1H, t), 3.15-3.10 (1H, m), 2.82 (1H, m), 2.40-2.22 (2H, m), 1.32 (3H, d) ppm.

Synthesis of 2-(1-((7-(3,4,5-trimethoxyphenyl)quinolin-5-yloxy)methyl)cyclopropyl)acetamide (Example 28)

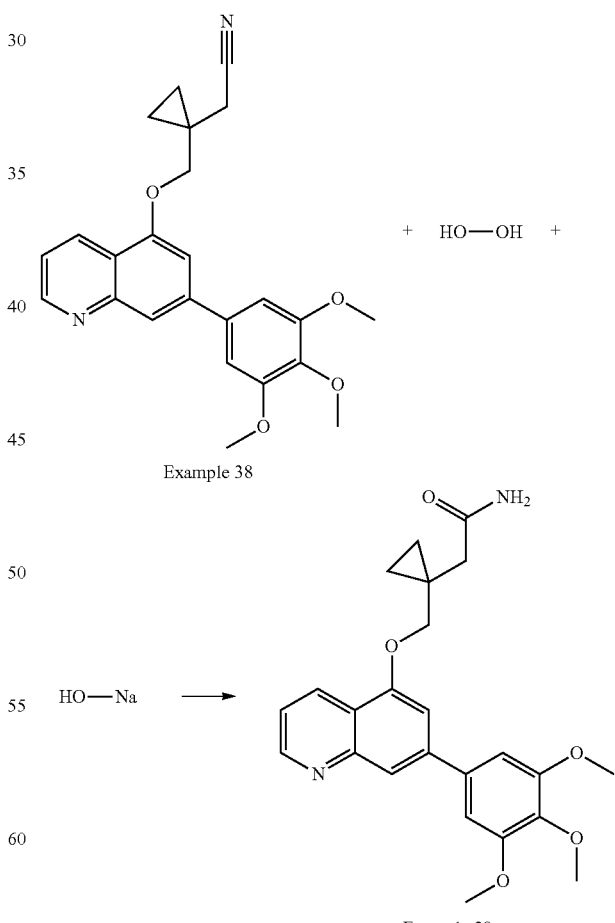

Example 38

Example 28

NaOH (1M, 0.37 mL) was added to a solution of 125 mg {1-[7-(3,4,5-Trimethoxy-phenyl)-quinolin-5-yloxymethyl]- cyclopropyl}-acetonitrile (Example 38) in EtOH (2 ml) under air at 0° C. followed by hydrogen peroxide (30% aq, ~50 mg). The mixture was stirred at 0° C. for 1 h then warmed to RT and stirred at that temperature for 48 hours. The reaction was quenched by addition of aq sat Na₂S₂O₃ and water then extracted with CH₂Cl₂ (3×). The combined extracts were washed with brine, dried (MgSO₄), filtered and concentrated.

Purification by HPLC gave 2-{1-[7-(3,4,5-Trimethoxyphenyl)-quinolin-5-yloxymethyl]-cyclopropyl}-acetamide 8.2 mg as a colourless solid.

HPLC-MS: Rt=3.05 min (method A), M+H=423.

Synthesis of (R)-4-((R)-1-(6,7'-biquinolin-5'-yloxy)ethyl)pyrrolidin-2-one (Example 29)

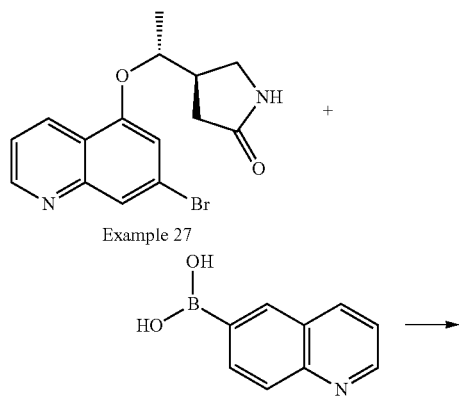

Example 27

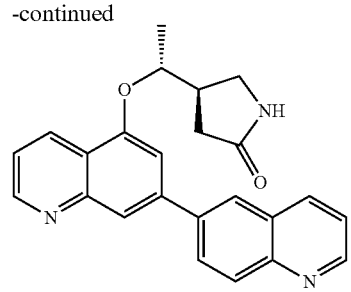

Example 29

40 mg Example 27, 31 mg quinoline-6-boronic acidboronic acid, 14 mg tetrakis-(triphenylphosphin)-palladium(0), 120 µL 2N aqueous sodium carbonate and 0.5 mL dioxan were heated in the microwave (MW) for 15 min at 140° C. The mixture was purified with HPLC (XbridgeC18, MeOH/water, TFA) and the desired fractions lyophilized to yield 30 mg (75%) of Example 29 as yellow solid.

HPLC-MS: Rt=0.54 min (method X001_002), M+H=384.

¹H-NMR (400 MHz, DMSO-d6): δ=9.05 (2H, d), 8.72 (2H, dd), 7.60 (1H, s), 8.40 (1H, d), 8.25 (1H, d), 8.05 (1H, s), 7.75 (1H, dd), 7.7-7.62 (2H, m), 7.6 (1H, s), 5.08 (1H, m), 3.48 (1H, t), 3.20 (1H, dd), 2.90 (1H, m), 2.45-2.3 (2H, m), 1.4 (3H, d) ppm.

The following Examples were synthesized in analogous manner to Example 29.

| Example | Boronic acid/ester | Yield | Analysis |
|---|---|---|---|
| Example 30 N-(5-(5-((R)-1-((R)-5-oxopyrrolidin-3-yl)ethoxy)quinolin-7-yl)pyridin-2-yl)acetamide | N-(5-(4,4,5,5-tetramethyl-1,3,2-dioxaborolan-2-yl)pyridin-2-yl)acetamide | 23 mg (38%) | HPLC-MS: Rt = 0.55 min (method X001_002), M + H = 391 |
| Example 31 (R)-4-((R)-1-(7-(6-(trifluoromethyl)pyridin-3-yl)quinolin-5-yloxy)ethyl)pyrrolidin-2-one | 6-(trifluoromethyl)pyridin-3-ylboronic acid | 38 mg (59%) | HPLC-MS: Rt = 0.74 min (method X001_002), M + H = 402 ¹H-NMR (400 MHz, DMSO-d6): δ = 9.29 (1H, s), 9.02 (1H, d), 8.65 (1H, d), 8.58 (1H, d), 8.1-8.0 (2H, m), 7.65 (1H, dd), 7.61-7.55 (2H, m), 5.05 (1H, m), 3.45 (1H, t), 3.18 (1H, dd), 2.88 (1H, m), 2.45-2.28 (2H, m), 1.38 (3H, d) ppm. |
| Example 33 (R)-4-((R)-1-(2-methyl-6,7'-biquinolin-5'-yloxy)ethyl)pyrrolidin-2-one | 2-methyl-6-(4,4,5,5-tetramethyl-1,3,2-dioxaborolan-2-yl)quinoline | 8 mg (17%) | HPLC-MS: Rt = 0.55 min (method X001_002), M + H = 398 |
| Example 41 (R)-4-((R)-1-(7-(1H-benzo[d]imidazol-5-yl)quinolin-5-yloxy)ethyl)pyrrolidin-2-one | 5-(4,4,5,5-tetramethyl-1,3,2-dioxaborolan-2-yl)-1H-benzo[d]imidazole | 32 mg (52%) | HPLC-MS: Rt = 0.42 min (method X001_003), M + H = 373 |
| Example 42 (R)-4-((R)-1-(7-(1-methyl-1H-indazol-6-yl)quinolin-5-yloxy)ethyl)pyrrolidin-2-one | 1-methyl-1H-indazol-6-ylboronic acid | 30 mg (47%) | HPLC-MS: Rt = 0.58 min (method X001_003), M + H = 387 |

-continued

| Example | Boronic acid/ester | Yield | Analysis |
|---|---|---|---|
| Example 43 (R)-4-((R)-1-(7-(4-(morpholinomethyl)phenyl)quinolin-5-yloxy)ethyl)pyrrolidin-2-one | 4-(morpholinomethyl)phenylboronic acid | 48 mg (69%) | HPLC-MS: Rt = 0.42 min (method X001_003), M + H = 432 |
| Example 47 (R)-4-((R)-1-(7-(1-methyl-1H-pyrazol-4-yl)quinolin-5-yloxy)ethyl)pyrrolidin-2-one | 1-methyl-4-(4,4,5,5-tetramethyl-1,3,2-dioxaborolan-2-yl)-1H-pyrazole | 25 mg (49%) | HPLC-MS: Rt = 0.50 min (method X001_002), M + H = 337 |
| Example 48 (R)-4-((R)-1-(7-(6-morpholinopyridin-3-yl)quinolin-5-yloxy)ethyl)pyrrolidin-2-one | 4-(5-(4,4,5,5-tetramethyl-1,3,2-dioxaborolan-2-yl)pyridin-2-yl)morpholine- | 36 mg (60%) | HPLC-MS: Rt = 0.48 min (method X001_002), M + H = 419 |
| Example 51 N-methyl-N-(4-(5-((R)-1-((R)-5-oxopyrrolidin-3-yl)ethoxy)quinolin-7-yl)benzyl)acetamide | N-methyl-N-(4-(4,4,5,5-tetramethyl-1,3,2-dioxaborolan-2-yl)benzyl)acetamide | 16 mg (30%) | HPLC-MS: Rt = 0.58 min (method X001_002), M + H = 418 |
| Example 53 6-(5-((R)-1-((R)-5-oxopyrrolidin-3-yl)ethoxy)quinolin-7-yl)-3,4-dihydroiso-quinolin-1(2H)-one | 6-(4,4,5,5-tetramethyl-1,3,2-dioxaborolan-2-yl)-3,4-dihydroiso-quinolin-1(2H)-one | 10 mg (29%) | HPLC-MS: Rt = 0.54 min (method X001_002), M + H = 402 |
| Example 55 (R)-4-((R)-1-(7-(4-((2-methylenepiperidin-1-yl)methyl)phenyl)quinolin-5-yloxy)ethyl)pyrrolidin-2-one | 6-(4,4,5,5-tetramethyl-1,3,2-dioxaborolan-2-yl)-3,4-dihydroiso-quinolin-1(2H)-one | 13 mg (17%) | HPLC-MS: Rt = 0.63 min (method X001_002), M + H = 444 |
| Example 56 N-methyl-5-(5-((R)-1-((R)-5-oxopyrrolidin-3-yl)ethoxy)quinolin-7-yl)picolinamide | N-methyl-5-(4,4,5,5-tetramethyl-1,3,2-dioxaborolan-2-yl)picolinamide | 30 mg (52%) | HPLC-MS: Rt = 0.54 min (method X001_002), M + H = 391 |
| Example 61 (R)-4-((R)-1-(7-(2-methylimidazo[1,2-a]pyridin-6-yl)quinolin-5-yloxy)ethyl)pyrrolidin-2-one | 2-methyl-6-(4,4,5,5-tetramethyl-1,3,2-dioxaborolan-2-yl)imidazo[1,2-a]pyridine | 16 mg (32%) | HPLC-MS: Rt = 0.50 min (method X001_004), M + H = 387 |
| Example 63 6-(5-((R)-1-((R)-5-oxopyrrolidin-3-yl)ethoxy)quinolin-7-yl)-1H-benzo[d][1,3]oxazin-2(4H)-one | 6-(4,4,5,5-tetramethyl-1,3,2-dioxaborolan-2-yl)-1H-benzo[d][1,3]oxazin-2(4H)-one | 10 mg (29%) | HPLC-MS: Rt = 0.45 min (method X001_004), M + H = 404 |
| Example 65 (R)-4-((R)-1-(7-(5-methoxypyridin-3-yl)quinolin-5-yloxy)ethyl)pyrrolidin-2-one | 5-methoxypyridin-3-ylboronic acid | 32 mg (70%) | HPLC-MS: Rt = 0.55 min (method X001_004), M + H = 364 |
| Example 66 (R)-4-((R)-1-(7-(6-isopropoxypyridin-3-yl)quinolin-5-yloxy)ethyl)pyrrolidin-2-one | 2-isopropoxy-5-(4,4,5,5-tetramethyl-1,3,2-dioxaborolan-2-yl)pyridine | 22 mg (46%) | HPLC-MS: Rt = 0.70 min (method X001_004), M + H = 392 |
| Example 67 (R)-4-((R)-1-(7-(5-fluoro-6-methoxy pyridin-3-yl)quinolin-5-yloxy)ethyl)pyrrolidin-2-one | 5-fluoro-6-methoxy-pyridin-3-ylboronic acid | 26 mg (55%) | HPLC-MS: Rt = 0.64 min (method X001_004), M + H = 382 |
| Example 68 N-ethyl-N-(4-(5-((R)-1-((R)-5-oxopyrrolidin-3-yl)ethoxy)quinolin-7-yl)benzyl)acetamide | N-ethyl-N-(4-(4,4,5,5-tetramethyl-1,3,2-dioxaborolan-2-yl)benzyl)acetamide | 8 mg (22%) | HPLC-MS: Rt = 0.62 min (method X001_004), M + H = 432 |

| Example | Boronic acid/ester | Yield | Analysis |
| --- | --- | --- | --- |
| Example 69<br>(R)-4-((R)-1-(7-(6-ethoxypyridin-3-yl)quinolin-5-yloxy)ethyl)pyrrolidin-2-one | 6-ethoxypyridin-3-ylboronic acid | 27 mg (58%) | HPLC-MS: Rt = 0.66 min (method X001_004), M + H = 378 |
| Example 72<br>(R)-4-((R)-1-(7-(6-(tetrahydro-2H-pyran-4-yloxy)pyridin-3-yl)quinolin-5-yloxy)ethyl)pyrrolidin-2-one | 2-(tetrahydro-2H-pyran-4-yloxy)-5-(4,4,5,5-tetramethyl-1,3,2-dioxaborolan-2-yl)pyridine | 26 mg (50%) | HPLC-MS: Rt = 0.63 min (method X001_004), M + H = 434 |
| Example 73<br>(R)-4-((R)-1-(7-(2-methoxypyridin-4-yl)quinolin-5-yloxy)ethyl)pyrrolidin-2-one | 2-methoxypyridin-4-ylboronic acid | 17 mg (37%) | HPLC-MS: Rt = 0.58 min (method X001_004), M + H = 364 |
| Example 76<br>(R)-4-((R)-1-(7-(4-(4-methylpiperazine-1-carbonyl)phenyl)quinolin-5-yloxy)ethyl)pyrrolidin-2-one | (4-methylpiperazin-1-yl)(4-(4,4,5,5-tetramethyl-1,3,2-dioxaborolan-2-yl)phenyl)methanone | 38 mg (70%) | HPLC-MS: Rt = 0.46 min (method X001_004), M + H = 459 |
| Example 78<br>(R)-4-((R)-1-(7-(1-ethyl-1H-pyrazol-4-yl)quinolin-5-yloxy)ethyl)pyrrolidin-2-one | 1-ethyl-4-(4,4,5,5-tetramethyl-1,3,2-dioxaborolan-2-yl)-1H-pyrazole | 20 mg (45%) | HPLC-MS: Rt = 0.53 min (method X001_004), M + H = 351 |
| Example 81<br>(R)-4-((R)-1-(7-(1-methyl-1H-benzo[d]imidazol-6-yl)quinolin-5-yloxy)ethyl)pyrrolidin-2-one | 1-methyl-1H-benzo[d]imidazol-6-ylboronic acid | 23 mg (48%) | HPLC-MS: Rt = 0.46 min (method X001_004), M + H = 387 |
| Example 83<br>(R)-4-((R)-1-(7-(2-(trifluoromethyl)imidazo[1,2-a]pyridin-6-yl)quinolin-5-yloxy)ethyl)pyrrolidin-2-one | 6-(4,4,5,5-tetramethyl-1,3,2-dioxaborolan-2-yl)-2-(trifluoromethyl)imidazo[1,2-a]pyridine | 26 mg (42%) | HPLC-MS: Rt = 0.59 min (method X001_004), M + H = 441 |
| Example 85<br>(R)-4-((R)-1-(7-(2-methylbenzo[d]thiazol-6-yl)quinolin-5-yloxy)ethyl)pyrrolidin-2-one | 2-methyl-6-(4,4,5,5-tetramethyl-1,3,2-dioxaborolan-2-yl)benzo[d]thiazole | 20 mg (41%) | HPLC-MS: Rt = 0.57 min (method X001_004), M + H = 404 |
| Example 86<br>(R)-4-((R)-1-(7-(4-(1-aminocyclopropyl)-3-chlorophenyl)quinolin-5-yloxy)ethyl)pyrrolidin-2-one | tert-butyl 1-(2-chloro-4-(4,4,5,5-tetramethyl-1,3,2-dioxaborolan-2-yl)phenyl)cyclopropyl-1 carbamate | 17 mg (33%) | HPLC-MS: Rt = 0.73 min (method X001_004), M + H = 422 |
| Example 87<br>(R)-4-((R)-1-(7-(1-(trifluoromethyl)-1H-pyrazol-4-yl)quinolin-5-yloxy)ethyl)pyrrolidin-2-one | 4-(4,4,5,5-tetramethyl-1,3,2-dioxaborolan-2-yl)-1-(trifluoromethyl)-1H-pyrazole | 19 mg (24%) | HPLC-MS: Rt = 0.55 min (method X001_002), M + H = 391<br>$^1$H-NMR (400 MHz, DMSO-d6):<br>δ = 9.25 (1H, s), 8.90 (1H, s), 8.70 (1H, s), 8.45 (1H, d), 8.00 (1H, d), 7.60 (1H, s), 7.48 (2H, m), 4.95 (1H, m), 3.45 (1H, t), 3.18 (1H, dd), 2.85 (1H, m), 2.45-2.25 (2H, m), 1.35 (3H, d) ppm. |
| Example 88<br>(R)-4-((R)-1-(7-(5-methoxypyridin-2-yl)quinolin-5-yloxy)ethyl)pyrrolidin-2-one | potassium trifluoro(5-methoxypyridin-2-yl)borate | 22 mg (48%) | HPLC-MS: Rt = 0.53 min (method X001_004), M + H = 364 |

| Example | Boronic acid/ester | Yield | Analysis |
| --- | --- | --- | --- |
| Example 89 (R)-4-((R)-1-(7-(6-tert-butoxypyridin-3-yl)quinolin-5-yloxy)ethyl)pyrrolidin-2-one | 2-tert-butoxy-5-(4,4,5,5-tetramethyl-1,3,2-dioxaborolan-2-yl)pyridine | 30 mg (78%) | HPLC-MS: Rt = 0.69 min (method X001_004), M + H = 406 |
| Example 90 (R)-4-((R)-1-(7-(6-cyclobutoxypyridin-3-yl)quinolin-5-yloxy)ethyl)pyrrolidin-2-one | 2-cyclobutoxy-5-(4,4,5,5-tetramethyl-1,3,2-dioxaborolan-2-yl)pyridine | 10 mg (26%) | HPLC-MS: Rt = 0.65 min (method X001_004), M + H = 404 |
| Example 91 3-methyl-7-(5-((R)-1-((R)-5-oxopyrrolidin-3-yl)ethoxy)quinolin-7-yl)quinazolin-4(3H)-one | 3-methyl-7-(4,4,5,5-tetramethyl-1,3,2-dioxaborolan-2-yl)quinazolin-4(3H)-one | 18 mg (32%) | HPLC-MS: Rt = 0.50 min (method X001_004), M + H = 415 |
| Example 93 (R)-4-((R)-1-(7-(2-(trifluoromethyl)-1H-benzo[d]imidazol-5-yl)quinolin-5-yloxy)ethyl)pyrrolidin-2-one | 5-(4,4,5,5-tetramethyl-1,3,2-dioxaborolan-2-yl)-2-(trifluoromethyl)-1H-benzo[d]imidazole | 16 mg (38%) | HPLC-MS: Rt = 0.59 min (method X001_004), M + H = 441 |
| Example 94 (R)-4-((R)-1-(7-(1-methyl-1H-benzo[d]imidazol-5-yl)quinolin-5-yloxy)ethyl)pyrrolidin-2-one | 1-methyl-5-(4,4,5,5-tetramethyl-1,3,2-dioxaborolan-2-yl)-1H-benzo[d]imidazole | 7 mg (19%) | HPLC-MS: Rt = 0.42 min (method X001_004), M + H = 387 |
| Example 95 (R)-4-((R)-1-(7-(6-(methylsulfonylmethyl)pyridin-3-yl)quinolin-5-yloxy)ethyl)pyrrolidin-2-one | 2-(methylsulfonylmethyl)-5-(4,4,5,5-tetramethyl-1,3,2-dioxaborolan-2-yl)pyridine | 23 mg (45%) | HPLC-MS: Rt = 0.42 min (method X001_004), M + H = 426 |
| Example 99 (R)-4-{(R)-1-[7-(5,6-Dimethoxy-pyridin-3-yl)-quinolin-5-yloxy]-ethyl}-pyrrolidin-2-one | 2,3-Dimethoxy-5-(4,4,5,5-tetramethyl-[1,3,2]dioxaborolan-2-yl)-pyridine | 66 mg (56%) | HPLC-MS: Rt = 2.91 min (method A), M + H = 394 |
| Example 100 (R)-4-{(R)-1-[7-(3,4-Dihydro-2H-pyrano[2,3-b]pyridine-6-yl)-quinolin-5-yloxy]-ethyl}-pyrrolidin-2-one | 6-(4,4,5,5-Tetramethyl-[1,3,2]dioxaborolan-2-yl)-3,4-dihydro-2H-pyrano[2,3-b]pyridine | 69 mg (59%) | HPLC-MS: Rt = 2.75 min (method A), M + H = 390 |
| Example 102 (R)-4-((R)-1-(7-(3-methoxy-4-(trifluoromethyl)phenyl)quinolin-5-yloxy)ethyl)pyrrolidin-2-one | 2-(3-methoxy-4-(trifluoromethyl)phenyl)-4,4,5,5-tetramethyl-1,3,2-dioxaborolane | 11 mg (27%) | HPLC-MS: Rt = 0.67 min (method X001_004), M + H = 431 |
| Example 104 (R)-4-((R)-1-(7-(6-(difluoromethoxy)pyridin-3-yl)quinolin-5-yloxy)ethyl)pyrrolidin-2-one | 2-(difluoromethoxy)-5-(4,4,5,5-tetramethyl-1,3,2-dioxaborolan-2-yl)pyridine | 19 mg (50%) | HPLC-MS: Rt = 0.56 min (method X001_004), M + H = 400 $^1$H-NMR (400 MHz, DMSO-d6): δ = 9.95 (1H, s), 8.80 (1H, s), 8.52 (1H, d), 8.45 (1H, d), 7.90 (1H, s), 7.80 (1H, t), 7.60 (1H, d), 7.52 (1H, dd), 7.45 (1H, s), 7.25 (1H, d), 4.95 (1H, m), 3.42 (1H, t), 3.18 (1H, dd), 2.85 (1H, m), 2.45-2.25 (2H, m), 1.35 (3H, d) ppm. |
| Example 105 (R)-4-((R)-1-(7-(1,2-dimethyl-1H-benzo[d]imidazol-5-yl)quinolin-5-yloxy)ethyl)pyrrolidin-2-one | 1,2-dimethyl-5-(4,4,5,5-tetramethyl-1,3,2-dioxaborolan-2-yl)-1H-benzo[d]imidazole | 12 mg (31%) | HPLC-MS: Rt = 0.38 min (method X001_004), M + H = 401 |

| Example | Boronic acid/ester | Yield | Analysis |
|---|---|---|---|
| Example 107 (R)-4-((R)-1-(7-(2,4-dimethylquinazolin-6-yl)quinolin-5-yloxy)ethyl)pyrrolidin-2-one | 2,4-dimethyl-6-(4,4,5,5-tetramethyl-1,3,2-dioxaborolan-2-yl)quinazoline | 14 mg (36%) | HPLC-MS: Rt = 0.47 min (method X001_004), M + H = 413 |
| Example 109 (R)-4-((R)-1-(7-(2-methyl-1H-benzo[d]imidazol-5-yl)quinolin-5-yloxy)ethyl)pyrrolidin-2-one | 2-methyl-5-(4,4,5,5-tetramethyl-1,3,2-dioxaborolan-2-yl)-1H-benzo[d]imidazole | 37 mg (77%) | HPLC-MS: Rt = 0.74 min (method X001_004), M + H = 387 |
| Example 111 (R)-4-((R)-1-(7-(6-(2,2,2-trifluoroethoxy)pyridin-3-yl)quinolin-5-yloxy)ethyl)pyrrolidin-2-one | 5-(4,4,5,5-tetramethyl-1,3,2-dioxaborolan-2-yl)-2-(2,2,2-trifluoro-ethoxy)pyridine | 13 mg (22%) | HPLC-MS: Rt = 0.62 min (method X001_004), M + H = 432 |
| Example 112 (R)-4-((R)-1-(7-(1,5-dimethyl-1H-pyrazol-4-yl)quinolin-5-yloxy)ethyl)pyrrolidin-2-one | 1,5-dimethyl-4-(4,4,5,5-tetramethyl-1,3,2-dioxaborolan-2-yl)-1H-pyrazole | 26 mg (59%) | HPLC-MS: Rt = 0.42 min (method X001_004), M + H = 351 |
| Example 114 (R)-4-((R)-1-(7-(1-propyl-1H-pyrazol-4-yl)quinolin-5-yloxy)ethyl)pyrrolidin-2-one | 1-propyl-4-(4,4,5,5-tetramethyl-1,3,2-dioxaborolan-2-yl)-1H-pyrazole | 28 mg (61%) | HPLC-MS: Rt = 0.49 min (method X001_004), M + H = 365 |
| Example 115 (R)-4-((R)-1-(7-(1-iso-propyl-1H-pyrazol-4-yl)quinolin-5-yloxy)ethyl)pyrrolidin-2-one | 1-isopropyl-4-(4,4,5,5-tetramethyl-1,3,2-dioxaborolan-2-yl)-1H-pyrazole | 20 mg (44%) | HPLC-MS: Rt = 0.49 min (method X001_004), M + H = 365 |
| Example 116 (R)-4-((R)-1-(7-(1-methyl-3-(trifluoro-methyl)-1H-pyrazol-4-yl)quinolin-5-yloxy)ethyl)pyrrolidin-2-one | 1-methyl-3-(trifluoromethyl)-1H-pyrazol-4-ylboronic acid | 33 mg (67%) | HPLC-MS: Rt = 0.51 min (method X001_004), M + H = 405 |
| Example 119 Acetic acid 2-(4-{5-[(R)-1-((R)-5-oxo-pyrrolidin-3-yl)-ethoxy]-quinolin-7-yl}-pyrazol-1-yl)-ethyl ester | Acetic acid 2-[4-(4,4,5,5-tetramethyl-[1,3,2]dioxaborolan-2-yl)-pyrazol-1-yl]-ethyl ester | 36 mg (31%) | HPLC-MS: Rt = 2.58 (method A), M + H = 409 |
| Example 120 (R)-4-((R)-1-(7-(6-(difluoromethyl)pyridin-3-yl)quinolin-5-yloxy)ethyl)pyrrolidin-2-one | 2-(difluoromethyl)-5-(4,4,5,5-tetramethyl-1,3,2-dioxaborolan-2-yl)pyridine | 19 mg (30%) | HPLC-MS: Rt = 0.47 min (method X001_004), M + H = 384 $^1$H-NMR (400 MHz, DMSO-d6): δ = 9.20 (1H, s), 9.10 (1H, d), 8.69 (1H, d), 8.50 (1H, d), 8.02 (1H, s), 7.90 (1H, d), 7.75 (1H, dd), 7.60 (m, 2H), 7.10 (t, 1H), 5.05 (1H, m), 3.42 (1H, t), 3.18 (1H, dd), 2.85 (1H, m), 2.45-2.25 (2H, m), 1.35 (3H, d) ppm. |

Synthesis of (R)-4-((R)-1-(7-iodoquinolin-5-yloxy)ethyl)pyrrolidin-2-one (Example 37)

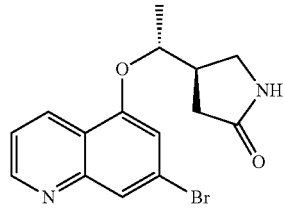

Example 27

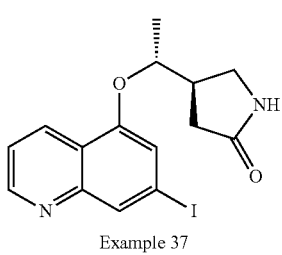

Example 37

50 mg of Example 27 and 9 mg of copper (I) iodide were suspended in 300 μL dioxane under argon. 9.6 μL N,N'dimethylethylendiamine and 45 mg of sodium iodide were added and the mixture heated to 110° C. over weekend. The mixture was diluted with DCM and extracted with aqueous ammonia and water, the organic phase was subsequently concentrated in vacuo and the residual purified with HPLC (XbridgeC18; MeOH/water, TFA) to yield 15 mg yellow solid as Example 37.

Analysis: HPLC-MS: Rt=1.25 min (method V003_003), M+H=383.

Synthesis of (R)-4-{(R)-1-[7-(5-Trifluoromethyl-pyridin-2-yl)-quinolin-5-yloxy]-ethyl}-pyrrolidin-2-one (Example 49)

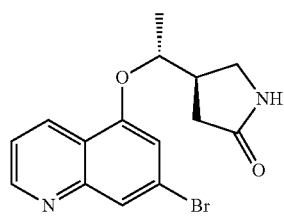

Example 27

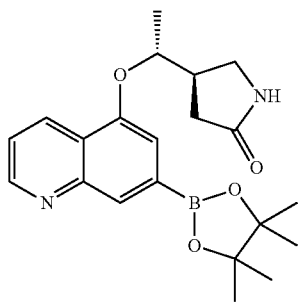

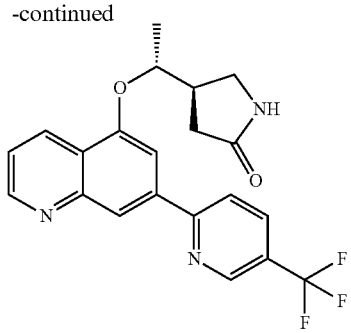

Example 49

Step 1 (=Reaction 9):

1 g (R)-4-[(R)-1-(7-Bromo-quinolin-5-yl-oxy)-ethyl]-pyrrolidin-2-one (example 27), 833 mg his (pinacolato) diboron, 105 mg Bis(triphenylphosphine)palladium(II) chloride and 878 mg potassium acetate were suspended in 10 ml dioxan and heated at 80° C. for 2 hours. The mixture was allowed to cool, then partitioned between DCM and water. The organic layer was separated, dried over Na₂SO₄, filtered and concentrated in vacuo. The residue was purified by chromatography using a Hept/EtOAc/MeOH gradient, the product eluting with 20% MeOH/EtOAc to give 976 mg of (R)-4-{(R)-1-[7-(4,4,5,5-Tetramethyl-[1,3,2]dioxaborolan-2-yl)-quinolin-5-yloxy]-ethyl}-pyrrolidin-2-one as a tan oil.

Analysis HPLC-MS: Rt=1.05 min (method B), M+H=301.

Step 2:

500 mg (R)-4-{(R)-1-[7-(4,4,5,5-Tetramethyl-[1,3,2]dioxaborolan-2-yl)-quinolin-5-yloxy]-ethyl}-pyrrolidin-2-one (325 mg 2-Bromo-5-trifluoromethyl-pyridine, 46 mg Bis (triphenylphosphine)palladium(II) chloride, 1.96 mL 2N aqueous sodium carbonate and 10 mL DMF were heated at 80° C. for 18 hours. The reaction was partitioned between DCM and NaHCO₃ (sat aq) then the organic layer was separated, dried over Na₂SO₄, filtered and concentrated in vacuo. The residue was purified by MPLC using a Hept/EtOAc/MeOH gradient to give 326 mg of (R)-4-{(R)-1-[7-(5-Trifluoromethyl-pyridin-2-yl)-quinolin-5-yloxy]-ethyl}-pyrrolidin-2-one as a yellow solid.

HPLC-MS: Rt=3.55 min (method A), M+H=402.

¹H NMR (500 MHz, Methanol-d4) δ ppm 1.55 (3H, d, J=6.15 Hz), 2.57 (1H, dd, J=17.18, 6.62 Hz), 2.69 (1H, dd, J=17.18, 9.46 Hz), 3.01-3.13 (1H, m), 3.40 (1H, dd, J=10.17, 5.75 Hz), 3.63-3.74 (1H, m), 5.17 (1H, quin, J=5.95 Hz), 8.07 (1H, t, J=6.94 Hz), 8.14-8.21 (1H, m), 8.33-8.40 (1H, m), 8.40-8.47 (1H, m), 8.50 (1H, s), 9.08-9.19 (1H, m), 9.21-9.28 (1H, m), 9.33-9.40 (1H, m).

Synthesis of (R)-4-((R)-1-(7-(1,2,3,4-tetrahydroisoquinolin-7-yl)quinolin-5-yloxy)ethyl)pyrrolidin-2-one (Example 101)

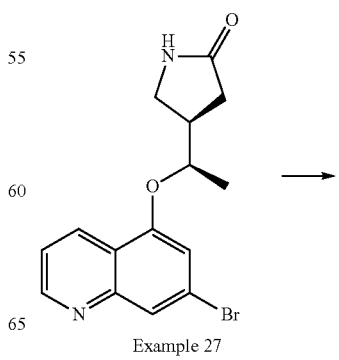

Example 27

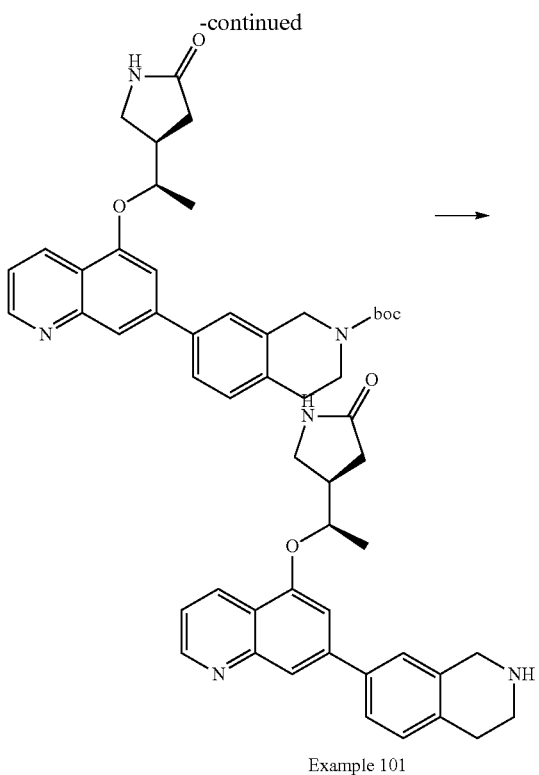

Example 101

150 mg Example 27, 241 mg 7-(4,4,5,5-Tetramethyl-[1,3,2]dioxaborolan-2-yl)-3,4-dihydro-1H-isoquinoline-2-carboxylic acid tert-butyl ester, 15 mg bis(triphenylphosphine) palladium(II) chloride, 671 µL 2N aqueous sodium carbonate and 2 mL DMF were heated for 2 hours at 90° C. The mixture was partitioned between DCM and NaHCO₃ (sat aq) and the organic layer was separated, dried (Na₂SO₄), filtered and concentrated in vacuo. The residue was dissolved in 10 ml 25% TFA in DCM and stirred at 25° C. overnight then concentrated in vacuo. Purification by flash chromatography using 0-25% MeOH/DCM gave 75 mg (43%) of Example 101 (R)-4-{(R)-1-[7-(1,2,3,4-Tetrahydroisoquinolin-7-yl)-quinolin-5-yloxy]-ethyl}-pyrrolidin-2-one as yellow solid.

HPLC-MS: Rt=2.28 min (method A), M+H=388.

Synthesis of (R)-4-(R)-1-(7-(1-(2-hydroxyethyl)-1H-pyrazol-4-yl)quinolin-5-yloxy)ethyl)pyrrolidin-2-one (Example 118)

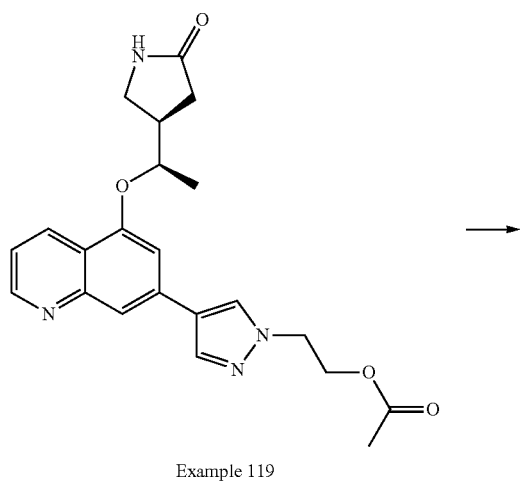

Example 119

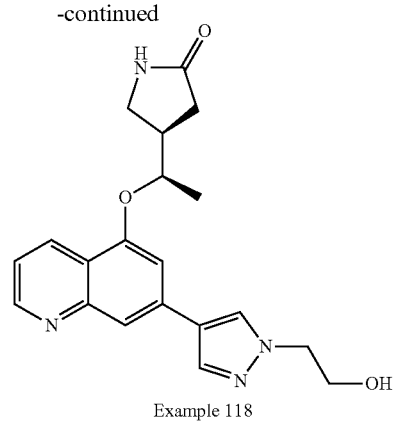

Example 118

21 mg of pure acetic acid 2-(4-{5-[(R)-1-((R)-5-oxo-pyrrolidin-3-yl)-ethoxy]-quinolin-7-yl}-pyrazol-1-yl)-ethyl ester (Example 119) and 26 mg of a 1:1 mixture of Example 119 and Example 118 was dissolved in 3 ml MeCN and 1 ml 1N NaOH(aq). The mixture was stirred overnight at 25° C. then partitioned between DCM and NaHCO₃(sat aq) and the organic layer was separated, dried (Na₂SO₄), filtered and concentrated in vacuo. Purification by reverse phase LC gave 26 mg (71%) of a crystalline solid.

HPLC-MS: Rt=2.37 min (method A), M+H=367.

4.5 Chromatographic Methods (HPLC-MS Methods)

The Example compounds prepared according to the foregoing synthesis scheme were characterised by the following chromatographic methods, which—if they were carried out—are specified individually in Table 6.

Method A:
Waters ZQ or Waters QT of micro, Agilent G1312A HPLC pump, Waters 2996 PDA detector, Waters 2420 ancillary detector
Eluent A: Water (0.1% formic acid)
Eluent B: Acetonitrile (0.1% formic acid)

| Time [min] | % A | % B | Flow rate [mL/min] |
|---|---|---|---|
| 0.00 | 95 | 5 | 0.60 |
| 5.00 | 0 | 100 | 0.60 |
| 5.40 | 0 | 100 | 0.60 |
| 5.42 | 95 | 5 | 0.60 |
| 7.00 | 95 | 5 | 0.60 |

The stationary phase used was a Waters Atlantis dC18 2.1 mm×100 mm, 3 µm, injection volume 3 µL (column temperature: constant at 40° C.).

Detector at a wavelength range 215 nm (nominal).

Method B:
Shimadzu LCMS2010EV, Shimadzu LC-20AB pump, SPD-M20A PDA detector, PL2100 ancillary
Eluent A: Water (0.1% formic acid)
Eluent B: Acetonitrile (0.1% formic acid)

| Time [min] | % A | % B | Flow rate [mL/min] |
|---|---|---|---|
| 0.00 | 95 | 5 | 1.00 |
| 2.50 | 0 | 100 | 1.00 |

| Time [min] | % A | % B | Flow rate [mL/min] |
|---|---|---|---|
| 2.70 | 0 | 100 | 1.00 |
| 2.71 | 95 | 5 | 1.00 |
| 3.50 | 95 | 5 | 1.00 |

The stationary phase used was a Waters Atlantis dC18 2.1 mm×50 mm, 3 μm, injection volume 3 μL (column temperature: constant at 40° C.).

Detector at a wavelength range 215 nm (nominal).

Method C:

Waters ZQ2000; Waters 1515 Pump, Waters PDA 996 Detector, Waters 2747 Injecor

Mobile Phase: A Wasser+0.1% formic acid
B Acetonitril+0.1% formic acid

Gradient:

| time in min | % A | % B | Flow rate in mL/min |
|---|---|---|---|
| 0.00 | 95.0 | 5.0 | 1.00 |
| 0.10 | 95.0 | 5.0 | 1.00 |
| 3.10 | 2.00 | 98.00 | 1.00 |
| 4.50 | 2.00 | 98.00 | 1.00 |
| 5.00 | 95.0 | 5.0 | 1.00 |

Stationary phase: Phase: X-terra MS C18 2.5 μm 4.6 mm×30 mm

Column temperature ca. 25° C.

Diode array detection took place in the wavelength range 210-400 nm.

Method D

Waters ZMD, Alliance 2690/2695 HPLC, Waters 996/2996 diode array detector

The mobile phase used was:
A: water with 0.10% TFA
B: acetonitrile with 0.10% TFA

| time in min | % A | % B | flow rate in mL/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

The stationary phase used was a Merck Chromolith™ Flash RP-18e column, 3 mm×100 mm (column temperature: constant at 25° C.).

Diode array detection took place in the wavelength range 210-400 nm.

Method E

Waters ZMD, Alliance 2690/2695 HPLC, Waters 996/2996 diode array detector

The mobile phase used was:
A: water with 0.10% TFA
D: methanol with 0.10% TFA

| time in min | % A | % D | flow rate in mL/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 |

The stationary phase used was a Waters XBridge™ C18 3.5 μM, 4.6×20 mm IS™ (column temperature: constant at 40° C.).

Diode array detection took place in the wavelength range 210-400 nm.

Method G:

Eluent A: Water/0.2% $KH_2PO_4$ pH=3
Eluent B: Acetonitrile

| Time [min] | % A | % B | Flow rate [mL/min] |
|---|---|---|---|
| 0.00 | 80 | 20 | 1.50 |
| 5.00 | 20 | 80 | 1.50 |
| 8.00 | 20 | 80 | 1.50 |

The stationary phase used was a Inertsil C8-3 (GL Sciences), 5 μm; dimension: 100×4.0 mm, (column temperature: constant at 30° C.).

Detection UV 220 nm

Method H:

Eluent A: Hexane
Eluent B: 2-Propanol

| Time [min] | % A | % B | Flow rate [mL/min] |
|---|---|---|---|
| 00.00 | 90 | 10 | 1.0 |
| 20.00 | 90 | 10 | 1.0 |

The stationary phase used was a Chiralpak AD-H (Daicel), 5 μm; dimension: 150×4.6 mm, (column temperature: constant at 10° C.).

Detection DAD 225 nm

Method I:

Eluent A: Hexane
Eluent B: 2-Propanol

| Time [min] | % A | % B | Flow rate [mL/min] |
|---|---|---|---|
| 00.00 | 90 | 10 | 1.0 |
| 25.00 | 90 | 10 | 1.0 |

The stationary phase used was a Chiralpak AD-H (Daicel), 5 μm; dimension: 150×4.6 mm, (column temperature: constant at 10° C.).

Detection DAD 225 nm

Method M:

Shimadzu LCMS2010EV, Shimadzu LC-20AB pump, SPD-M20A PDA detector, PL2100 ancillary Eluent A: Water (0.1% formic acid)
Eluent B: Acetonitrile (0.1% formic acid)

| Time [min] | % A | % B | Flow rate [mL/min] |
|---|---|---|---|
| 0.00 | 95 | 5 | 1.00 |
| 1.50 | 0 | 100 | 1.00 |
| 1.6 | 0 | 100 | 1.00 |
| 1.61 | 95 | 5 | 1.00 |
| 2.00 | 95 | 5 | 1.00 |

The stationary phase used was a Waters Atlantis dC18 2.1 mm×50 mm, 3 μm, injection volume 3 μL (column temperature: constant at 40° C.).

Detector at a wavelength range 215 nm (nominal).

Method XBM:

Waters ZMD, Alliance 2690/2695 HPLC, Waters 996/2996 diode array detector

The mobile phase used was:

C: water with 0.10% NH$_3$

D: methanol

| time in min | % C | % D | flow rate in mL/min |
|---|---|---|---|
| 0.00 | 95 | 5 | 4.00 |
| 0.20 | 95 | 5 | 4.00 |
| 1.60 | 2 | 100 | 4.00 |
| 1.90 | 2 | 100 | 4.00 |

The stationary phase used was a Waters XBridge™ C18 3.5 μm, 4.6×20 mm IS™ (column temperature: constant at 40° C.).

Diode array detection took place in the wavelength range 210-400 nm.

Method X001__002:

| method: | X001__002 |
| column: | XBridge BEH C18, 2.1 × 30 mm, 1.7 μm |
| company: | Waters |

| time [min] | % Sol [H2O, 0.13% TFA] | % Sol [Methanol, 0.05% TFA] | Flow [ml/min] | Temp [° C.] |
|---|---|---|---|---|
| 0.0 | 99 | 1 | 1.3 | 60 |
| 0.05 | 99 | 1 | 1.3 | 60 |
| 1.05 | 0 | 100 | 1.3 | 60 |
| 1.2 | 0 | 100 | 1.3 | 60 |

Diode array detection took place in the wavelength range 210-400 nm.

Method X001__003:

| method: | X001__003 |
| column: | XBridge BEH C18, 2.1 × 30 mm, 1.7 μm |
| company: | Waters |

| time [min] | % Sol [H2O, 0.10% TFA] | % Sol [Methanol] | Flow [ml/min] | Temp [° C.] |
|---|---|---|---|---|
| 0.0 | 99 | 1 | 1.5 | 60 |
| 0.05 | 99 | 1 | 1.5 | 60 |
| 1.05 | 0 | 100 | 1.5 | 60 |
| 1.2 | 0 | 100 | 1.5 | 60 |

Diode array detection took place in the wavelength range 210-400 nm.

Method X001__004:

| method: | X001__004 |
| column: | XBridge C18, 2.1 × 20 mm, 2.5 μm |
| company: | Waters |

| time [min] | % Sol [H2O, 0.10% TFA] | % Sol [Methanol] | Flow [ml/min] | Temp [° C.] |
|---|---|---|---|---|
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

Diode array detection took place in the wavelength range 210-400 nm.

Method V003__002:

| method: | V003__002 |
| column: | XBridge C18, 4.6 × 30 mm, 3.5 μm |
| company: | Waters |

| time [min] | % Sol [H2O, 0.1% NH3] | % Sol [Methanol, 0.1% NH3] | Flow [ml/min] | Temp [° C.] |
|---|---|---|---|---|
| 0.0 | 95 | 5 | 4 | 60 |
| 0.2 | 95 | 5 | 4 | 60 |
| 1.5 | 0 | 100.0 | 4 | 60 |
| 1.75 | 0 | 100 | 4 | 60 |

Diode array detection took place in the wavelength range 210-400 nm.

Method V003__003:

| method: | V003__003 |
| column: | XBridge C18, 4.6 × 30 mm, 3.5 μm |
| company: | Waters |

| time [min] | % Sol [H2O, 0.1% NH3] | % Sol [Methanol] | Flow [ml/min] | Temp [° C.] |
|---|---|---|---|---|
| 0.0 | 95 | 5 | 4 | 60 |
| 0.2 | 95 | 5 | 4 | 60 |
| 1.5 | 0 | 100.0 | 4 | 60 |
| 1.75 | 0 | 100 | 4 | 60 |

Diode array detection took place in the wavelength range 210-400 nm.

4.6 NMR Methods

Configuration of the Bruker DRX 500 MHz NMR:

High performance digital NMR spectrometer, 2-channel microbay console and Windows XP host workstation running Topspin version 1.3.

Equipped with:
Oxford instruments magnet 11.74 Tesla (500 MHz proton resonance frequency)
B-VT 3000 temperature controller
GRASP II gradient spectroscopy accessory for fast acquisition of 2D pulse sequences
Deuterium lock switch for gradient shimming
5 mm Broad Band Inverse geometry double resonance probe with automated tuning and matching (BBI ATMA). Allows $^1$H observation with pulsing/decoupling of nuclei in the frequency range $^{15}$N and $^{31}$P with $^2$H lock and shielded z-gradient coils.

Configuration of the Bruker DPX 250 MHz NMR

High performance one bay Bruker 250 MHz digital two channel NMR spectrometer console and Windows XP host workstation running XwinNMR version 3.5.

Equipped with:
Oxford instruments magnet 5.87 Tesla (250 MHz proton resonance frequency)
B-VT 3300 variable temperature controller unit
Four nucleus (QNP) switchable probe for observation of $^1$H, $^{13}$C, $^{19}$F and $^{31}$P with $^2$H lock Configuration of the Bruker DPX 400 MHz NMR
High performance digital NMR spectrometer controlled by a Windows XP workstation running Topspin 1.3p18
Equipped with:
Bruker UltraShield Plus magnet 9.40 Tesla (400 MHz proton resonance frequency)
B-VT 3300 temperature controller
GRASP II gradient spectroscopy accessory for fast acquisition of 2D pulse sequences
Deuterium lock switch for gradient shimming
5 mm Selective Inverse Probe (SEI). Allows $^1$H observation with pulsing/decoupling of $^{13}$C with $^2$H lock and shielded z-gradient coils.

5. EXAMPLES

The following Examples were prepared analogously to the methods of synthesis described above. These compounds are suitable as SYK inhibitors and have IC$_{50}$-values of less than or equal to 1 µmol. The IC$_{50}$-values of the individual example substances are shown in the following Table 1 and were experimentally determined as follows:

Syk Kinase Test

Recombinant human Syk (amino acids 342-635) was expressed as a fusion protein with an N-terminal GST tag, affinity-purified and deep-frozen at a concentration of approx. 50-100 µM in test buffer (25 mM HEPES pH7.5; 25 mM MgCl$_2$; 5 mM MnCl$_2$; 50 mM KCl; either 0.2% BSA or 0.2% HSA; 0.01% CHAPS; 100 µM Na$_3$VO$_4$; 0.5 mM DTT) and 10% glycerol at −80° C. until use.

The catalytic activity of the GST-Syk kinase fusion protein was determined using the Kinase Glo® Luminescence Kinase test (Promega; V6712). In this homogeneous test the amount of ATP remaining after the kinase reaction is quantified by a luciferin-luciferase reaction using luminescence. The luminescence signal obtained correlates with the amount of ATP still present and thus correlates inversely with the activity of the protein kinase.

Method

The test compounds were dissolved in 100% DMSO at a concentration of 10 mM and diluted in DMSO to a concentration of 1 mM. All further dilutions of the substances were carried out with 7.5% DMSO in test buffer until a concentration was reached which was 7.5 times above the final test concentration (final concentration of the compounds: 30 µM to 1 nM). 2 µl aliquots of these dilutions were transferred into a 384-well Optiplate (Perkin Elmer, #6007290). GST-Syk was diluted to 6.0 nM in the test buffer and 10 µl of this dilution were used in the kinase test (final concentration of Syk=4 nM in a total volume of 15 µl). After 15 minutes incubation at room temperature 3 µl of a mixture of 750 nM ATP and 100 µg/ml poly (L-Glutamic acid L-Tyrosine 4:1), Fluka #81357) in test buffer were added to each well and the incubation was continued for a further 60 minutes at room temperature.

Positive controls are the reaction mixtures that contain no test substance; negative controls (blanks) are reaction mixtures that contain no kinase.

After 60 minutes, 10 µl Kinase-Glo® solution (Promega, Cat. #V6712) (heated to room temperature) were added to each well and incubation was continued for a further 15 minutes. The plates were read in a Microplate Scintillation and Luminescence Counter (Canberra Packard GmbH).

Data Evaluation and Calculation:

The output file of the "Counter" is a text file that contains the well number and measured counts in two columns. For data evaluation and calculation, the measurement of the negative control was set as 100% inhibition and the measurement of the positive control was set as 0% inhibition. Based on this values the % inherent value for the measurement of each substance concentration was calculated using an "MS-Excel-VB macro". Normally, the % inhibition values calculated are between 100% and 0% inhibition values but may also occur outside these limits in individual cases. The IC$_{50}$ values were calculated from the % inhibition values using "GraphPad-Prism" software (Version 5) (GraphPad Software Inc.).

The following Examples of formula 1

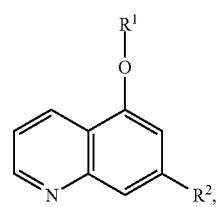

having the following properties were prepared according to the methods of synthesis described above, wherein * denotes the position where the each of the groups R$^1$ and R$^2$ are linked to the rest of the molecule of formula 1:

TABLE 1

| No. | Structure | R$^1$ | R$^2$ | IC$_{50}$-value (+0.2% HSA in µM) | IC$_{50}$-value (+0.2% BSA in µM) |
|---|---|---|---|---|---|
| 1 | (structure: 5-oxy-7-phenylquinoline with chiral CH$_3$-CH-O- linker to pyrrolidinone) | Chiral, CH$_3$-CH(O*)- attached to pyrrolidinone (C=O) | *-CH(CH$_3$)- attached to pyrrolidinone (C=O) | — | 0.0004 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 2 | Chiral | | | 0.0010 | 0.0004 |
| 3 | 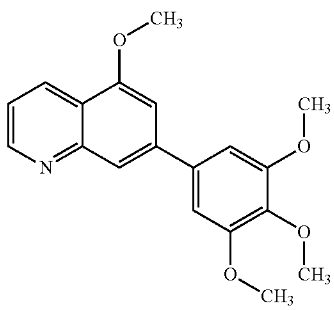 [SMILES: COc1cc(-c2cc(OC)c3cccnc3c2)cc(OC)c1OC] | | | — | 1.2110 |
| 4 | 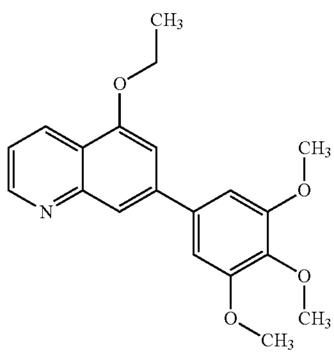 [SMILES: CCOc1cc(-c2cc(OC)c(OC)c(OC)c2)cc2ncccc12] | | | — | 1.0960 |
| 5 | 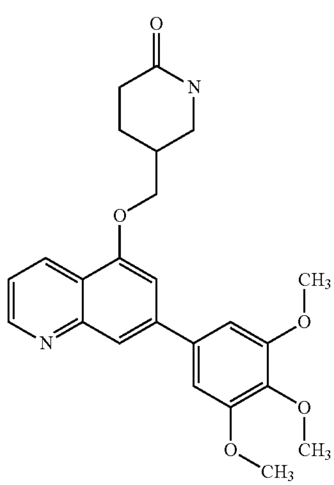 [SMILES: COc1cc(-c2cc(OCC3CCC(=O)NC3)c3cccnc3c2)cc(OC)c1OC] | | | — | — |

TABLE 1-continued

| No. | Structure | | R¹ | R² | IC₅₀-value (+0.2% HSA in µM) | IC₅₀-value (+0.2% BSA in µM) |
|---|---|---|---|---|---|---|
| 6 | [structure] | Chiral | [R¹ group] | [2-pyridyl] | — | 0.0017 |
| 7 | [structure] | Chiral | [R¹ group] | [3,4-dimethoxyphenyl] | — | 0.0084 |
| 8 | [structure] | Chiral | [R¹ group] | [3,4-dimethoxyphenyl] | — | 0.0006 |
| 9 | [structure] | Chiral | [R¹ group] | [3,4,5-trimethoxyphenyl] | — | 0.0311 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 10 | 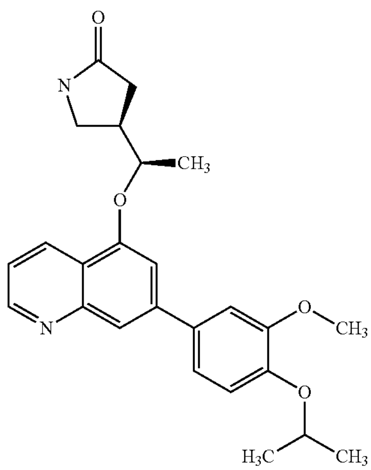 | | | — | 0.0004 |
| 11 | 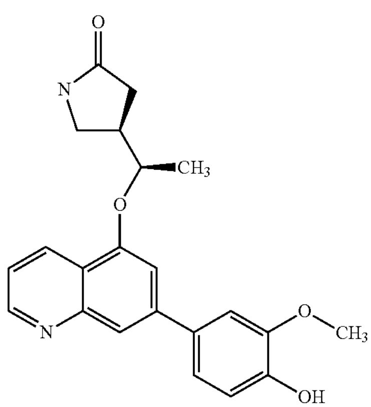 | | | — | 0.0006 |
| 12 | 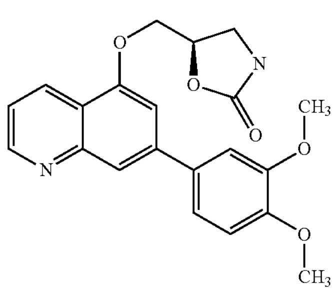 | | | — | 0.0020 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 13 | (Chiral) quinoline with 5-O-CH2-(oxazolidinone) and 7-(3-methoxy-4-hydroxyphenyl) | oxazolidinone-CH2-* | *-phenyl-3-OCH3-4-OH | — | 0.0010 |
| 14 | (Chiral) quinoline with 5-O-CH(CH3)-(pyrrolidinone) and 7-(3,5-difluoro-4-methoxyphenyl) | pyrrolidinone-CH(CH3)-* | *-phenyl-3,5-F2-4-OCH3 | — | 0.0025 |
| 15 | (Chiral) quinoline with 5-O-CH2-(oxazolidinone) and 7-(3,5-difluoro-4-methoxyphenyl) | oxazolidinone-CH2-* | *-phenyl-3,5-F2-4-OCH3 | — | 0.0162 |

TABLE 1-continued

| No. | Structure | | R¹ | R² | IC₅₀-value (+0.2% HSA in μM) | IC₅₀-value (+0.2% BSA in μM) |
|---|---|---|---|---|---|---|
| 16 | [structure: quinoline with 5-O-CH₂-(S)-oxazolidinone and 7-(3-methoxy-4-isopropoxyphenyl)] | Chiral | [(S)-4-methyl-oxazolidin-2-one, attached via CH₂] | [3-methoxy-4-isopropoxyphenyl] | — | 0.0025 |
| 17 | [structure: quinoline with 5-O-CH₂-(pyrrolidinone) and 7-(3,5-difluoro-4-methoxyphenyl)] | Chiral | [4-methyl-pyrrolidin-2-one, attached via CH₂] | [3,5-difluoro-4-methoxyphenyl] | — | 0.1084 |
| 18 | [structure: quinoline with 5-O-CH₂-(S)-oxazolidinone and 7-(3,4,5-trimethoxyphenyl)] | Chiral | [(S)-4-methyl-oxazolidin-2-one, attached via CH₂] | [3,4,5-trimethoxyphenyl] | — | 0.0060 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 19 | (Chiral) quinoline with 5-O-CH2-(4-pyrrolidinone) and 7-(3-methoxy-4-hydroxyphenyl) | 4-(pyrrolidin-2-one-4-yl)methyl | 3-methoxy-4-hydroxyphenyl | — | 0.0208 |
| 20 | (Chiral) quinoline with 5-O-CH2-(oxazolidinone) and 7-(6-methoxypyridin-3-yl) | (oxazolidin-2-one-5-yl)methyl | 6-methoxypyridin-3-yl | — | 0.0123 |
| 21 | (Chiral) quinoline with 5-O-CH(CH3)-(pyrrolidinone) and 7-(6-methoxypyridin-3-yl) | 1-(pyrrolidin-2-one-4-yl)ethyl | 6-methoxypyridin-3-yl | — | 0.0009 |
| 22 | 7-bromoquinolin-5-yloxymethyl-(3-carbamoylpyridin-2-yl) | 2-(3-carbamoylpyridin-2-yl)methyl | Br | — | 0.3997 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 23 | 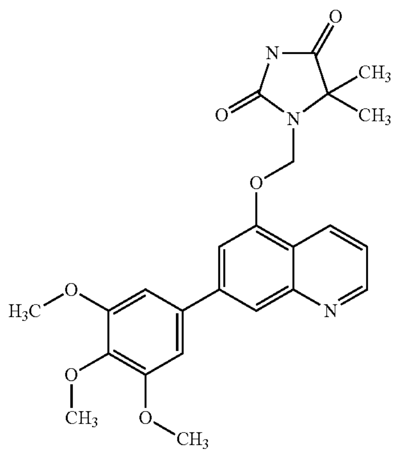 [SMILES: COc1cc(-c2cc(OCN3C(=O)NC(=O)C3(C)C)c3cccnc3c2)cc(OC)c1OC] | | | — | 0.4000 |
| 24 | 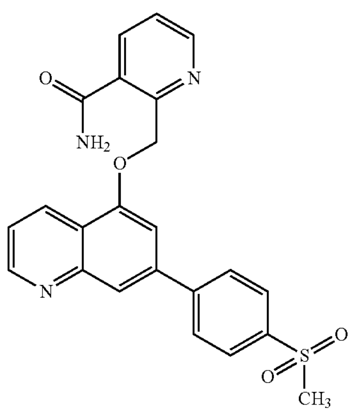 [SMILES: CS(=O)(=O)c1ccc(-c2cc(OCc3ncccc3C(N)=O)c3cccnc3c2)cc1] | | | — | 0.0027 |
| 25 | 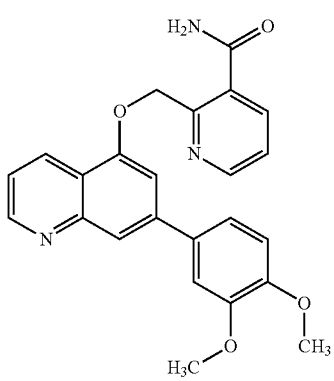 [SMILES: COc1ccc(-c2cc(OCc3ncccc3C(N)=O)c3cccnc3c2)cc1OC] | | | — | 0.0006 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 26 | 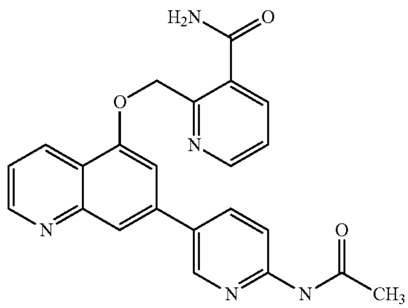 [SMILES: CC(=O)Nc1ccc(-c2cc(OCc3ncccc3C(N)=O)c3cccnc3c2)cn1] | | | — | 0.0142 |
| 27 | Chiral | | | — | 0.0551 |
| 28 | 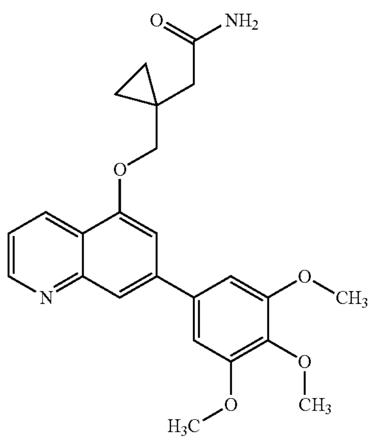 [SMILES: COc1cc(-c2cc(OCC3(CC(N)=O)CC3)c3cccnc3c2)cc(OC)c1OC] | | | — | 0.4086 |
| 29 | Chiral | | | — | 0.0003 |
| 30 | Chiral | | | — | 0.0018 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 31 | Chiral | | | — | 0.0025 |
| 32 | 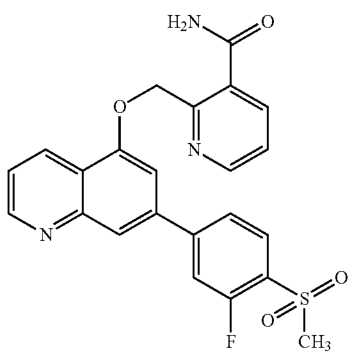 [SMILES: CS(=O)(=O)c1ccc(-c2cc(OCc3ncccc3C(N)=O)c3cccnc3c2)cc1F] | | | — | 0.0155 |
| 33 | Chiral | | | — | 0.0007 |
| 34 | Chiral | | | — | 0.0004 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 35 | 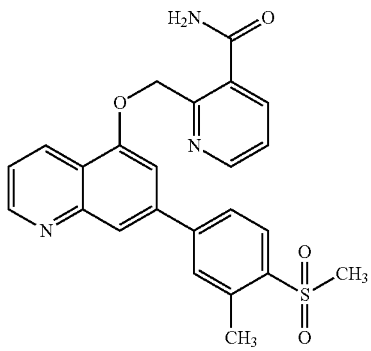 [SMILES: Cc1cc(-c2cc(OCc3ncccc3C(N)=O)c3cccnc3c2)ccc1S(C)(=O)=O] | | | — | 0.0017 |
| 36 | 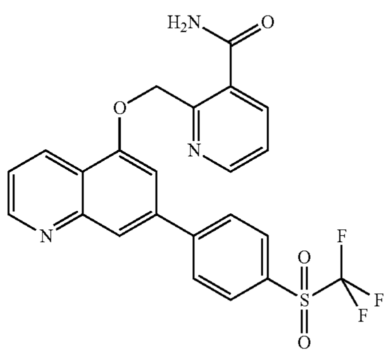 [SMILES: NC(=O)c1cccnc1COc1cc(-c2ccc(S(=O)(=O)C(F)(F)F)cc2)cc2ncccc12] | | | — | 0.0118 |
| 37 | 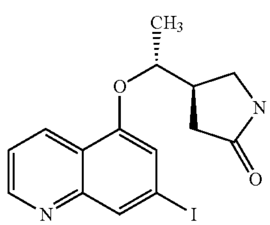 | | | — | 0.0319 |
| 38 | 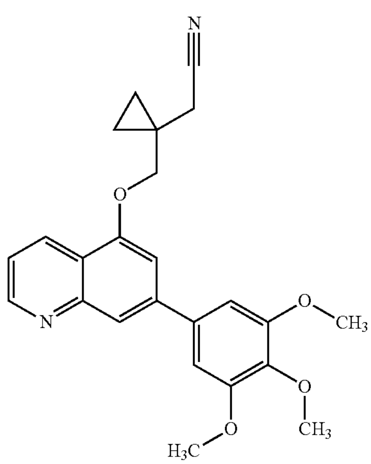 [SMILES: COc1cc(-c2cc(OCC3(CC#N)CC3)c3cccnc3c2)cc(OC)c1OC] | | | — | 0.5031 |

TABLE 1-continued
| No. | Structure | R¹ | R² | IC$_{50}$-value (+0.2% HSA in μM) | IC$_{50}$-value (+0.2% BSA in μM) |
|---|---|---|---|---|---|
| 39 | 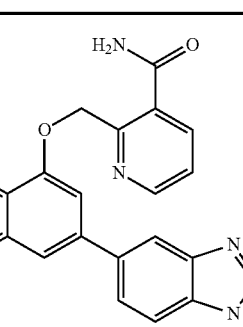 | 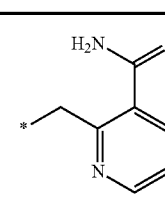 | 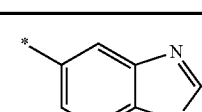 | — | 0.0040 |
| 40 | 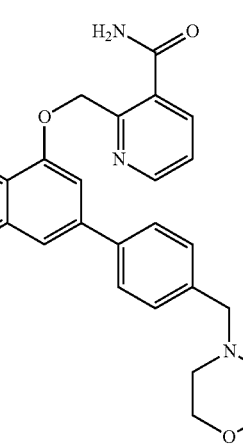 | 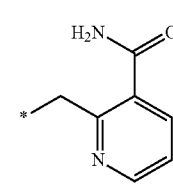 | 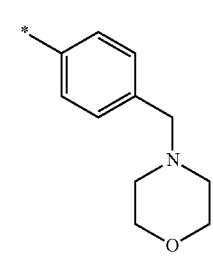 [SMILES: *c1ccc(CN2CCOCC2)cc1] | 0.0012 | 0.0034 |
| 41 | 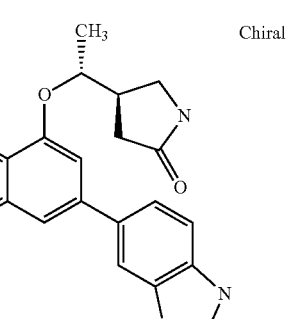 Chiral | 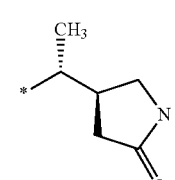 | 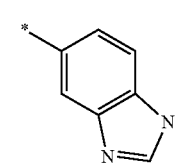 | — | 0.0003 |
| 42 | 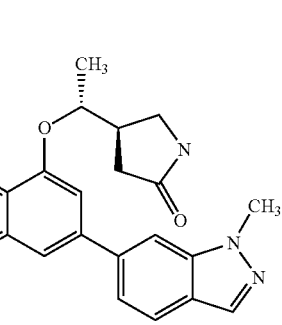 Chiral | 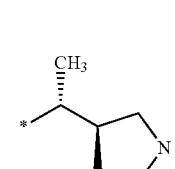 | 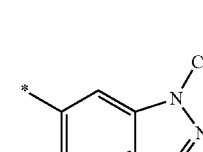 | — | 0.0009 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 43 | (chiral structure) | (chiral pyrrolidinone with CH₃) | 4-(morpholinomethyl)phenyl | — | 0.0003 |
| 44 | (structure) | 2-(CH₂-)-3-carbamoylpyridine | 1-methyl-1H-indazol-6-yl | — | 0.0010 |
| 45 | (structure) | 2-(CH₂-)-3-carbamoylpyridine | 6-morpholinopyridin-3-yl | — | 0.0016 |
| 46 | (structure) | 2-(CH₂-)-3-carbamoylpyridine | 1-methyl-1H-pyrazol-4-yl | — | 0.0020 |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 47 | 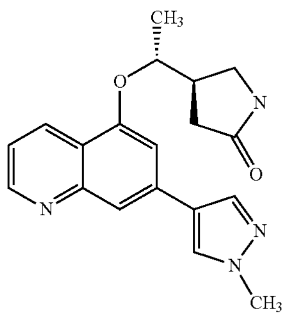 | | | — | 0.0002 |
| 48 | 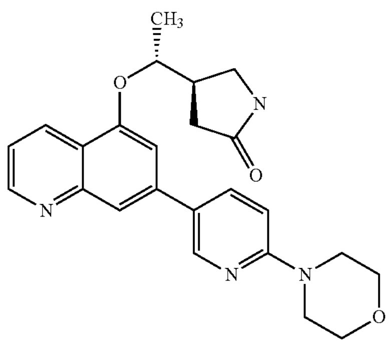 | | | — | 0.0001 |
| 49 | 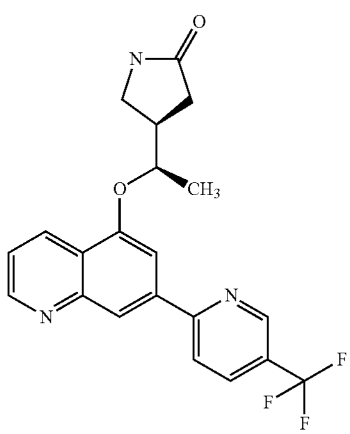 | | | — | 0.0005 |
| 50 | 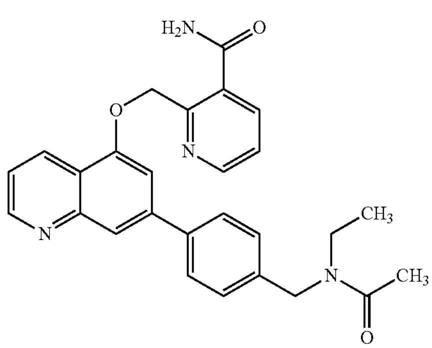 [SMILES: CCN(Cc1ccc(-c2cc(OCc3ncccc3C(N)=O)c3cccnc3c2)cc1)C(C)=O] | | | — | 0.0016 |

TABLE 1-continued

| No. | Structure | R¹ | R² | IC₅₀-value (+0.2% HSA in μM) | IC₅₀-value (+0.2% BSA in μM) |
|---|---|---|---|---|---|
| 51 | (Chiral structure) | (Chiral) | | — | 0.0000 |
| 52 | 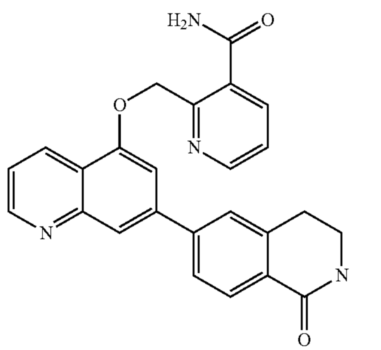 [SMILES: NC(=O)c1cccnc1COc1cc(-c2ccc3c(c2)CCNC3=O)cc2ncccc12] | | | — | 0.0077 |
| 53 | (Chiral structure) | (Chiral) | | — | 0.0009 |
| 54 | 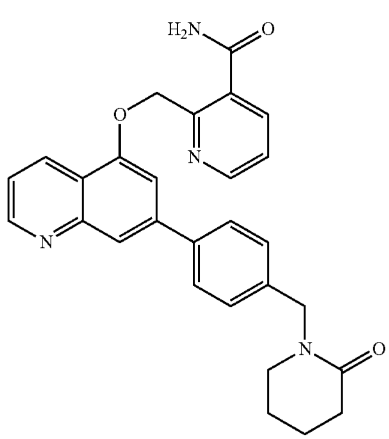 [SMILES: NC(=O)c1cccnc1COc1cc(-c2ccc(CN3CCCCC3=O)cc2)cc2ncccc12] | | | — | 0.0022 |

TABLE 1-continued

| No. | Structure | R¹ | R² | IC$_{50}$-value (+0.2% HSA in μM) | IC$_{50}$-value (+0.2% BSA in μM) |
| --- | --- | --- | --- | --- | --- |
| 55 | Chiral | | | — | 0.0003 |
| 56 | Chiral | | | — | 0.0014 |
| 57 | 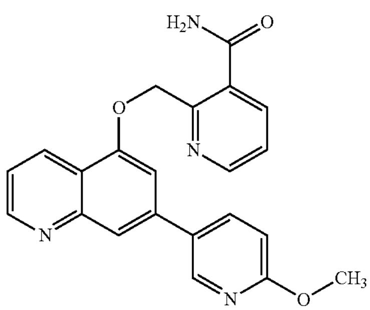 [SMILES: COc1ccc(-c2cc(OCc3ncccc3C(N)=O)c3cccnc3c2)cn1] | | | — | 0.0223 |
| 58 | 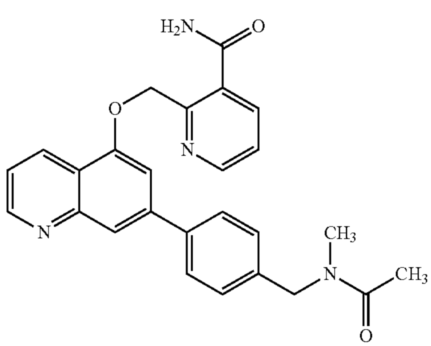 [SMILES: CC(=O)N(C)Cc1ccc(-c2cc(OCc3ncccc3C(N)=O)c3cccnc3c2)cc1] | | | — | 0.0016 |

TABLE 1-continued

| No. | Structure | R¹ | R² | IC₅₀-value (+0.2% HSA in μM) | IC₅₀-value (+0.2% BSA in μM) |
|---|---|---|---|---|---|
| 59 | 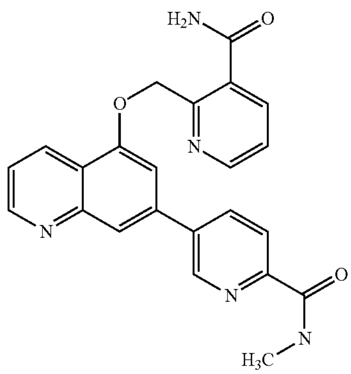 [SMILES: CNC(=O)c1ccc(-c2cc(OCc3ncccc3C(N)=O)c3cccnc3c2)cn1] | | | — | 0.0391 |
| 60 | 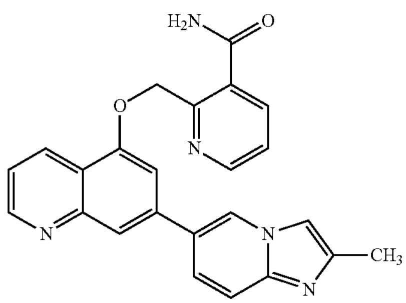 [SMILES: Cc1cn2cc(-c3cc(OCc4ncccc4C(N)=O)c4cccnc4c3)ccc2n1] | | | 0.0646 | — |
| 61 | Chiral | | | 0.0019 | — |
| 62 | 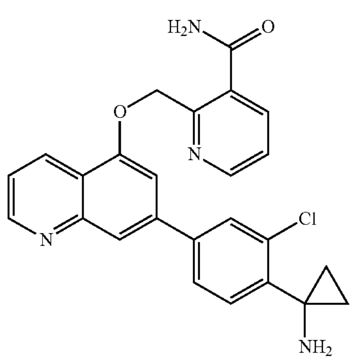 [SMILES: NC(=O)c1cccnc1COc1cc(-c2ccc(C3(N)CC3)c(Cl)c2)cc2ncccc12] | | | 0.0004 | — |

TABLE 1-continued

| No. | Structure | R¹ | R² | IC₅₀-value (+0.2% HSA in μM) | IC₅₀-value (+0.2% BSA in μM) |
|---|---|---|---|---|---|
| 63 | 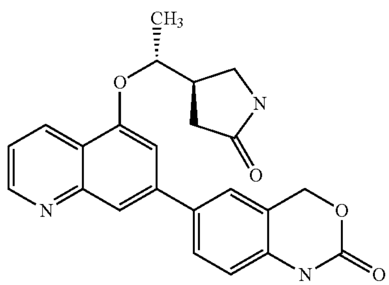 | Chiral | | 0.0001 | — |
| 64 | 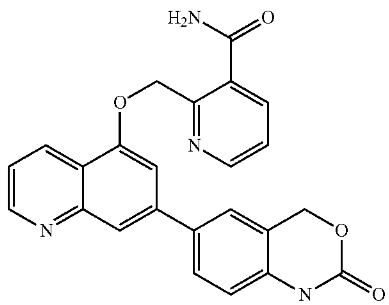 [SMILES: NC(=O)c1cccnc1COc1cc(-c2ccc3c(c2)COC(=O)N3)cc2ncccc12] | | | 0.0024 | — |
| 65 | 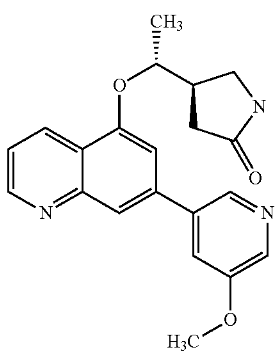 | Chiral | | 0.0159 | — |
| 66 | 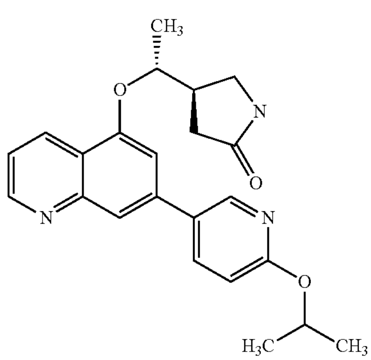 | Chiral | | 0.0010 | — |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 67 | (Chiral structure) | Chiral | (substituent) | 0.0079 | — |
| 68 | (Chiral structure) | Chiral | (substituent) | — | 0.0002 |
| 69 | (Chiral structure) | Chiral | (substituent) | 0.0003 | — |
| 70 | (structure) | (substituent) | (substituent) | 0.0355 | — |

TABLE 1-continued
| No. | Structure | R¹ | R² | IC₅₀-value (+0.2% HSA in μM) | IC₅₀-value (+0.2% BSA in μM) |
|---|---|---|---|---|---|
| 71 | 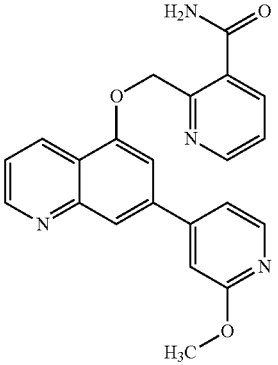 [SMILES: COc1cc(-c2cc(OCc3ncccc3C(N)=O)c3cccnc3c2)ccn1] | 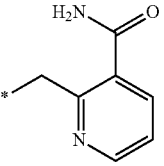 [SMILES: *Cc1ncccc1C(N)=O] | 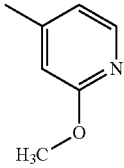 | 0.0795 | — |
| 72 | 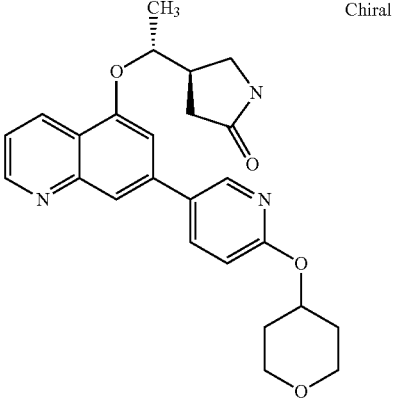 [SMILES: C[C@@H](Oc1cc(-c2ccc(OC3CCOCC3)nc2)cc2ncccc12)[C@H]1CNC(=O)C1] Chiral | 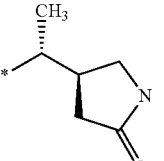 | 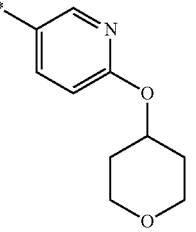 | 0.0013 | — |
| 73 | 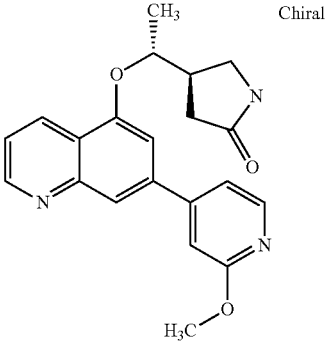 [SMILES: COc1cc(-c2cc(O[C@H](C)[C@H]3CNC(=O)C3)c3cccnc3c2)ccn1] Chiral | 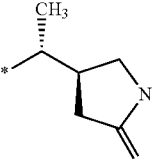 | 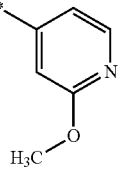 | 0.0031 | — |
| 74 | 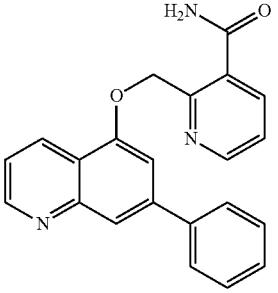 [SMILES: NC(=O)c1cccnc1COc1cc(-c2ccccc2)cc2ncccc12] | 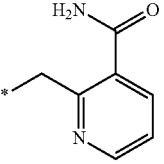 [SMILES: *Cc1ncccc1C(N)=O] | 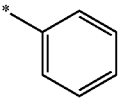 | 0.0463 | — |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 75 | 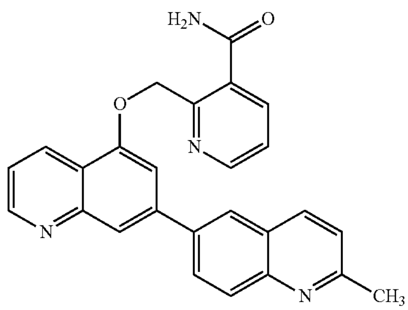 [SMILES: Cc1ccc2cc(-c3cc(OCc4ncccc4C(N)=O)c4cccnc4c3)ccc2n1] | | | 0.0151 | — |
| 76 | Chiral | | | 0.0015 | — |
| 77 | 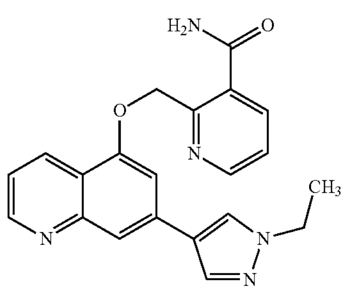 [SMILES: CCn1cc(-c2cc(OCc3ncccc3C(N)=O)c3cccnc3c2)cn1] | | | 0.0010 | — |
| 78 | Chiral | | | 0.0002 | — |

TABLE 1-continued

| No. | Structure | R¹ | R² | IC₅₀-value (+0.2% HSA in μM) | IC₅₀-value (+0.2% BSA in μM) |
|---|---|---|---|---|---|
| 79 | (structure) | (structure) | (structure) | 2.6326 | — |
| 80 | (structure) | (structure) | (structure) | 0.0632 | — |
| 81 | (structure) Chiral | (structure) | (structure) | 0.0016 | — |
| 82 | (structure) | (structure) | (structure) | 0.0081 | — |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 83 | 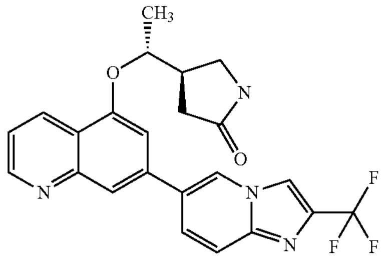 | Chiral | | 0.0053 | — |
| 84 | 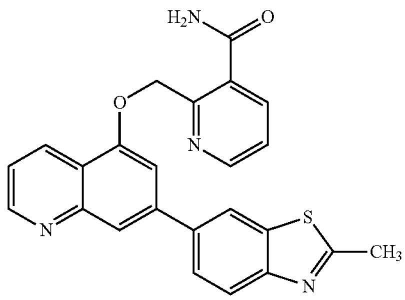 [SMILES: Cc1nc2ccc(-c3cc(OCc4ncccc4C(N)=O)c4cccnc4c3)cc2s1] | | | 0.0117 | — |
| 85 | 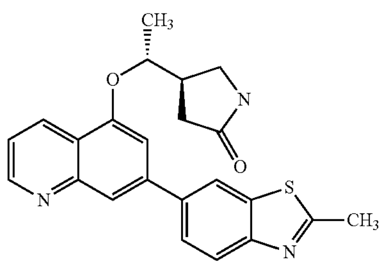 | Chiral | | 0.0002 | — |
| 86 | 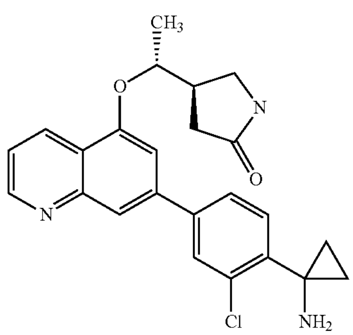 | Chiral | | 0.0002 | — |
| 87 | 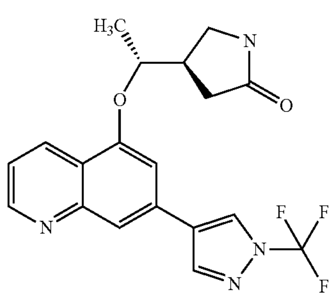 | Chiral | | 0.0014 | — |

TABLE 1-continued

| No. | Structure | R¹ | R² | IC₅₀-value (+0.2% HSA in μM) | IC₅₀-value (+0.2% BSA in μM) |
|---|---|---|---|---|---|
| 88 | 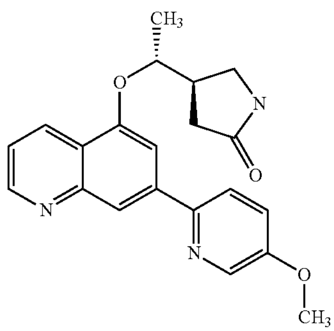 | Chiral | | 0.0003 | — |
| 89 | 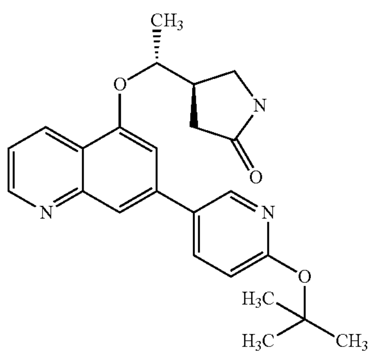 | Chiral | | 0.0026 | — |
| 90 | 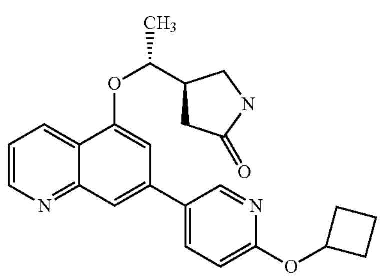 | Chiral | | 0.0006 | — |
| 91 | 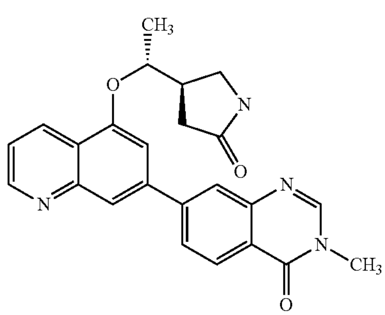 | Chiral | | 0.0036 | — |

TABLE 1-continued

| No. | Structure | R¹ | R² | IC₅₀-value (+0.2% HSA in μM) | IC₅₀-value (+0.2% BSA in μM) |
|---|---|---|---|---|---|
| 92 | 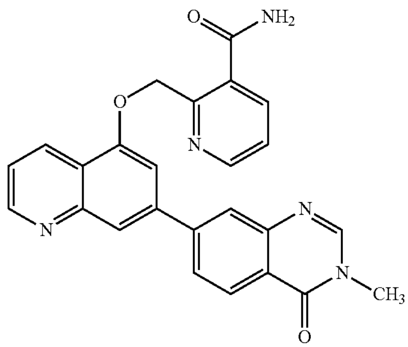 [SMILES: Cn1cnc2cc(-c3cc(OCc4ncccc4C(N)=O)c4cccnc4c3)ccc2c1=O] | | | 0.1049 | — |
| 93 | 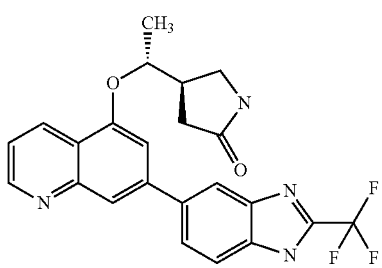 | Chiral | | 0.0004 | — |
| 94 | 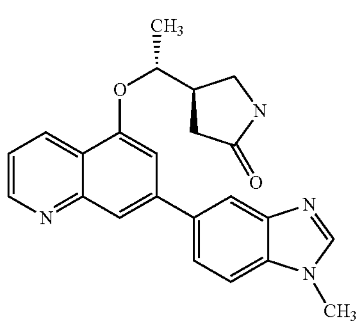 | Chiral | | 0.0003 | — |
| 95 | 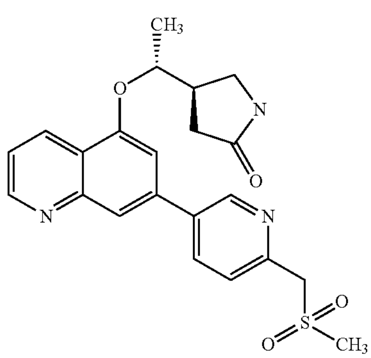 | Chiral | | 0.0011 | — |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 96 | 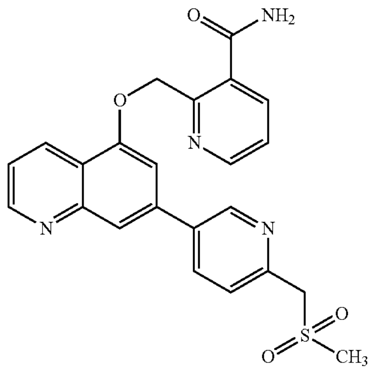 [SMILES: CS(=O)(=O)Cc1ccc(-c2cc(OCc3ncccc3C(N)=O)c3cccnc3c2)cn1] | | | 0.0343 | — |
| 97 | 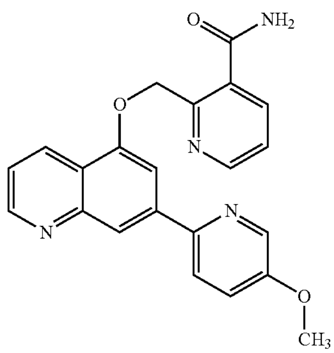 [SMILES: COc1ccc(-c2cc(OCc3ncccc3C(N)=O)c3cccnc3c2)nc1] | | | 0.0701 | — |
| 98 | 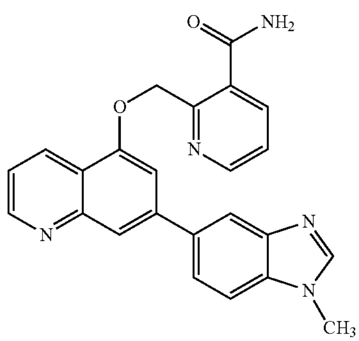 [SMILES: Cn1cnc2cc(-c3cc(OCc4ncccc4C(N)=O)c4cccnc4c3)ccc21] | | | 0.0167 | — |
| 99 | Chiral | | | 0.0274 | — |

TABLE 1-continued

| No. | Structure | R¹ | R² | IC₅₀-value (+0.2% HSA in μM) | IC₅₀-value (+0.2% BSA in μM) |
|-----|-----------|-----|-----|------|------|
| 100 | 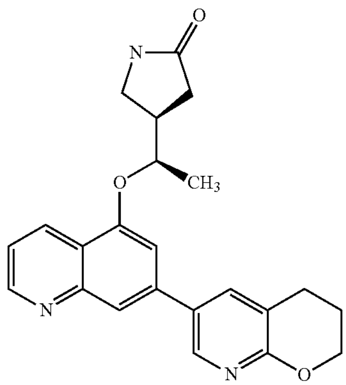 | Chiral | | 0.0009 | — |
| 101 | 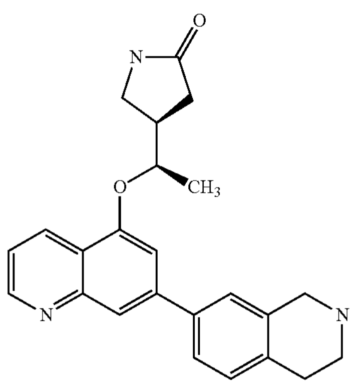 | Chiral | | 0.0004 | — |
| 102 | 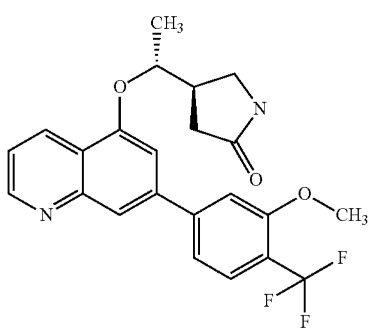 | Chiral | | 0.0045 | — |
| 103 | 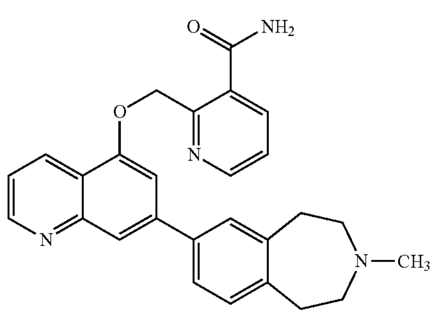 [SMILES: CN1CCc2ccc(-c3cc(OCc4ncccc4C(N)=O)c4cccnc4c3)cc2CC1] | | | 0.0211 | — |

TABLE 1-continued

| No. | Structure | R¹ | R² | IC₅₀-value (+0.2% HSA in μM) | IC₅₀-value (+0.2% BSA in μM) |
|---|---|---|---|---|---|
| 104 | 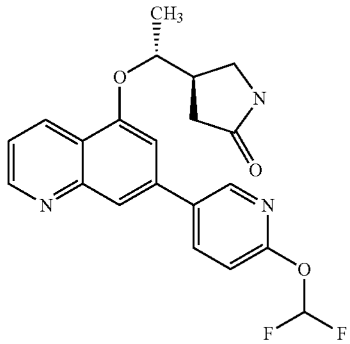 | Chiral | | 0.0054 | — |
| 105 | 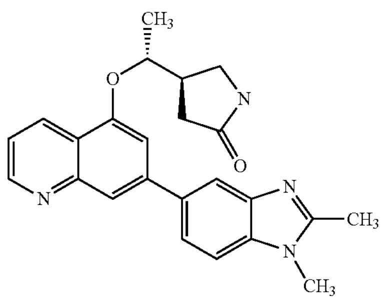 | Chiral | | 0.0002 | — |
| 106 | 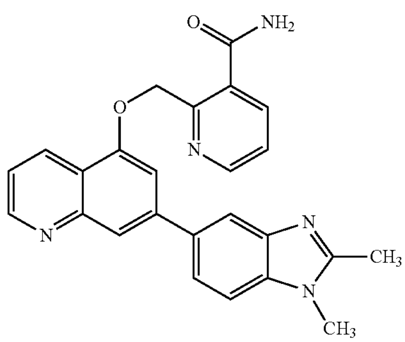 [SMILES: Cc1nc2cc(-c3cc(OCc4ncccc4C(N)=O)c4cccnc4c3)ccc2n1C] | | | 0.0013 | — |
| 107 | 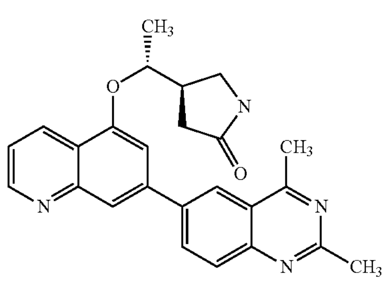 | Chiral | | 0.0049 | — |

TABLE 1-continued

| No. | Structure | R¹ | R² | IC₅₀-value (+0.2% HSA in μM) | IC₅₀-value (+0.2% BSA in μM) |
|---|---|---|---|---|---|
| 108 | 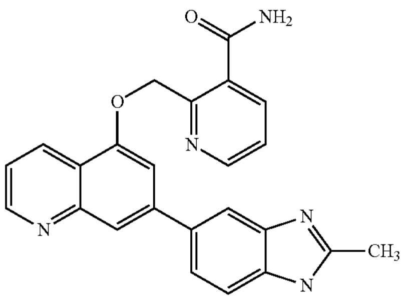 [SMILES: Cc1nc2cc(-c3cc(OCc4ncccc4C(N)=O)c4cccnc4c3)ccc2[nH]1] | | | 0.0025 | — |
| 109 | Chiral | | | 0.0004 | — |
| 110 | 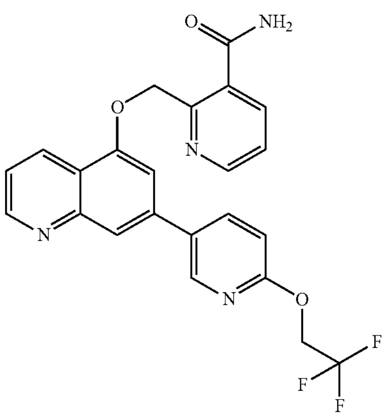 [SMILES: NC(=O)c1cccnc1COc1cc(-c2ccc(OCC(F)(F)F)nc2)cc2ncccc12] | | | 0.0787 | — |
| 111 | Chiral | | | 0.0034 | — |

TABLE 1-continued

| No. | Structure | R¹ | R² | IC₅₀-value (+0.2% HSA in μM) | IC₅₀-value (+0.2% BSA in μM) |
|-----|-----------|-----|-----|---------|---------|
| 112 | 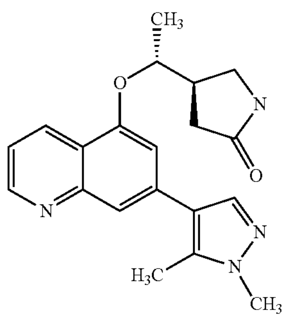 | | | 0.0012 | — |
| 113 | 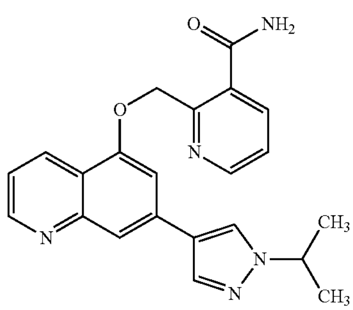 [SMILES: CC(C)n1cc(-c2cc(OCc3ncccc3C(N)=O)c3cccnc3c2)cn1] | | | 0.0005 | — |
| 114 | 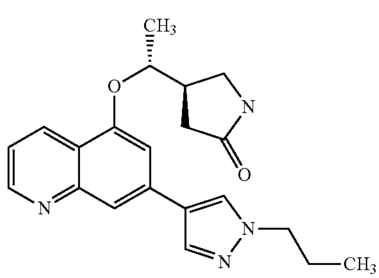 | | | 0.0000 | — |
| 115 | 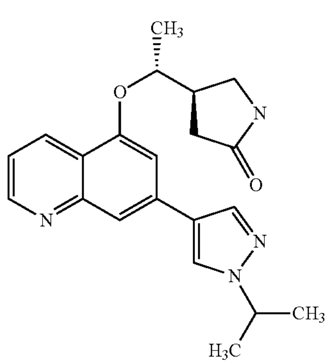 | | | 0.0000 | — |

TABLE 1-continued

| No. | Structure | | R¹ | R² | IC₅₀-value (+0.2% HSA in μM) | IC₅₀-value (+0.2% BSA in μM) |
|---|---|---|---|---|---|---|
| 116 | [structure] | Chiral | [structure] | [structure] | 0.0465 | — |
| 117 | [structure] | | [structure] | [structure] | 0.0015 | — |
| 118 | [structure] | Chiral | [structure] | [structure] | 0.0001 | — |
| 119 | [structure] | Chiral | [structure] | [structure] | 0.0001 | — |

TABLE 1-continued

| No. | Structure | R¹ | R² | IC$_{50}$-value (+0.2% HSA in μM) | IC$_{50}$-value (+0.2% BSA in μM) |
|---|---|---|---|---|---|
| 120 | [quinoline-pyrrolidinone structure with pyridine-CHF₂], Chiral | [H₃C-CH-pyrrolidinone structure] | [pyridine-CHF₂] | 0.0006 | — |

6. INDICATIONS

As has been found, the compounds of formula 1 are characterised by their range of applications in the therapeutic field. Particular mention should be made of those applications for which the compounds of formula 1 according to the invention are preferably used on the basis of their pharmaceutical activity as SYK-inhibitors. Examples include respiratory complaints, allergic diseases, osteoporosis, gastrointestinal diseases or complaints, immune or autoimmune diseases, allergic diseases, inflammatory diseases, e.g. inflammatory diseases of the joints, skin and eyes and diseases of the peripheral or central nervous system.

Particular mention should be made of the prevention and treatment of respiratory tract and pulmonary diseases which are accompanied by increased mucus production, inflammation and/or obstructive diseases of the airways. Examples of these include asthma, paediatric asthma, ARDS (Adult Respiratory Distress Syndrome), acute, allergic or chronic bronchitis, autoimmune haemolytic anemia, chronic obstructive bronchitis (COPD) (including the treatment of Rhinovirus-induced exacerbations), coughs, allergic rhinitis or sinusitis, allergic rhinoconjunctivitis, chronic rhinitis or sinusitis, alveolitis, farmers' lung, hyperreactive airways, infectious bronchitis or pneumonitis, bronchiectasis, pulmonary fibrosis, bronchial oedema, pulmonary oedema, pneumonia or interstitial pneumonia triggered by various causes such as aspiration, inhalation of toxic gases or bronchitis, pneumonia or interstitial pneumonia triggered by cardiac insufficiency, radiation, chemotherapy, cystic fibrosis or mucoviscidosis, alpha1-antitrypsin deficiency, artheriosclerosis and pulmonary hypertension.

The compounds according to the invention are preferably also suitable for the treatment of allergic diseases such as for example allergic rhinitis, allergic rhinoconjunctivitis, allergic conjunctivitis, and contact dermatitis, urticaria/angiooedema and allergic dermatitis.

Mention should also preferably be made of the treatment of inflammatory diseases of the gastrointestinal tract. Examples of these are Crohn's disease and ulcerative colitis.

The compounds according to the invention are preferably also suitable for the treatment of inflammatory diseases of the joints or inflammatory diseases of the skin and eyes. Examples of these are rheumatoid arthritis, antibody-based glomerulonephritis, psoriasis, Kawasaki syndrome, coeliac disease (sprue), artheriosclerosis (see Hilgendorf et al, Arterioscler Thromb Vasc Biol. 2011, vol. 31; pp. 1991-1999) and Wegener's granulomatosis.

The compounds according to the invention are preferably also suitable for the treatment of autoimmune diseases. Examples of these are hepatitis (autoimmune-based), lupus erythematodes, anti-phospholipid syndrome, Berger's disease, Evans's syndrome, immunohaemolytic anaemia, ITP (idiopathic thrombocytopenic purpura; adult, neonatal and paediatric), myasthenia gravis, Sjögren's syndrome, sclerodermy, Bullous pemphigoid and Pemphigus vulgaris.

The compounds according to the invention are preferably also suitable for the treatment of B-cell lymphomas, like chronic lymphocytic leukaemia and non Hodgkin's lymphomas or T cell lymphomas.

Mention may preferably also be made of the prevention and treatment of diseases of the peripheral or central nervous system. Examples of these are acute and chronic multiple sclerosis or non-familial lateral sclerosis.

Mention may preferably also be made of the prevention and treatment of osteoporotic diseases such as for example disease-associated osteopenia, osteoporosis and osteolytic diseases.

The present invention relates particularly preferably to the use of compounds of formula 1 for preparing a pharmaceutical composition for the treatment of diseases selected from among asthma, COPD, allergic rhinitis, Adult Respiratory Distress Syndrome, bronchitis, allergic dermatitis, contact dermatitis, ITP, rheumatoid arthritis and allergic rhinoconjunctivitis.

Most preferably, the compounds of formula 1 may be used for the treatment of a disease selected from among asthma, allergic rhinitis, rheumatoid arthritis, allergic dermatitis, pulmonary hypertension and COPD.

7. COMBINATIONS

The compounds of formula 1 may be used on their own or in conjunction with other active substances of formula 1 according to the invention. The compounds of formula 1 may optionally also be used in conjunction with other pharmacologically active substances. Preferably the active substances used here may be selected for example from among the betamimetics, anticholinergics, corticosteroids, NSAIDS, COX2-inhibitors (Coxibe), folic acid antagonists (or dihydrofolate reductase inhibitors), PDE4-inhibitors, LTD4-antagonists, EGFR-inhibitors, MRP4-inhibitors, dopamine agonists, H1-antihistamines, PAF-antagonists, iNos-inhibitors, HMG-CoA reductase inhibitors (statins), PI3-kinase-inhibitors, CCR3-antagonists, CCR2-antagonists, CCR1-antagonists, IKK2-inhibitors, A2a agonists, alpha-4-integrin-inhibitors, CRTH2-antagonists, histamine 1, combined H1/H3-antagonists, p38 kinase inhibitors, methylxanthines, ENaC-inhibitors, CXCR1-antagonists, CXCR2-antagonists, Bruton's tyrosine kinase inhibitors (BTK-inhibitors), Janus kinase-inhibitors (JAK-inhibitor), IA phosphoinositide-3-kinase delta-inhibitors (PI3K-delta-inhibitors), dihydroorotate dehydrogenase inhibitors, ICE-inhibitors, LTB4-antagonists, 5-LO antagonists, FLAP-antagonists. LTB4-antagonists; cromoglycine, dissociated glucocorticoid mimetics, anti-TNF-antibodies, TNF-receptor Fc, pegylated anti-TNF-Fab, Anti-IL6 receptor antibodies, Anti-CD20 antibodies, anti-GM-CSF antibodies, anti-CD46-antibodies, anti-IL-1-antibodies, anti-IL-2-antibodies, anti-IL-4-antibodies, anti-IL-5-antibodies, anti-IL-13-antibodies, anti-IL-4/IL-13-antibodies, or double or triple combinations thereof, such as for example combinations of one, two or three compounds selected from among the

- SYK-inhibitors of formula 1, corticosteroids, CCR1-antagonists, COX2-inhibitors (Coxibe) and folic acid antagonists such as methotrexate
- SYK-inhibitors of formula 1, corticosteroids, betamimetics, CCR3-antagonists and CRTH2-antagonists
- SYK-inhibitors of formula 1, betamimetics, corticosteroids, EGFR-inhibitors and PDE4-antagonists,
- SYK-inhibitors of formula 1, anticholinergics, betamimetics, corticosteroids, EGFR-inhibitors and PDE4-antagonists,
- SYK-inhibitors of formula 1, PDE4-inhibitors, corticosteroids and EGFR-inhibitors,
- SYK-inhibitors of formula 1, EGFR-inhibitors and PDE4-inhibitors,
- SYK-inhibitors of formula 1 and EGFR-inhibitors,
- SYK-inhibitors of formula 1, betamimetics and anticholinergics
- SYK-inhibitors of formula 1, anticholinergics, betamimetics, corticosteroids and PDE4-inhibitors,
- SYK-inhibitors of formula 1, anticholinergics, betamimetics, corticosteroids, iNOS inhibitors, HMG-CoA reductase inhibitors.

Combinations of three active substances each taken from one of the above-mentioned categories of compounds are also an object of the invention.

Suitable betamimetics used are preferably compounds selected from among arformoterol, carmoterol, formoterol, indacaterol, salmeterol, albuterole, bambuterol, bitolterol, broxaterol, carbuterol, clenbuterol, fenoterol, hexoprenalin, ibuterol, isoetharin, isoprenalin, levosalbutamol, mabuterol, meluadrin, metaproterenol, milveterol, orciprenalin, pirbuterol, procaterol, reproterol, rimiterol, ritodrin, salmefamol, soterenol, sulphonterol, terbutalin, tiaramide, tolubuterol, zinterol, 6-Hydroxy-8-{1-hydroxy-2-[2-(4-methoxy-phenyl)-1,1-dimethyl-ethylamino]-ethyl}-4H-benzo[1,4]oxazine-3-one; 8-{2-[2-(2,4-Difluor-phenyl)-1,1-dimethyl-ethylamino]-1-hydroxy-ethyl}-6-hydroxy-4H-benzo[1,4]oxazine-3-one; 8-{2-[2-(3,5-Difluor-phenyl)-1,1-dimethyl-ethylamino]-1-hydroxy-ethyl}-6-hydroxy-4H-benzo[1,4]oxazine-3-one; 8-{2-[2-(4-Ethoxy-phenyl)-1,1-dimethyl-ethylamino]-1-hydroxy-ethyl}-6-hydroxy-4H-benzo[1,4]oxazine-3-one; 8-{2-[2-(4-Fluor-phenyl)-1,1-dimethyl-ethylamino]-1-hydroxy-ethyl}-6-hydroxy-4H-benzo[1,4]oxazine-3-one; N-(5-{2-[3-(4,4-Diethyl-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-fluoro-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[3-(4,4-Diethyl-6-methoxy-2-oxo-4H-benzo[d][1,3]oxazine-1-yl)-1,1-dimethyl-propylamino]-1-hydroxy-ethyl}-2-hydroxy-phenyl)-methansulfonamide; N-(5-{2-[1,1-Dimethyl-3-(2-oxo-4,4-dipropyl-4H-benzo[d][1,3]oxazine-1-yl)-propylamino]-1-hydroxy-ethyl}-2-hydroxy-phenyl)-methansulfonamide; 8-{2-[1,1-Dimethyl-3-(2-oxo-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(6-methyl-2-oxo-2,3-dihydro-benzoimidazole-1-yl)-propylamino]-1-hydroxy-ethyl}-6-hydroxy-4H-benzo[1,4]oxazine-3-one; 8-{2-[1,1-Dimethyl-3-(2-oxo-5-trifluormethyl-2,3-dihydro-benzoimidazol-1-yl)-propylamino]-1-hydroxy-ethyl}-6-hydroxy-4H-benzo[1,4]oxazine-3-one; 8-{2-[1,1-Dimethyl-3-(3-methyl-2-oxo-2,3-dihydro-benzoimidazol-1-yl)-propylamino]-1-hydroxy-ethyl}-6-hydroxy-4H-benzo[1,4]oxazine-3-one; N-[2-Hydroxy-5-((1R)-1-hydroxy-2-{2-[4-(2-hydroxy-2-phenyl-ethylamino)-phenyl]-ethylamino}-ethyl)-phenyl]-formamide; 8-Hydroxy-5-((1R)-1-hydroxy-2-{2-[4-(6-methoxy-biphenyl-3-ylamino)-phenyl]-ethylamino}-ethyl)-1H-quinoline-2-one; 8-Hydroxy-5-[(1R)-1-hydroxy-2-(6-phenethylamino-hexylamino)-ethyl]-1H-quinoline-2-one; 5-[(1R)-2-(2-{4-[4-(2-Amino-2-methyl-propoxy)-phenylamino]-phenyl}-ethylamino)-1-hydroxy-ethyl]-8-hydroxy-1H-quinoline-2-one; [3-(4-{6-[(2R)-2-Hydroxy-2-(4-hydroxy-3-hydroxymethyl-phenyl)-ethylamino]-hexyloxy}-butyl)-5-methyl-phenyl]-urea; 4-((1R)-2-{6-[2-(2,6-Dichlor-benzyloxy)-ethoxy]-hexylamino}-1-hydroxy-ethyl)-2-hydroxymethyl-phenol; 3-(4-{6-[(2R)-2-Hydroxy-2-(4-hydroxy-3-hydroxymethyl-phenyl)-ethylamino]-hexyloxy}-butyl)-benzenesulfonamide; 3-(3-{7-[(2R)-2-Hydroxy-2-(4-hydroxy-3-hydroxymethyl-phenyl)-ethylamino]-heptyloxy}-propyl)-benzenesulfonamide; 4-((1R)-2-{6-[4-(3-Cyclopentanesulfonyl-phenyl)-butoxy]-hexylamino}-1-hydroxy-ethyl)-2-hydroxymethyl-phenol, 4-(2-{6-[2-(2,6-dichloro-benzyloxy)-ethoxy]-hexylamino}-1-hydroxy-ethyl)-2-hydroxymethyl-phenol; Vilanterol; N-1-Adamantanyl-2-{3-[(2R)-2-({(2R)-2-hydroxy-2-[4-hydroxy-3-(hydroxymethyl)phenyl]ethyl}amino)propyl]phenyl}acetamide; 2-(3-{2-[2-hydroxy-3-methanesulfonylamino-phenyl)-ethylamino]-propyl}-phenyl)-N-[4-(4-hydroxy-phenyl)-2-vinyl-penta-2,4-dienyl]-acetamide; (1R)-5-{2-[6-(2,2-Difluor-2-phenyl-ethoxy)-hexylamino]-1-hydroxy-ethyl}-8-hydroxy-1H-quinoline-2-one; (R,S)-4-(2-{[6-(2,2-Difluor-4-phenylbutoxy)hexyl]amino}-1-hydroxy-ethyl)-2-(hydroxymethyl)phenol; (R,S)-4-(2-{[6-(2,2-Difluor-2-phenylethoxy)hexyl]amino}-1-hydroxy-ethyl)-2-(hydroxymethyl)phenol; (R,S)-4-(2-{[4,4-Difluor-6-(4-phenylbutoxy)hexyl]amino}-1-hydroxy-ethyl)-2-(hydroxymethyl)phenol; (R,S)-4-(2-{[6-(4,4-Difluor-4-phenylbutoxy)hexyl]amino}-1-hydroxy-ethyl)-2-(hydroxymethyl)phenol; (R,S)-5-(2-{[6-(2,2-Difluor-2-phenylethoxy)hexyl]amino}-1-hydroxy-ethyl)-8-hydroxyquinoline-2(1H)-one; (R,S)-2-({6-[2,2-Difluor-2-(3-methylphenyl)ethoxy]hexyl}amino)-1-hydroxyethyl]-2-(hydroxymethyl)phenol; 4-(1R)-2-{[6-(2,2-Difluor-2-phenylethoxy)hexyl]amino}-1-hydroxyethyl)-2-(hydroxymethyl)phenol; (R,S)-2-(Hydroxymethyl)-4-(1-hydroxy-2-{[4,4,5I5-tetrafluor-6-(3-phenylpropoxy)hexyl]amino}ethyl)phenol; (R,S)-[5-(2-{[6-(2,2-Difluor-2- phenylethoxy)hexyl]amino}-1-hydroxy-ethyl)-2-hydroxyphenyl]formamide; (R,S)-4-[2-({6-[2-(3-Bromophenyl)-2,2-difluoroethoxy]hexyl}amino)-1-hydroxyethyl]-2-(hydroxymethyl)phenol; (R,S)—N-[3-(1,1-Difluor-2-{[6-({2-hydroxy-2-[4-hydroxy-3-(hydroxymethyl)phenyl]ethyl}amino)hexyl]oxy}ethyl)phenyl]-urea; 3-[3-(1,1-Difluor-2-{[6-({2-hydroxy-2-[4-hydroxy-3-(hydroxymethyl)phenyl]ethyl}-amino)hexyl]oxy}ethyl)phenyl]imidazolidine-2,4-dione; (R,S)-4-[2-({6-[2,2-Difluor-2-(3-methoxyphenyl)ethoxy]hexyl}amino)-1-hydroxyethyl]-2-(hydroxymethyl)phenol; 5-((1R)-2-{[6-(2,2-Difluor-2-phenylethoxy)hexyl]amino}-1-hydroxyethyl)-8-hydroxyquinoline-2(1H)-one; 4-((1R)-2-{[4,4-Difluor-6-(4-phenylbutoxy)hexyl]amino}-1-hydroxy-ethyl)-2-(hydroxymethyl)phenol; (R,S)-4-(2-{[6-(3,3-Difluor-3-phenylpropoxy)hexyl]amino}-1-hydroxy-ethyl)-2-(hydroxymethyl)phenol; (R,S)-(2-{[6-(2,2-Difluor-2-phenylethoxy)-4,4-difluorohexyl]amino}-1-hydroxyethyl)-2-(hydroxymethyl)phenol; (R,S)-4-(2-{[6-(2,2-Difluor-3-phenylpropoxy)hexyl]amino}-1-hydroxy ethyl)-2-(hydroxymethyl)phenol; 3-[2-(3-Chlor-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide; N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide; 7-[2-(2-{3-[2-(2-Chlor-phenyl)-ethylamino]-propylsulfanyl}-ethylamino)-1-hydroxy-ethyl]-4-hydroxy-3H-benzothiazol-2-one, optionally in the form of the racemates, enantiomers, diastereomers and optionally in the form of the pharmacologically acceptable acid addition salts, solvates or hydrates thereof.

According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate, preferably the hydrochloride, hydrobromide, hydrosulphate, hydrophosphate, hydrofumarate and hydromethanesulphonate. Of the above-mentioned acid addition salts the salts of hydrochloric acid, methanesulphonic acid, benzoic acid and acetic acid are particularly preferred according to the invention.

The anticholinergics used are preferably compounds selected from among
tiotropium salts, particularly the bromide salt, oxitropium salts, particularly the bromide salt, flutropium salts, particularly the bromide salt, ipratropium salts, particularly the bromide salt, Aclidinium salts, particularly the bromide salt, glycopyrronium salts, particularly the bromide salt, trospium salts, particularly the chloride salt, tolterodin, (3R)-1-Phenethyl-3-(9H-xanthene-9-carbonyloxy)-1-azoniabicyclo[2.2.2]octan-salts; 2,2-Diphenyl propionic acid tropenole ester-methobromide; 2,2-Diphenyl propionic acid scopine ester-methobromide; 2-Fluor-2,2-Diphenyl acetic acid scopine ester-methobromide; 2-Fluor-2,2-Diphenyl acetic acid tropenole ester-methobromide; 3,3',4,4'-Tetrafluor benzilic acid tropenole ester-methobromide; 3,3',4,4'-Tetrafluor benzilic acid scopine ester-methobromide; 4,4'-Difluor benzilic acid tropenole ester-methobromide; 4,4'-Difluor benzilic acid scopine ester-methobromide; 3,3'-Difluor benzilic acid tropenole ester-methobromide; 3,3'-Difluor benzilic acid scopine ester-methobromide; 9-Hydroxy-fluorene-9-carboxylic acid tropenole ester-methobromide; 9-Fluor-fluorene-9-carboxylic acid tropenole ester-methobromide; 9-Hydroxy-fluorene-9-carboxylic acid scopine ester-methobromide; 9-Fluor-fluorene-9-carboxylic acid scopine ester-methobromide; 9-Methyl-fluorene-9-carboxylic acid tropenole ester-methobromide; 9-Methyl-fluorene-9-carboxylic acid scopine ester-methobromide; Benzilic acid cyclopropyl tropine ester-methobromide; 2,2-Diphenyl propionic acid cyclopropyltropine ester-methobromide; 9-Hydroxy-xanthene-9-carboxylic acid cyclopropyltropine ester-methobromide; 9-Methyl-fluorene-9-carboxylic acid cyclopropyltropine ester-methobromide; 9-Methyl-xanthene-9-carboxylic acid cyclopropyltropine ester-methobromide; 9-Hydroxy-fluorene-9-carboxilic acid cyclopropyltropine ester-methobromide; 4,4'-Difluor benzilic acid methyl ester cyclopropyltropine ester-methobromide; 9-Hydroxy-xanthene-9-carboxylic acid tropenole ester-methobromide; 9-Hydroxy-xanthene-9-carboxylic acid scopine ester-methobromide; 9-Methyl-xanthene-9-carboxylic acid tropenole ester-methobromide; 9-Methyl-xanthene-9-carboxylic acid scopine ester-methobromide; 9-Ethyl-xanthene-9-carboxylic acid tropenole ester-methobromide; 9-Difluormethyl-xanthene-9-carboxylic acid tropenole ester-methobromide; 9-Hydroxymethyl-xanthene-9-carboxylic acid scopine ester-methobromide;

3-[2-(3-Chloro-phenyl)-ethoxy]-N-(2-diethylamino-ethyl)-N-{2-[2-(4-hydroxy-2-oxo-2,3-dihydro-benzothiazol-7-yl)-ethylamino]-ethyl}-propionamide;

N-(2-Diethylamino-ethyl)-N-{2-[2-(4-hydroxy-2-oxo-2,3-dihydro-benzothiazol-7-yl)-ethylamino]-ethyl}-3-(2-naphthalen-1-yl-ethoxy)-propionamide;

7-[2-(2-{3-[2-(2-Chloro-phenyl)-ethylamino]-propylsulfanyl}-ethylamino)-1-hydroxy-ethyl]-4-hydroxy-3H-benzothiazol-2-one and Darotropium;

optionally in the form of the solvates or hydrates thereof.

In the above-mentioned salts the cations tiotropium, oxitropium, flutropium, ipratropium, glycopyrronium, aclidinium and trospium are the pharmacologically active ingredients. As anions, the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts, the chlorides, bromides, iodides and methanesulphonate are particularly preferred.

Of particular importance is tiotropium bromide. In the case of tiotropium bromide the pharmaceutical combinations according to the invention preferably contain it in the form of the crystalline tiotropium bromide monohydrate, which is known from WO 02/30928. If the tiotropium bromide is used in anhydrous form in the pharmaceutical combinations according to the invention, it is preferable to use anhydrous crystalline tiotropium bromide, which is known from WO 03/000265.

Corticosteroids used here are preferably compounds selected from among
beclomethasone, betamethasone, budesonide, butixocort, ciclesonide, deflazacort, dexamethasone, etiprednole, flunisolide, fluticasone, loteprednole, mometasone, prednisolone, prednisone, rofleponide, triamcinolone, tipredane; Pregna-1,4-diene-3,20-dione, 6-fluoro-11-hydroxy-16,17-[(1-methylethylidene)bis(oxy)]-21-[[4-[(nitrooxy)methyl]benzoyl]oxy]-, (6-alpha,11-beta,16-alpha)- (9CI); 16,17-butylidenedioxy-6,9-difluoro-11-hydroxy-17-(methylthio)androst-4-en-3-one; 6,9-Difluor-17-[(2-furanylcarbonyl)oxy]-11-hydroxy-16-methyl-3-oxo-androsta-1,4-dien-17-carbothione acid (S)-fluoromethylester; (S)-fluoromethyl 6,9-difluoro-17-[(2-furanylcarbonyl)oxy]-11-hydroxy-16-methyl-3-oxo-androsta-1,4-diene-17-carbothionate; 6-alpha,9-alpha-difluoro-11-beta-hydroxy-16alpha-methyl-3-oxo-17alpha-(2,2,3,3-tetramethylcyclopropylcarbonyl)oxy-androsta-1,4-diene-17beta-carboxylic acid cyanomethyl ester, each optionally in the form of the racemates, enantiomers or diastereomers thereof and optionally in the form of the salts and derivatives, solvates and/or hydrates thereof.

Particularly preferably the steroid is selected from among budesonide, fluticasone, mometasone, ciclesonide and (S)-fluoromethyl 6,9-difluoro-17-[(2-furanylcarbonyl)oxy]-11-hydroxy-16-methyl-3-oxo-androsta-1,4-diene-17-carbothionate, optionally in the form of the racemates, enantiomers or diastereomers thereof and optionally in the form of the salts and derivatives, solvates and/or hydrates thereof.

Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogen phosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, apremilast, arofyllin, atizoram, oglemilast, tetomilast; 5-[(N-(2,5-dichloro-3-pyridinyl)-carboxamide]-8-methoxy-Quinoline (D-4418); 5-[N-(3,5-dichloro-1-oxido-4-pyridinyl)-carboxamide]-8-methoxy-2-(trifluoromethyl)-Quinoline (D-4396 (Sch-351591)); N-(3,5-dichloropyrid-4-yl)-[1-(4-fluorobenzyl)-5-hydroxy-indol-3-yl]glyoxylic acid amide (AWD-12-281 (GW-842470)); 9-[(2-fluorophenyl)methyl]-N-methyl-2-(trifluoromethyl)-9H-Purin-6-amine (NCS-613); 4-[(2R)-2-[3-(cyclopentyloxy)-4-methoxyphenyl]-2-phenylethyl]-Pyridine (CDP-840); N-[(3R)-3,4,6,7-tetrahydro-9-methyl-4-oxo-1-phenylpyrrolo[3,2,1-jk][1,4]benzodiazepin-3-yl]-4-Pyridinecarboxamide (PD-168787); 4-[6,7-diethoxy-2,3-bis(hydroxymethyl)-1-naphthalenyl]-1-(2-methoxyethyl)-2(1H)-Pyridinone (T-440); 2-[4-[6,7-diethoxy-2,3-bis(hydroxymethyl)-1-naphthalenyl]-2-pyridinyl]-4-(3-pyridinyl)-1(2H)-Phthalazinone (T-2585); (3-(3-cyclopenyloxy-4-methoxybenzyl)-6-ethylamino-8-isopropyl-3H-purine (V-11294A); beta-[3-(cyclopentyloxy)-4-methoxyphenyl]-1,3-dihydro-1,3-dioxo-2H-Isoindole-2-propanamide (CDC-801); Imidazo[1,5-a]pyrido[3,2-e]pyrazine-6(5H)-one, 9-ethyl-2-methoxy-7-methyl-5-propyl-(D-22888); 5-[3-(cyclopentyloxy)-4-methoxyphenyl]-3-[(3-methylphenyl)methyl]-, (3S,5S)-2-Piperidinon (HT-0712); 4-[1-[3,4-bis(difluoromethoxy)phenyl]-2-(3-methyl-1-oxido-4-pyridinyl)ethyl]-alpha,alpha-bis(trifluoromethyl)-Benzenemethanol (L-826141); N-(3,5-Dichloro-1-oxo-pyridin-4-yl)-4-difluormethoxy-3-cyclopropylmethoxybenzamide; (−)p-[(4aR*,10bS*)-9-Ethoxy-1,2,3,4,4a,10b-hexahydro-8-methoxy-2-methylbenzo[s][1,6]naphthyridin-6-yl]-N,N-diisopropylbenzamide; (R)-(+)-1-(4-Brombenzyl)-4-[(3-cyclopentyloxy)-4-methoxyphenyl]-2-pyrrolidon; 3-(Cyclopentyloxy-4-methoxyphenyl)-1-(4-N'-[N-2-cyano-5-methyl-isothioureido]benzyl)-2-pyrrolidon; cis[4-Cyano-4-(3-cyclopentyloxy-4-methoxyphenyl)cyclohexan-1-carboxylic acid]; 2-carbomethoxy-4-cyano-4-(3-cyclopropylmethoxy-4-difluoromethoxyphenyl)cyclohexan-1-one; cis[4-Cyano-4-(3-cyclopropylmethoxy-4-difluormethoxyphenyl)cyclohexan-1-ol]; (R)-(+)-Ethyl[4-(3-cyclopentyloxy-4-methoxyphenyl)pyrrolidin-2-yliden]acetat; (S)-(−)-Ethyl[4-(3-cyclopentyloxy-4-methoxyphenyl)pyrrolidin-2-yliden]acetat; 9-Cyclopentyl-5,6-dihydro-7-ethyl-3-(2-thienyl)-9H-pyrazolo[3,4-c]-1,2,4-triazolo[4,3-a]pyridin; 9-Cyclopentyl-5,6-dihydro-7-ethyl-3-(tert-butyl)-9H-pyrazolo[3,4-c]-1,2,4-triazolo[4,3-a]pyridin,
optionally in the form of the racemates, enantiomers or diastereomers and optionally in the form of the pharmacologically acceptable acid addition salts, solvates and/or hydrates thereof.

By acid addition salts with pharmacologically acceptable acids which the above-mentioned PDE4-inhibitors might be in a position to form are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

CRTH2 antagonists which may be used are preferably compounds selected from among Ramatroban, Setipiprant, Laropiprant and
ODC-9101 (2-(1-ethyl-5-fluoro-2-methyl-1H-indole-3-ylmethyl)-quinoline; see www.chemietek.com/products.aspx?pid=132), optionally in the form of the racemates, enantiomers or diastereomers and optionally in the form of the pharmacologically acceptable acid addition salts, solvates and/or hydrates thereof.

CCR3 antagonists which may be used are preferably compounds selected from among 1-(4-acetyl-benzyl)-3-[4-(3,4-dichloro-benzyl)-morpholin-2-ylmethyl]-urea (GW766994)

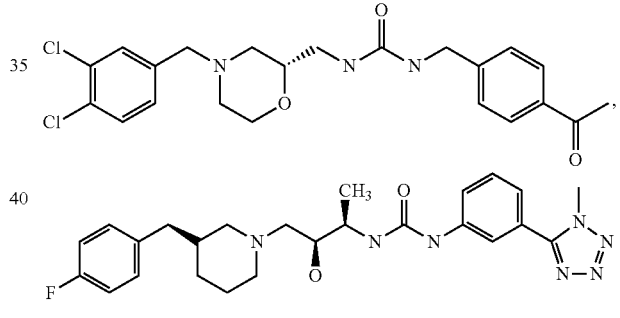

(BMS 639623), AZD 1744, AZD 3778 and YM-344031 as disclosed in Bioorganic & Medicinal Chemistry Letters (2008), 18(2), 576-585.

NSAIDS which may be used are preferably compounds selected from among Aceclofenac, Acemetacin, Acetylsalicylsaure, Alclofenac, Alminoprofen, Amfenac, Ampiroxicam, Antolmetinguacil, Anirolac, Antrafenin, Azapropazon, Benorilat, Bermoprofen, Bindarit, Bromfenac, Bucloxinsaure, Bucolom, Bufexamac, Bumadizon, Butibufen, Butixirat, Carbasalatcalcium, Carprofen, Cholin Magnesium Trisalicylat, Celecoxib, Cinmetacin, Cinnoxicam, Clidanac, Clobuzarit, Deboxamet, Dexibuprofen, Dexketoprofen, Diclofenac, Diflunisal, Droxicam, Eltenac, Enfenaminsaure, Etersalat, Etodolac, Etofenamat, Etoricoxib, Feclobuzon, Felbinac, Fenbufen, Fenclofenac, Fenoprofen, Fentiazac, Fepradinol, Feprazon, Flobufen, Floctafenin, Flufenaminsaure, Flufenisal, Flunoxaprofen, Flurbiprofen, Flurbiprofenaxetil, Furofenac, Furprofen, Glucametacin, Ibufenac, Ibuprofen, Indobufen, Indometacin, Indometacinfarnesil, Indoprofen, Isoxepac, Isoxicam, Ketoprofen, Ketorolac, Lobenzarit, Lonazolac, Lornoxicam, Loxoprofen, Lumiracoxib, Meclofenaminsaure, Meclofen, Mefenaminsaure, Meloxicam, Mesalazin, Miroprofen, Mofezolac, Nabumeton, Naproxen, Nifluminsaure, Olsalazin, Oxaprozin, Oxipinac, Oxyphenbutazon, Parecoxib, Phenylbutazon, Pelubiprofen, Pimeprofen, Pirazolac, Priroxicam, Pirprofen, Pranoprofen, Prifelon, Prinomod, Proglumetacin, Proquazon, Protizininsaure, Rofecoxib, Romazarit, Salicylamid, Salicylsaure, Salmistein, Salnacedin, Salsalat, Sulindac, Sudoxicam, Suprofen, Talniflumat, Tenidap, Tenosal, Tenoxicam, Tepoxalin, Tiaprofensaure, Taramid, Tilnoprofenarbamel, Timegadin, Tinoridin, Tiopinac, Tolfenaminsaure, Tolmetin, Ufenamat, Valdecoxib, Ximoprofen, Zaltoprofen and Zoliprofen.

COX2-inhibitors (Coxibe) which may be used are preferably compounds selected from among Celecoxib, Meloxicam, Etoricoxib, Lumiracoxib, Parecoxib, Rofecoxib and Valdecoxib.

Folic acid antagonists (or dihydrofolate reductase inhibitors) which may be used are preferably compounds selected from among methotrexate, trimethoprim, brodimoprim, pemetrexed and iclaprim.

A CCR1 antagonist which may be used for combination with the SYK inhibitors of formula 1 is preferably selected from among CCX354 (GSK) and BMS-817399 (BMS).

A Bruton's tyrosine kinase inhibitor (BTK-inhibitors) which may be combined with the SYK-inhibitors of formula I is preferably selected from among PCI-32765 (Pharmacyclic, see Honigberg et al, PNAS, (2010), vol. 107, No. 29, pp. 13075-13080), AVL-292 (Avila) and 6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one (=RN486) (Roche), see Hu Daigen et al. JPET 341: 90-103, 2012).

A Janus kinase-inhibitors (JAK-inhibitor) which may be combined with the SYK-inhibitors of formula I is preferably selected from among GLPG-0634 (Abbott/Galapagos), Baricitinib (Lilly), VX-509 (Vertex) and Tofacitinib (Pfizer).

A IA phosphoinositide-3-kinase-delta inhibitors (PI3K-delta-inhibitors) which may be combined with the SYK-inhibitors of formula I is preferably selected from among Cal-101 (Calistoga) and GS-1101.

A dihydroorotate dehydrogenase inhibitor which may be combined with the SYK-inhibitors of formula I is preferably Leflunomid (Aventis).

Furthermore the SYK-inhibitors of formula I may be combined with either Hydroxychloroquine, Sulfasalizine or Abatacept (CTLA-41 g).

An anti-TNF-antibody which may be combined with the SYK-inhibitors of formula I is preferably selected from amgong Adalimumab and golimumab.

A TNF-receptor Fc which may be combined with the SYK-inhibitors of formula I is preferably Etanercept.

A pegylated anti-TNF-Fab which may be combined with the SYK-inhibitors of formula I is preferably certolizumab pegol.

An anti-IL6 receptor antibody which may be combined with the SYK-inhibitors of formula I is preferably selected from among Actemra and Roactemra.

An anti-CD20 antibody which may be combined with the SYK-inhibitors of formula I is preferably Rituximab.

LTD4-antagonists which may be used are preferably compounds selected from among montelukast, pranlukast, zafirlukast; (E)-8-[2-[4-[4-(4-Fluorophenyl)butoxy]phenyl]ethenyl]-2-(1H-tetrazol-5-yl)-4H-1-benzopyran-4-one (MEN-91507); 4-[6-Acetyl-3-[3-(4-acetyl-3-hydroxy-2-propylphenylthio)propoxy]-2-propylphenoxy]-butyric acid (MN-001); 1-(((R)-(3-(2-(6,7-Difluor-2-quinolinyl)ethenyl)phenyl)-3-(2-(2-hydroxy-2-propyl)phenyl)thio)methylcyclopropane-acetic acid; 1-(((1(R)-3(3-(2-(2,3-Dichlorthieno[3,2-b]pyridin-5-yl)-(E)-ethenyl)phenyl)-3-(2-(1-hydroxy-1-methylethyl)phenyl) propyl)thio)methyl)cyclopropane acetic acid; [2-[[2-(4-tert-Butyl-2-thiazolyl)-5-benzofuranyl]oxymethyl]phenyl]acetic acid, optionally in the form of the racemates, enantiomers or diastereomers, optionally in the form of the pharmacologically acceptable acid addition salts and optionally in the form of the salts and derivatives, solvates and/or hydrates thereof.

By acid addition salts with pharmacologically acceptable acids which the LTD4-antagonists may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate. By salts or derivatives which the LTD4-antagonists may be capable of forming are meant, for example: alkali metal salts, such as, for example, sodium or potassium salts, alkaline earth metal salts, sulphobenzoates, phosphates, isonicotinates, acetates, propionates, dihydrogen phosphates, palmitates, pivalates or furoates.

The EGFR-inhibitors used are preferably compounds selected from among 4-[(3-chloro-4-fluorophenyl)amino]-6-{[4-(morpholine-4-yl)-1-oxo-2-butene-1-yl]amino}-7-cyclopropylmethoxy-quinazoline, 4-[(3-chloro-4-fluorophenyl)amino]-6-{[4-(N,N-diethylamino)-1-oxo-2-butene-1-yl]amino}-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopropylmethoxy-quinazoline, 4-[(R)-(1-phenyl-ethyl)amino]-6-{[4-(morpholine-4-yl)-1-oxo-2-butene-1-yl]amino}-7-cyclopentyloxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-cyclopropylmethoxy-quinazoline, 4-[(3-chloro-4-fluoro-phenyl)amino]-6-{[4-((R)-6-methyl-2-oxo-morpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholine-4-yl)-1-oxo-2-butene-1-yl]amino}-7-cyclopropylmethoxy-quinazoline, 4-[(3-chloro-4-fluoro-phenyl)amino]-6-[2-((S)-6-methyl-2-oxo-morpholine-4-yl)-ethoxy]-7-methoxy-quinazoline, 4-[(3-chloro-4-fluorophenyl)amino]-6-({4-[N-(2-methoxyethyl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2-butene-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-butene-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-butene-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(R)-(1-Phenyl-ethyl)amino]-6-({4-[N-(2-methoxy-ethyl)-N-methyl-amino]-1-oxo-2-butene-1-yl}amino)-7-cyclopropylmethoxy-quinazoline, 4-[(R)-(1-Phenyl-ethyl)amino]-6-({4-[N-(tetrahydropyran-4-yl)-N-methyl-amino]-1-oxo-2-butene-1-yl}amino)-7-cyclopropylmethoxy-quinazoline, 4-[(3-chloro-4-fluorophenyl)amino]-6-{[4-(N,N-dimethylamino)-1-oxo-2- butene-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-butene-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-butene-1-yl}amino)-7-cyclopentyloxy-quinazoline, 4-[(3-chloro-4-fluorophenyl)amino]-6-{[4-(N-cyclopropyl-N-methyl-amino)-1-oxo-2-butene-1-yl]amino}-7-cyclopentyloxy-quinazoline, 4-[(3-chloro-4-fluorophenyl)amino]-6-{[4-(N,N-dimethylamino)-1-oxo-2-butene-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-butene-1-yl]amino}-7-[(S)-(tetrahydrofuran-2-yl)methoxy]-quinazoline, 4-[(3-ethynyl-phenyl)amino]-6.7-bis-(2-methoxy-ethoxy)-quinazoline, 4-[(3-chloro-4-fluorophenyl)amino]-7-[3-(morpholine-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-butene-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholine-4-yl)-1-oxo-2-butene-1-yl]amino}-7-methoxy-quinazoline, 4-[(3-chloro-4-fluorophenyl)amino]-6-{[4-(morpholine-4-yl)-1-oxo-2-butene-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-butene-1-yl}amino)-7-[(tetrahydrofuran-2-yl)methoxy]-quinazoline, 4-[(3-ethynyl-phenyl)amino]-6-{[4-(5.5-dimethyl-2-oxo-morpholine-4-yl)-1-oxo-2-butene-1-yl]amino}-quinazoline, 4-[(3-chloro-4-fluoro-phenyl)amino]-6-[2-(2.2-dimethyl-6-oxo-morpholine-4-yl)-ethoxy]-7-methoxy-quinazoline, 4-[(3-chloro-4-fluoro-phenyl)amino]-6-[2-(2.2-dimethyl-6-oxo-morpholine-4-yl)-ethoxy]-7-[(R)-(tetrahydrofuran-2-yl)methoxy]-quinazoline, 4-[(3-chloro-4-fluoro-phenyl)amino]-7-[2-(2.2-dimethyl-6-oxo-morpholine-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholine-4-yl)-piperidine-1-yl]-ethoxy}-7-methoxy-quinazoline, 4-[(3-chloro-4-fluoro-phenyl)amino]-6-[1-(tert.-butyloxycarbonyl)-piperidine-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidine-4-yloxy)-7-methoxy-quinazoline, 4-[(3-chloro-4-fluoro-phenyl)amino]-6-{1-[(morpholine-4-yl)carbonyl]-piperidine-4-yloxy}-7-methoxy-quinazoline, 4-[(3-chloro-4-fluoro-phenyl)amino]-6-{1-[(methoxymethyl)carbonyl]-piperidine-4-yloxy}-7-methoxy-quinazoline, 4-[(3-chloro-4-fluoro-phenyl)amino]-6-(piperidine-3-yloxy)-7-methoxy-quinazoline, 4-[(3-chloro-4-fluoro-phenyl)amino]-6-[1-(2-acetylamino-ethyl)-piperidine-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholine-4-yl)carbonylamino]-cyclohexan-1-yloxy}-7-methoxy-quinazoline, 4-[(3-chloro-4-fluoro-phenyl)amino]-6-{trans-4-[(morpholine-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidine-1-yl)carbonyl]-piperidine-4-yloxy}-7-methoxy-quinazoline, 4-[(3-chloro-4-fluoro-phenyl)amino]-6-(1-aminocarbonylmethyl-piperidine-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholine-4-yl)carbonyl]-N-methyl-amino}-cyclohexan-1-yloxy)-7-methoxy-quinazolin; 4-{2-[4-(3-chloro-4-fluoro-phenylamino)-7-methoxy-quinazolin-6-yloxy]-ethyl}-6-methyl-morpholine-2-one, 4-{4-[4-(3-chloro-2-fluoro-phenylamino)-7-methoxy-quinazolin-6-yloxy]-cyclohexyl}-1-methyl-piperazine-2-one, 4-[(3-chloro-4-fluoro-phenyl)amino]-6-(cis-4-{N-[(morpholine-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidine-4-yloxy)-7-ethoxy-quinazoline, 4-[(3-chloro-4-fluoro-phenyl)amino]-6-(1-methanesulphonyl-piperidine-4-yloxy)-7-(2-methoxy-ethoxy)-quinazoline, 4-[(3-chloro-4-fluoro-phenyl)amino]-6-[1-(2-methoxy-acetyl)-piperidine-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidine-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidine-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazine-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholine-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidine-4-yloxy}-7-methoxy-quinazoline, 4-[(3-chloro-4-fluoro-phenyl)amino]-6-{1-[(morpholine-4-yl)carbonyl]-piperidine-4-yloxy}-7-(2-methoxy-ethoxy)-quinazoline, 4-[(3-ethynyl-phenyl)amino]-6-(1-acetyl-piperidine-4-yloxy)-7-methoxy-quinazoline, 4-[(3-ethynyl-phenyl)amino]-6-(1-methyl-piperidine-4-yloxy)-7-methoxy-quinazoline, 4-[(3-ethynyl-phenyl)amino]-6-(1-methanesulphonyl-piperidine-4-yloxy)-7-methoxy-quinazoline, 4-[(3-chloro-4-fluoro-phenyl)amino]-6-(1-methyl-piperidine-4-yloxy)-7(2-methoxy-ethoxy)-quinazoline, 4-[(3-chloro-4-fluoro-phenyl)amino]-6-(1-isopropyloxycarbonyl-piperidine-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidine-4-yloxy)-7-methoxy-quinazoline, 4-[(3-ethynyl-phenyl)amino]-6-[1-(2-methoxy-acetyl)-piperidine-4-yloxy]-7-methoxy-quinazoline, 4-[(3-ethynyl-phenyl)amino]-6-{1-[(morpholine-4-yl)carbonyl]- piperidine-4-yloxy}-7-methoxy-quinazoline, 4-[(3-chloro-4-fluoro-phenyl)amino]-6-{1-[(cis-2,6-dimethyl-morpholine-4-yl)carbonyl]-piperidine-4-yloxy}-7-methoxy-quinazoline, 4-[(3-chloro-4-fluoro-phenyl)amino]-6-{1-[(2-methyl-morpholine-4-yl)carbonyl]-piperidine-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidine-4-yloxy}-7-methoxy-quinazoline, 4-[(3-chloro-4-fluoro-phenyl)amino]-6-{1-[(N-methyl-N-2-methoxyethyl-amino)carbonyl]-piperidine-4-yloxy}-7-methoxy-quinazoline, 4-[(3-chloro-4-fluoro-phenyl)amino]-6-(1-ethyl-piperidine-4-yloxy)-7-methoxy-quinazoline, 4-[(3-chloro-4-fluoro-phenyl)amino]-6-{1-[(2-methoxyethyl)carbonyl]-piperidine-4-yloxy}-7-methoxy-quinazoline, 4-[(3-chloro-4-fluoro-phenyl)amino]-6-{1-[(3-methoxypropyl-amino)-carbonyl]-piperidine-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholine-4-yl)carbonyl]-N-methyl-amino}-cyclohexan-1-yloxy)-7-methoxy-quinazoline, 4-[(3-chloro-4-fluoro-phenyl)amino]-6-[2-(2.2-dimethyl-6-oxo-morpholine-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidine-4-yloxy)-7-methoxy-quinazoline, 4-[(3-chloro-4-fluoro-phenyl)amino]-6-(1-cyano-piperidine-4-yloxy)-7-methoxy-quinazoline, 3-Cyano-4-[(3-chlor-4-fluorphenyl)amino]-6-{[4-(N,N-dimethylamino)-1-oxo-2-butene-1-yl]amino}-7-ethoxy-quinoline, [4-[(3-chloro-4-fluoro-phenyl)amino]-6-{[4-(homomorpholine-4-yl)-1-oxo-2-butene-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)-carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, 4-[(3-chloro-4-fluoro-phenyl)amino]-7-(2-{4-[(S)-(2-oxo-tetrahydrofuran-5-yl)carbonyl]-piperazine-1-yl}-ethoxy)-6-[(vinylcarbonyl)amino]-quinazoline, 4-[(3-chloro-4-fluoro-phenyl)amino]-7-[2-((S)-6-methyl-2-oxo-morpholine-4-yl)-ethoxy]-6-[(vinylcarbonyl)amino]-quinazoline, 4-[(3-chloro-4-fluoro-phenyl)amino]-7-[4-((R)-6-methyl-2-oxo-morpholine-4-yl)-butyloxy]-6-[(vinylcarbonyl)amino]-quinazoline, 4-[(3-chloro-4-fluoro-phenyl)amino]-7-[4-((S)-6-methyl-2-oxo-morpholine-4-yl)-butyloxy]-6-[(vinylcarbonyl)amino]-quinazoline, cetuximab, trastuzumab, panitumumab (=ABX-EGF), Mab ICR-62, gefitinib, pelitinib, canertinib and erlotinib, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the EGFR-inhibitors may be capable of forming are meant, for example, salts selected from among the hydrochloride, hydrobromide, hydroiodide, hydrosulphate, hydrophosphate, hydromethanesulphonate, hydronitrate, hydromaleate, hydroacetate, hydrobenzoate, hydrocitrate, hydrofumarate, hydrotartrate, hydrooxalate, hydrosuccinate, hydrobenzoate and hydro-p-toluenesulphonate, preferably hydrochloride, hydrobromide, hydrosulphate, hydrophosphate, hydrofumarate and hydromethanesulphonate.

Examples of dopamine agonists which may be used preferably include compounds selected from among bromocriptine, cabergoline, alpha-dihydroergocryptine, lisuride, pergolide, pramipexol, roxindol, ropinirol, talipexol, terguride and viozan. Any reference to the above-mentioned dopamine agonists within the scope of the present invention includes a reference to any pharmacologically acceptable acid addition salts and optionally hydrates thereof which may exist. By the physiologically acceptable acid addition salts which may be formed by the above-mentioned dopamine agonists are meant, for example, pharmaceutically acceptable salts which are selected from the salts of hydrochloric acid, hydrobromic acid, sulphuric acid, phosphoric acid, methanesulphonic acid, acetic acid, fumaric acid, succinic acid, lactic acid, citric acid, tartaric acid and maleic acid.

Examples of H1-antihistamines preferably include compounds selected from among epinastine, cetirizine, azelastine, fexofenadine, levocabastine, loratadine, mizolastine, ketotifen, emedastine, dimetinden, clemastine, bamipin, cexchlorpheniramine, pheniramine, doxylamine, chlorophenoxamine, dimenhydrinate, diphenhydramine, promethazine, ebastine, olopatadine, desloratidine and meclozine. Any reference to the above-mentioned H1-antihistamines within the scope of the present invention includes a reference to any pharmacologically acceptable acid addition salts which may exist.

Examples of PAF-antagonists preferably include compounds selected from among lexipafant, 4-(2-chlorophenyl)-9-methyl-2-[3 (4-morpholinyl)-3-propanon-1-yl]-6H-thieno-[3,2-f]-[1,2,4]triazolo[4,3-a][1,4]diazepines, 6-(2-chlorophenyl)-8,9-dihydro-1-methyl-8-[(4-morpho-linyl)carbonyl]-4H,7H-cyclo-penta-[4,5]thieno-[3,2-f][1,2,4]triazolo[4,3-a][1,4]diazepines. Any reference to the above-mentioned above-mentioned PAF-antagonists includes within the scope of the present invention a reference to any pharmacologically acceptable acid addition salts thereof which may exist.

MRP4-inhibitors used are preferably compounds selected from among N-acetyl-dinitrophenyl-cysteine, cGMP, cholate, diclofenac, dehydroepiandrosterone 3-glucuronide, dehydroepiandrosterone 3-sulphate, dilazep, dinitrophenyl-s-glutathione, estradiol 17-beta-glucuronide, estradiol 3,17-disulphate, estradiol 3-glucuronide, estradiol 3-sulphate, estrone 3-sulphate, flurbiprofen, folate, N5-formyl-tetrahydrofolate, glycocholate, glycolithocholic acid sulphate, ibuprofen, indomethacin, indoprofen, ketoprofen, lithocholic acid sulphate, methotrexate, ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulfinpyrazone, taurochenodeoxycholate, taurocholate, taurodeoxycholate, taurolithocholate, taurolithocholic acid sulphate, topotecan, trequinsin and zaprinast, dipyridamole, optionally in the form of the racemates, enantiomers, diastereomers and the pharmacologically acceptable acid addition salts and hydrates thereof.

The invention relates more preferably to the use of MRP4-inhibitors for preparing a pharmaceutical composition for treating respiratory complaints, containing the SYK-inhibitors of formula 1 and MRP4-inhibitors according to the invention, the MRP4-inhibitors preferably being selected from among dehydroepiandrosterone 3-sulphate, estradiol 3,17-disulphate, flurbiprofen, indomethacin, indoprofen, taurocholate, optionally in the form of the racemates, enantiomers, diastereomers and the pharmacologically acceptable acid addition salts and hydrates thereof. The separation of enantiomers from the racemates can be carried out using methods known from the art (e.g. chromatography on chiral phases, etc.).

By acid addition salts with pharmacologically acceptable acids are meant, for example, salts selected from among the hydrochlorides, hydrobromides, hydroiodides, hydrosulphates, hydrophosphates, hydromethanesulphonates, hydronitrates, hydromaleates, hydroacetates, hydrobenzoates, hydrocitrates, hydrofumarates, hydrotartrates, hydrooxalates, hydrosuccinates, hydrobenzoates and hydro-p-toluenesulphonates, preferably the hydrochlorides, hydrobromides, hydrosulphates, hydrophosphates, hydrofumarates and hydromethanesulphonates.

The invention further relates to pharmaceutical preparations which contain a triple combination of the SYK-inhibitors of formula 1, MRP4-inhibitors and another active substance according to the invention, such as, for example, an anticholinergic, a PDE4 inhibitor, a steroid, an LTD4-antagonist or a betamimetic, and the preparation thereof and the use thereof for treating respiratory complaints.

Compounds which may be used as iNOS inhibitors are compounds selected from among: S-(2-aminoethyl)isothiourea, aminoguanidine, 2-aminomethylpyridine, 5,6-dihydro-6-methyl-4H-1,3-Thiazine-2-amine (=AMT), L-canavanine, 2-iminopiperidine, S-isopropylisothiourea, S-methylisothiourea, S-ethylisothiourea, S-methyltiocitrullin, S-ethylthiocitrulline, L-NA ($N^\omega$-nitro-L-arginine), L-NAME ($N^\omega$-nitro-L-argininemethylester), L-NMMA ($N^G$-monomethyl-L-arginine), L-NIO ($N^\omega$-iminoethyl-L-ornithine), L-NIL ($N^\omega$-iminoethyl-lysine), (S)-6-acetimidoylamino-2-amino-hexanoic acid (1H-tetrazol-5-yl)-amide (SC-51) (*J. Med. Chem.* 2002, 45, 1686-1689), N-[[3-(aminomethyl)phenyl]methyl]-Ethanimidamide (=1400W), (S)-4-(2-acetimidoylamino-ethylsulphanyl)-2-amino-butyric acid (GW274150) (*Bioorg. Med. Chem. Lett.* 2000, 10, 597-600), 2-[2-(4-methoxy-pyridin-2-yl)-ethyl]-3H-imidazo[4,5-b]pyridine (BYK191023) (*Mol. Pharmacol.* 2006, 69, 328-337), 2-((R)-3-amino-1-phenyl-propoxy)-4-chloro-5-fluorobenzonitrile (WO 01/62704), 2-((1R,3S)-3-amino-4-hydroxy-1-thiazol-5-yl-butylsulphanyl)-6-trifluoromethyl-nicotinonitrile (WO 2004/041794), 2-((1R,3S)-3-amino-4-hydroxy-1-thiazol-5-yl-butylsulphanyl)-4-chloro-benzonitrile (WO 2004/041794), 2-((1R,3S)-3-amino-4-hydroxy-1-thiazol-5-yl-butylsulphanyl)-5-chloro-benzonitrile (WO 2004/041794), (2S,4R)-2-amino-4-(2-chloro-5-trifluoromethyl-phenylsulphanyl)-4-thiazol-5-yl-butan-1-ol (WO 2004/041794), 2-((1R,3S)-3-amino-4-hydroxy-1-thiazol-5-yl-butylsulphanyl)-5-chloro-nicotinonitrile (WO 2004/041794), 4-((S)-3-amino-4-hydroxy-1-phenyl-butylsulphanyl)-6-methoxy-nicotinonitrile (WO 02/090332), substituted 3-phenyl-3,4-dihydro-1-isoquinolinamine such as e.g. (1S,5S,6R)-7-chloro-5-methyl-2-aza-bicyclo[4.1.0]hept-2-en-3-ylamine (ONO-1714) (*Biochem. Biophys. Res. Commun.* 2000, 270, 663-667), (4R,5R)-5-ethyl-4-methyl-thiazolidin-2-ylideneamine (*Bioorg. Med. Chem.* 2004, 12, 4101), (4R,5R)-5-ethyl-4-methyl-selenazolidin-2-ylideneamine (*Bioorg. Med. Chem. Lett.* 2005, 15, 1361), 4-aminotetrahydrobiopterine (*Curr. Drug Metabol.* 2002, 3, 119-121), (E)-3-(4-chloro-phenyl)-N-(1-{2-oxo-2-[4-(6-trifluoromethyl-pyrimidin-4-yloxy)-piperidine-1-yl]-ethylcarbamoyl}-2-pyridin-2-yl-ethyl)-acrylamide (FR260330) (*Eur. J. Pharmacol.* 2005, 509, 71-76), 3-(2,4-difluoro-phenyl)-6-[2-(4-imidazol-1-yl-methyl-phenoxy)-ethoxy]-2-phenyl-pyridine (PPA250) (*J. Pharmacol. Exp. Ther.* 2002, 303, 52-57), 3-{[(benzo[1,3]-dioxol-5-ylmethyl)-carbamoyl]-methyl}-4-(2-imidazol-1-yl-pyrimidin-4-yl)-piperazine-1-carboxylate (BBS-1) (*Drugs Future* 2004, 29, 45-52), (R)-1-(2-imidazol-1-yl-6-methyl-pyrimidin-4-yl)-pyrrolidine-2-carboxylic acid (2-benzo[1,3]dioxol-5-yl-ethyl)-amide (BBS-2) (*Drugs Future* 2004, 29, 45-52) and the pharmaceutical salts, prodrugs or solvates thereof.

Examples of iNOS-inhibitors within the scope of the present invention may also include antisense oligonucleotides, particularly those antisense oligonucleotides which bind iNOS-coding nucleic acids. For example, WO 01/52902 describes antisense oligonucleotides, particularly antisense oligonucleotides, which bind iNOS coding nucleic acids, for modulating the expression of iNOS. iNOS-antisense oligonucleotides as described particularly in WO 01/52902 may therefore also be combined with the PDE4-inhibitors of the present invention on account of their similar effect to the iNOS-inhibitors.

Suitable HMG-CoA reductase inhibitors (also called statins) which may be preferably used in double or triple combinations with the compounds of formula 1 are selected from among Atorvastatin, Cerivastatin, Flurvastatin, Lovastatin, Pitavastatin, Pravastatin, Rosuvastatin, Simvastatin, optionally in form of their pharmaceutically available acid addition salts, prodrugs, solvates or hydrates thereof.

8. FORMULATIONS

Suitable forms for administration are for example tablets, capsules, solutions, syrups, emulsions or inhalable powders or aerosols. The content of the pharmaceutically effective compound(s) in each case should be in the range from 0.1 to 90 wt. %, preferably 0.5 to 50 wt. % of the total composition, i.e. in amounts which are sufficient to achieve the dosage range specified hereinafter.

The preparations may be administered orally in the form of a tablet, as a powder, as a powder in a capsule (e.g. a hard gelatine capsule), as a solution or suspension. When administered by inhalation the active substance combination may be given as a powder, as an aqueous or aqueous-ethanolic solution or using a propellant gas formulation.

Preferably, therefore, pharmaceutical formulations are characterised by the content of one or more compounds of formula 1 according to the preferred embodiments above.

It is particularly preferable if the compounds of formula 1 are administered orally, and it is also particularly preferable if they are administered once or twice a day. Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

For oral administration the tablets may, of course, contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

It is also preferred if the compounds of formula 1 are administered by inhalation, particularly preferably if they are administered once or twice a day. For this purpose, the compounds of formula 1 have to be made available in forms suitable for inhalation. Inhalable preparations include inhalable powders, propellant-containing metered-dose aerosols or propellant-free inhalable solutions, which are optionally present in admixture with conventional physiologically acceptable excipients.

Within the scope of the present invention, the term propellant-free inhalable solutions also includes concentrates or sterile ready-to-use inhalable solutions. The preparations which may be used according to the invention are described in more detail in the next part of the specification.

Inhalable Powders

If the active substances of formula 1 are present in admixture with physiologically acceptable excipients, the following physiologically acceptable excipients may be used to prepare the inhalable powders according to the invention: monosaccharides (e.g. glucose or arabinose), disaccharides (e.g. lactose, saccharose, maltose), oligo- and polysaccharides (e.g. dextran), polyalcohols (e.g. sorbitol, mannitol, xylitol), salts (e.g. sodium chloride, calcium carbonate) or mixtures of these excipients with one another. Preferably, mono- or disaccharides are used, while the use of lactose or glucose is preferred, particularly, but not exclusively, in the form of their hydrates. For the purposes of the invention, lactose is the particularly preferred excipient, while lactose monohydrate is most particularly preferred. Methods of preparing the inhalable powders according to the invention by grinding and micronising and by finally mixing the components together are known from the prior art.

Propellant-Containing Inhalable Aerosols

The propellant-containing inhalable aerosols which may be used according to the invention may contain the compounds of formula 1 dissolved in the propellant gas or in dispersed form. The propellant gases which may be used to prepare the inhalation aerosols according to the invention are known from the prior art. Suitable propellant gases are selected from among hydrocarbons such as n-propane, n-butane or isobutane and halohydrocarbons such as preferably fluorinated derivatives of methane, ethane, propane, butane, cyclopropane or cyclobutane. The propellant gases mentioned above may be used on their own or in mixtures thereof. Particularly preferred propellant gases are fluorinated alkane derivatives selected from TG134a (1,1,1,2-tetrafluoroethane), TG227 (1,1,1,2,3,3,3-heptafluoropropane) and mixtures thereof. The propellant-driven inhalation aerosols used within the scope of the use according to the invention may also contain other ingredients such as co-solvents, stabilisers, surfactants, antioxidants, lubricants and pH adjusters. All these ingredients are known in the art.

Propellant-Free Inhalable Solutions

The compounds of formula 1 according to the invention are preferably used to prepare propellant-free inhalable solutions and inhalable suspensions. Solvents used for this purpose include aqueous or alcoholic, preferably ethanolic solutions. The solvent may be water on its own or a mixture of water and ethanol. The solutions or suspensions are adjusted to a pH of 2 to 7, preferably 2 to 5, using suitable acids. The pH may be adjusted using acids selected from inorganic or organic acids. Examples of particularly suitable inorganic acids include hydrochloric acid, hydrobromic acid, nitric acid, sulphuric acid and/or phosphoric acid. Examples of particularly suitable organic acids include ascorbic acid, citric acid, malic acid, tartaric acid, maleic acid, succinic acid, fumaric acid, acetic acid, formic acid and/or propionic acid etc. Preferred inorganic acids are hydrochloric and sulphuric acids. It is also possible to use the acids which have already formed an acid addition salt with one of the active substances. Of the organic acids, ascorbic acid, fumaric acid and citric acid are preferred. If desired, mixtures of the above acids may also be used, particularly in the case of acids which have other properties in addition to their acidifying qualities, e.g. as flavourings, antioxidants or complexing agents, such as citric acid or ascorbic acid, for example. According to the invention, it is particularly preferred to use hydrochloric acid to adjust the pH.

Co-solvents and/or other excipients may be added to the propellant-free inhalable solutions used for the purpose according to the invention. Preferred co-solvents are those which contain hydroxyl groups or other polar groups, e.g. alcohols—particularly isopropyl alcohol, glycols—particularly propyleneglycol, polyethyleneglycol, polypropyleneglycol, glycolether, glycerol, polyoxyethylene alcohols and polyoxyethylene fatty acid esters. The terms excipients and additives in this context denote any pharmacologically acceptable substance which is not an active substance but which can be formulated with the active substance or substances in the pharmacologically suitable solvent in order to improve the qualitative properties of the active substance formulation. Preferably, these substances have no pharmacological effect or, in connection with the desired therapy, no appreciable or at least no undesirable pharmacological effect.

The excipients and additives include, for example, surfactants such as soya lecithin, oleic acid, sorbitan esters, such as polysorbates, polyvinylpyrrolidone, other stabilisers, complexing agents, antioxidants and/or preservatives which guarantee or prolong the shelf life of the finished pharmaceutical formulation, flavourings, vitamins and/or other additives known in the art. The additives also include pharmacologically acceptable salts such as sodium chloride as isotonic agents. The preferred excipients include antioxidants such as ascorbic acid, for example, provided that it has not already been used to adjust the pH, vitamin A, vitamin E, tocopherols and similar vitamins or provitamins occurring in the human body. Preservatives may be used to protect the formulation from contamination with pathogens. Suitable preservatives are those which are known in the art, particularly cetyl pyridinium chloride, benzalkonium chloride or benzoic acid or benzoates such as sodium benzoate in the concentration known from the prior art.

For the treatment forms described above, ready-to-use packs of a medicament for the treatment of respiratory complaints are provided, containing an enclosed description including for example the words respiratory disease, COPD or asthma, together with a naphthyridine according to formula 1 and one or more combination partners selected from those described above.

The invention claimed is:

1. A compound of the formula 1

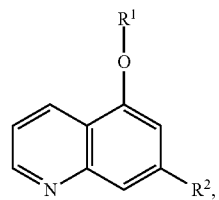

wherein
  $R^1$ is a linear or branched $C_{1-6}$-alkyl,
  wherein $R^1$ is substituted by $R^3$ which is selected from the group consisting of a three-, four-, five-, six- or seven-membered cycloalkyl; a five-, six- or seven-membered, saturated heterocycle comprising one, two or three heteroatoms each independently selected from the group consisting of N, S and O; and a five- or six-membered heteroaryl comprising one, two or three heteroatoms each independently selected from the group consisting of N, S and O;
  wherein the $R^3$ may optionally be substituted by one, two, three or four substituents each independently selected from the group consisting of oxo, OH, —CO—NH$_2$, —CO—NH(CH$_3$), —CO—N(CH$_3$)$_2$, —C$_{1-5}$-alkyl, —C$_{1-3}$-alkylene-CO—NH$_2$, —C$_{1-3}$-alkylene-CO—NH(CH$_3$), —C$_{1-3}$-alkylene-CO—N(CH$_3$)$_2$, —C$_{1-3}$-alkylene-CN and —CN, and wherein
  $R^2$ is selected from the group consisting of halogen, phenyl, a five- or six-membered monocyclic heteroaryl comprising one, two or three heteroatoms each independently selected from the group consisting of N, S and O; a bicyclic nine-, ten- or eleven-membered, either aromatic or non-aromatic, but not fully saturated heterocycle comprising one, two, three or four heteroatoms each independently selected from the group consisting of N, S and O;
  wherein the $R^2$ may optionally be substituted by one, two, three or four substituents $R^4$ which independently from one another are selected from the group consisting of linear or branched —O—C$_{1-5}$-alkyl, —OH, oxo, halogen, —C$_{1-5}$-haloalkyl, —SO$_2$CH$_3$, —C$_{1-3}$-alkylene-SO$_2$—C$_{1-3}$-alkyl), —SO$_2$—CF$_3$, —CN, —C$_{3-6}$-cycloalkyl, linear or branched —C$_{1-5}$-alkyl, a four, five- or six-membered saturated heterocycle comprising one, two or three heteroatoms each independently from one another selected from the group of N, S, —SO$_2$ and O; —C$_{1-3}$-alkylene-N(C$_{1-3}$-alkyl)-CO—C$_{1-3}$-alkyl, —NH—CO—C$_{1-3}$-alkyl, —CO—NH(CH$_3$), —CO—NH$_2$, —CO—N(CH$_3$)$_2$, —O—R$^5$, —CO—R$^5$, —C$_{1-3}$-alkylene-O—CO—C$_{1-3}$-alkyl and

wherein the $R^4$ may optionally be substituted by one or two substituents $R^5$,
  wherein each $R^5$ is independently from one another selected from the group consisting of linear or branched —C$_{1-4}$-alkyl, oxo, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl, a five- or six-membered heteroaryl comprising one or two heteroatoms each independently selected from the group consisting of N, O and S,
  wherein the $R^5$ may optionally be substituted by a group consisting of oxo, —C$_{1-3}$-alkyl and —C$_{1-3}$-haloalkyl,
  or a pharmacologically acceptable salt thereof.

2. The compound of formula I according to claim 1, wherein
  $R^1$ is selected from the group consisting of —CH$_3$ and —CH$_2$—(CH$_3$) which is substituted by $R^3$ which is selected from the group consisting of a three-, four-, five-, six- or seven-membered cycloalkl; a five-, six- or seven-membered, saturated heterocycle comprising one, two or three heteroatoms each independently selected from the group consisting of N, S and O; and a five- or six-membered heteroaryl comprising one, two or three heteroatoms each independently selected from the group consisting of N, S and O;
  wherein the $R^3$ may optionally be substituted by one, two, three or four substituents each independently selected from the group consisting of oxo, OH, —CO—NH$_2$, —CO—NH(CH$_3$), —CO—N(CH$_3$)$_2$, —C$_{1-5}$-alkyl, —C$_{1-3}$-alkylene-CO—NH$_2$, —C$_{1-3}$-alkylene-CO—NH(CH$_3$), —C$_{1-3}$-alkylene-CO—N(CH$_3$)$_2$, —C$_{1-3}$-alkylene-CN and —CN,
  or a pharmacologically acceptable salt thereof.

3. The compound of formula I according to claim 2, wherein $R^1$ is substituted by $R^3$ which is selected from the group consisting of a five- or six-membered saturated heterocycle comprising one or two heteroatoms each independently selected from the group consisting of N, S and O,
  wherein the $R^3$ may optionally be substituted by one, two, three or four substituents each independently selected from the group consisting of oxo, OH, —CO—NH$_2$, —CO—NH(CH$_3$), —CO—N(CH$_3$)$_2$, —C$_{1-5}$-alkyl, —C$_{1-3}$-alkylene-CO—NH$_2$, —C$_{1-3}$-alkylene-CO—NH(CH$_3$), —C$_{1-3}$-alkylene-CO—N(CH$_3$)$_2$, —C$_{1-3}$-alkylene-CN and —CN, or a pharmacologically acceptable salt thereof.

4. The compound of formula 1 according to claim 2, wherein R$^1$ is substituted by R$^3$ which is selected from the group consisting of a five- or six-membered heteroaryl comprising one or two heteroatoms each independently selected from the group consisting of N, S and O, wherein the R$^3$ may optionally be substituted by one, two, three or four substituents each independently selected from the group consisting of oxo, OH, —CO—NH$_2$, —CO—NH(CH$_3$), —CO—N(CH$_3$)$_2$, —C$_{1-5}$-alkyl, —C$_{1-3}$-alkylene-CO—NH$_2$, —C$_{1-3}$-alkylene-CO—NH(CH$_3$), —C$_{1-3}$-alkylene-CO—N(CH$_3$)$_2$, —C$_{1-3}$-alkylene-CN and —CN, or a pharmacologically acceptable salt thereof.

5. The compound of formula 1 according claim 4, wherein R$^1$ is a selected from the group consisting of —CH$_3$ or —CH$_2$(CH$_3$), wherein R$^1$ is substituted by R$^3$ which is selected from the group consisting of a three-, four-, five- or six-membered cycloalkl; a five- or six-membered saturated heterocycle comprising one or two heteroatoms each independently selected from the group consisting of N, S and O; and a five- or six-membered heteroaryl comprising one or two heteroatoms each independently selected from the group consisting of N, S and O;

wherein the R$^3$ may optionally be substituted by one, two, three or four substituents each independently selected from the group consisting of oxo, —CO—NH$_2$, —CH$_2$—CO—NH$_2$, methyl and —CH$_2$—CN, or a pharmacologically acceptable salt thereof.

6. The compound of formula 1 according to claim 5, wherein

R$^1$ is selected from the group consisting of —CH$_3$ and —CH$_2$—CH$_3$, wherein R$^1$ is substituted by R$^3$ which is a five-membered saturated heterocycle comprising one nitrogen-atom, wherein the R$^3$ is substituted by one oxo-group or a pharmacologically acceptable salt thereof.

7. The compound of formula 1 according to claim 5, wherein

R$^1$ including its substitution with R$^3$ is the group

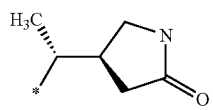

or a pharmacologically acceptable salt thereof.

8. The compound of formula 1 according to claim 5, wherein

R$^1$ is selected from the group consisting of —CH$_3$ and —CH$_2$—CH$_3$, wherein R$^1$ is substituted by R$^3$ which is a six-membered heteroaryl comprising one nitrogen-atom, wherein the R$^3$ is substituted by —CO—NH$_2$, or a pharmacologically acceptable salt thereof.

9. The compound of formula 1 according to claim 5, wherein

R$^1$ including its substitution with R$^3$ is the group

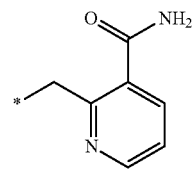

or a pharmacologically acceptable salt thereof.

10. The compound of formula 1 according to claim 9, wherein

R$^2$ is selected from the group consisting of phenyl, a five- or six-membered monocyclic heteroaryl comprising one, two or three heteroatoms each independently selected from the group consisting of N, S and O; a bicyclic, nine- or ten-membered, either aromatic or non-aromatic, but not fully saturated heterocycle comprising one, two, three or four heteroatoms each independently selected from the group consisting of N, S and O;

wherein the R$^2$ may optionally be substituted by one, two, three or four substituents R$^4$ which independently from one another are selected from the group consisting of linear or branched —O—C$_{1-3}$-alkyl, oxo, —OH, —F, —Cl, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently selected from the group of N, S, SO$_2$ and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein the R$^4$ may optionally be substituted by one or two substituents R$^5$, wherein each R$^5$ is independently from one another selected from the group consisting of methyl, ethyl, propyl, isopropyl, isopropyl, n-butyl, isobutyl, tert-butyl, —C$_{1-3}$-haloalkyl, oxo, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl, a five- or six-membered heteroaryl comprising one or two heteroatoms each independently selected from the group consisting of N, S and O, wherein the R$^5$ may optionally be substituted by a group consisting of oxo, methyl, ethyl, —CF$_3$, or a pharmacologically acceptable salt thereof.

11. The compound of formula 1 according to claim 10, wherein

R$^2$ is phenyl, wherein the R$^2$ may optionally be substituted by one, two, three or four substituents R$^4$ which independently from one another are selected from the group consisting of linear or branched —O—C$_{1-3}$-alkyl, oxo, —OH, —F, —Cl, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently selected from the group of N, S and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein the R$^4$ may optionally be substituted by one or two substituents R$^5$,
wherein each R$^5$ is independently selected from the group consisting of methyl, ethyl, propyl, isopropyl, n-butyl, isobutyl, tert-butyl, oxo, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl, a five- or six-membered heteroaryl comprising one or two heteroatoms each independently selected from the group consisting of N, S and O, wherein the R$^5$ may optionally be substituted by a group consisting of oxo, methyl,
or a pharmacologically acceptable salt thereof.

12. The compound of formula 1 according to claim 11, wherein
R$^2$ is phenyl,
and wherein the R$^2$ may optionally be substituted by one, two, three or four substituents R$^4$ which independently from one another are selected from the group consisting of —OCH$_3$, oxo, —OH, —F, Cl, —CF$_3$, —CHF$_2$, —SO$_2$CH$_3$, —SO$_2$—CF$_3$, —CH$_3$, —CH$_2$—CH$_3$, propyl, isopropyl; —NH—CO—CH$_3$, —C$_{1-3}$-alkylene-N(C$_{1-3}$-alkyl)-CO—CH$_3$, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein the R$^4$ may optionally be substituted by one or two substituents R$^5$,
wherein each R$^5$ is independently selected from the group consisting of methyl, ethyl, propyl, isopropyl, isopropyl, n-butyl, isobutyl, tert-butyl, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently from one another selected from the group of N, S and O, a three, four-, five-, six- or seven-membered cycloalkyl,
wherein the R$^5$ may optionally be substituted by a group consisting of oxo, methyl, or a pharmacologically acceptable salt thereof.

13. The compound of formula 1 according to claim 10, wherein
R$^2$ is a five- or six-membered monocyclic heteroaryl comprising one, two or three heteroatoms each independently selected from the group consisting of N, S and O;
wherein the R$^2$ may optionally be substituted by one, two, three or four substituents R$^4$ which independently from one another are selected from the group consisting of —O-methyl, —O-ethyl, —O-propyl, —O-isopropyl, oxo, —OH, —F, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently selected from the group of N, S and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$, —C$_{1-3}$-alkylene-O—CO—C$_{1-3}$-alkyl and

wherein the R$^4$ may optionally be substituted by one or two substituents R$^5$,
wherein each R$^5$ is independently selected from the group consisting of methyl, ethyl, propyl, isopropyl, n-butyl, isobutyl, tert-butyl, —C$_{1-3}$-haloalkyl, —OH, halogen, —C$_{1-2}$-alkylene-C$_{1-3}$-haloalkyl, a five- or six-membered saturated heterocycle comprising one, two or three heteroatoms each independently selected from the group of N, S and O, a three, four-, five-, six- or seven-membered cycloalkyl,
wherein the R$^5$ may optionally be substituted by a group consisting of oxo, methyl and —CF$_3$,
or a pharmacologically acceptable salt thereof.

14. The compound of formula 1 according to claim 13, wherein
R$^2$ is a five- or six-membered monocyclic heteroaryl comprising one, two or three heteroatoms each independently selected from the group consisting of N, S and O;
wherein the R$^2$ may optionally be substituted by one, two, three or four substituents R$^4$ which independently from one another are selected from the group consisting of —O—CH$_3$, oxo, —OH, —F, —CF$_3$, —CHF$_2$, —SO$_2$CH$_3$, —CH$_2$—SO$_2$—CH$_3$, —SO$_2$—CF$_3$, —CH$_3$, —CH$_2$—CH$_3$, propyl, isopropyl, a five- or six-membered saturated heterocycle comprising one or two heteroatoms each independently from one another selected from the group of N, S and O; —NH—CO—CH$_3$, —C$_{1-3}$-alkylene-N(C$_{1-3}$-alkyl)-CO—C$_{1-3}$-alkyl, —CO—NH(CH$_3$), —(C$_{1-3}$-alkylene)-O—CO—CH$_3$, —CO—NH$_2$, —CO—N(CH$_3$)$_2$, —O—R$^5$, —CO—R$^5$,
wherein the R$^4$ may optionally be substituted by one or two substituents R$^{59}$
wherein each R$^5$ is independently selected from the group consisting of methyl, ethyl, propyl, isopropyl, n-butyl, isobutyl, tert-butyl, —CF$_3$, —CH$_2$—CF$_3$, —CHF$_2$, CH$_2$F, —CF$_2$—CF$_3$, —OH, halogen, -ethylen-CF$_3$, a five- or six-membered saturated heterocycle comprising one, two or three heteroatoms each independently from one another selected from the group of N, S and O, a three, four-, five-, six- or seven-membered cycloalkyl,
wherein the R$^5$ may optionally be substituted by a group consisting of oxo, methyl and —CF$_3$,
or a pharmacologically acceptable salt thereof.

15. The compound of formula 1 according to claim 14, wherein
R$^2$ is a five-membered monocyclic heteroaryl comprising one, two or three heteroatoms each independently selected from the group consisting of N, S and O;

whereby this five-membered monocyclic heteroaryl is linked to the quinoline core structure via a carbon atom and wherein this five-membered monocyclic heteroaryl optionally may be further substituted as identified in claim 14,
or a pharmacologically acceptable salt thereof.

16. The compound of formula 1 according to claim 14, wherein
$R^2$ is a five-membered monocyclic heteroaryl comprising at least one nitrogen atom and optionally one or two further heteroatoms each independently selected from the group consisting of N, S and O;
whereby this five-membered monocyclic heteroaryl is linked to the quinoline core structure via a nitrogen atom,
and wherein this five-membered monocyclic heteroaryl optionally may be further substituted as identified in claim 14,
or a pharmacologically acceptable salt thereof.

17. The compound of formula 1 according to claim 10, wherein
$R^2$ is a bicyclic, nine- or ten-membered, either aromatic or non-aromatic, but not fully saturated heterocycle comprising one, two, three or four heteroatoms each independently selected from the group consisting of N, S and O;
wherein the $R^2$ may optionally be substituted by one, two, three or four substituents $R^4$ which independently from one another are selected from the group consisting of linear or branched —O—$C_{1-3}$-alkyl, oxo, —OH, —F, —$CF_3$, —$CHF_2$, —$SO_2CH_3$, —$CH_2$—$SO_2$—$CH_3$, —$SO_2$—$CF_3$, —$CH_3$, —$CH_2$—$CH_3$, propyl, isopropyl, a five- or six-membered saturated heterocycle comprising one or two heteroatoms each independently from one another selected from the group of N, S and O; —NH—CO—$CH_3$, —$C_{1-3}$-alkylene-N($C_{1-3}$-alkyl)-CO—$C_{1-3}$-alkyl, —CO—NH($CH_3$), —($C_{1-3}$-alkylene)-O—CO—$CH_3$, —CO—$NH_2$, —CO—N($CH_3$)$_2$, —O—$R^5$, —CO—$R^5$, —$C_{1-3}$-alkylene-O—CO—$C_{1-3}$-alkyl and

wherein the $R^4$ may optionally be substituted by one or two substituents $R^5$,
wherein each $R^5$ is independently selected from the group consisting of methyl, ethyl, propyl, isopropyl, —$C_{1-3}$-haloalkyl, —OH, halogen, —$C_{1-2}$-alkylene-$C_{1-3}$-haloalkyl, a five- or six-membered saturated heterocycle comprising one, two or three heteroatoms each independently from one another selected from the group of N, S and O, a three, four-, five-, six- or seven-membered cycloalkyl,
wherein the $R^5$ may optionally be substituted by a group consisting of oxo, methyl and —$CF_3$,
or a pharmacologically acceptable salt thereof.

18. The compound of formula 1 according to one of claims 17, wherein
$R^2$ is a bicyclic, nine- or ten-membered, either aromatic or non-aromatic, but not fully saturated heterocycle comprising one, two, three or four heteroatoms each independently selected from the group consisting of N, S and O;
wherein the $R^2$ may optionally be substituted by one, two, three or four substituents $R^4$ which independently from one another are selected from the group consisting of —O—$CH_3$, —O-ethyl, —O-propyl, —O-isopropyl, oxo, —OH, —F, —$CF_3$, methyl, ethyl, propyl and isopropyl,
or a pharmacologically acceptable salt thereof.

19. The compound of formula 1 according to claim 14, wherein
$R^2$ is pyridine,
wherein the $R^2$ may optionally be substituted by one, two, three or four substituents $R^4$ which independently from one another are selected from the group consisting of —O—$CH_3$, oxo, —OH, —F, —$CF_3$, —$CHF_2$, —$SO_2CH_3$, —$CH_2$—$SO_2$—$CH_3$, —$SO_2$—$CF_3$, —$CH_3$, —$CH_2$—$CH_3$, propyl, isopropyl, a five- or six-membered saturated heterocycle comprising one or two heteroatoms each independently selected from the group of N, S and O; —NH—CO—$CH_3$, —$C_{1-3}$-alkylene-N($C_{1-3}$-alkyl)-CO—$C_{1-3}$-alkyl, —CO—NH($CH_3$), —($C_{1-3}$-alkylene)-O—CO—$CH_3$, —CO—$NH_2$, —CO—N($CH_3$)$_2$, —O—$R^5$, —CO—$R^5$,
wherein the $R^4$ may optionally be substituted by one or two substituents $R^5$,
wherein each $R^5$ is independently from one another selected from the group consisting of methyl, ethyl, propyl, isopropyl, n-butyl, isobutyl, tert-butyl, —$CF_3$, —$CH_2$—$CF_3$, —$CHF_2$, $CH_2F$, —$CF_2$—$CF_3$, —OH, halogen, —$C_{1-2}$-alkylene-$CF_3$, a five- or six-membered saturated heterocycle comprising one, two or three heteroatoms each independently from one another selected from the group of N, S and O, a three, four-, five-, six- or seven-membered cycloalkyl,
wherein the $R^5$ may optionally be substituted by a group consisting of oxo, methyl and —$CF_3$
or a pharmacologically acceptable salt thereof.

20. The compound of formula 1 according to claim 19, wherein
$R^2$ is pyridine,
wherein the $R^2$ is substituted by one or two $R^4$ which independently from one another are selected from the group consisting of —O—$CH_3$, —OH, —F, —$CF_3$, —$CHF_2$, —$CH_3$, —$CH_2$—$CH_3$, propyl, isopropyl and —O—$R^5$,
wherein $R^5$ is selected from the group consisting of methyl, ethyl, propyl, isopropyl, —$CF_3$, —$CHF_2$, $CH_2F$, —$CH_2$—$CF_3$, —$CF_2$—$CF_3$
or a pharmacologically acceptable salt thereof.

21. The compound according to formula 1 according to claim 1, wherein
$R^1$ including its substitution with $R^3$ is selected from the group consisting of

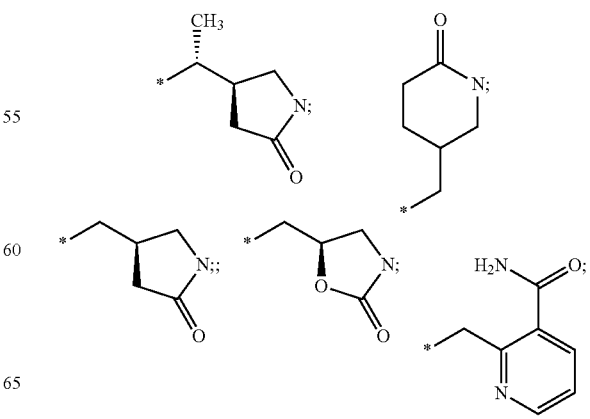

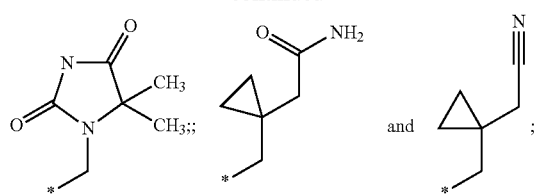
and wherein
$R^2$ is selected from the group consisting of
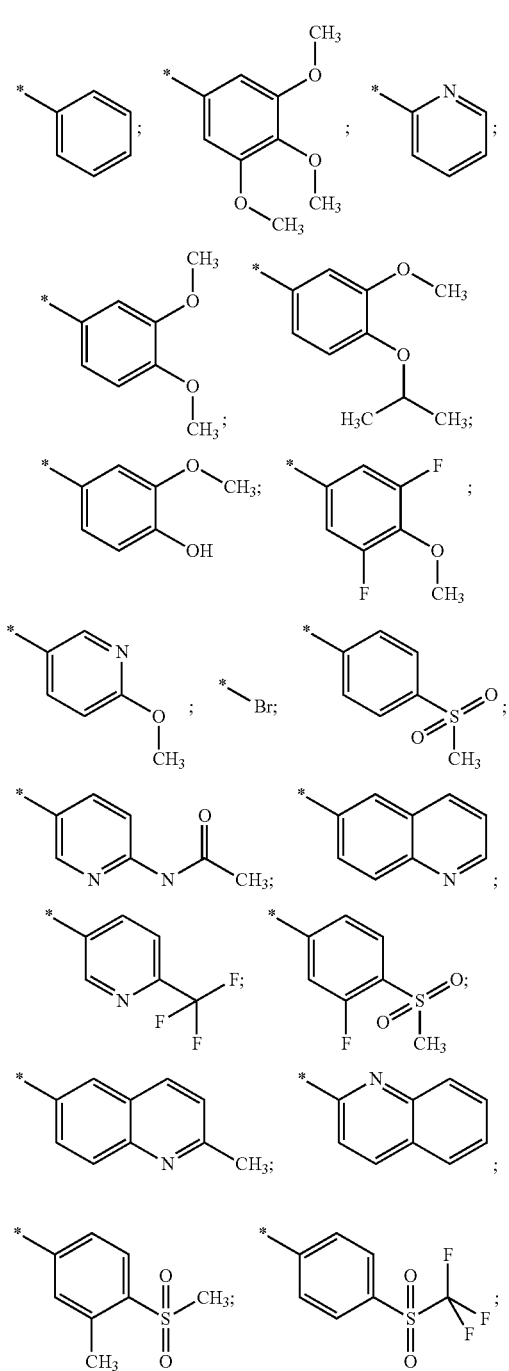
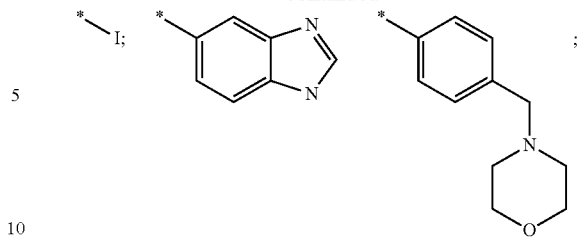
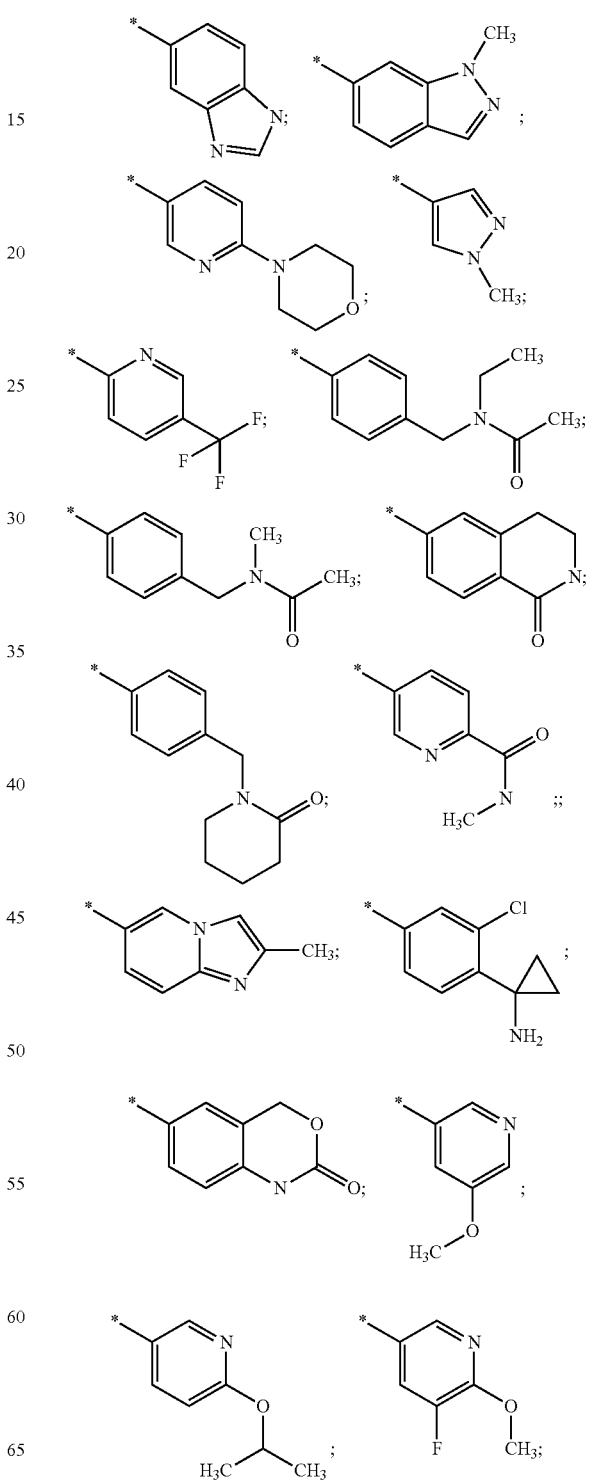

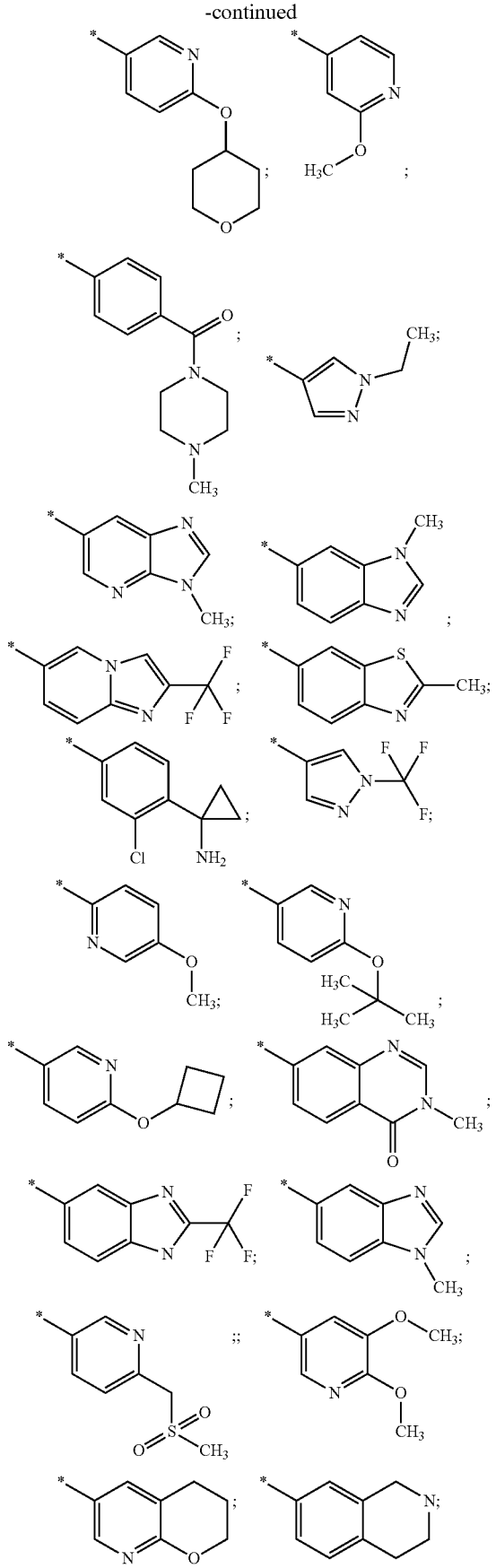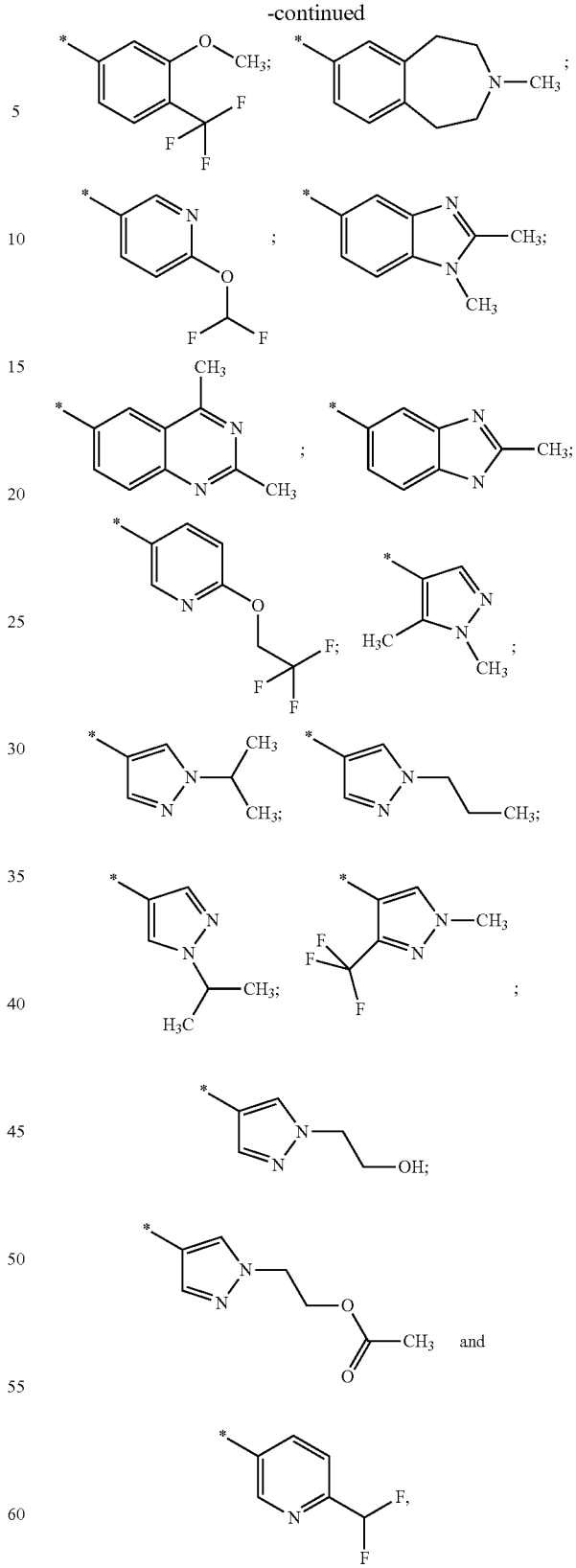
or a pharmacologically acceptable salt thereof.
22. The compound according to formula 1 according to claim 1 selected from the group consisting of

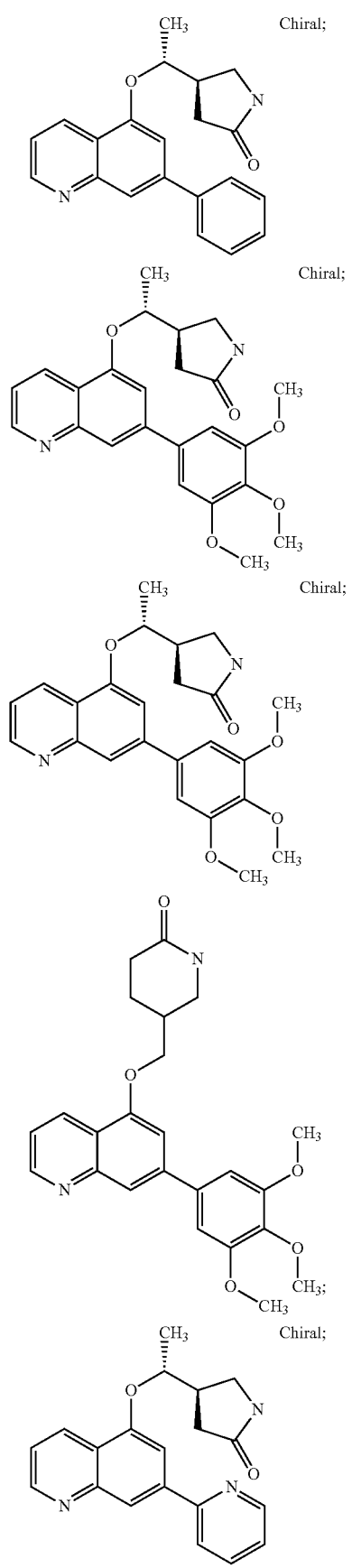
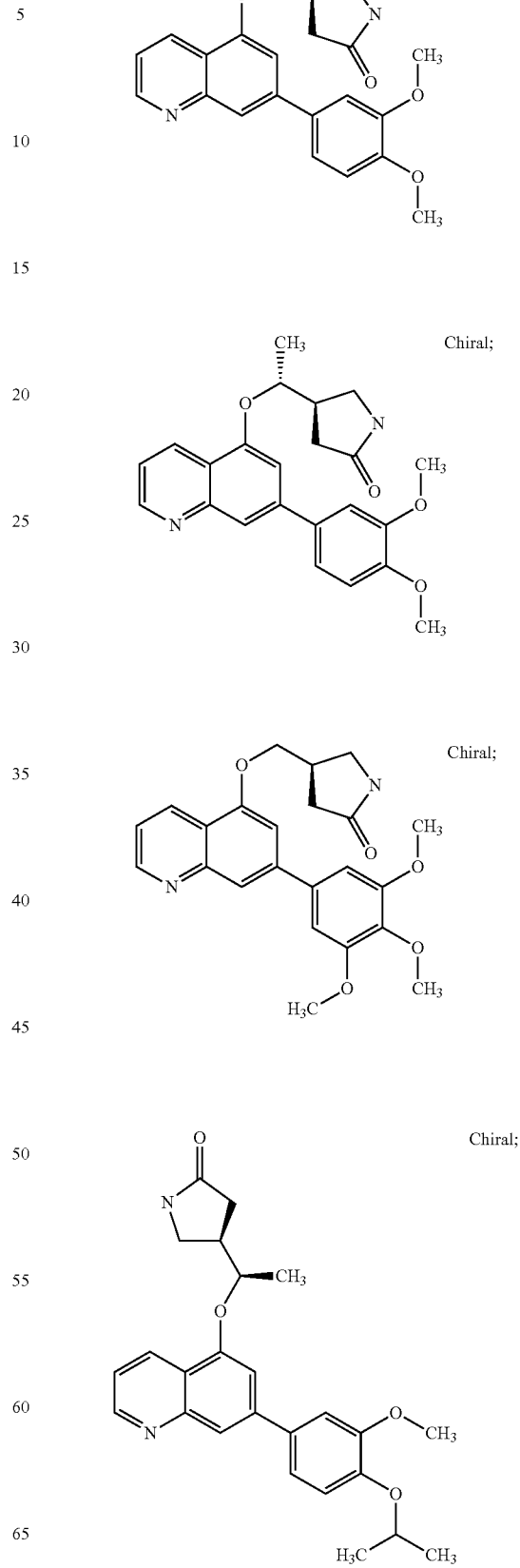

213
-continued
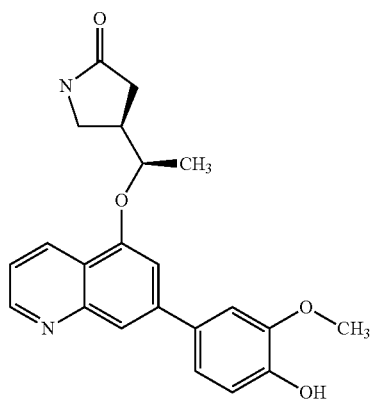
Chiral;
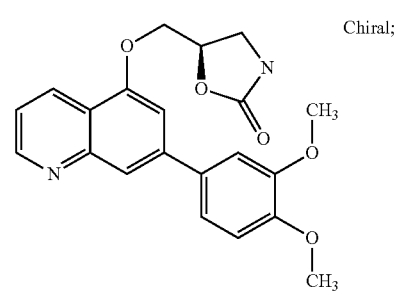
Chiral;
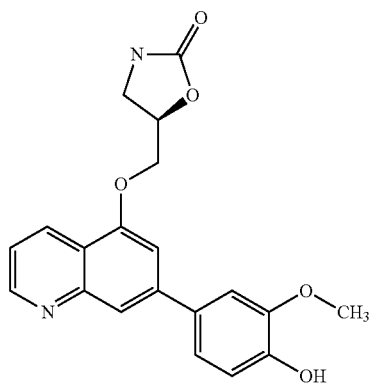
Chiral;
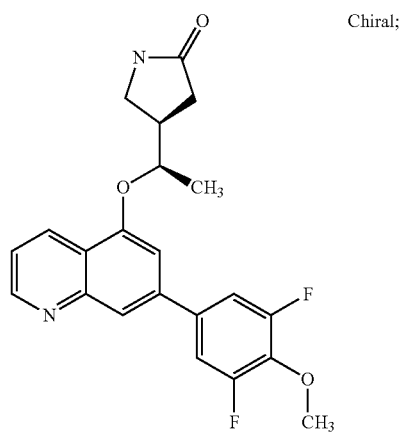
Chiral;
214
-continued
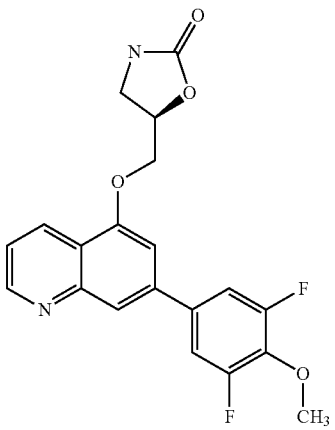
Chiral;
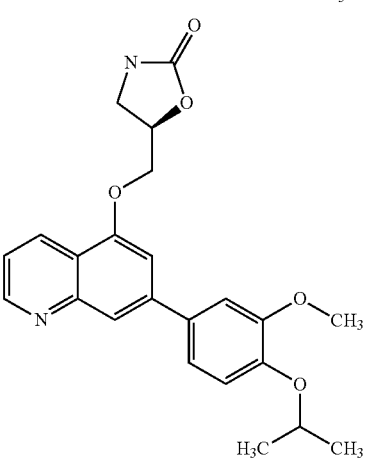
Chiral;
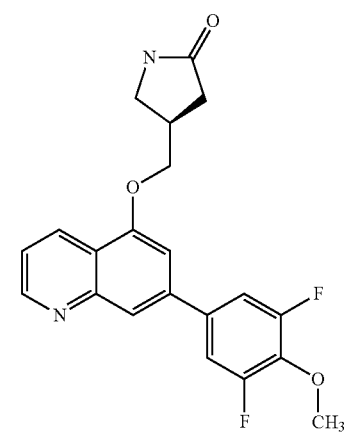
Chiral;
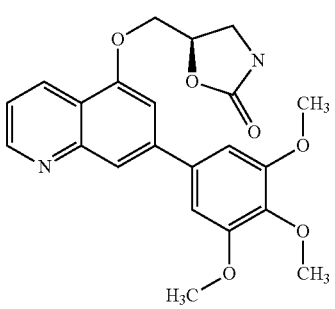
Chiral;

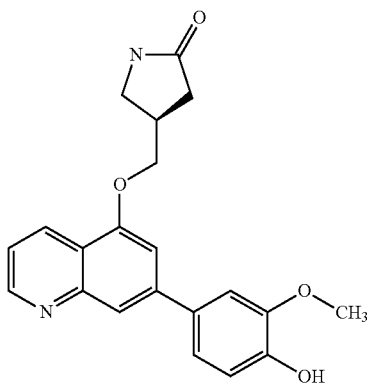 Chiral;
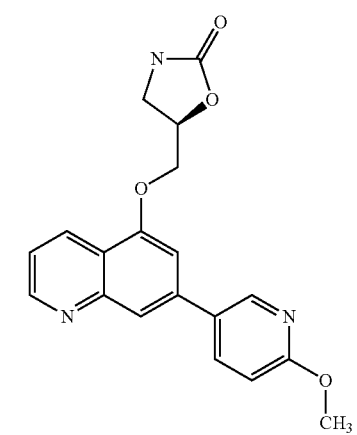 Chiral;
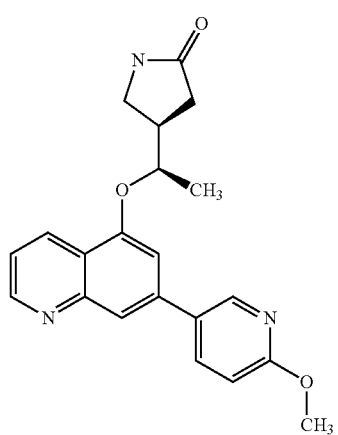 Chiral;
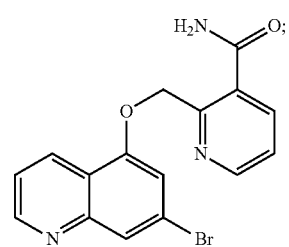
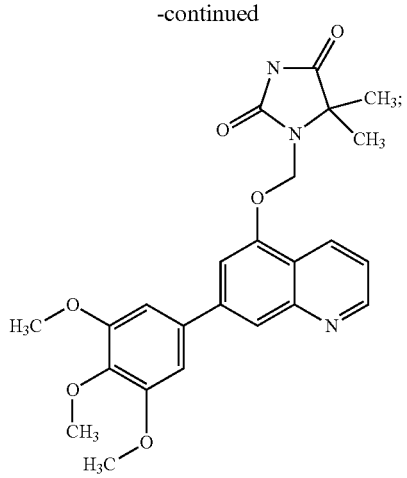
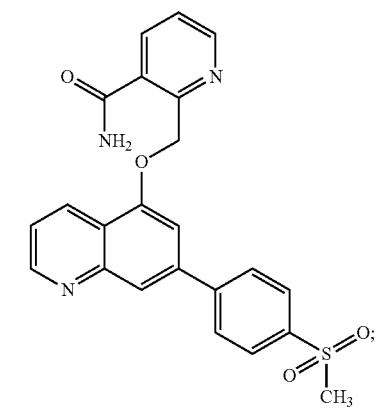
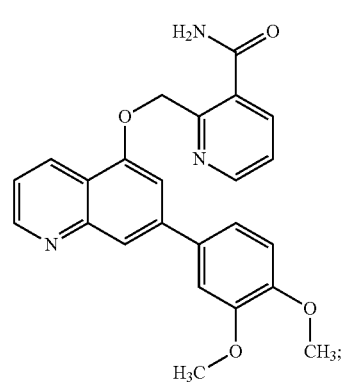
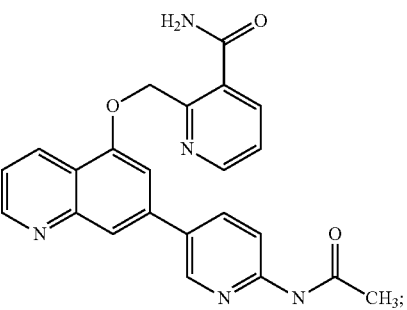

217
-continued
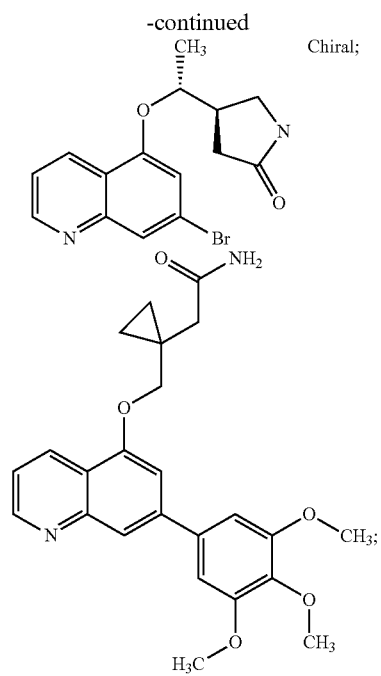
Chiral;
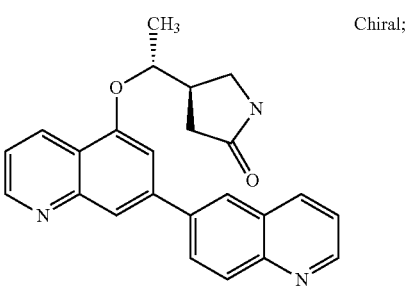
Chiral;
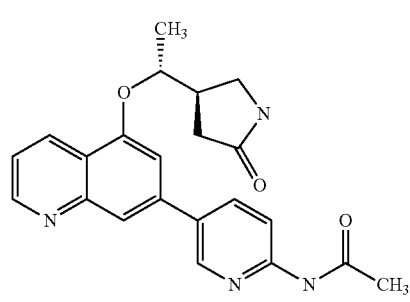
Chiral;
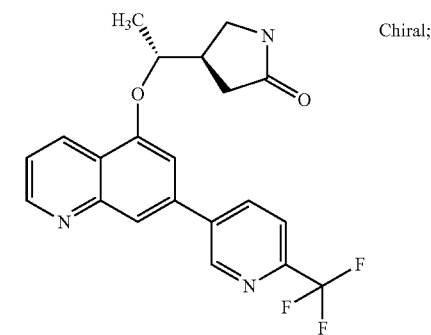
Chiral;
218
-continued
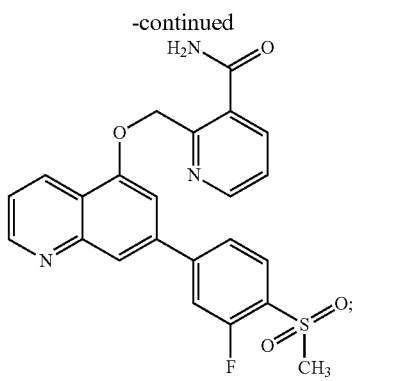
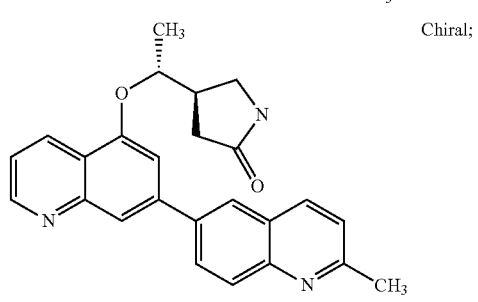
Chiral;
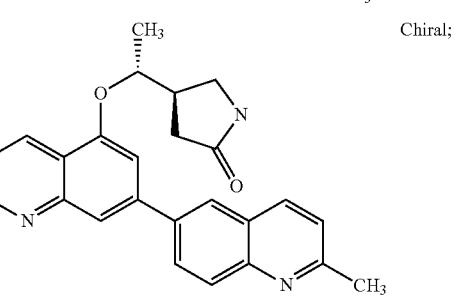
Chiral;
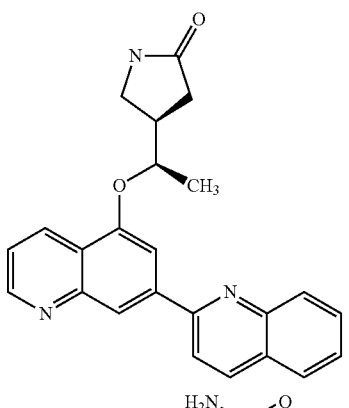
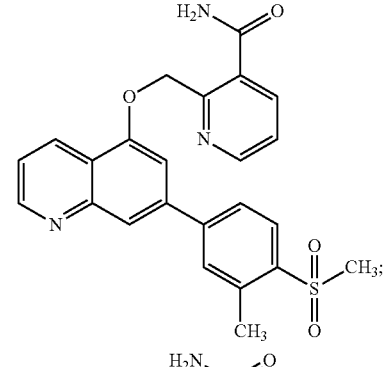
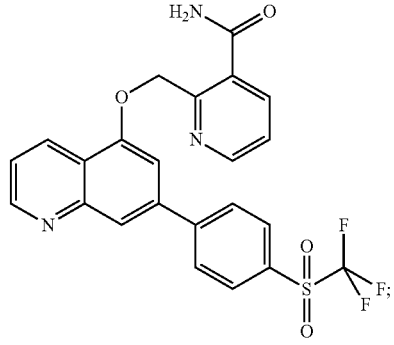

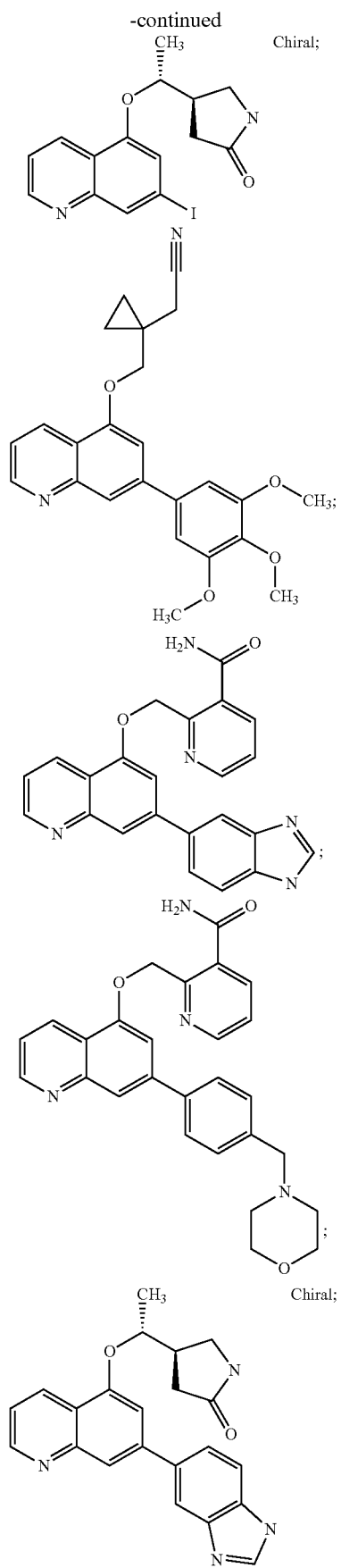
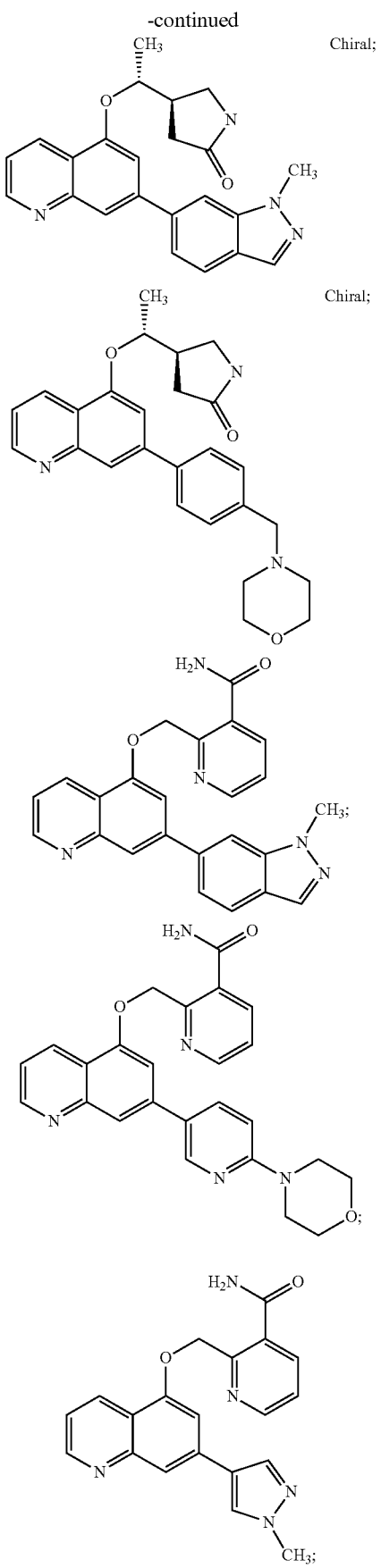

221 -continued
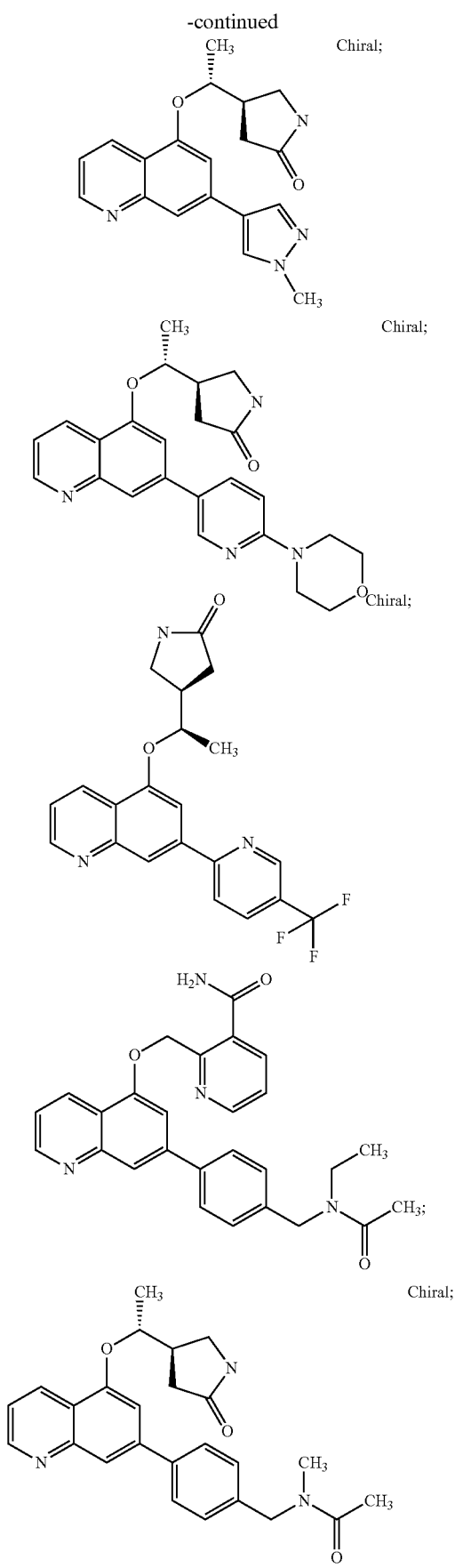
222 -continued
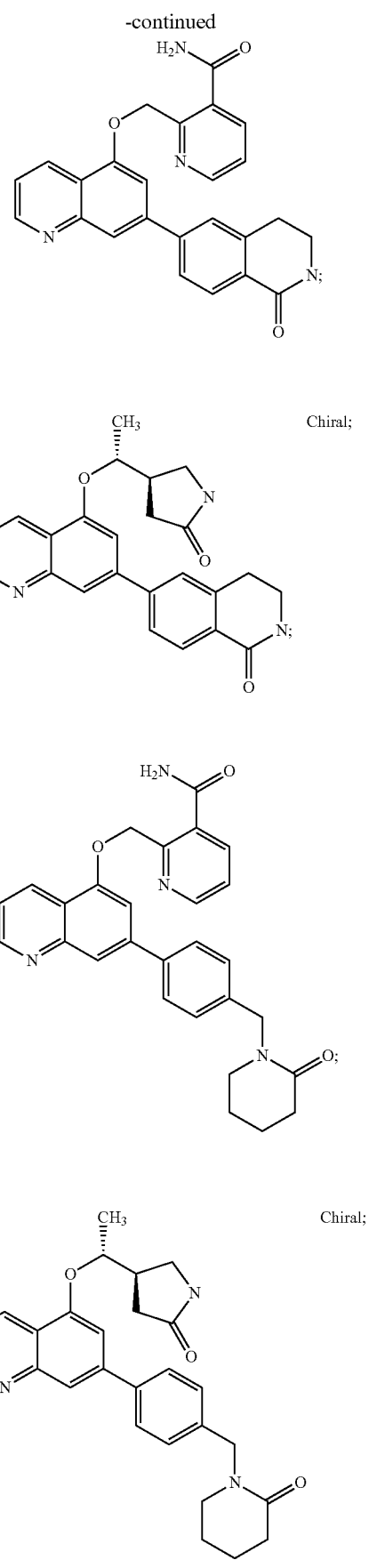

-continued
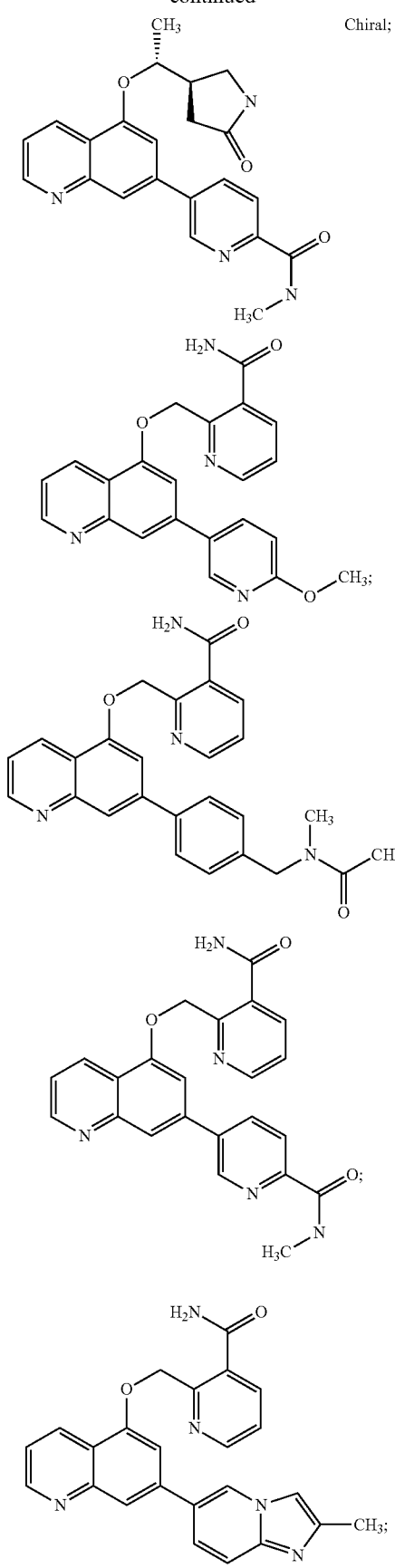
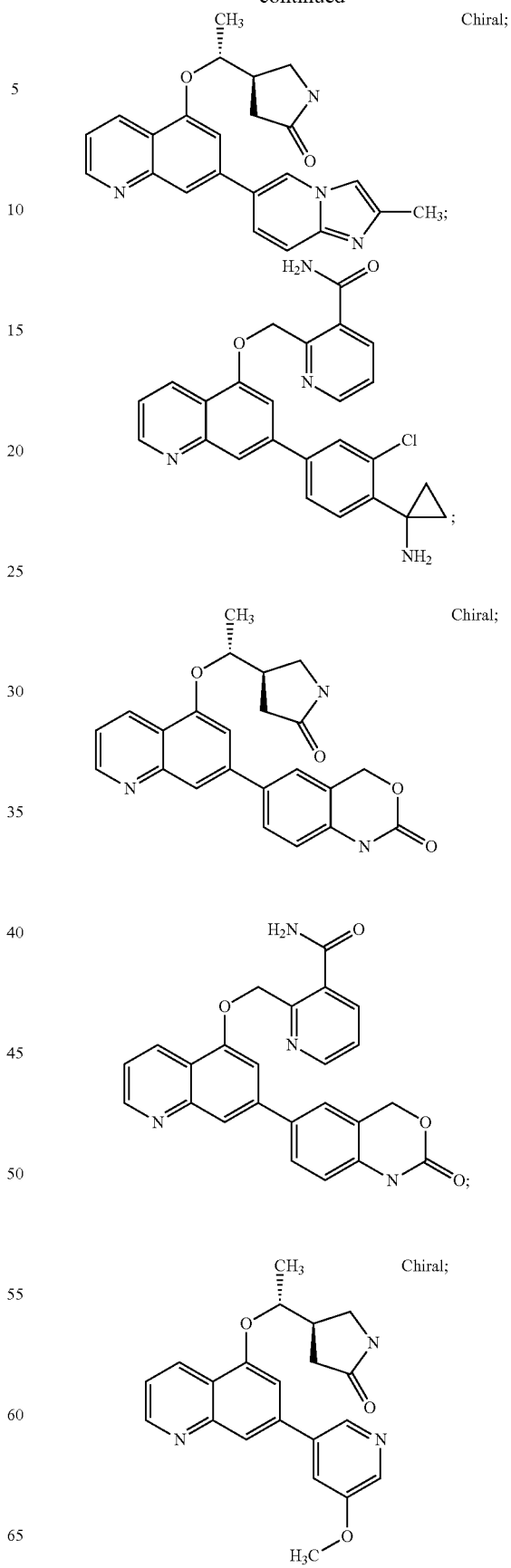

-continued
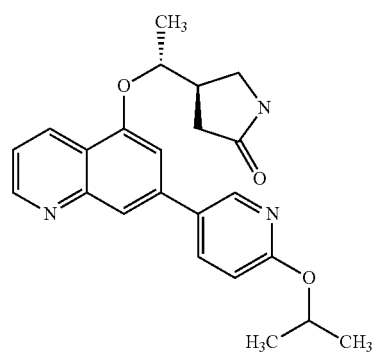
Chiral;
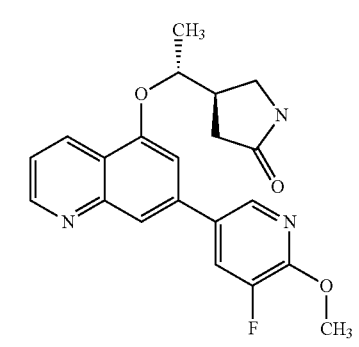
Chiral;
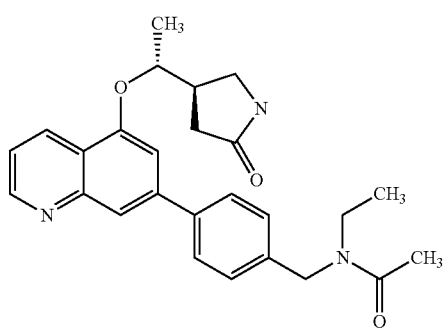
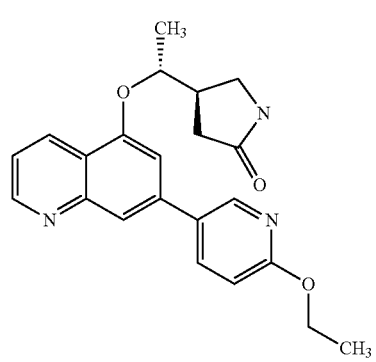
Chiral;
-continued
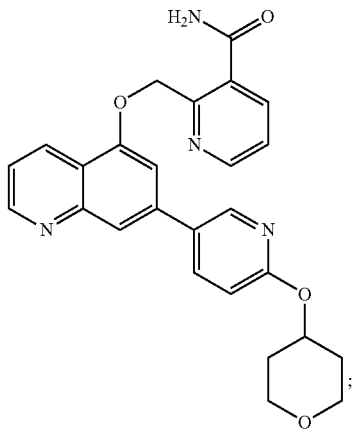
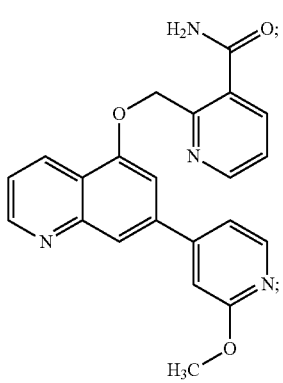
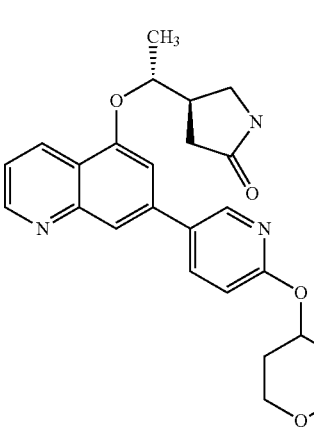
Chiral;
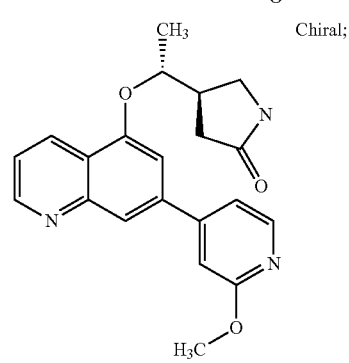
Chiral;

227
-continued
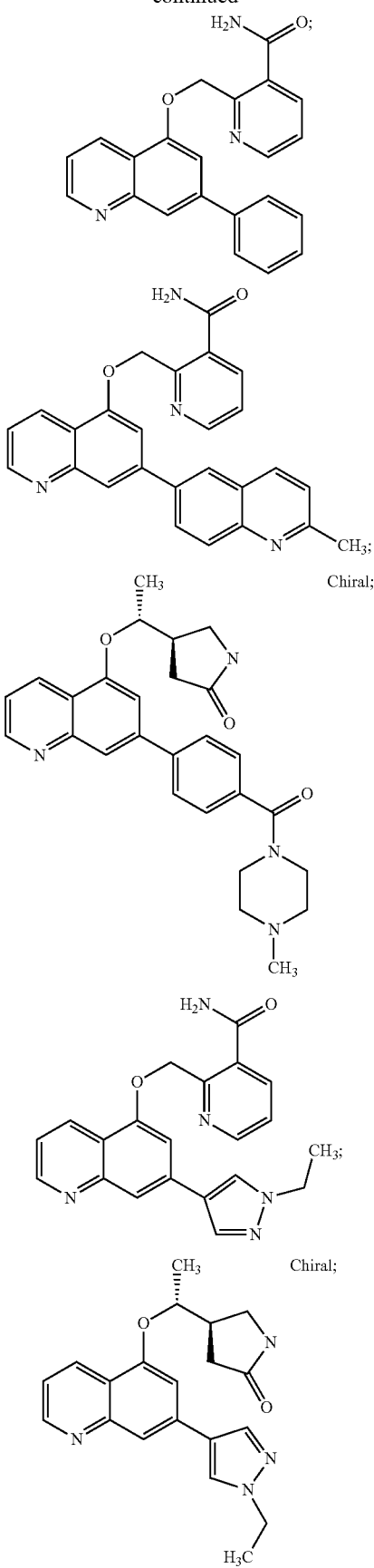
228
-continued
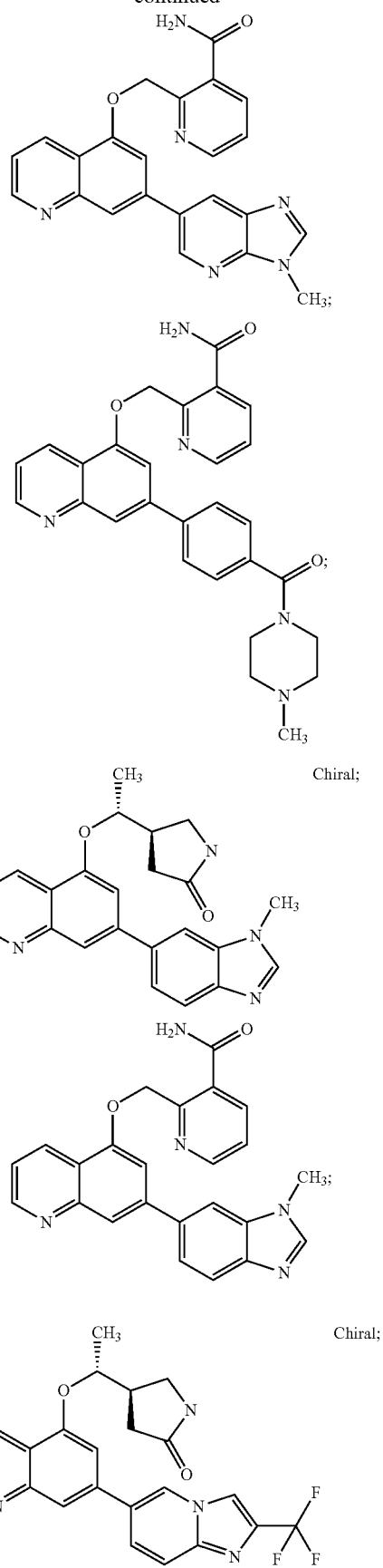

229
-continued
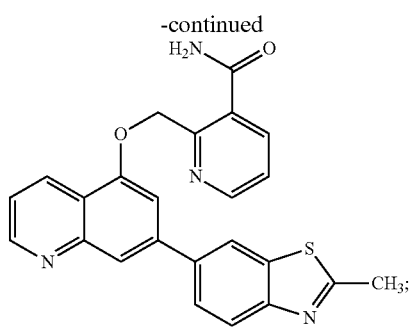
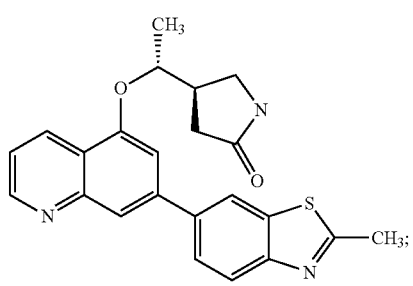
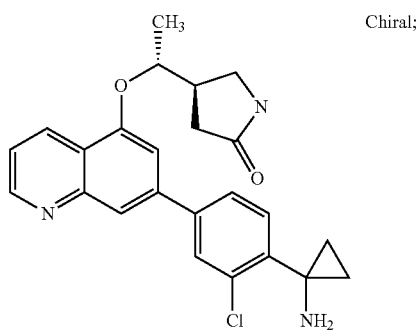
Chiral;
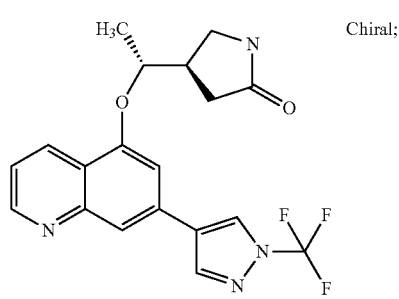
Chiral;
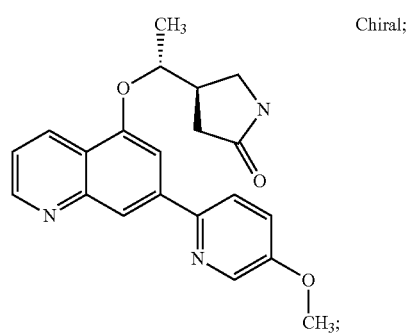
Chiral;
230
-continued
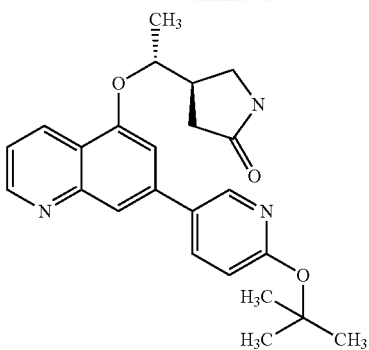
Chiral;
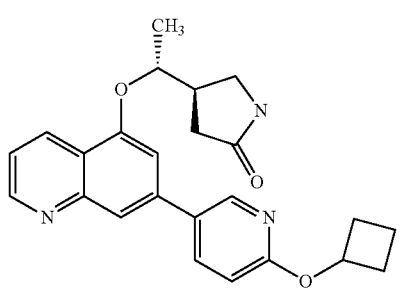
Chiral;
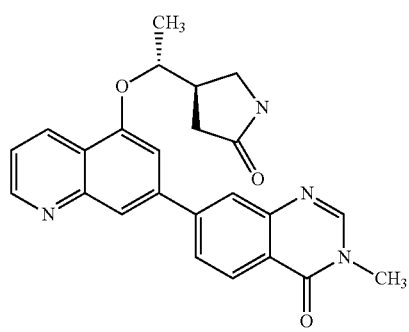
Chiral;
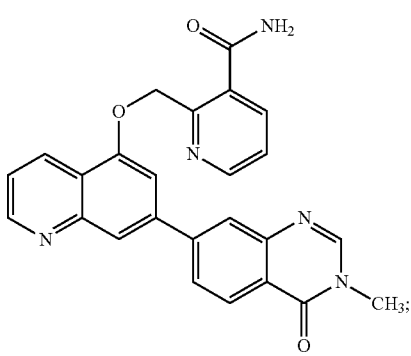
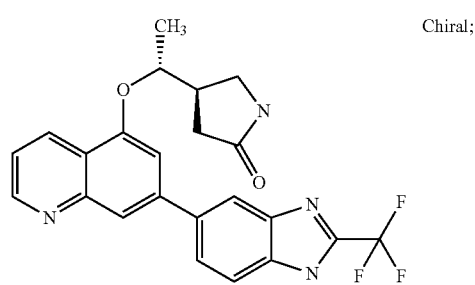
Chiral;

231
-continued
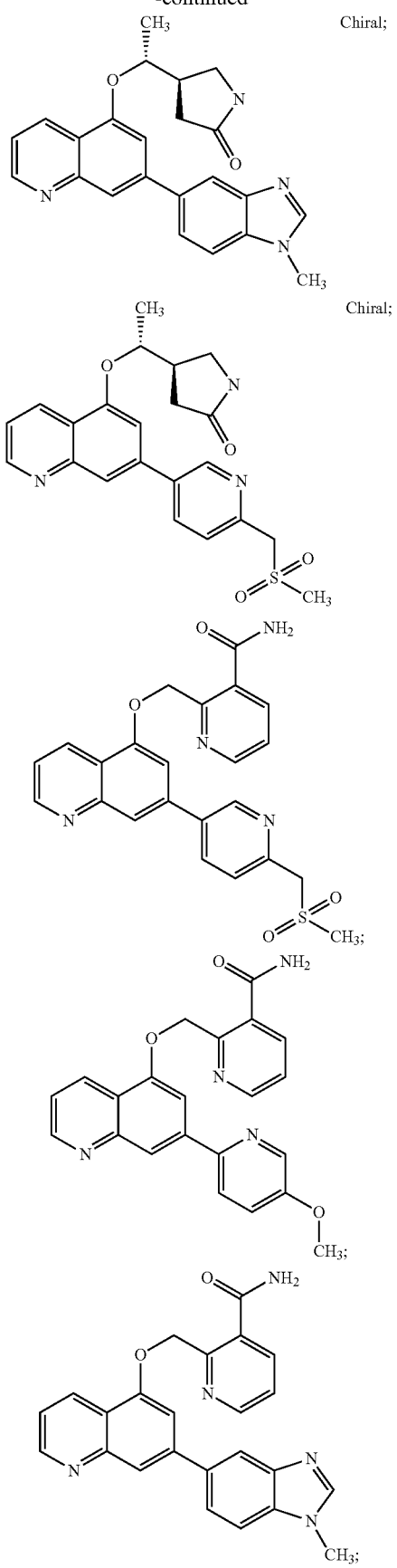
232
-continued
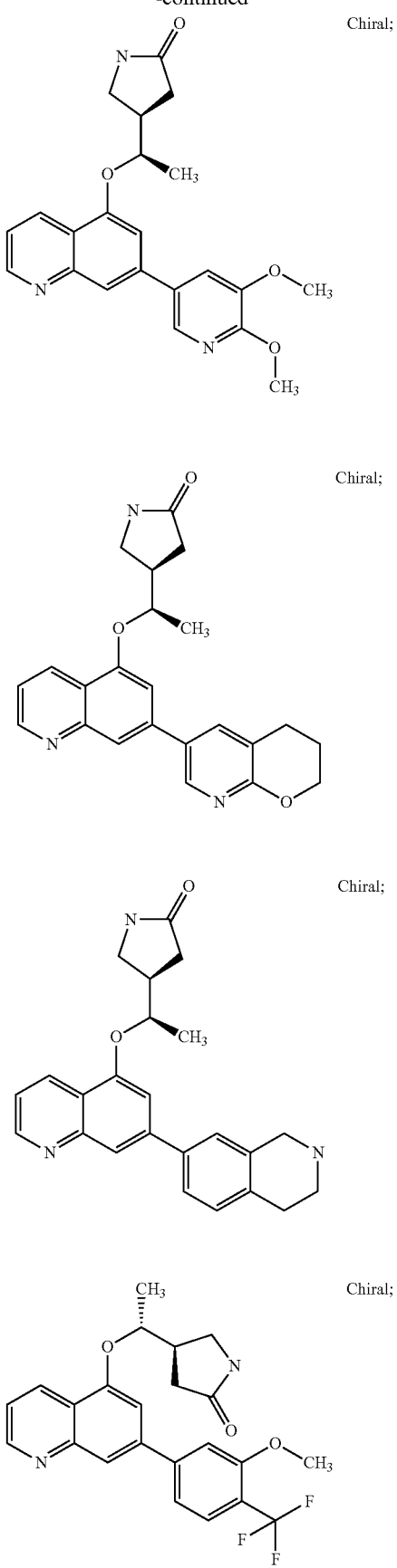

233
-continued
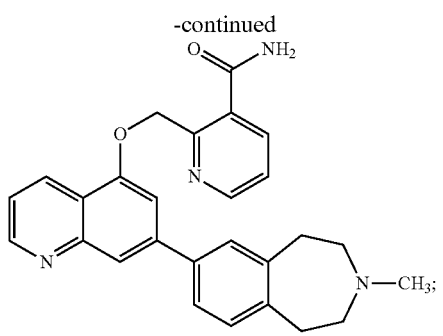
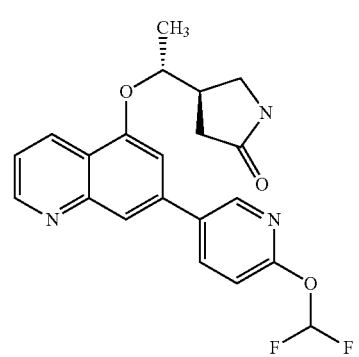
Chiral;
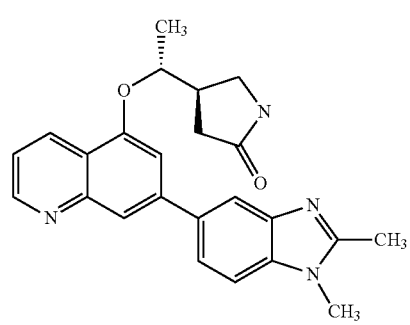
Chiral;
234
-continued
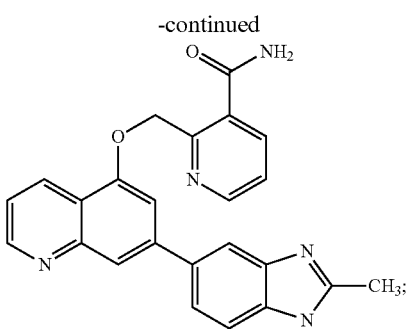
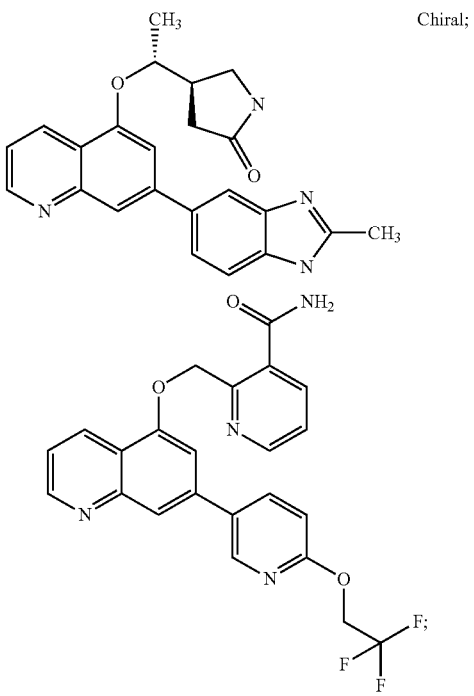
Chiral;
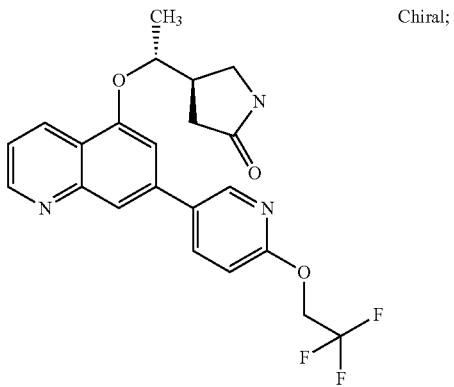
Chiral;
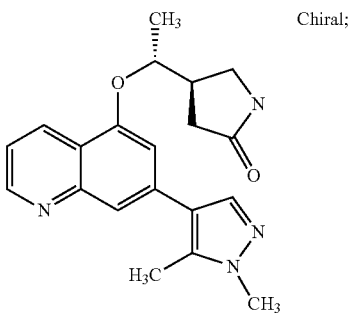
Chiral;

-continued

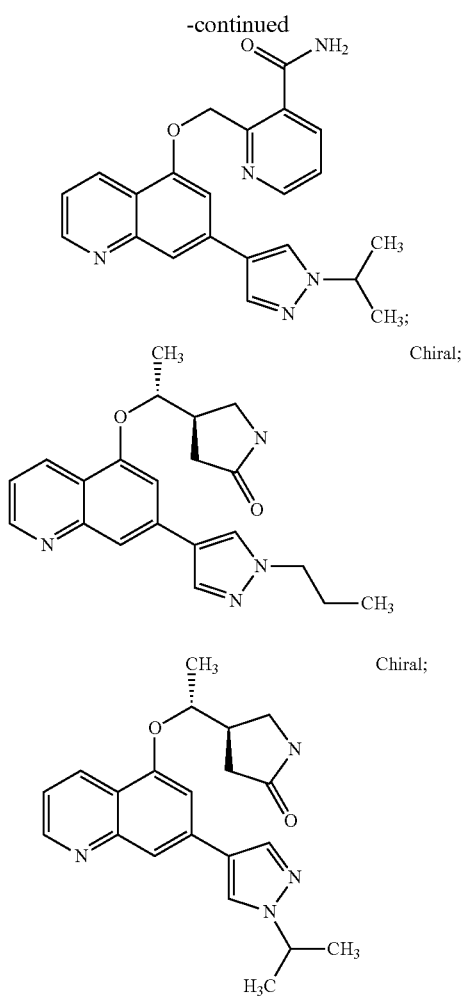

-continued

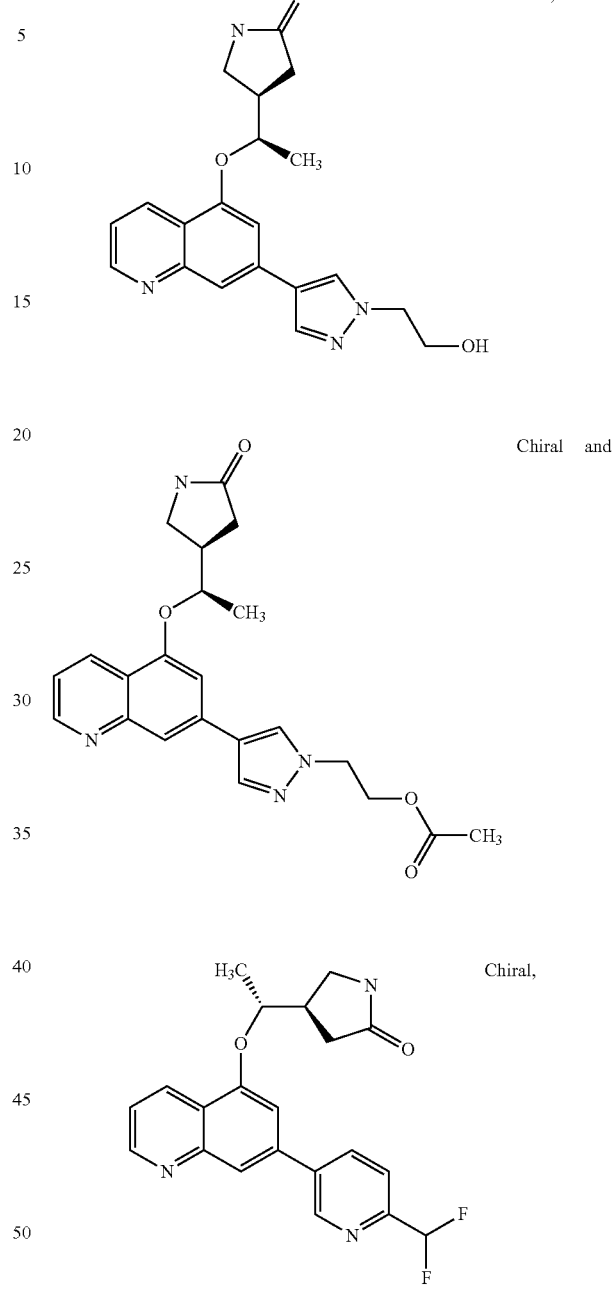

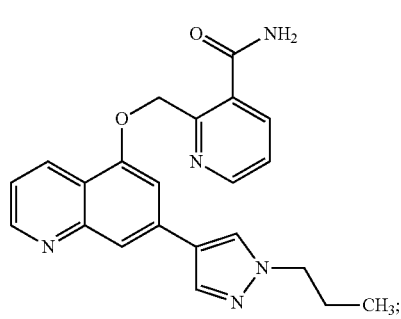 [SMILES: CCCn1cc(-c2cc(OCc3ncccc3C(N)=O)c3cccnc3c2)cn1]

or a pharmacologically acceptable salt thereof.

23. A pharmaceutical formulation comprising a therapeutically affective amount of a compound of formula 1 according to claim 1 and one or more pharmaceutically acceptable carriers and/or adjuvants.

24. The pharmaceutical formulation according to claim 23 in combination with an active substance selected from the group consisting of anticholinergics, betamimetics, corticosteroids, PDE4-inhibitors, EGFR-inhibitors, LTD4-antagonists, CCR3-inhibitors, CRTH2-antagonists, CCR1-antagonists, NSAIDS, COX 2-inhibitors (Coxibe), iNOS-inhibitors, HMG-CoA reductase inhibitors and folic acid antagonists.

25. A compounds selected from formula 7
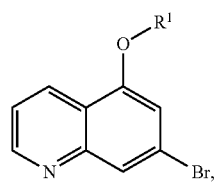
from formula A
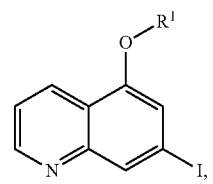
from formula B
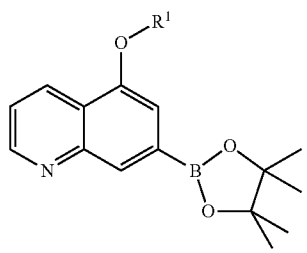
and from formula C
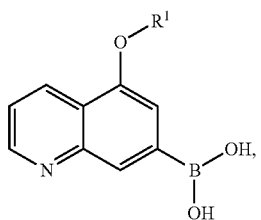
wherein R¹ and R² are defined as in one of claim 1.
26. A compound of formula 1 selected from a group consisting of:
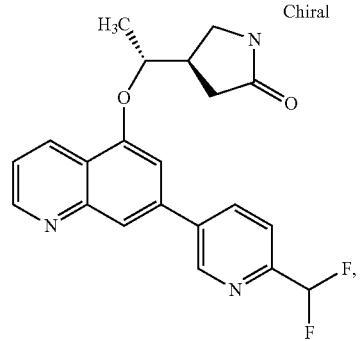
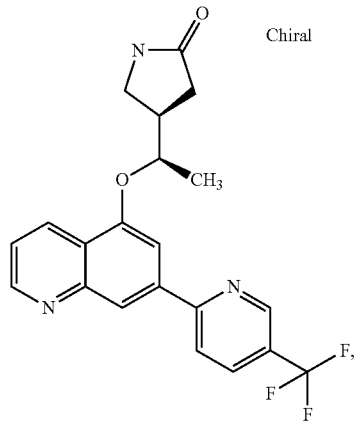
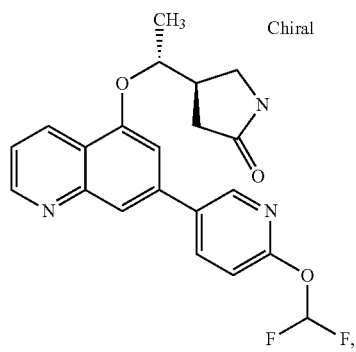
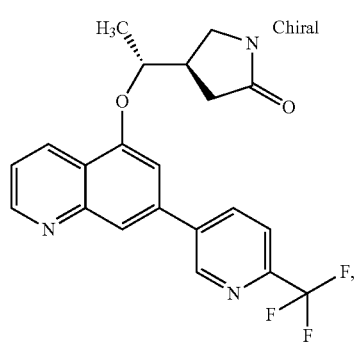
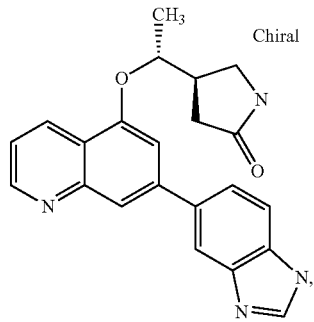

-continued
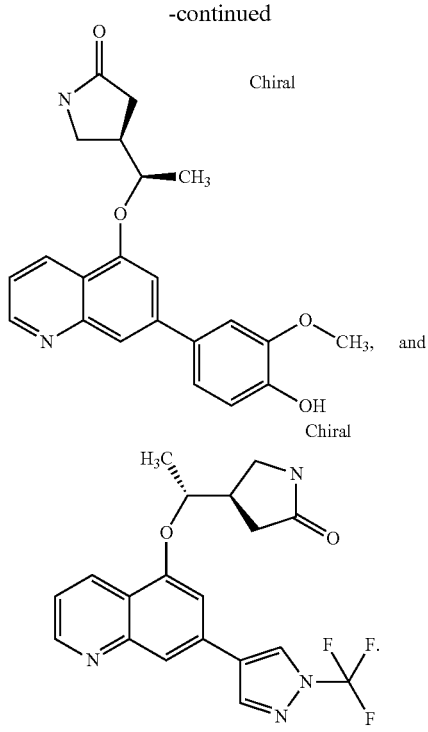
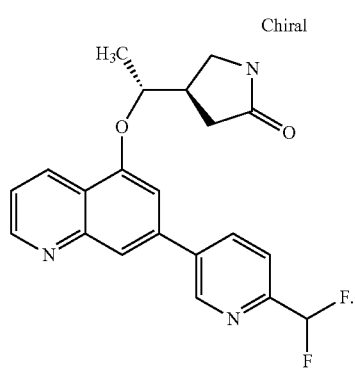 [SMILES: C[C@@H](Oc1cc(-c2ccc(C(F)F)nc2)cc2ncccc12)[C@H]1CNC(=O)C1]
27. The compound according to claim 26 wherein the compound is:
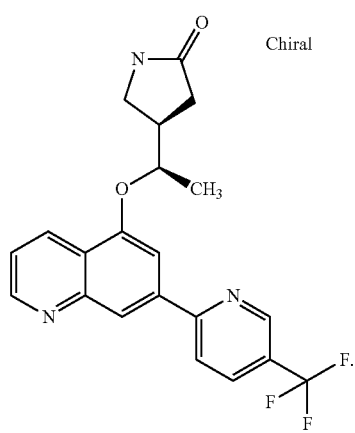 [SMILES: C[C@@H](Oc1cc(-c2ccc(C(F)(F)F)cn2)cc2ncccc12)[C@H]1CNC(=O)C1]
28. The compound according to claim 26 wherein the compound is:
29. The compound according to claim 26 wherein the compound is:
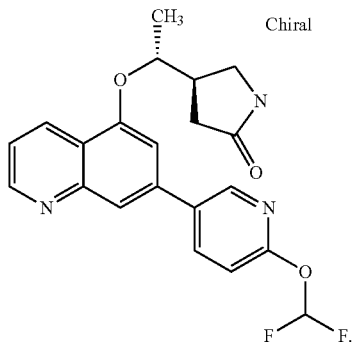 [SMILES: C[C@@H](Oc1cc(-c2ccc(OC(F)F)nc2)cc2ncccc12)[C@H]1CNC(=O)C1]
30. The compound according to claim 26 wherein the compound is:
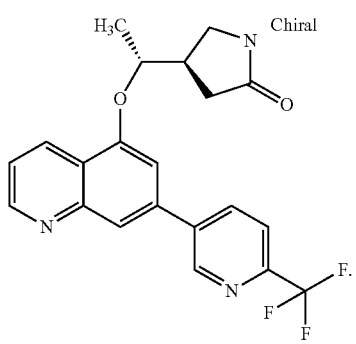 [SMILES: C[C@@H](Oc1cc(-c2ccc(C(F)(F)F)nc2)cc2ncccc12)[C@H]1CNC(=O)C1]
31. The compound according to claim 26 wherein the compound is:
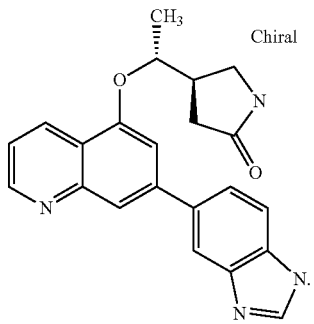
32. The compound according to claim 26 wherein the compound is:
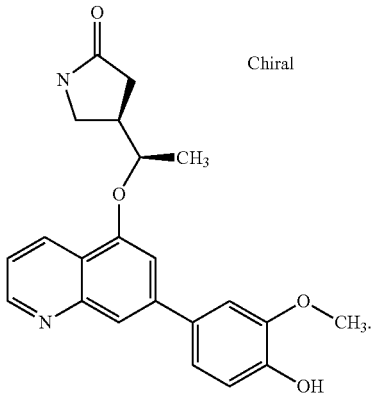 [SMILES: COc1cc(-c2cc(O[C@H](C)[C@H]3CNC(=O)C3)c3cccnc3c2)ccc1O]

33. The compound according to claim 26 wherein the compound is:

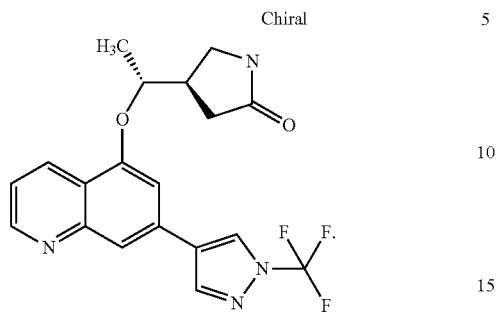

34. A pharmaceutical formulation comprising a therapeutically affective amount of a compound of formula 1 according to claim 26 and one or more pharmaceutically acceptable carriers and/or adjuvants.

35. The pharmaceutical formulation according to claim 34 in combination with an active substance selected from the group consisting of anticholinergics, betamimetics, corticosteroids, PDE4-inhibitors, EGFR-inhibitors, LTD4-antagonists, CCR3-inhibitors, CRTH2-antagonists, CCR1-antagonists, NSAIDS, COX 2-inhibitors (Coxibe), iNOS-inhibitors, HMG-CoA reductase inhibitors and folic acid antagonists.

* * * * *